(12) United States Patent
Kamo

(10) Patent No.: US 9,079,907 B2
(45) Date of Patent: Jul. 14, 2015

(54) FUSED HETEROCYCLIC COMPOUND AND USE THEREOF

(75) Inventor: Izumi Kamo, Osaka (JP)

(73) Assignee: TAKEDA PHARMACEUTICAL COMPANY LIMITED, Osaka (JP)

(*) Notice: Subject to any disclaimer, the term of this patent is extended or adjusted under 35 U.S.C. 154(b) by 0 days.

(21) Appl. No.: 13/410,774

(22) Filed: Mar. 2, 2012

(65) Prior Publication Data
US 2012/0165312 A1 Jun. 28, 2012

Related U.S. Application Data

(62) Division of application No. 12/227,333, filed as application No. PCT/JP2007/059944 on May 15, 2007, now Pat. No. 8,158,617.

(30) Foreign Application Priority Data

May 16, 2006 (JP) .................................. 2006/136236

(51) Int. Cl.
*A61B 5/00* (2006.01)
*A61B 5/103* (2006.01)
(Continued)

(52) U.S. Cl.
CPC .............. *C07D 487/04* (2013.01); *A61K 31/00* (2013.01); *A61K 31/4353* (2013.01);
(Continued)

(58) Field of Classification Search
USPC .......................................... 600/561, 587, 591
See application file for complete search history.

(56) References Cited

U.S. PATENT DOCUMENTS 6,995,153 B2 2/2006 Seto et al.
7,030,107 B2 4/2006 Seto et al.
(Continued)

FOREIGN PATENT DOCUMENTS

EP 1 591 120 A1 11/2005
EP 1 970 373 A1 9/2008
(Continued)

OTHER PUBLICATIONS

Peng et al., "External Urethral Sphincter Activity in a Rat Model of Pudendal Nerve Injury", Apr. 24, 2006, Neurourology and Urodynamics, 25: 388-396.*
(Continued)

*Primary Examiner* — Devin Henson
(74) *Attorney, Agent, or Firm* — Wenderoth, Lind & Ponack, L.L.P.

(57) ABSTRACT

The present invention relates to a serotonin 5-HT$_{2C}$ receptor activator containing a compound represented by the formula (I)

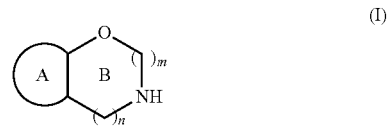

wherein ring A is a 5- or 6-membered aromatic heterocycle optionally having substituent(s), and ring B is a 7- to 9-membered ring optionally having substituent(s) other than an oxo group wherein the combination of m and n (m,n) is (1,2), (2,1), (2,2), (3,1), (3,2) or (4,1), or a salt thereof or a prodrug thereof, and a fused heterocyclic compound having a serotonin 5-HT$_{2C}$ receptor activating action and the like.

2 Claims, 1 Drawing Sheet

(51) Int. Cl.

| | |
|---|---|
| *A61B 5/117* | (2006.01) |
| *C07D 487/04* | (2006.01) |
| *A61K 31/00* | (2006.01) |
| *A61K 31/4353* | (2006.01) |
| *A61K 31/553* | (2006.01) |
| *C07D 223/16* | (2006.01) |
| *C07D 498/04* | (2006.01) |
| *C07D 519/00* | (2006.01) |
| *G01N 33/94* | (2006.01) |
| *A61N 1/36* | (2006.01) |
| *A61B 5/20* | (2006.01) |
| *A61B 5/0488* | (2006.01) |

(52) U.S. Cl.
CPC ........... *A61K 31/553* (2013.01); *C07D 223/16* (2013.01); *C07D 498/04* (2013.01); *C07D 519/00* (2013.01); *G01N 33/942* (2013.01); *A61B 5/04882* (2013.01); *A61B 5/202* (2013.01); *A61B 5/205* (2013.01); *A61N 1/36007* (2013.01)

(56) References Cited

U.S. PATENT DOCUMENTS

| | | | |
|---|---|---|---|
| 2004/0235856 | A1 | 11/2004 | McMurray et al. |
| 2005/0085469 | A1 | 4/2005 | Seto et al. |
| 2005/0107375 | A1 | 5/2005 | Seto et al. |
| 2006/0199795 | A1 | 9/2006 | Itoh et al. |
| 2007/0142357 | A1 | 6/2007 | Smith et al. |
| 2007/0274913 | A1 | 11/2007 | Kamo et al. |
| 2008/0045502 | A1 | 2/2008 | Wolgast et al. |
| 2008/0146583 | A1 | 6/2008 | McMurray et al. |
| 2008/0305162 | A1 | 12/2008 | Lluel et al. |
| 2009/0062253 | A1 | 3/2009 | Gahman et al. |
| 2009/0182140 | A1 | 7/2009 | Furukubo et al. |
| 2010/0173894 | A1 | 7/2010 | Brian et al. |
| 2010/0286120 | A1 | 11/2010 | Matsumoto et al. |
| 2010/0317651 | A1 | 12/2010 | Sasaki et al. |

FOREIGN PATENT DOCUMENTS

| | | |
|---|---|---|
| JP | 9-151186 | 6/1997 |
| JP | 2003-277384 | 10/2003 |
| JP | 2004/159919 | 6/2004 |
| JP | 2004-524029 | 8/2004 |
| JP | 2004-346059 | 12/2004 |
| JP | 2006-056881 | 3/2006 |
| WO | 00/64904 | 11/2000 |
| WO | 02/067867 | 9/2002 |
| WO | 02/074746 | 9/2002 |
| WO | 03/050123 | 6/2003 |
| WO | 03/062245 | 7/2003 |
| WO | 2004/067008 | 8/2004 |
| WO | 2004/096196 | 11/2004 |
| WO | 2005/044822 | 5/2005 |
| WO | 2006/022420 | 3/2006 |
| WO | 2007/074291 | 7/2007 |
| WO | 2009/032754 | 3/2009 |

OTHER PUBLICATIONS

Kamo et al. "The role of baldder-to-urethral reflexes in urinary incontinence", AJP-Renal Physiol. Volume 287, Sep. 2004, pp. F434-F441.*

Cueva-Rolon et al. "Vagotomy Blocks Responses to Vaginocervical Stimulation After Genitospinal Neurectomy in Rats", Physiology & Behavior, vol. 60, Issue 1, Jul. 1996, pp. 19-24.*

Opposition to Letters Patent (with English translation) issued in Costa Rican Application No. 2011-0021, published Mar. 8, 2012.

European Search Report issued Apr. 4, 2014 in corresponding European Application No. 13 19 5352.

Kaiho et al., "Role of noradrenergic pathways in sneeze-induced urethral continence reflex in rats", American Journal of Physiology—Renal Physiology, vol. 292, 2007, pp. F639-F646.

Torimoto et al., "Effects of Serotonin and Noreinephrine Reuptake Inhibitors on the Bladder-to-Urethral Reflexes (BURS) Preventing Stress Urinary Incontinence (SUI)", The Journal of Urology, vol. 171, No. 4, Supplement, May 9, 2004, pp. 130-131.

Torimoto et al., "The urethral closing mechanism preventing stress urinary incontinence (SUI) induced by the bladdertourethral reflexes", Abstracts of the Annual Meeting of the Society for Neuroscience; 33rd Annual Meeting of the Society of Neuroscience, Presentation No. 189.2, Nov. 9, 2003.

Kamo et al., "Urethral closure mechanisms under sneeze-induced stress condition in rats: a new animal model for evaluation of stress urinary incontinence", American Journal of Physiology—Regulatory, Integrative and Comparative Physiology, vol. 285, May 15, 2003, pp. R356-R365.

Conway et al., "Comparison of leak point pressure methods in an animal model of stress urinary incontinence", International Urogynecology Journal, vol. 16, 2005, pp. 359-363.

Hijaz et al., "Efficacy of Vaginal Sling Procedure in a Rat Model of Stress Urinary Incontinence", The Journal of Urology, vol. 172, Nov. 2004, pp. 2065-2068.

Hijaz et al., "Long-Term Efficacy of a Vaginal Sling Procedure in a Rat Model of Stress Urinary Incontinence", The Journal of Urology, vol. 173, May 2005, pp. 1817-1819.

Hijaz et al., "Role of Sling Integrity in the Restoration of Leak Point Pressure in the Rat Vaginal Sling Model", The Journal of Urology, vol. 174, Aug. 2005, pp. 771-775.

Kamo et al., "Involvement of reflex urethral closure mechanisms in urethral resistance under momentary stress condition induced by electrical stimulation of rat abdomen", American Journal of Physiology—Renal Physiology, vol. 293, 2007, pp. F920-F926.

Hijaz et al., "Animal Models of Female Stress Urinary Incontinence", The Journal of Urology, vol. 179, Jun. 2008, pp. 2103-2110.

Miyazato et al., "Effect of duloxetine, a norepinephrine and serotonin reuptake inhibitor, on sneeze-induced urethral continence reflex in rats", American Journal of Physiology—Renal Physiology, vol. 295, 2008, pp. F264-F271.

Miyazato et al., "Role of spinal serotonergic pathways in sneeze-induced urethral continence reflex in rats", American Journal of Physiology—Renal Physiology, vol. 297, Jul. 29, 2009, pp. F1024-F1031.

European Search Report issued May 19, 2014 in corresponding Application No. 13195343.2.

J. Eric Jelovsek et al., "Pelvic organ prolapse", The Lancet, vol. 369, Mar. 24, 2007, pp. 1027-1038.

Michael J. Bishop et al., "New 5-$HT_{2c}$ receptor agonists", Expert Opinion on Therapeutic Patents, vol. 13, No. 11, 2003, pp. 1691-1705.

Methvin Isaac et al., "Pyrrolo[3,2,1-*ij*]quinoline Derivatives, a 5-$HT_{2c}$ Receptor Agonist with Selectivity over the 5-$HT_{2a}$ Receptor: Potential Therapeutic Applications for Epilepsy and Obesity", Bioorganic & Medicinal Chemistry Letters, vol. 10, Feb. 16, 2000, pp. 919-921.

Methvin Isaac, "The 5-$HT_{2c}$ receptor as a potential therapeutic target for the design of antiobesity and antiepileptic drugs", Drugs of the Future, vol. 26, No. 4, 2001, pp. 383-393.

J. Paterson et al., "Pelvic floor exercises as a treatment for postmicturition dribble", British Journal of Urology, vol. 79, No. 6, pp. 892-897, Jun. 1997.

X. G. Yang et al., "Synthese von Pyridazino[3,4-f][1,4]oxazepinen durch intramolekulare [4+2]-Cycloaddition mit inversem Elektronenbedarf", Chemiker-Zeitung, vol. 115, No. 12, pp. 367-369, 1991.

I. Ito et al., "Synthesis of Pyrazolone Derivatives. XXX. Synthesis of Pyrazolo[3,4-*b*][1,4]oxazepines", Chemical & Pharmaceutical Bulletin, vol. 25, No. 6, pp. 1443-1446, 1977.

(56) References Cited

OTHER PUBLICATIONS

S. Seto et al., "Design, synthesis, and evaluation of novel 2-substituted-4-aryl-6,7,8,9-tetrahydro-5H-pyrimido-[4,5-b][1,5]oxazocin-5-ones as NK$_1$ antagonists", Bioorganic & Medicinal Chemistry, vol. 13, No. 20, pp. 5717-5732, 2005.

Supplementary European Search Report issued Jun. 7, 2010 in European Application No. 07743379.5.

Nicolaus, B.J.R. "Symbiotic Approach to Drug Design," Decision Making in Drug Research, XX, XX, Jan. 1983, pp. 173-186, XP001111439.

Office Action mailed Mar. 10, 2015 in corresponding Japanese Application No. 2014-029593 (with English translation).

"Gynecologic and Obstetric Surgery", 2004, No. 15, pp. 75-82.

"Surgical Therapy", 2000, vol. 83, No. 2, pp. 153-159.

\* cited by examiner

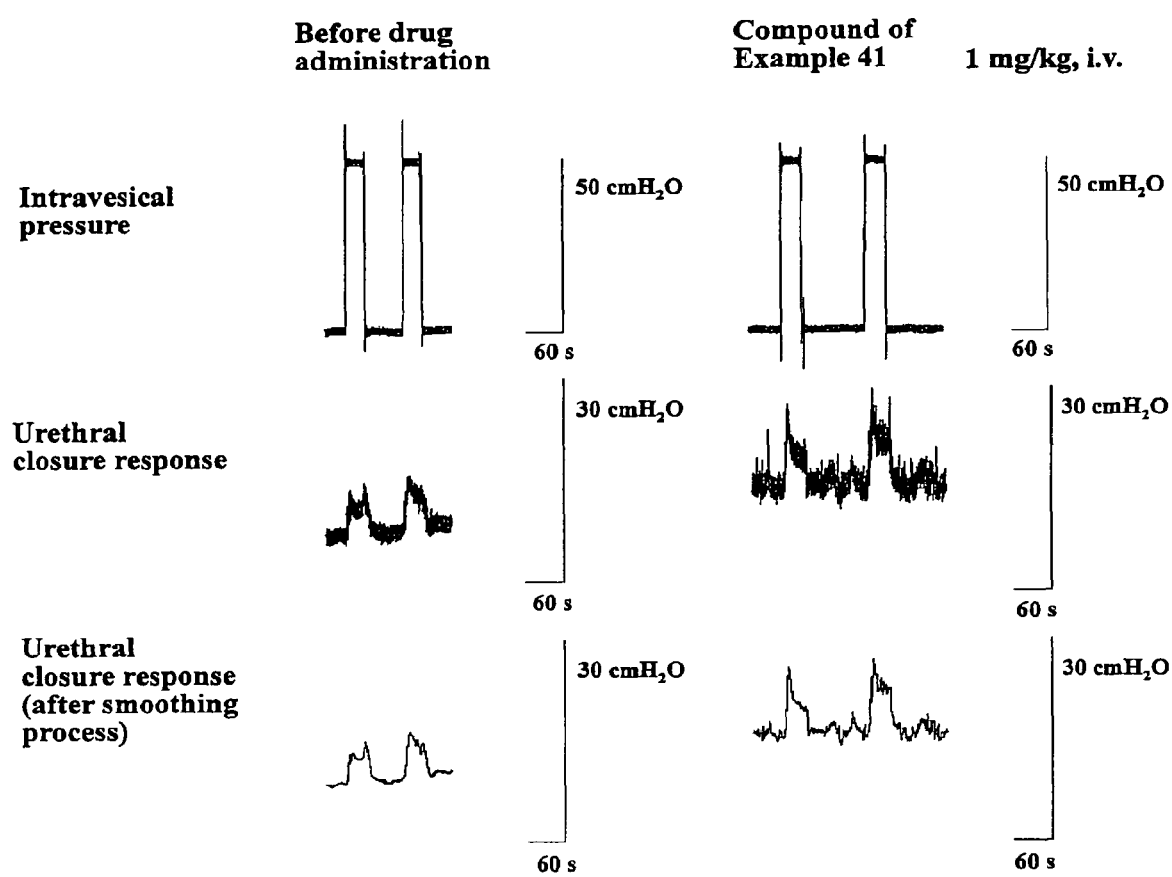

FUSED HETEROCYCLIC COMPOUND AND USE THEREOF

This application is a divisional application of U.S. application Ser. No. 12/227,333, filed Nov. 14, 2008, now U.S. Pat. No. 8,158,617 now allowed, which is the national phase filing of International Patent Application No. PCT/JP2007/059944, filed May 15, 2007.

TECHNICAL FIELD

The present invention relates to a fused heterocyclic compound that possesses excellent serotonin $5\text{-HT}_{2C}$ receptor activation action, and that is useful as a therapeutic or prophylactic drug and the like for stress urinary incontinence and/or obesity and the like, a prophylactic or therapeutic agent for pelvic organ prolapse (genital organ prolapse), rectal prolapse or post-micturition dribble comprising a compound that possesses serotonin $5\text{-HT}_{2C}$ receptor activation action, and a screening method for a substance that increases the contraction of the pelvic floor muscles.

BACKGROUND OF THE INVENTION

The serotonin $5\text{-HT}_{2C}$ receptor, one of the receptors of the biological transmitter serotonin, is distributed mainly in the central nervous system and controls many physiological functions in vivo. A representative example is the control of appetite; it has been demonstrated in a study with rodents that when the central serotonin $5\text{-HT}_{2C}$ receptor is stimulated, eating behavior lessons and body weight is lost. In humans as well, it has been reported that when a serotonin $5\text{-HT}_{2C}$ receptor activator is administered, appetite is suppressed and body weight is lost (see non-patent document 1). In addition, stimulation of the central serotonin $5\text{-HT}_{2C}$ receptor has been shown to suppress depression-related behavior in a rat study using a serotonin $5\text{-HT}_{2C}$ receptor activator (see non-patent document 2), and has also been reported to be effective on many central nervous diseases such as anxiety (see non-patent document 3). The serotonin $5\text{-HT}_{2C}$ receptor is also highly expressed in the parasympathetic nucleus and motorial nerve cell bodies in the sacral spinal cord, and is thought to control peripheral nervous functions (see non-patent document 4). It has been reported that when a serotonin $5\text{-HT}_{2C}$ receptor activator is administered to rats, penile erection is induced (see non-patent document 5), and urethral resistance is increased (see patent document 1); all these actions are attributed to stimulation of the serotonin $5\text{-HT}_{2C}$ receptor in the sacral spinal cord. For serotonin $5\text{-HT}_{2C}$ receptor activators, many clinical applications are likely, with particular expectations for anti-obesity drugs, antidepressants, anti-anxiety drugs, therapeutic drugs for male erectile dysfunction, and therapeutic drugs for stress urinary incontinence and the like.

As a heterocyclic amine compound, the following compounds have been reported.

(1) A compound represented by the formula

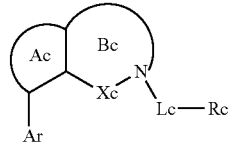

wherein ring Ac is an optionally substituted aromatic ring; ring Bc is a nitrogen-containing 6- to 9-membered ring optionally further having substituent(s) other than -Lc-Rc; Xc is an optionally substituted methylene group; Ar is an optionally substituted aromatic group; Rc is an optionally substituted cyclic group; Lc is an optionally substituted $C_{1\text{-}3}$ alkylene group, —CONH—, —SO$_2$NH— or —SO$_2$—, and Xc is not a methylene group substituted by an oxo group, or a salt thereof (see patent document 2).

(2) A compound represented by the formula

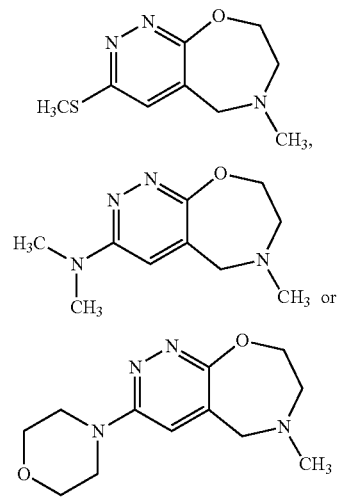

(see non-patent document 6).

(3) A compound represented by the formula

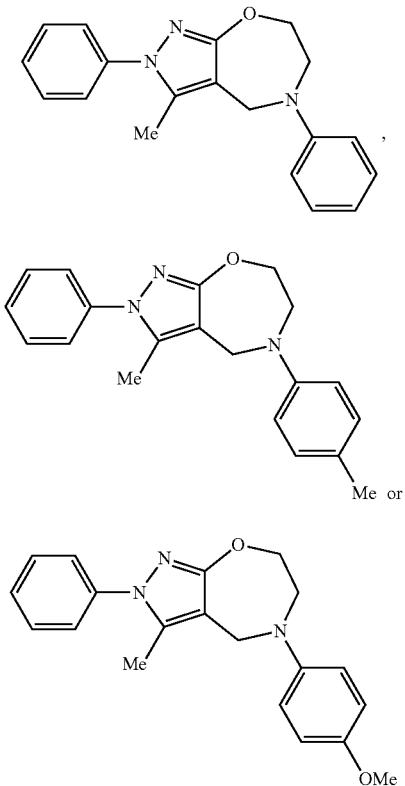

(see non-patent document 7).

(4) A compound represented by the formula

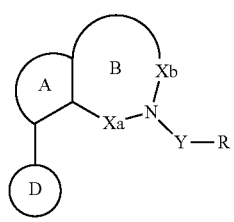

wherein ring A is an optionally further substituted aromatic heterocycle;
ring B is an optionally further substituted nitrogen-containing 6- to 9-membered ring;
Xa is an optionally substituted methylene group (excluding —C(=O)—);
Xb is an optionally substituted methylene group;
Y is an optionally substituted $C_{1-3}$ alkylene group, —CONH—, —SO$_2$NH— or —SO$_2$—,
R is an optionally substituted aromatic group; and
ring D is an optionally substituted aromatic ring or an optionally substituted non-aromatic heterocycle,
provided that when ring D is an optionally substituted benzene ring, then the benzene ring has a substituent at the ortho-position relative to the bond with ring A, or Xb is a substituted methylene group,
or a salt thereof (see patent document 3).

However, no reference is made to the serotonin 5-HT$_{2C}$ receptor-activating action of the compound.

"Pelvic organ prolapse" is a disease wherein the anterior wall of the vagina, the posterior wall of the vagina, the uterus, the vaginal stump after hysterectomy or the urinary bladder descends and protrudes beyond the vaginal orifice (see, for example, non-patent document 8 and non-patent document 9); this descent becomes conspicuous when abdominal pressure rises transiently as a result of straining or bearing a heavy load and the like. "Rectal prolapse" is characterized by the symptom in which the rectum likewise descends and protrudes beyond the anus (see, for example, non-patent document 8). These diseases are prevalent in females, with childbirth, aging, and obesity being known as risk factors, and one of suggested causes thereof is the weakening of the pelvic floor muscles and perivisceral connective tissue that support the vagina, the uterus and the like. The pelvic floor muscles are skeletal muscles that unite with the pelvis in a hammock-like way, serving constantly to maintain some contraction and support the organs in the pelvis from below. In pelvic organ prolapse and rectal prolapse, organ weights reportedly become unendurable because of the weakening of these pelvic floor muscles, resulting in the descent of the pelvic organs and the rectum (see, for example, non-patent document 8 and non-patent document 9); it is thought that when abdominal pressure rises particularly, the increased pressure becomes unendurable and the protrusion becomes more conspicuous. On the other hand, it has been reported that when abdominal pressure rises, the urinary bladder is compressed, reflex via the urinary bladder-spinal cord-pelvic floor muscles and the urethra causes the pelvic floor muscles and the urethral sphincter to contract to increase urethral internal pressure, whereby urinary incontinence is prevented (see, for example, non-patent document 10). For this reason, it is thought that upon a rise in abdominal pressure, the pelvic floor muscles contract reflexly to prevent not only urinary incontinence, but also the descent of the pelvic organs. If there is a disorder in this reflex pathway or the pelvic floor muscles, sufficient contraction of the pelvic floor muscles cannot be obtained and support for the pelvic organs becomes inadequate. Therefore, in screening for a therapeutic drug for pelvic organ prolapse or rectal prolapse, a test system for evaluating the contractile responses of the pelvic floor muscles is useful. However, almost no basic studies have been conducted on these prolapses (pelvic organ prolapse and rectal prolapse), and currently there is no evaluation system. Nor is there any reported method of evaluating the contractile force of the pelvic floor muscles in vivo.

Lower urinary tract symptoms consist of storage symptoms, voiding symptoms and post-micturition symptoms, and one of the major post-micturition symptoms is post-micturition dribble. Post-micturition dribble is a complaint of involuntary voiding immediately after micturition, occurring usually after leaving the toilet bowl for males, and after standing up for females. For post-micturition dribble as such, it has been reported that pelvic floor muscle exercise is effective (see non-patent documents 11 to 13); the weakening of the pelvic floor muscles is thought to be a cause thereof.

Many compounds are known to bind to the serotonin 5-HT$_{2C}$ receptor; patent documents 4 to 9 state that compounds that bind to the serotonin 5-HT$_{2C}$ receptor are useful in the treatment of stress urinary incontinence and the like, but there is no statement on their therapeutic effects on pelvic organ prolapse, rectal prolapse or post-micturition dribble.

non-patent document 1: Expert Opinion on Investigational Drugs, 2006, vol. 15, p. 257-266
non-patent document 2: J. Pharmacol. Exp. Ther., 1998, vol. 286, p. 913-924
non-patent document 3: Pharmacology Biochemistry Behavior, 2002, vol. 71, p. 533-554
non-patent document 4: Neuroscience, 1999, vol. 92, p. 1523-1537
non-patent document 5: Eur. J. Pharmacol., 2004, vol. 483, p. 37-43
non-patent document 6: Chemiker-Zeitung, 1991, vol. 115, No. 12, p. 367-369
non-patent document 7: Chem. Pharm. Bull., 1977, vol. 25, No. 6, p. 1443-1446
non-patent document 8: Lancet 2007, vol. 369, p. 1027-38
non-patent document 9: European Urology 2007, vol. 51, p. 884-886
non-patent document 10: American Journal of Physiology Renal Physiology 2004, vol. 287, p. F434-441
non-patent document 11: British Journal of Urology 1997, vol. 79, p. 892-897
non-patent document 12: Urologic Nursing 2004, vol. 24, p. 490-497, 512
non-patent document 13: British Journal of Nursing 2005, vol. 14, p. 1014-1018, 1020-1021
patent document 1: WO04/096196
patent document 2: WO04/067008
patent document 3: JP-A-2006-056881
patent document 4: WO02/040457
patent document 5: WO02/083863
patent document 6: WO03/097636
patent document 7: WO04/000829
patent document 8: WO04/000830
patent document 9: WO02/008178

DISCLOSURE OF THE INVENTION

Problems to be Solved by the Invention

There is a demand for the development of a compound that possesses serotonin 5-HT$_{2C}$ receptor activation action, that is useful as a therapeutic or prophylactic drug and the like for stress urinary incontinence, obesity and the like, and that has excellent profiles in terms of receptor selectivity, pharmacological efficacy, duration of action, specificity, low toxicity and the like.

It is an object of the present invention to provide a prophylactic or therapeutic agent for diseases such as stress urinary incontinence and obesity, comprising a fused heterocyclic compound that has a chemical structure different from that of any of commonly known compounds including the aforementioned compound, and that possesses serotonin 5-$HT_{2C}$ receptor activation action and the like.

It is an important task to construct an in vivo evaluation system that is convenient, useful and efficient in designing and screening for a novel therapeutic drug. However, currently, there is no established method for evaluating the reflex contractile force of the pelvic floor muscles in vivo. For this reason, if a new evaluation system allowing efficient screening for the reflex contractile force of the pelvic floor muscles is constructed, an excellent therapeutic drug for prolapse (pelvic organ prolapse or rectal prolapse) or post-micturition dribble can be provided.

Means for Solving the Problems

The present inventors have conducted intensive studies and succeeded for the first time in the creation of a serotonin 5-$HT_{2C}$ receptor activator comprising a compound represented by the formula

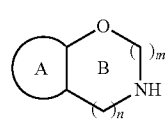

(I)

wherein ring A is a 5- or 6-membered aromatic heterocycle optionally having substituent(s), and ring B is a 7- to 9-membered ring optionally having substituent(s) other than an oxo group wherein the combination of m and n (m,n) is (1,2), (2,1), (2,2), (3,1), (3,2) or (4,1), or a salt thereof (hereinafter to be abbreviated as compound (I)) or a prodrug thereof and further found that compound (I) unexpectedly has superior properties as a serotonin 5-$HT_{2C}$ receptor activator and is sufficiently satisfactory as a pharmaceutical agent. Based on these findings, they have completed the present invention. In the above-mentioned compound (I), a compound represented by the formula

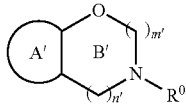

wherein ring A' is a 5- or 6-membered aromatic heterocycle optionally having substituent(s) (wherein ring A' does not include rings represented by

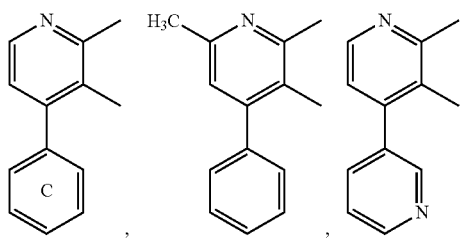

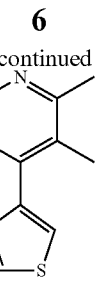

wherein ring C is a benzene ring optionally having substituent(s)), ring B' is a 7- to 9-membered ring optionally having substituent(s) other than an oxo group, a thioxo group and an imino group optionally having a substituent wherein the combination of m' and n' (m',n') is (1,2), (2,1), (2,2), (3,1), (3,2) or (4,1), and $R^0$ is a hydrogen atom or a hydrocarbon group optionally having substituent(s) other than an oxo group, excluding the compounds represented by the formulas

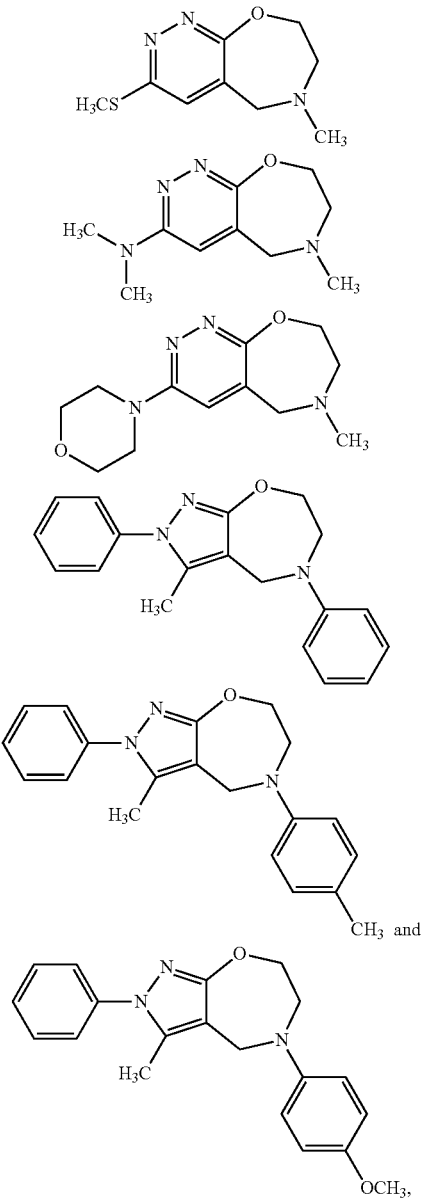

or a salt thereof is a novel compound.

The present inventors also found that in a state wherein the spinal cord is cut at the thoracic spinal cord, and wherein the hypogastric nerve and the pudendal nerve are cut bilaterally, the urethral closure responses observed upon a rise in the intravesical pressure in an anesthetized female rat are remarkably decreased by cutting the nerves that lead to the iliococcygeus muscle and the pubococcygeus muscle bilaterally, and are reactions by the iliococcygeus muscle and the pubococcygeus muscle, which are the pelvic floor muscles. That is, it was found that by raising intravesical pressure in a state wherein the hypogastric nerve and the pudendal nerve are cut bilaterally, and monitoring the urethral closure responses, it is possible to evaluate the contractile responses of the pelvic floor muscles in vivo, and that by introducing this item for evaluation, a new method of in vivo evaluation of pharmacological efficacy for seeking a therapeutic drug for pelvic organ prolapse, rectal prolapse or post-micturition dribble is provided. On the basis of the same principle as this method, by raising intravesical pressure in a state wherein the hypogastric nerve and the pudendal nerve are cut bilaterally, and measuring the closure responses of rectal internal pressure or vaginal internal pressure, it is also possible to evaluate the contractile responses of the iliococcygeus muscle and the pubococcygeus muscle, which are the pelvic floor muscles. Urethral resistance in the urine storage phase can also be evaluated instead of urethral closure responses. As an index of urethral resistance, leak point pressure, which is an intravesical pressure that causes urine leakage, can be used. By raising intravesical pressure in a state wherein the hypogastric nerve and the pudendal nerve are cut bilaterally, and evaluating leak point pressure, it is possible to evaluate the contractile responses of the pelvic floor muscles.

Furthermore, the present inventors found that by using these methods of in vivo evaluation of pharmacological efficacy and the like, it is possible to allow a substance that activates the serotonin 5-$HT_{2C}$ receptor to increase the reflex contractile responses of the pelvic floor muscles, and to prevent or treat pelvic organ prolapse, rectal prolapse or post-micturition dribble. The present inventors conducted further investigations based on these findings, and developed the present invention.

Accordingly, the present invention relates to

[1] a serotonin 5-$HT_{2C}$ receptor activator comprising a compound represented by the formula

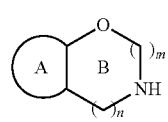
(I)

wherein ring A is a 5- or 6-membered aromatic heterocycle optionally having substituent(s), and ring B is a 7- to 9-membered ring optionally having substituent(s) other than an oxo group wherein the combination of m and n (m,n) is (1,2), (2,1), (2,2), (3,1), (3,2) or (4,1), or a salt thereof or a prodrug thereof;

[2] the serotonin 5-$HT_{2C}$ receptor activator of [1] which is an agent for the prophylaxis or treatment of stress urinary incontinence and/or obesity;

[3] a compound represented by the formula

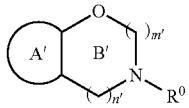

wherein ring A' is a 5- or 6-membered aromatic heterocycle optionally having substituent(s) (wherein ring A' does not include rings represented by

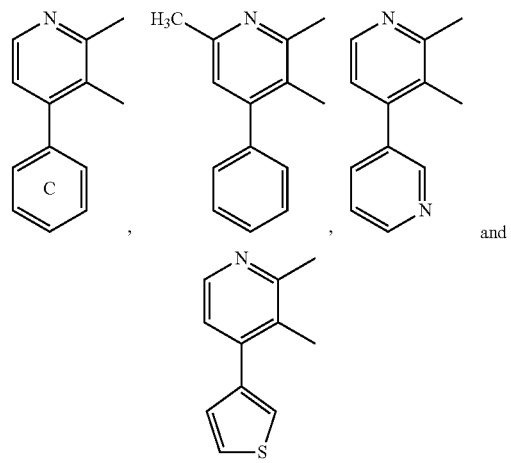

wherein ring C is a benzene ring optionally having substituent(s)), ring B' is a 7- to 9-membered ring optionally having substituent(s) other than an oxo group, a thioxo group and an imino group optionally having a substituent wherein the combination of m' and n' (m',n') is (1,2), (2,1), (2,2), (3,1), (3,2) or (4,1), and $R^0$ is a hydrogen atom or a hydrocarbon group optionally having substituent(s) other than an oxo group, excluding the compounds represented by the formulas

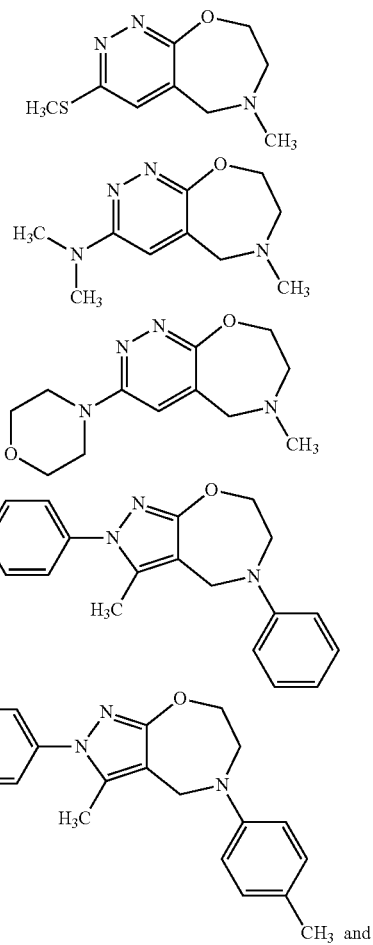

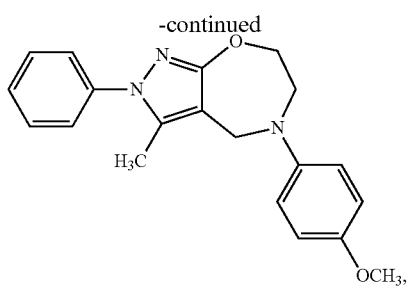

or a salt thereof;

[4] the compound of [3], wherein ring A' is a ring represented by the formula

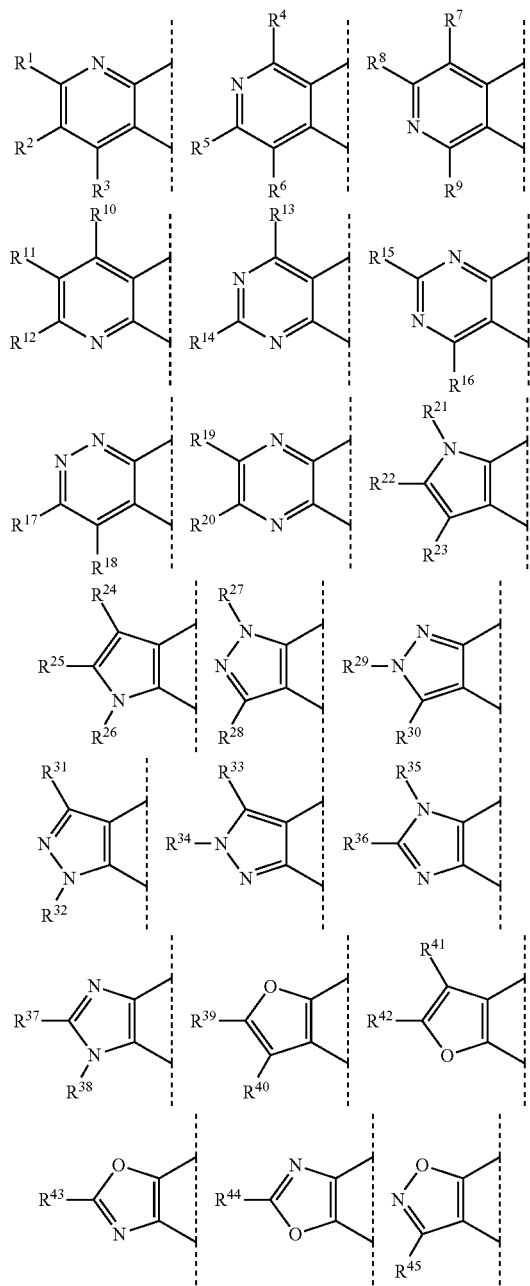

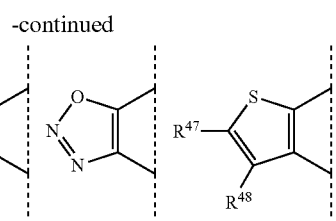

wherein $R^1$, $R^2$, $R^4$-$R^{16}$, $R^{18}$-$R^{26}$, $R^{28}$ and $R^{30}$-$R^{54}$ are each a hydrogen atom, a halogen atom, a nitro group, a cyano group, a hydrocarbon group optionally having substituent(s), a hydroxyl group optionally having a substituent, a thiol group optionally having a substituent, an amino group optionally having substituent(s) or a heterocyclic group optionally having substituent(s), $R^3$, $R^{27}$ and $R^{29}$ are each a hydrogen atom, a halogen atom, a nitro group, a cyano group, an alkyl group optionally having substituent(s), an alkenyl group optionally having substituent(s), an alkynyl group optionally having substituent(s), an aralkyl group optionally having substituent(s), a hydroxyl group optionally having a substituent, a thiol group optionally having a substituent, an amino group optionally having substituent(s) or a heterocyclic group optionally having substituent(s), $R^{17}$ is a hydrogen atom, a halogen atom, a nitro group, a cyano group, a hydrocarbon group optionally having substituent(s), a hydroxyl group optionally having a substituent, a thiol group, an alkenylthio group optionally having substituent(s), an alkynylthio group optionally having substituent(s), an aralkylthio group optionally having substituent(s), an arylthio group optionally having substituent(s), an amino group optionally having substituent(s) or a heterocyclic group optionally having substituent(s);

[5] the compound of [4], wherein ring A' is a ring represented by the formula

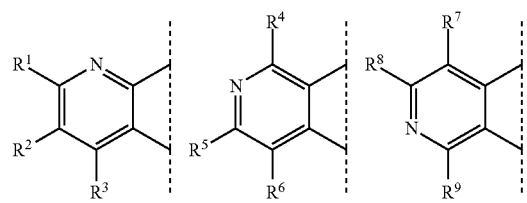

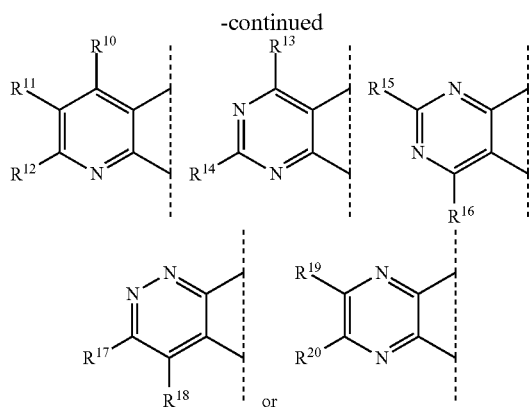

wherein each symbol is as defined in [4];

[6] the compound of [4], wherein ring A' is a ring represented by the formula

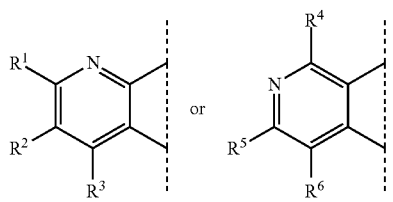

wherein each symbol is as defined in [4];

[7] the compound of [3], wherein a combination of m' and n' (m',n') is (2,1) or (2,2);

[8] the compound of [3] which is a compound represented by the formula

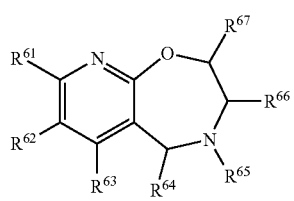

wherein
$R^{61}$ is
(1) a hydrogen atom,
(2) a halogen atom,
(3) a $C_{1-6}$ alkyl group,
(4) a $C_{2-6}$ alkenyl group,
(5) a $C_{3-6}$ cycloalkyl group,
(6) a $C_{6-12}$ aryl group optionally substituted by substituent(s) selected from (i) a halogen atom, (ii) a cyano group, (iii) an amino group, (iv) a hydroxy group, (v) a di-$C_{1-6}$ alkylamino group, (vi) a $C_{1-6}$ alkyl group optionally substituted by halogen atom(s), (vii) a $C_{1-6}$ alkoxy group optionally substituted by halogen atom(s), (viii) a $C_{1-6}$ alkylthio group, (ix) $C_{1-4}$ alkylenedioxy, (x) a $C_{1-6}$ alkyl-carbonyl group, (xi) a $C_{1-6}$ alkyl-carbonylamino group, (xii) a carbamoyl group, (xiii) a $C_{1-6}$ alkoxy-carbonyl group, (xiv) a $C_{7-12}$ aralkyloxy group and (xv) a $C_{6-12}$ aryl group, and optionally condensed with a benzofuran ring, a pyrrole ring or a tetrahydrofuran ring,
(7) a group represented by the formula —$NR^{68}R^{69}$
wherein $R^{68}$ is (i) a hydrogen atom, (ii) a $C_{1-6}$ alkyl group optionally having $C_{1-6}$ alkoxy group(s) or $C_{3-6}$ cycloalkyl group(s), (iii) a $C_{3-6}$ cycloalkyl group, (iv) a $C_{7-12}$ aralkyl group optionally having $C_{6-12}$ aryl group(s), (v) a pyrrolidinyl group optionally having $C_{7-12}$ aralkyl group(s) or (vi) a tetrahydropyranyl group, and
$R^{69}$ is a hydrogen atom or a $C_{1-6}$ alkyl group,
(8) a pyrrolidinyl group optionally substituted by substituent(s) selected from (i) a $C_{1-6}$ alkyl group optionally having $C_{1-6}$ alkoxy group(s) and (ii) a $C_{6-12}$ aryl group,
(9) a piperidinyl group optionally substituted by 1 or 2 substituents selected from (i) a $C_{1-6}$ alkyl group optionally having imidazopyridyl group(s), (ii) a $C_{1-6}$ alkoxy group, (iii) a $C_{6-12}$ aryloxy group and (iv) a pyrrolidinyl group, and optionally condensed with a $C_{3-8}$ cycloalkyl ring or a $C_{6-12}$ aryl ring, or optionally forming a spiro bond with an indane ring,
(10) a morpholinyl group optionally substituted by 1 or 2 substituents selected from (i) a $C_{1-6}$ alkyl group and (ii) a $C_{6-12}$ aryl group optionally substituted by substituent(s) selected from a halogen atom and a $C_{1-6}$ alkoxy group,
(11) an optionally oxidized thiomorpholinyl group,
(12) a thienyl group optionally having cyano group(s) and optionally condensed with a benzene ring,
(13) a furyl group,
(14) a tetrahydropyranyl group,
(15) a pyridyl group optionally having substituent(s) selected from (i) a morpholinyl group and (ii) a pyrrolidinyl group,
(16) a pyrazolyl group optionally having $C_{1-6}$ alkyl group(s),
(17) an isoxazolyl group optionally having $C_{1-6}$ alkyl group(s),
(18) an azepanyl group optionally having $C_{1-6}$ alkyl group(s), and optionally condensed with a benzene ring,
(19) an oxazepanyl group,
(20) a group represented by the formula

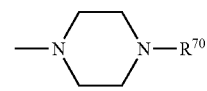

wherein $R^{70}$ is
(i) a hydrogen atom,
(ii) a $C_{1-6}$ alkyl group optionally having substituent(s) selected from (a) a $C_{1-6}$ alkoxy-carbonyl group, (b) a $C_{6-12}$ arylsulfonyl group, (c) a morpholinyl group and (d) a pyridyl group,
(iii) a $C_{7-12}$ aralkyl group,
(iv) a $C_{1-6}$ alkyl-carbonyl group,
(v) a $C_{1-6}$ alkoxy-carbonyl group,
(vi) a $C_{7-12}$ aralkyloxy-carbonyl group,
(vii) an N—$C_{1-6}$ alkyl-carbamoyl group,
(viii) a $C_{1-6}$ alkylsulfonyl group,
(ix) a pyrimidinyl group or
(x) a thienylcarbonyl group, or
(21) a group represented by the formula

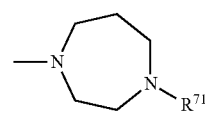

wherein $R^{71}$ is a hydrogen atom or a $C_{1-6}$ alkoxy-carbonyl group;
$R^{62}$ is a hydrogen atom or a halogen atom;
$R^{63}$ is a hydrogen atom;
$R^{64}$ is a hydrogen atom;

R$^{65}$ is a hydrogen atom, a C$_{1-6}$ alkyl group or a C$_{7-12}$ aralkyl group;
R$^{66}$ is a hydrogen atom or a C$_{1-6}$ alkyl group; and
R$^{67}$ is a hydrogen atom or a C$_{1-6}$ alkyl group;

[9] a compound selected from tert-butyl 4-(2,3,4,5-tetrahydropyrido[3,2-f][1,4]oxazepin-8-yl)piperazine-1-carboxylate,
8-piperidin-1-yl-2,3,4,5-tetrahydropyrido[3,2-f][1,4]oxazepine,
8-morpholin-4-yl-2,3,4,5-tetrahydropyrido[3,2-f][1,4]oxazepine,
8-pyrrolidin-1-yl-2,3,4,5-tetrahydropyrido[3,2-f][1,4]oxazepine,
N,N-diethyl-2,3,4,5-tetrahydropyrido[3,2-f][1,4]oxazepin-8-amine,
8-azepan-1-yl-2,3,4,5-tetrahydropyrido[3,2-f][1,4]oxazepine,
8-(2-methylpiperidin-1-yl)-2,3,4,5-tetrahydropyrido[3,2-f][1,4]oxazepine,
8-[4-(2-phenylethyl)piperazin-1-yl]-2,3,4,5-tetrahydropyrido[3,2-f][1,4]oxazepine,
8-[4-(4-phenylbutyl)piperazin-1-yl]-2,3,4,5-tetrahydropyrido[3,2-f][1,4]oxazepine,
8-(4-chlorophenyl)-2,3,4,5-tetrahydropyrido[3,2-f][1,4]oxazepine,
8-(4-fluorophenyl)-2,3,4,5-tetrahydropyrido[3,2-f][1,4]oxazepine,
8-[4-(methylthio)phenyl]-2,3,4,5-tetrahydropyrido[3,2-f][1,4]oxazepine,
methyl 4-(2,3,4,5-tetrahydropyrido[3,2-f][1,4]oxazepin-8-yl)benzoate,
8-[4-(trifluoromethoxy)phenyl]-2,3,4,5-tetrahydropyrido[3,2-f][1,4]oxazepine,
8-(3-furyl)-2,3,4,5-tetrahydropyrido[3,2-f][1,4]oxazepine,
tert-butyl 4-(7-fluoro-2,3,4,5-tetrahydropyrido[3,2-f][1,4]oxazepin-8-yl)piperazine-1-carboxylate,
tert-butyl 4-(2-methyl-2,3,4,5-tetrahydropyrido[3,2-f][1,4]oxazepin-8-yl)piperazine-1-carboxylate,
2-methyl-8-morpholin-4-yl-2,3,4,5-tetrahydropyrido[3,2-f][1,4]oxazepine,
2-methyl-8-piperidin-1-yl-2,3,4,5-tetrahydropyrido[3,2-f][1,4]oxazepine,
8-(2,5-dimethylpyrrolidin-1-yl)-2,3,4,5-tetrahydropyrido[3,2-f][1,4]oxazepine,
N-(sec-butyl)-N-methyl-2,3,4,5-tetrahydropyrido[3,2-f][1,4]oxazepin-8-amine,
N-isopropyl-N-methyl-2,3,4,5-tetrahydropyrido[3,2-f][1,4]oxazepin-8-amine,
8-isopropyl-2,3,4,5-tetrahydropyrido[3,2-f][1,4]oxazepine,
8-cyclopropyl-2,3,4,5-tetrahydropyrido[3,2-f][1,4]oxazepine,
8-cyclobutyl-2,3,4,5-tetrahydropyrido[3,2-f][1,4]oxazepine, and
8-cyclopentyl-2,3,4,5-tetrahydropyrido[3,2-f][1,4]oxazepine, or a salt thereof;
[10] a prodrug of the compound of [3];
[11] a pharmaceutical agent comprising a compound represented by the formula

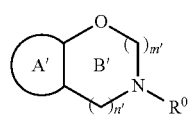

wherein ring A' is a 5- or 6-membered aromatic heterocycle optionally having substituent(s) (wherein ring A' does not include rings represented by

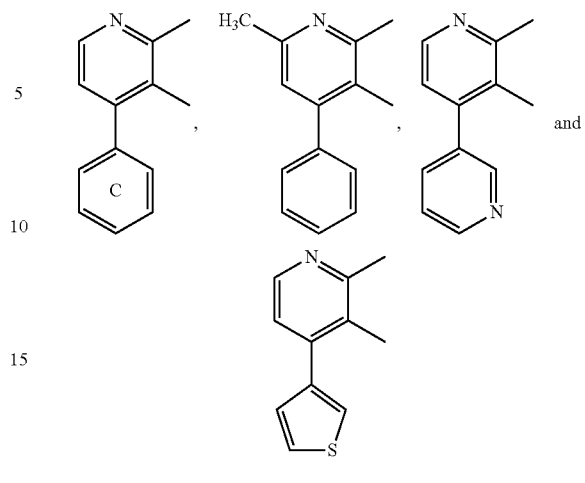

wherein ring C is a benzene ring optionally having substituent(s)), ring B' is a 7- to 9-membered ring optionally having substituent(s) other than an oxo group, a thioxo group and an imino group optionally having a substituent wherein the combination of m' and n' (m',n') is (1,2), (2,1), (2,2), (3,1), (3,2) or (4,1), and R$^o$ is a hydrogen atom or a hydrocarbon group optionally having substituent(s) other than an oxo group, excluding the compounds represented by the formulas

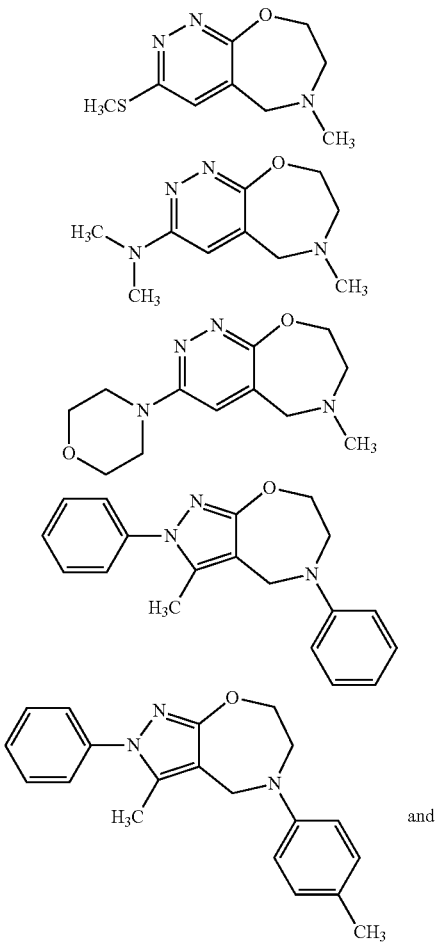

-continued

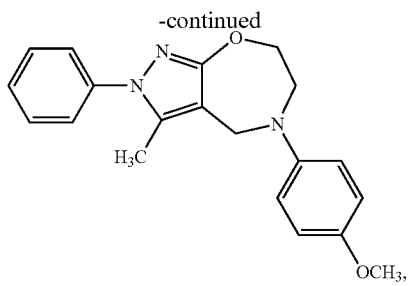

or a salt thereof or a prodrug thereof;
[12] a method of preventing or treating stress urinary incontinence and/or obesity, comprising administering an effective amount of a compound represented by the formula

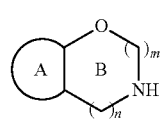  (I)

wherein ring A is a 5- or 6-membered aromatic heterocycle optionally having substituent(s), and ring B is a 7- to 9-membered ring optionally having substituent(s) other than an oxo group wherein the combination of m and n (m,n) is (1,2), (2,1), (2,2), (3,1), (3,2) or (4,1), or a salt thereof or a prodrug thereof to a mammal;
[13] use of a compound represented by the formula

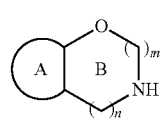  (I)

wherein ring A is a 5- or 6-membered aromatic heterocycle optionally having substituent(s), and ring B is a 7- to 9-membered ring optionally having substituent(s) other than an oxo group wherein the combination of m and n (m,n) is (1,2), (2,1), (2,2), (3,1), (3,2) or (4,1), or a salt thereof or a prodrug thereof, for the production of an agent for the prophylaxis or treatment of stress urinary incontinence and/or obesity;
[14] an agent for the prophylaxis or treatment of pelvic organ prolapse, rectal prolapse or post-micturition dribble, comprising a serotonin 5-$HT_{2C}$ receptor activator;
[15] a method of preventing or treating pelvic organ prolapse, rectal prolapse or post-micturition dribble, comprising administering an effective amount of a serotonin 5-$HT_{2C}$ receptor activator to a mammal;
[16] use of a serotonin 5-$HT_{2C}$ receptor activator for the production of an agent for the prophylaxis or treatment of pelvic organ prolapse, rectal prolapse or post-micturition dribble;
[17] a method of screening for a substance that increases pelvic floor muscles contraction, comprising increasing an intravesical pressure after bilateral transection of the hypogastric nerve and pudendal nerve of an animal, and measuring a closure response in the urinary tract, rectum or vagina observed at that time;
[18] a method of screening for a substance that increases pelvic floor muscles contraction, comprising increasing an intravesical pressure after bilateral transection of the hypogastric nerve and pudendal nerve of an animal, and measuring the leak point pressure at that time; and the like.

Moreover, the present invention relates to
[19] a method of screening for a therapeutic drug for pelvic organ prolapse, rectal prolapse or post-micturition dribble, comprising increasing an intravesical pressure after bilateral transection of the hypogastric nerve and pudendal nerve of an animal, and measuring a closure response in the urinary tract, rectum or vagina observed at that time;
[20] a method of screening for a therapeutic drug for pelvic organ prolapse, rectal prolapse or post-micturition dribble, comprising increasing an intravesical pressure after bilateral transection of the hypogastric nerve and pudendal nerve of an animal, and measuring the leak point pressure at that time;
[21] the method of the above-mentioned [19] or [20], wherein the closure response in the urinary tract, rectum or vagina or urethral resistance (decreased leak point pressure) upon increase of an intravesical pressure after bilateral transection of the hypogastric nerve and pudendal nerve of an animal is based on the unilateral transection or injury of the nerve involved in the reflex contraction of pelvic floor muscles, birth, ovariectomy, a mechanical vaginal expansion treatment, diabetes, a drug administration or a combination of these;
[22] the method of any of the above-mentioned [19]-[21], wherein the animal is female; and the like.

BRIEF DESCRIPTION OF THE DRAWING

FIG. 1 shows a typical example of the action of a 5-$HT_{2C}$ receptor agonist on a urethral closure response induced by an increased intravesical pressure after bilateral transection of the hypogastric nerve and pudendal nerve of a female rat under urethane anesthesia.

DETAILED DESCRIPTION OF THE INVENTION

The present invention is explained in detail in the following.

Since compound (I) or a prodrug thereof of the present invention has a superior serotonin 5-$HT_{2C}$ receptor activation action, it is useful as a safe prophylactic or therapeutic drug for any serotonin 5-$HT_{2C}$ associated disease, such as stress urinary incontinence, obesity and the like.

In addition, a serotonin 5-$HT_{2C}$ receptor activator is useful as a prophylactic or therapeutic drug for pelvic organ prolapse, rectal prolapse or post-micturition dribble.

In compound (I) and a compound represented by the formula

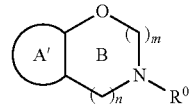

wherein ring A' is a 5- or 6-membered aromatic heterocycle optionally having substituent(s) (wherein ring A' does not include rings represented by

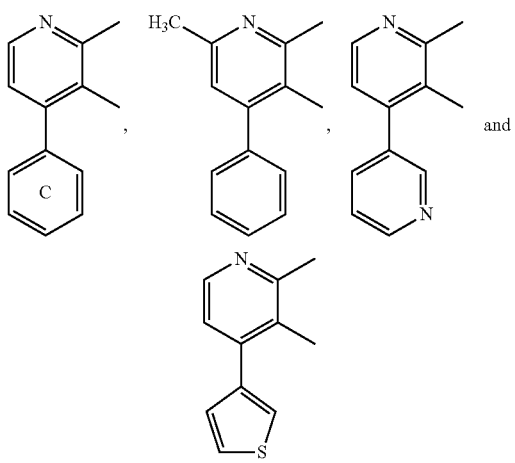

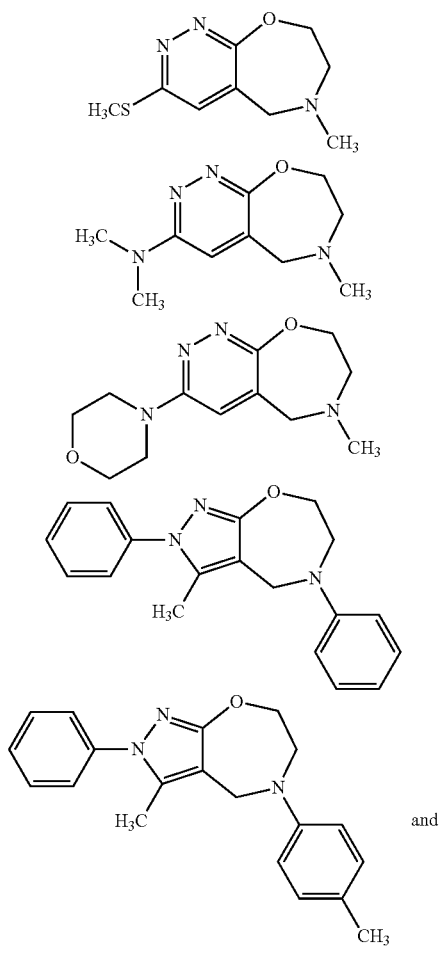

wherein ring C is a benzene ring optionally having substituent(s)), ring B is a 7- to 9-membered ring optionally having substituent(s) other than an oxo group, a thioxo group and an imino group optionally having a substituent wherein the combination of m and n (m,n) is (1,2), (2,1), (2,2), (3,1), (3,2) or (4,1), and $R^0$ is a hydrogen atom or a hydrocarbon group optionally having substituent(s) other than an oxo group, excluding the compounds represented by the formulas

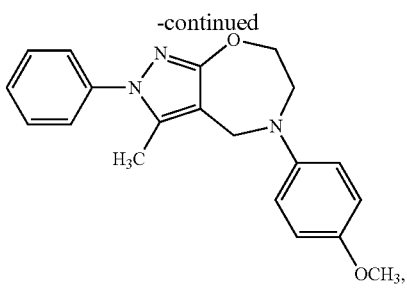

encompassed in compound (I) or a salt thereof, examples of the substituent that "a 5- or 6-membered aromatic heterocycle optionally having substituent(s)" for ring A or ring A' include a halogen atom, a nitro group, a cyano group, a hydrocarbon group optionally having substituent(s), a hydroxyl group optionally having a substituent, a thiol group optionally having a substituent, an amino group optionally having substituent(s) or a heterocyclic group optionally having substituent(s).

In the present specification, examples of the "halogen atom" include fluorine atom, chlorine atom, bromine atom and iodine atom.

In the present specification, examples of the "hydrocarbon group optionally having substituent(s)" include "alkyl group optionally having substituent(s)", "alkenyl group optionally having substituent(s)", "alkynyl group optionally having substituent(s)", "aralkyl group optionally having substituent(s)", "aryl group optionally having substituent(s)", "cycloalkyl group optionally having substituent(s)" and the like.

In the present specification, examples of the "alkyl group optionally having substituent(s)" include a $C_{1-6}$ alkyl group (e.g., methyl, ethyl, propyl, isopropyl, butyl, isobutyl, sec-butyl, tert-butyl, pentyl, hexyl etc.) optionally having substituent(s) selected from (i) a halogen atom (e.g., fluorine atom, chlorine atom, bromine atom, iodine atom), (ii) a cyano group, (iii) a hydroxy group, (iv) a nitro group, (v) a formyl group, (vi) an amino group, (vii) a mono- or di-$C_{1-6}$ alkylamino group (e.g., methylamino, ethylamino, propylamino, dimethylamino, diethylamino, dipropylamino etc.), (viii) a $C_{1-6}$ alkyl-carbonylamino group (e.g., acetylamino, ethylcarbonylamino etc.), (ix) a $C_{1-6}$ alkoxy-carbonylamino group (e.g., methoxycarbonylamino, ethoxycarbonylamino, propoxycarbonylamino etc.), (x) a $C_{1-6}$ alkyl group (e.g., methyl, ethyl, propyl, isopropyl, butyl, isobutyl, sec-butyl, tert-butyl, pentyl, hexyl etc.) optionally substituted by substituent(s) selected from a halogen atom (e.g., fluorine atom, chlorine atom, bromine atom, iodine atom), $C_{1-6}$ alkoxy group (e.g., methoxy, ethoxy, propoxy etc.), $C_{6-12}$ arylsulfonyl group (e.g., phenylsulfonyl etc.), and heterocyclic group (e.g., morpholinyl group, pyridyl group, imidazopyridyl group, benzimidazolyl group etc.), (xi) a $C_{7-12}$ aralkyl group (e.g., benzyl, 2-phenylethyl, 1-phenylethyl, 3-phenylpropyl, 4-phenylbutyl etc.), (xii) a $C_{3-8}$ cycloalkyl group (e.g., cyclopropyl, cyclobutyl, cyclopentyl, cyclohexyl etc.), (xiii) a $C_{6-12}$ aryl group (e.g., phenyl, 1-naphthyl, 2-naphthyl etc.) optionally substituted by substituent(s) selected from a halogen atom (e.g., fluorine atom, chlorine atom, bromine atom, iodine atom) and a $C_{1-6}$ alkoxy group (e.g., methoxy, ethoxy, propoxy etc.), (xiv) a $C_{1-6}$ alkoxy group (e.g., methoxy, ethoxy, propoxy, isopropoxy, butoxy, isobutoxy, sec-butoxy, tert-butoxy etc.) optionally substituted by halogen atom(s) (e.g., fluorine atom, chlorine atom, bromine atom, iodine atom), (xv) a $C_{7-12}$ aralkyloxy group (e.g., benzyloxy etc.), (xvi) a $C_{6-12}$ aryloxy group (e.g., phenoxy etc.), (xvii) a carboxyl group, (xviii) a $C_{1-6}$ alkoxy-carbonyl group (e.g., methoxycarbonyl, ethoxycarbonyl, propoxycarbonyl, isopropoxycarbonyl, tert-butoxycarbonyl etc.), (xix) a $C_{7-12}$ aralkyloxy-carbonyl group (e.g., benzyloxycarbonyl etc.), (xx) a $C_{6-12}$ aryloxy-carbonyl group (e.g., phenyloxycarbonyl etc.), (xxi) a $C_{1-6}$ alkyl-carbonyl group (e.g., acetyl, ethylcarbonyl, propylcarbonyl, isopropylcarbonyl, 2,2-dimethylpropylcarbonyl etc.), (xxii) a $C_{3-8}$ cycloalkyl-carbonyl group (e.g., cyclopropylcarbonyl, cyclobutylcarbonyl, cyclopentylcarbonyl, cyclohexylcarbonyl etc.), (xxiii) a $C_{7-12}$ aralkyl-carbonyl group (e.g., benzylcarbonyl etc.), (xxiv) a carbamoyl group, (xxv) a thiocarbamoyl group, (xxvi) a mono- or di-$C_{1-6}$ alkyl-carbamoyl group (e.g., methylcarbamoyl, ethylcarbamoyl, propylcarbamoyl, isopropylcarbamoyl, dimethylcarbamoyl, diethylcarbamoyl, dipropylcarbamoyl etc.), (xxvii) a mono- or di-$C_{7-12}$ aralkyl-carbamoyl group (e.g., benzylcarbamoyl, dibenzylcarbamoyl etc.), (xxviii) a thiol group, (xxix) a $C_{1-6}$ alkylthio group (e.g., methylthio, ethylthio, propylthio etc.), (xxx) a $C_{7-12}$ aralkylthio group (e.g., benzylthio etc.), (xxxi) a $C_{1-6}$ alkylsulfonyl group (e.g., methylsulfonyl, ethylsulfonyl, propylsulfonyl, isopropylsulfonyl etc.), (xxxii) a $C_{3-8}$ cycloalkylsulfonyl group (e.g., cyclopropylsulfonyl, cyclobutylsulfonyl, cyclopentylsulfonyl etc.), (xxxiii) a $C_{6-12}$ arylsulfonyl group (e.g., phenylsulfonyl, 1-naphthylsulfonyl, 2-naphthylsulfonyl etc.), (xxxiv) $C_{7-12}$ aralkylsulfonyl group (e.g., benzylsulfonyl etc.), (xxxv) a 5- to 8-membered non-aromatic heterocyclic group containing, besides carbon atom, 1 to 4 hetero atoms selected from nitrogen atom, sulfur atom and oxygen atom (for example, pyrrolidinyl, tetrahydrofuryl, tetrahydrothienyl, piperidyl, tetrahydropyranyl, morpholinyl, thiomorpholinyl, piperazinyl, azepanyl, oxazepanyl etc.), (xxxvi) a 5- to 8-membered aromatic heterocyclic group containing, besides carbon atom, 1 to 4 hetero atoms selected from nitrogen atom, sulfur atom and oxygen atom (for example, furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, imidazopyridyl etc.), (xxxvii) a 5- to 8-membered non-aromatic heterocyclyl-carbonyl group containing, besides carbon atom, 1 to 4 hetero atoms selected from nitrogen atom, sulfur atom and oxygen atom (for example, pyrrolidinylcarbonyl, tetrahydrofurylcarbonyl, tetrahydrothienylcarbonyl, piperidylcarbonyl, tetrahydropyranylcarbonyl, morpholinylcarbonyl, thiomorpholinylcarbonyl, piperazinylcarbonyl etc.), (xxxviii) a 5- to 8-membered aromatic heterocyclyl-carbonyl group containing, besides carbon atom, 1 to 4 hetero atoms selected from nitrogen atom, sulfur atom and oxygen atom (for example, furylcarbonyl, thienylcarbonyl, pyrrolylcarbonyl, oxazolylcarbonyl, isoxazolylcarbonyl, thiazolylcarbonyl, isothiazolylcarbonyl, imidazolylcarbonyl, pyrazolylcarbonyl, 1,2,3-oxadiazolylcarbonyl, 1,2,4-oxadiazolylcarbonyl, 1,3,4-oxadiazolylcarbonyl, furazanylcarbonyl, 1,2,3-thiadiazolylcarbonyl, 1,2,4-thiadiazolylcarbonyl, 1,3,4-thiadiazolylcarbonyl, 1,2,3-triazolylcarbonyl, 1,2,4-triazolylcarbonyl, tetrazolylcarbonyl, pyridylcarbonyl, pyridazinylcarbonyl, pyrimidinylcarbonyl, pyrazinylcarbonyl, triazinylcarbonyl etc.), (xxxix) a ureido group, (xxxx) a $C_{1-6}$ alkylureido group (e.g., methylureido, ethylureido, propylureido etc.), (xxxxi) a $C_{6-12}$ arylureido group (e.g., phenylureido, 1-naphthylureido, 2-naphthylureido etc.) and (xxxxii) a $C_{1-4}$ alkylenedioxy group (e.g., methylenedioxy, ethylenedioxy, propylenedioxy etc.), and the like, wherein the number of the substituents is 1 to 4, preferably 1 to 3.

In the present specification, examples of the "alkenyl group optionally having substituent(s)" include a $C_{2-6}$ alkenyl group (e.g., vinyl, 1-propenyl, allyl, isopropenyl, butenyl, isobutenyl etc.) optionally having 1 to 4, preferably 1 to 3, substituents optionally possessed by the above-mentioned "alkyl group optionally having substituent(s)" and the like.

In the present specification, examples of the "alkynyl group optionally having substituent(s)" include a $C_{2-6}$ alkynyl group (e.g., ethynyl, propargyl, butynyl, 1-hexynyl etc.) optionally having 1 to 4, preferably 1 to 3, substituents optionally possessed by the above-mentioned "alkyl group optionally having substituent(s)" and the like.

In the present specification, examples of the "aralkyl group optionally having substituent(s)" include a $C_{7-12}$ aralkyl group (e.g., benzyl, 2-phenylethyl, 1-phenylethyl, 3-phenylpropyl etc.) optionally having 1 to 4, preferably 1 to 3, substituents optionally possessed by the above-mentioned "alkyl group optionally having substituent(s)".

In the present specification, examples of the "aryl group optionally having substituent(s)" include a $C_{6-12}$ aryl group (e.g., phenyl, naphthyl etc.) optionally having 1 to 4, preferably 1 to 3, substituents optionally possessed by the abovementioned "alkyl group optionally having substituent(s)".

The "aryl group optionally having substituent(s)" is optionally condensed with a benzofuran ring, a pyrrole ring, a tetrahydrofuran ring and the like.

In the present specification, examples of the "cycloalkyl group optionally having substituent(s)" include a $C_{3-6}$ cycloalkyl group (e.g., cyclopropyl, cyclobutyl, cyclopentyl, cyclohexyl) optionally having 1 to 4, preferably 1 to 3, substituents optionally possessed by the above-mentioned "alkyl group optionally having substituent(s)".

In the present specification, examples of the "hydroxyl group optionally having a substituent" include a hydroxyl group and a hydroxyl group having a substituent.

In the present specification, examples of the "hydroxyl group having a substituent" include a hydroxyl group having the aforementioned "hydrocarbon group optionally having substituent(s)".

In the present specification, examples of the "thiol group optionally having a substituent" include a thiol group and a thiol group having a substituent.

In the present specification, examples of the "thiol group having a substituent" include alkylthio group optionally having substituent(s), alkenylthio group optionally having substituent(s), alkynylthio group optionally having substituent(s), aralkylthio group optionally having substituent(s), arylthio group optionally having substituent(s) and the like.

In the present specification, examples of the "alkylthio group optionally having substituent(s)" include a thiol group having the aforementioned "alkyl group optionally having substituent(s)".

In the present specification, examples of the "alkenylthio group optionally having substituent(s)" include a thiol group having the aforementioned "alkenyl group optionally having substituent(s)".

In the present specification, examples of the "alkynylthio group optionally having substituent(s)" include a thiol group having the aforementioned "alkynyl group optionally having substituent(s)".

In the present specification, examples of the "aralkylthio group optionally having substituent(s)" include a thiol group having the aforementioned "aralkyl group optionally having substituent(s)".

In the present specification, examples of the "arylthio group optionally having substituent(s)" include a thiol group having the aforementioned "aryl group optionally having substituent(s)".

In the present specification, examples of the "amino group optionally having substituent(s)" include an amino group and an amino group having substituent(s).

In the present specification, examples of the "an amino group having substituent(s)" include an amino group having 1 or 2 substituents selected from the aforementioned "hydrocarbon group optionally having substituent(s)" and the below-mentioned "heterocyclic group optionally having substituent(s)".

In the present specification, examples of the "heterocyclic group optionally having substituent(s)" include (1) a 5- to 8-membered non-aromatic heterocyclic group containing, besides carbon atom, 1 to 4 hetero atoms selected from nitrogen atom, sulfur atom and oxygen atom (e.g., pyrrolidinyl, tetrahydrofuryl, tetrahydrothienyl, piperidyl, tetrahydropyranyl, morpholinyl, thiomorpholinyl, piperazinyl, azepanyl, 1,4-diazepanyl, oxazepanyl (e.g., 1,4-oxazepanyl) etc.) and optionally having 1 to 3 substituents optionally possessed by the aforementioned "alkyl group optionally having substituent(s)", (2) a 5- to 8-membered aromatic heterocyclic group containing, besides carbon atom, 1 to 4 hetero atoms selected from nitrogen atom, sulfur atom and oxygen atom (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl etc.) and optionally having 1 to 3 substituents optionally possessed by the aforementioned "alkyl group optionally having substituent(s)". In addition, the "heterocyclic group optionally having substituent(s)" is optionally oxidized. For example, when the heterocyclic group contains a nitrogen atom and/or a sulfur atom, the nitrogen atom and/or sulfur atom are/is optionally oxidized.

The "heterocyclic group optionally having substituent(s)" is optionally condensed with a $C_{3-8}$ cycloalkyl ring (e.g., cyclopropane ring, cyclobutane ring, cyclopentane ring, cyclohexane ring, cycloheptane ring, cyclooctane ring), or a $C_{6-12}$ aryl ring (e.g., benzene ring, naphthalene ring etc.), and optionally form a spiro bond with a $C_{3-8}$ cycloalkyl ring (e.g., cyclopropane ring, cyclobutane ring, cyclopentane ring, cyclohexane ring, cycloheptane ring, cyclooctane ring), fused cycloalkyl ring (e.g., indane ring etc.) and the like.

Ring A and ring A' are preferably a ring represented by the formula

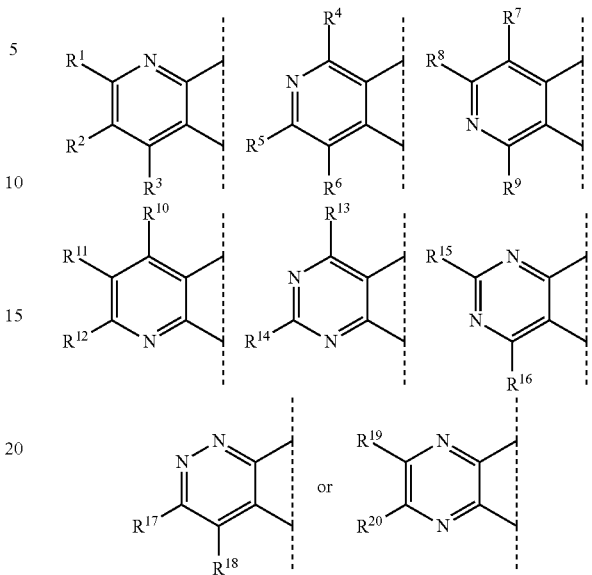

wherein $R^1$, $R^2$, $R^4$-$R^{16}$ and $R^{18}$-$R^{20}$ are each a hydrogen atom, a halogen atom, a nitro group, a cyano group, a hydrocarbon group optionally having substituent(s), a hydroxyl group optionally having a substituent, a thiol group optionally having a substituent, an amino group optionally having substituent(s) or a heterocyclic group optionally having substituent(s), $R^3$ is a hydrogen atom, a halogen atom, a nitro group, a cyano group, an alkyl group optionally having substituent(s), an alkenyl group optionally having substituent(s), an alkynyl group optionally having substituent(s), an aralkyl group optionally having substituent(s), a hydroxyl group optionally having a substituent, a thiol group optionally having a substituent, an amino group optionally having substituent(s) or a heterocyclic group optionally having substituent(s), and $R^{17}$ is a hydrogen atom, a halogen atom, a nitro group, a cyano group, a hydrocarbon group optionally having substituent(s), a hydroxyl group optionally having a substituent, a thiol group, alkenylthio group optionally having substituent(s), an alkynylthio group optionally having substituent(s), an aralkylthio group optionally having substituent(s), an arylthio group optionally having substituent(s), an amino group optionally having substituent(s) or a heterocyclic group optionally having substituent(s), and particularly preferably a ring represented by the formula

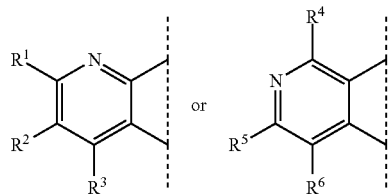

wherein $R^1$, $R^2$ and $R^4$-$R^6$ are each a hydrogen atom, a halogen atom, a nitro group, a cyano group, a hydrocarbon group optionally having substituent(s), a hydroxyl group optionally having a substituent, a thiol group optionally having a substituent, an amino group optionally having substituent(s) or a heterocyclic group optionally having substituent(s), and $R^3$ is a hydrogen atom, a halogen atom, a nitro group, a cyano group, an alkyl group optionally having substituent(s), an alkenyl group optionally having substituent(s), an alkynyl group optionally having substituent(s), an aralkyl group optionally having substituent(s), a hydroxyl group optionally having a substituent, a thiol group optionally having a substituent, an amino group optionally having substituent(s) or a heterocyclic group optionally having substituent(s).

$R^1$ is preferably a hydrogen atom, a halogen atom, a hydrocarbon group optionally having substituent(s), an amino group optionally having substituent(s) or a heterocyclic group optionally having substituent(s).

$R^2$ is preferably a hydrogen atom or a halogen atom.

$R^3$ is preferably a hydrogen atom.

$R^4$ is preferably a hydrogen atom, a halogen atom, a hydrocarbon group optionally having substituent(s), an amino group optionally having substituent(s) or a heterocyclic group optionally having substituent(s).

$R^5$ is preferably a hydrogen atom or a halogen atom.

$R^6$ is preferably a hydrogen atom.

In addition, $R^7$-$R^{54}$ is preferably a hydrogen atom.

Ring B is a 7- to 9-membered ring optionally having substituent(s) other than an oxo group wherein the combination of m and n (m,n) is (1,2), (2,1), (2,2), (3,1), (3,2) or (4,1). Ring B optionally has substituent(s) other than an oxo group at substitutable position(s) and optionally has such substituent(s) on a nitrogen atom. Examples of the substituent(s) ring B optionally has include a substituent selected from a halogen atom, a nitro group, a cyano group, a hydrocarbon group optionally having substituent(s), a hydroxyl group optionally having a substituent, a thiol group optionally having a substituent, an amino group optionally having substituent(s) and a heterocyclic group optionally having substituent(s), wherein the number of the substituents is 1 to 6, preferably 1 to 3.

The combination of m and n constituting ring B (m,n) is preferably (2,1) or (2,2).

Ring B' is a 7- to 9-membered ring optionally having substituent(s) other than an oxo group, a thioxo group and an imino group optionally having a substituent wherein the combination of m' and n' (m',n') is (1,2), (2,1), (2,2), (3,1), (3,2) or (4,1). Ring B' optionally has substituent(s) other than an oxo group, a thioxo group and an imino group optionally having a substituent at substitutable position(s). Examples of the substituent(s) that ring B' optionally has include a substituent selected from a halogen atom, a nitro group, a cyano group, a hydrocarbon group optionally having substituent(s), a hydroxyl group optionally having a substituent, a thiol group optionally having a substituent, an amino group optionally having substituent(s) and a heterocyclic group optionally having substituent(s), wherein the number of the substituents is 1 to 6, preferably 1 to 3.

$R^0$ on the nitrogen atom constituting ring B' is (1) a hydrogen atom or (2) hydrocarbon group optionally having substituent(s) other than an oxo group.

The combination of m' and n' constituting ring B' (m',n') is preferably (2,1) or (2,2).

As compound (I), (A) a compound represented by the formula

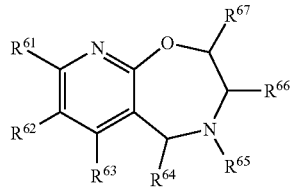

wherein
$R^{61}$ is
(1) a hydrogen atom,
(2) a halogen atom,
(3) a $C_{1-6}$ alkyl group,
(4) a $C_{2-6}$ alkenyl group,
(5) a $C_{3-6}$ cycloalkyl group,
(6) a $C_{6-12}$ aryl group optionally substituted by substituent(s) selected from (i) a halogen atom, (ii) a cyano group, (iii) an amino group, (iv) a hydroxy group, (v) a di-$C_{1-6}$ alkylamino group, (vi) a $C_{1-6}$ alkyl group optionally substituted by halogen atom(s), (vii) a $C_{1-6}$ alkoxy group optionally substituted by halogen atom(s), (viii) a $C_{1-6}$ alkylthio group, (ix) $C_{1-4}$ alkylenedioxy, (x) a $C_{1-6}$ alkyl-carbonyl group, (xi) a $C_{1-6}$ alkyl-carbonylamino group, (xii) a carbamoyl group, (xiii) a $C_{1-6}$ alkoxy-carbonyl group, (xiv) a $C_{7-12}$ aralkyloxy group and (xv) a $C_{6-12}$ aryl group, and optionally condensed with a benzofuran ring, a pyrrole ring or a tetrahydrofuran ring,
(7) a group represented by the formula —$NR^{68}R^{69}$ wherein $R^{68}$ is (i) a hydrogen atom, (ii) a $C_{1-6}$ alkyl group optionally having $C_{1-6}$ alkoxy group(s) or $C_{3-6}$ cycloalkyl group(s), (iii) a $C_{3-6}$ cycloalkyl group, (iv) a $C_{7-12}$ aralkyl group optionally having $C_{6-12}$ aryl group(s), (v) a pyrrolidinyl group optionally having $C_{7-12}$ aralkyl group(s) or (vi) a tetrahydropyranyl group, and
$R^{69}$ is a hydrogen atom or a $C_{1-6}$ alkyl group,
(8) a pyrrolidinyl group optionally substituted by substituent(s) selected from (i) a $C_{1-6}$ alkyl group optionally having $C_{1-6}$ alkoxy group(s) and (ii) a $C_{6-12}$ aryl group,
(9) a piperidinyl group optionally substituted by 1 or 2 substituents selected from (i) a $C_{1-6}$ alkyl group optionally having imidazopyridyl group(s), (ii) a $C_{1-6}$ alkoxy group, (iii) a $C_{6-12}$ aryloxy group and (iv) a pyrrolidinyl group, and optionally condensed with a $C_{3-8}$ cycloalkyl ring or a $C_{6-12}$ aryl ring, or optionally forming a spiro bond with an indane ring,
(10) a morpholinyl group optionally substituted by 1 or 2 substituents selected from (i) a $C_{1-6}$ alkyl group and (ii) a $C_{6-12}$ aryl group optionally substituted by substituent(s) selected from a halogen atom and a $C_{1-6}$ alkoxy group,
(11) an optionally oxidized thiomorpholinyl group (e.g., thiomorpholinyl group wherein the sulfur atom is optionally oxidized),
(12) a thienyl group optionally having cyano group(s) and optionally condensed with a benzene ring,
(13) a furyl group,
(14) a tetrahydropyranyl group,
(15) a pyridyl group optionally having substituent(s) selected from (i) a morpholinyl group and (ii) a pyrrolidinyl group,
(16) a pyrazolyl group optionally having $C_{1-6}$ alkyl group(s),
(17) an isoxazolyl group optionally having $C_{1-6}$ alkyl group(s),
(18) an azepanyl group optionally having $C_{1-6}$ alkyl group(s), and optionally condensed with a benzene ring,
(19) an oxazepanyl group,
(20) a group represented by the formula

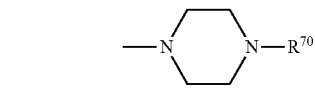

wherein $R^{70}$ is
(i) a hydrogen atom,
(ii) a $C_{1-6}$ alkyl group optionally having substituent(s) selected from (a) a $C_{1-6}$ alkoxy-carbonyl group, (b) a $C_{6-12}$ arylsulfonyl group, (c) a morpholinyl group and (d) a pyridyl group,
(iii) a $C_{7-12}$ aralkyl group,
(iv) a $C_{1-6}$ alkyl-carbonyl group,
(v) a $C_{1-6}$ alkoxy-carbonyl group, (vi) a $C_{7-12}$ aralkyloxy-carbonyl group,
(vii) an N—$C_{1-6}$ alkyl-carbamoyl group,
(viii) a $C_{1-6}$ alkylsulfonyl group,
(ix) a pyrimidinyl group or
(x) a thienylcarbonyl group, or
(21) a group represented by the formula

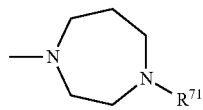

wherein $R^{71}$ is a hydrogen atom or a $C_{1-6}$ alkoxy-carbonyl group;
$R^{62}$ is a hydrogen atom or a halogen atom;
$R^{63}$ is a hydrogen atom;
$R^{64}$ is a hydrogen atom;
$R^{65}$ is a hydrogen atom, a $C_{1-6}$ alkyl group or a $C_{7-12}$ aralkyl group;
$R^{66}$ is a hydrogen atom or a $C_{1-6}$ alkyl group; and
$R^{67}$ is a hydrogen atom or a $C_{1-6}$ alkyl group, or a salt thereof,
(B) a compound represented by the formula

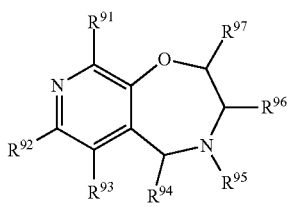

wherein $R^{91}$ is
(1) a hydrogen atom,
(2) a halogen atom,
(3) a $C_{1-6}$ alkyl group,
(4) a $C_{6-12}$ aryl group optionally substituted by substituent(s) selected from (i) a halogen atom, (ii) a cyano group, (iii) an amino group, (iv) a hydroxy group, (v) a di-$C_{1-6}$ alkylamino group, (vi) a $C_{1-6}$ alkyl group optionally substituted by halogen atom(s), (vii) a $C_{1-6}$ alkoxy group optionally substituted by halogen atom(s), (viii) a $C_{1-6}$ alkylthio group, (ix) $C_{1-4}$ alkylenedioxy, (x) a $C_{1-6}$ alkyl-carbonyl group, (xi) a $C_{1-6}$ alkyl-carbonylamino group, (xii) a carbamoyl group, (xiii) a $C_{1-6}$ alkoxy-carbonyl group, (xiv) a $C_{7-12}$ aralkyloxy group and
(xv) a $C_{6-12}$ aryl group, and optionally condensed with a benzofuran ring,
(5) a group represented by the formula —$NR^{98}R^{99}$ wherein $R^{98}$ is (i) a $C_{1-6}$ alkyl group optionally having $C_{1-6}$ alkoxy group(s), (ii) a $C_{3-6}$ cycloalkyl group, (iii) a $C_{7-12}$ aralkyl group optionally having $C_{6-12}$ aryl group(s) or (iv) a pyrrolidinyl group optionally having $C_{7-12}$ aralkyl group(s), and $R^{99}$ is a $C_{1-6}$ alkyl group,
(6) a pyrrolidinyl group optionally substituted by substituent(s) selected from (i) a $C_{1-6}$ alkyl group optionally having $C_{1-6}$ alkoxy group(s) and (ii) a $C_{6-12}$ aryl group,
(7) a piperidinyl group optionally substituted by 1 or 2 substituents selected from (i) a $C_{1-6}$ alkyl group optionally having imidazopyridyl group(s), (ii) a $C_{6-12}$ aryloxy group and (iii) a pyrrolidinyl group, and optionally condensed with a $C_{3-8}$ cycloalkyl ring or a $C_{6-12}$ aryl ring, or optionally forming a spiro bond with an indane ring, (8) a morpholinyl group optionally substituted by 1 or 2 substituents selected from (i) a $C_{1-6}$ alkyl group and (ii) a $C_{6-12}$ aryl group optionally substituted by substituent(s) selected from a halogen atom and a $C_{1-6}$ alkoxy group,
(9) a thienyl group optionally having cyano group(s) and optionally condensed with a benzene ring,
(10) a furyl group,
(11) a pyridyl group optionally having substituent(s) selected from (i) a morpholinyl group and (ii) a pyrrolidinyl group,
(12) a pyrazolyl group optionally having $C_{1-6}$ alkyl group(s),
(13) an azepanyl group optionally having $C_{1-6}$ alkyl group(s), and optionally condensed with a benzene ring,
(14) a group represented by the formula

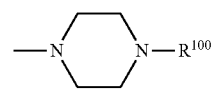

wherein $R^{100}$ is
(i) a hydrogen atom,
(ii) a $C_{1-6}$ alkyl group optionally having substituent(s) selected from (a) a $C_{6-12}$ arylsulfonyl group, (b) a morpholinyl group and (c) a pyridyl group,
(iii) a $C_{7-12}$ aralkyl group,
(iv) a $C_{1-6}$ alkyl-carbonyl group,
(v) a $C_{1-6}$ alkoxy-carbonyl group,
(vi) a $C_{7-12}$ aralkyloxy-carbonyl group,
(vii) an N—$C_{1-6}$ alkyl-carbamoyl group,
(viii) a $C_{1-6}$ alkylsulfonyl group,
(ix) a pyrimidinyl group or
(x) a thienylcarbonyl group, or
(15) a group represented by the formula

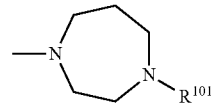

wherein $R^{101}$ is a hydrogen atom or a $C_{1-6}$ alkoxy-carbonyl group;
$R^{92}$, $R^{93}$, $R^{94}$, $R^{96}$ and $R^{97}$ are each a hydrogen atom; and
$R^{95}$ is a hydrogen atom, a $C_{1-6}$ alkyl group or a $C_{7-12}$ aralkyl group, or a salt thereof,
(C) a compound represented by the formula

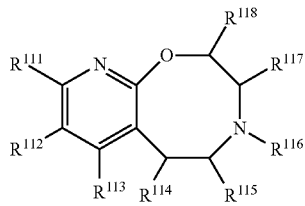

wherein $R^{111}$ is
(1) a hydrogen atom,
(2) a halogen atom,
(3) a $C_{1-6}$ alkyl group,
(4) a $C_{6-12}$ aryl group optionally substituted by substituent(s) selected from (i) a halogen atom, (ii) a cyano group, (iii) an amino group, (iv) a hydroxy group, (v) a di-$C_{1-6}$ alkylamino group, (vi) a $C_{1-6}$ alkyl group optionally substituted by halogen atom(s), (vii) a $C_{1-6}$ alkoxy group optionally substituted by halogen atom(s) (viii) a $C_{1-6}$ alkylthio group, (ix) $C_{1-4}$ alkylenedioxy, (x) a $C_{1-6}$ alkyl-carbonyl group, (xi) a $C_{1-6}$ alkyl-carbonylamino group, (xii) a carbamoyl group, (xiii) a $C_{1-6}$ alkoxy-carbonyl group, (xiv) a $C_{7-12}$ aralkyloxy group and (xv) a $C_{6-12}$ aryl group, and optionally condensed with a benzofuran ring,
(5) a group represented by the formula —$NR^{119}R^{120}$ wherein $R^{119}$ is (i) a $C_{1-6}$ alkyl group optionally having $C_{1-6}$ alkoxy group(s), (ii) a $C_{3-6}$ cycloalkyl group, (iii) a $C_{7-12}$ aralkyl group optionally having $C_{6-12}$ aryl group(s) or (iv) a pyrrolidinyl group optionally having $C_{7-12}$ aralkyl group(s), and $R^{120}$ is a $C_{1-6}$ alkyl group,
(6) a pyrrolidinyl group optionally substituted by substituent(s) selected from (i) a $C_{1-6}$ alkyl group optionally having a $C_{1-6}$ alkoxy group and (ii) a $C_{6-12}$ aryl group,
(7) a piperidinyl group optionally substituted by 1 or 2 substituents selected from (i) a $C_{1-6}$ alkyl group optionally having imidazopyridyl group(s), (ii) a $C_{6-12}$ aryloxy group and (iii) a pyrrolidinyl group, and optionally condensed with a $C_{3-8}$ cycloalkyl ring or a $C_{6-12}$ aryl ring, or optionally forming a spiro bond with an indane ring,
(8) a morpholinyl group optionally substituted by 1 or 2 substituents selected from (i) a $C_{1-6}$ alkyl group and (ii) a $C_{6-12}$ aryl group optionally substituted by substituent(s) selected from a halogen atom and a $C_{1-6}$ alkoxy group,
(9) a thienyl group optionally having cyano group(s) and optionally condensed with a benzene ring,
(10) a furyl group,
(11) a pyridyl group optionally having substituent(s) selected from (i) a morpholinyl group and (ii) a pyrrolidinyl group,
(12) a pyrazolyl group optionally having $C_{1-6}$ alkyl group(s),
(13) an azepanyl group optionally having $C_{1-6}$ alkyl group(s), and optionally condensed with a benzene ring,
(14) a group represented by the formula

wherein $R^{121}$ is
(i) a hydrogen atom,
(ii) a $C_{1-6}$ alkyl group optionally having substituent(s) selected from (a) a $C_{6-12}$ arylsulfonyl group, (b) a morpholinyl group and (c) a pyridyl group,
(iii) a $C_{7-12}$ aralkyl group,
(iv) a $C_{1-6}$ alkyl-carbonyl group,
(v) a $C_{1-6}$ alkoxy-carbonyl group,
(vi) a $C_{7-12}$ aralkyloxy-carbonyl group,
(vii) an N—$C_{1-6}$ alkyl-carbamoyl group,
(viii) a $C_{1-6}$ alkylsulfonyl group,
(ix) a pyrimidinyl group or
(x) a thienylcarbonyl group, or
(15) a group represented by the formula

wherein $R^{122}$ is a hydrogen atom or a $C_{1-6}$ alkoxy-carbonyl group;
$R^{112}$ is a hydrogen atom or a halogen atom;
$R^{113}$ is a hydrogen atom or a halogen atom;
$R^{114}$ is a hydrogen atom or a $C_{1-6}$ alkyl group;
$R^{115}$ is a hydrogen atom or a $C_{1-6}$ alkyl group;
$R^{116}$ is a hydrogen atom, a $C_{1-6}$ alkyl group or a $C_{7-12}$ aralkyl group;
$R^{117}$ is a hydrogen atom or a $C_{1-6}$ alkyl group; and
$R^{118}$ is a hydrogen atom or a $C_{1-6}$ alkyl group, or a salt thereof and the like can be mentioned.

Particularly,
tert-butyl 4-(2,3,4,5-tetrahydropyrido[3,2-f][1,4]oxazepin-8-yl)piperazine-1-carboxylate (Example 30),
8-piperidin-1-yl-2,3,4,5-tetrahydropyrido[3,2-f][1,4]oxazepine (Example 40),
8-morpholin-4-yl-2,3,4,5-tetrahydropyrido[3,2-f][1,4]oxazepine (Example 41),
8-pyrrolidin-1-yl-2,3,4,5-tetrahydropyrido[3,2-f][1,4]oxazepine bis(trifluoroacetate) (Example 43),
N,N-diethyl-2,3,4,5-tetrahydropyrido[3,2-f][1,4]oxazepin-8-amine bis(trifluoroacetate) (Example 44),
8-azepan-1-yl-2,3,4,5-tetrahydropyrido[3,2-f][1,4]oxazepine bis(trifluoroacetate) (Example 46),
8-(2-methylpiperidin-1-yl)-2,3,4,5-tetrahydropyrido[3,2-f][1,4]oxazepine bis(trifluoroacetate) (Example 49),
8-[4-(2-phenylethyl)piperazin-1-yl]-2,3,4,5-tetrahydropyrido[3,2-f][1,4]oxazepine tris(trifluoroacetate) (Example 58),
8-[4-(4-phenylbutyl)piperazin-1-yl]-2,3,4,5-tetrahydropyrido[3,2-f][1,4]oxazepine tris(trifluoroacetate) (Example 67),
8-(4-chlorophenyl)-2,3,4,5-tetrahydropyrido[3,2-f][1,4]oxazepine (Example 79),
8-(4-fluorophenyl)-2,3,4,5-tetrahydropyrido[3,2-f][1,4]oxazepine bis(trifluoroacetate) (Example 81),
8-[4-(methylthio)phenyl]-2,3,4,5-tetrahydropyrido[3,2-f][1,4]oxazepine bis(trifluoroacetate) (Example 96),
methyl 4-(2,3,4,5-tetrahydropyrido[3,2-f][1,4]oxazepin-8-yl)benzoate bis(trifluoroacetate) (Example 102),
8-[4-(trifluoromethoxy)phenyl]-2,3,4,5-tetrahydropyrido[3,2-f][1,4]oxazepine bis(trifluoroacetate) (Example 104),
8-(3-furyl)-2,3,4,5-tetrahydropyrido[3,2-f][1,4]oxazepine bis(trifluoroacetate) (Example 112),
tert-butyl 4-(7-fluoro-2,3,4,5-tetrahydropyrido[3,2-f][1,4]oxazepin-8-yl)piperazine-1-carboxylate (Example 122),
tert-butyl 4-(2-methyl-2,3,4,5-tetrahydropyrido[3,2-f][1,4]oxazepin-8-yl)piperazine-1-carboxylate (Example 126),
2-methyl-8-morpholin-4-yl-2,3,4,5-tetrahydropyrido[3,2-f][1,4]oxazepine (Example 128),
2-methyl-8-piperidin-1-yl-2,3,4,5-tetrahydropyrido[3,2-f][1,4]oxazepine (Example 129),
(+)-2-methyl-8-morpholin-4-yl-2,3,4,5-tetrahydropyrido[3,2-f][1,4]oxazepine (Example 130), and
(−)-2-methyl-8-morpholin-4-yl-2,3,4,5-tetrahydropyrido[3,2-f][1,4]oxazepine (Example 131)
are preferable.

When compound (I) is a salt, examples of the salt include salt with inorganic base, ammonium salt, salt with organic base, salt with inorganic acid, salt with organic acid, salt with basic or acidic amino acid and the like.

Preferable examples of the salt with inorganic base include alkali metal salts such as sodium salt, potassium salt and the like; alkaline earth metal salts such as calcium salt, magnesium salt, barium salt and the like; aluminum salt and the like.

Preferable examples of the salt with organic base include salts with trimethylamine, triethylamine, pyridine, picoline, ethanolamine, diethanolamine, triethanolamine, dicyclohexylamine, N,N'-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Of these salts, pharmaceutically acceptable salts are preferable.

Compound (I) encompasses a solvate, for example, hydrate. In addition, compound (I) may be labeled with an isotope (e.g., $^3H$, $^{14}C$, $^{35}S$, $^{125}I$ and the like) and the like.

When compound (I) of the present invention has an asymmetric center, isomers such as enantiomer, diastereomer and the like may be present. Such isomers and a mixture thereof are all encompassed in the scope of the present invention. When an isomer due to conformation is present, such isomer and a mixture thereof are also encompassed in compound (I) of the present invention.

The production methods of the compound of the present invention are explained in the following.

A compound represented by the formula (I) or a salt thereof and a starting material compound thereof can be produced by a means known per se, for example, a method shown by the following scheme and the like. In the following, the "room temperature" generally means 10-30° C. and, unless otherwise specified, each symbol in the chemical structural formulas in the scheme is as defined above. The compounds in the formulas encompass salts thereof, and examples of such salt include those similar to the salt of compound (I) and the like.

While the compound obtained in each step can be used for the next reaction in the form of a reaction mixture or a crude product. Alternatively, it can also be isolated from a reaction mixture according to a conventional method, and easily purified by a separation means such as recrystallization, distillation, chromatography and the like.

Now, the production methods of the compounds represented by the formula (I) and the formula (Ix) of the present invention or a salt thereof (hereinafter referred to as compound (I) and compound (Ix), respectively) are explained (wherein x is a, b, c, d, e, f, g or h).

Compound (I), compound (Ia), compound (Ib) and compound (Ic) of the present invention can be produced by, for example, the following Method A, Method B, Method C, Method D or Method E.

[Method A]

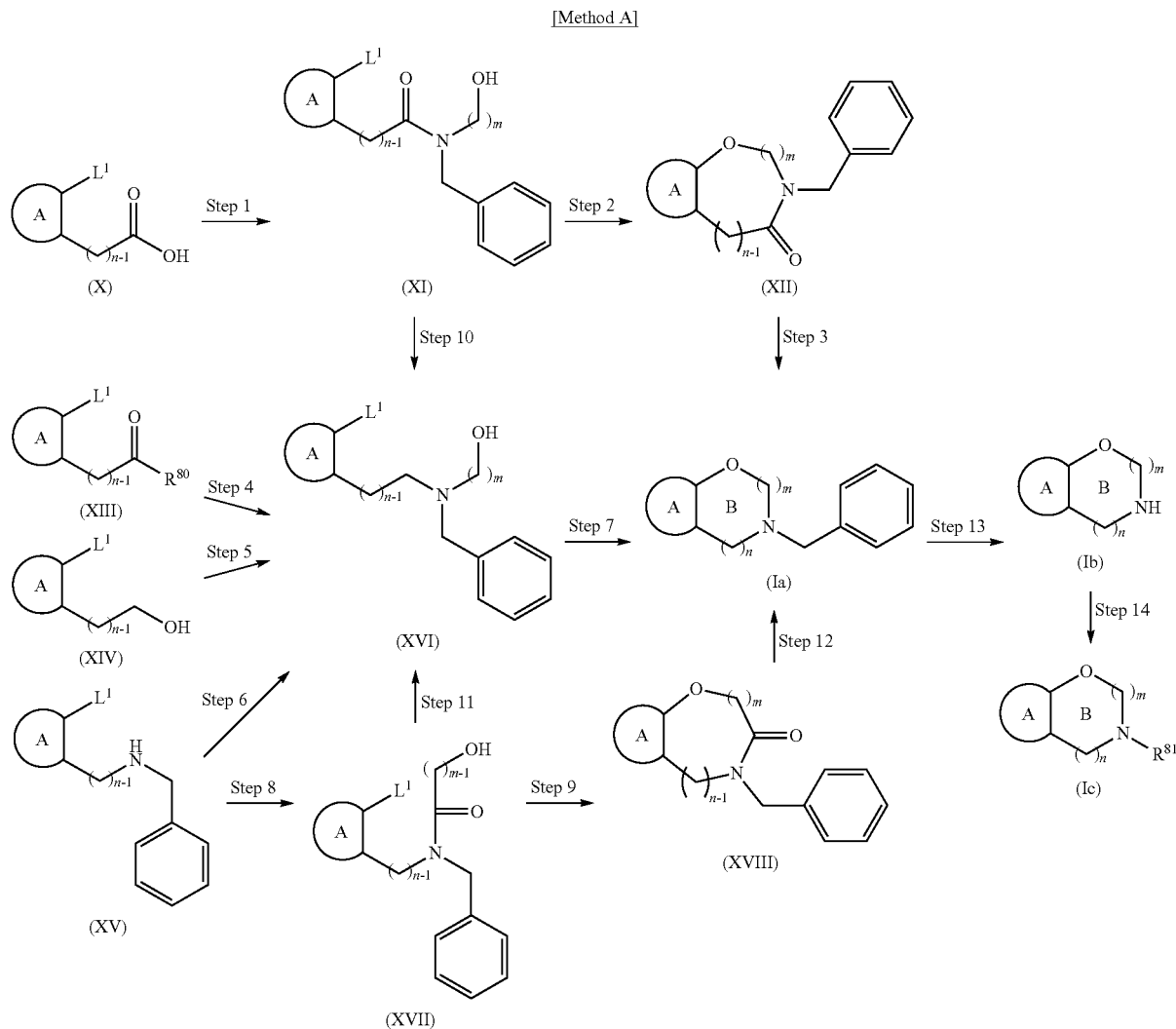

wherein $L^1$ is a leaving group, $R^{80}$ is a hydrogen atom, $R^{81}$ is a $C_{1-6}$ alkyl group optionally having substituent(s) or a $C_{7-12}$ aralkyl group optionally having substituent(s), and other symbols are as defined above.

The leaving group for $L^1$ is, for example, a halogen atom (e.g., fluorine atom, chlorine atom, bromine atom, iodine atom), a substituted sulfonyloxy group (e.g., $C_{1-6}$ alkylsulfonyloxy group such as methanesulfonyloxy, ethanesulfonyloxy, trifluoromethanesulfonyloxy and the like; $C_{6-14}$ arylsulfonyloxy group such as benzenesulfonyloxy, p-toluenesulfonyloxy and the like; $C_{7-16}$ aralkylsulfonyloxy group such as benzylsulfonyloxy and the like; and the like), substituted sulfinyl group (e.g., methanesulfinyl and the like), acyloxy (acetoxy, benzoyloxy and the like), carbonic acid esters, trichloroacetimidic acid esters, oxalic acid esters, phosphorous acid esters (e.g., methyl phosphite and the like), phosphoranes, oxy group substituted by hetero ring or aryl group (succinimide, benzotriazole, quinoline, 4-nitrophenyl and the like), a hetero ring (imidazole and the like) and the like.

(Step 1)

In this step, a compound represented by the formula (X) or a salt thereof (hereinafter to be referred to as compound (X)) and a compound represented by the formula (XX):

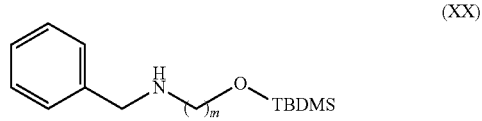

wherein TBDMS is a tert-butyldimethylsilyl group, and other symbols are as defined above, or a salt thereof (hereinafter to be referred to as amine compound (XX)) are subjected to a dehydrative condensation, and then the TBDMS group is removed to give a compound represented by the formula (XI) or a salt thereof (hereinafter to be referred to as compound (XI)).

Compound (X) and amine compound (XX) are commercially available, or can be produced by a known method. The amount of amine compound (XX) to be used is about 1 to about 10 molar equivalents, preferably about 1 to about 2 molar equivalents, per 1 mol of compound (X).

The dehydrative condensation can be performed by a method known per se, for example, the method described in The Chemical Society of Japan Ed., 1991 "4th Ed. Jikken Kagaku Koza (Courses in Experimental Chemistry) 22, Organic Synthesis IV" and the like, or a method analogous thereto. Such method is, for example, a method using a condensation agent or a method using a reactive derivative and the like.

Examples of the condensation agent used for the "method using a condensation agent" include dicyclohexylcarbodiimide, diisopropylcarbodiimide, N-ethyl-N'-(3-dimethylaminopropyl)carbodiimide and hydrochloride thereof, benzotriazol-1-yl-tris(dimethylamino)phosphonium hexafluorophosphate, diphenylphosphoryl azide and the like. They may be used alone, or in combination with an additive (e.g., N-hydroxysuccinimide, 1-hydroxybenzotriazole, 3-hydroxy-4-oxo-3,4-dihydro-1,2,3-benzotriazine and the like). The amount of the condensation agent to be used is about 1 to about 10 molar equivalents, preferably about 1 to about 2 molar equivalents, per 1 mol of compound (X). The amount of the additive to be used is about 1 to about 10 molar equivalents, preferably about 1 to about 2 molar equivalents, per 1 mol of compound (X). The above-mentioned reaction is generally performed in a solvent that does not adversely influence the reaction, and an appropriate base for promotion of the reaction may be added. Examples of the solvent include hydrocarbons (e.g., benzene, toluene and the like), ethers (e.g., diethyl ether, dioxane, tetrahydrofuran and the like), esters (e.g., ethyl acetate and the like), halogenated hydrocarbons (e.g., chloroform, dichloromethane and the like), amides (e.g., N,N-dimethylformamide and the like), aromatic amines (e.g., pyridine and the like), water and the like, which may be mixed as appropriate. Examples of the base include alkali metal hydroxide (e.g., sodium hydroxide, potassium hydroxide and the like), hydrogen carbonate (e.g., sodium hydrogen carbonate, potassium hydrogen carbonate and the like), carbonate (e.g., sodium carbonate, potassium carbonate and the like), acetate (e.g., sodium acetate and the like), tertiary amines (e.g., trimethylamine, triethylamine, N-methylmorpholine and the like), aromatic amines (e.g., pyridine, picoline, N,N-dimethylaniline and the like) and the like. The amount of the base to be used is generally about 1 to about 100 molar equivalents, preferably about 1 to about 5 molar equivalents, per 1 mol of compound (X). The reaction temperature is generally about $-80°$ C. to about $150°$ C., preferably about $-80°$ C. to about $50°$ C., and the reaction time is generally about 0.1 to about 48 hr, preferably about 0.5 to about 16 hr.

As the reactive derivative used for the "method using a reactive derivative", for example, acid halide, acid anhydride, mixed acid anhydride, active ester and the like can be mentioned. The conversion to a reactive derivative can be performed according to a method known per se. For example, for conversion to an acid halide, a method using acid halide (e.g., thionyl chloride, oxalyl chloride and the like), a method using halide of phosphorus and phosphoric acid (e.g., phosphorus trichloride, phosphorus pentachloride and the like) and the like can be mentioned. While the above-mentioned reaction using a "reactive derivative" varies depending on the kind of the reactive derivative or compound (X), it is generally performed in a solvent that does not adversely influence the reaction, and an appropriate base may be added to promote the reaction. The kind and amount of the solvent and base to be used for the reaction, reaction temperature and reaction time are the same as those described for the above-mentioned "method using a condensation agent".

The TBDMS group can be removed by a method known per se or the method described in Wiley-InterScience, 1999 "Protective Groups in Organic Synthesis, 3rd Ed." (by Theodora W. Greene, Peter G. M. Wuts) and the like, or a method analogous thereto. For example, a method using an acid (e.g., hydrochloric acid, sulfuric acid, acetic acid, hydrogen fluoride, trifluoroacetic acid, p-toluenesulfonic acid and the like), a salt (e.g., tetrabutylammonium fluoride, pyridine-hydrogen fluoride complex, lithium tetrafluoroborate and the like), a peroxide (e.g., tert-butyl peroxide and the like), a palladium catalyst (e.g., palladium(II) chloride and the like) and the like can be used.

(Step 2)

In this step, compound (XI) is converted to a compound represented by the formula (XII) or a salt thereof (hereinafter to be referred to as compound (XII)) by subjecting to an intramolecular ring closure reaction. This reaction can be performed by a method known per se, generally in the presence of a base and, where necessary, in a solvent that does not adversely influence the reaction.

Examples of the base include metal hydride (e.g., potassium hydride, sodium hydride and the like), inorganic base (e.g., alkali metal hydroxide such as lithium hydroxide, sodium hydroxide, potassium hydroxide and the like; alkali metal hydrogen carbonate such as sodium hydrogen carbonate, potassium hydrogen carbonate and the like; alkali metal carbonate such as sodium carbonate, potassium carbonate and the like; alkoxide such as sodium methoxide, sodium ethoxide and the like; and the like), organic base (e.g., trimethylamine, triethylamine, diisopropylethylamine, N-methylmorpholine, 1,8-diazabicyclo[5.4.0]undec-7-ene, pyridine, N,N-dimethylaniline, pyridazine, 4-dimethylaminopyridine and the like) and the like. Particularly, metal hydrides such as sodium hydride and the like are preferable. While the amount of the base to be used varies depending on the kind of the solvent and other reaction conditions, it is generally about 0.1 to about 10 molar equivalents, preferably about 0.1 to about 5 molar equivalents, per 1 mol of compound (XI).

Examples of the solvent that does not adversely influence the reaction include alcohols (e.g., methanol, ethanol, propanol, 2-propanol, butanol, isobutanol, tert-butanol and the like), hydrocarbons (e.g., benzene, toluene, xylene, hexane, heptane and the like), halogenated hydrocarbons (e.g., dichloromethane, chloroform and the like), ethers (e.g., diethyl ether, diisopropyl ether, tert-butyl methyl ether, tetrahydrofuran, dioxane, dimethoxyethane and the like), nitriles (e.g., acetonitrile and the like), amides (e.g., N,N-dimethylformamide, N,N-dimethylacetamide and the like), sulfoxides (e.g., dimethyl sulfoxide and the like), water and the like. These solvents may be used in a mixture of two or more kinds at an appropriate ratio.

The reaction temperature is, for example, about −50° C. to about 200° C., preferably about 0° C. to about 150° C., and the reaction time varies depending on the kind of compound (XI), reaction temperature and the like and is, for example, about 0.1 to about 100 hr, preferably about 0.5 to about 24 hr.
(Step 3)

In this step, compound (XII) is converted to a compound represented by the formula (Ia) or a salt thereof (hereinafter to be referred to as compound (Ia)) by a reduction reaction. This reaction can be performed by a method known per se generally in the presence of a reducing agent, where necessary, in a solvent that does not adversely influence the reaction.

Examples of the reducing agent include aluminum reagent (e.g., lithium aluminum hydride (LiAlH$_4$), diisobutylaluminum hydride (DIBAL-H), sodium bis(2-methoxyethoxy)aluminum hydride (Red-Al), alane (AlH$_3$) and the like) or boron reagent (e.g., borane (BH$_3$), 9-borabicyclo[3.3.1]nonane (9-BBN), sodium tetrahydroborate (NaBH$_4$), sodium cyanoborohydride (NaBH$_3$CN), sodium triacetoxyborohydride (NaBH(OAc)$_3$) and the like) and the like. Particularly, lithium aluminum hydride and borane are preferable. While the amount of the reducing agent to be used varies depending on the kind of the solvent and other reaction conditions, it is generally about 1 to about 10 molar equivalents, preferably about 1 to about 5 molar equivalents, per 1 mol of compound (XII).

Examples of the solvent that does not adversely influence the reaction include alcohols (e.g., methanol, ethanol, propanol, 2-propanol, butanol, isobutanol, tert-butanol and the like), hydrocarbons (e.g., benzene, toluene, xylene, hexane, heptane and the like), halogenated hydrocarbons (e.g., dichloromethane, chloroform and the like), ethers (e.g., diethyl ether, diisopropyl ether, tert-butyl methyl ether, tetrahydrofuran, dioxane, dimethoxyethane and the like), carboxylic acids (e.g., acetic acid, trifluoroacetic acid and the like) and the like. These solvents may be used in a mixture of two or more kinds at an appropriate ratio.

The reaction temperature is, for example, about −80° C. to about 200° C., preferably about −80° C. to about 100° C. The reaction time varies depending on the kind of compound (XII), reaction temperature and the like and is, for example, about 0.1 to about 100 hr, preferably about 0.5 to about 24 hr.
(Step 4)

In this step, a compound represented by the formula (XIII) or a salt thereof (hereinafter to be referred to as compound (XIII)) is converted to a compound represented by the formula (XVI) or a salt thereof (hereinafter to be referred to as compound (XVI)) by a reductive amination reaction using amine compound (XX), and then removing the TBDMS group.

Compound (XIII) is commercially available, or can be produced by a known method. The amount of amine compound (XX) to be used is generally about 1 to about 10 molar equivalents, preferably about 1 to about 2 molar equivalents, per 1 mol of compound (XIII).

The reductive amination reaction can be performed by a method known per se. For example, it can be performed by reacting compound (XIII) with amine compound (XX), and reducing the resulting imine or iminium ion.

Compound (XIII) can be converted to an imine or iminium ion by a known method, for example, in a solvent inert to the reaction, and using an additive as necessary.

Examples of the solvent inert to the reaction include aromatic hydrocarbons (e.g., toluene, xylene and the like), aliphatic hydrocarbons (e.g., heptane, hexane and the like), halogenated hydrocarbons (e.g., chloroform, dichloromethane and the like), ethers (e.g., diethyl ether, tetrahydrofuran, dioxane and the like), alcohols (e.g., methanol, ethanol, 2-propanol, butanol, benzyl alcohol and the like), nitriles (e.g., acetonitrile and the like), esters (e.g., ethyl acetate and the like), amides (e.g., N,N-dimethylformamide and the like), sulfoxides (e.g., dimethyl sulfoxide and the like) and a mixture thereof.

The reaction can be advantageously performed by adding a catalyst as necessary. Examples of the catalyst include mineral acids (e.g., hydrochloric acid, hydrobromic acid, sulfuric acid and the like), carboxylic acids (e.g., formic acid, acetic acid, propionic acid, trifluoroacetic acid and the like), sulfonic acids (e.g., methanesulfonic acid, p-toluenesulfonic acid and the like), Lewis acids (e.g., aluminum chloride, zinc chloride, zinc bromide, boron trifluoride, titanium chloride and the like), acetate (e.g., sodium acetate, potassium acetate and the like), molecular sieves (e.g., molecular sieves 3A, 4A, 5A and the like), dehydrating agent (e.g., magnesium sulfate and the like) and the like. The amount of the catalyst to be used is, for example, about 0.01 to about 50 molar equivalents, preferably about 0.1 to about 10 molar equivalents, per 1 mol of compound (XIII).

The reaction temperature is generally about 0° C. to about 200° C., preferably about 20° C. to about 150° C., and the reaction time is generally about 0.5 hr to about 48 hr, preferably about 0.5 hr to about 24 hr.

The reduction reaction of the resulting imine or iminium ion can be performed by a known method, for example, in a solvent inert to the reaction, and using various reducing agents. Examples of the reduction reaction include a method using a metal hydride and a method using a catalytic hydrogenation reaction.

Examples of the metal hydride include boron reagent (e.g., sodium borohydride, lithium borohydride, zinc borohydride, sodium cyanoborohydride, sodium triacetoxyborohydride, lithium cyanoborohydride and the like), aluminum reagent (e.g., diisobutylaluminum hydride, aluminum hydride, lithium aluminum hydride and the like), borane complex (e.g., borane-THF complex, catechol borane and the like) and the like, and sodium borohydride, sodium cyanoborohydride, sodium triacetoxyborohydride and the like are preferable. The amount of the metal hydride to be used is, for example, about 1 to about 50 molar equivalents, preferably about 1 to about 10 molar equivalents, per 1 mol of imine or iminium ion.

The reduction reaction with metal hydride is generally performed in a solvent inert to the reaction. Examples of the solvent include aromatic hydrocarbons (e.g., toluene, xylene and the like), aliphatic hydrocarbons (e.g., heptane, hexane and the like), halogenated hydrocarbons (e.g., chloroform, dichloromethane and the like), ethers (e.g., diethyl ether, tetrahydrofuran, dioxane and the like), nitriles (e.g., acetonitrile and the like) and a mixture thereof. These solvents may be used in a mixture at an appropriate ratio.

The reaction temperature is generally about −80° C. to about 200° C., preferably about −40° C. to about 100° C., and the reaction time is generally about 5 min to about 48 hr, preferably about 1 hr to about 24 hr.

The catalytic hydrogenation reaction can be performed in the presence of a catalyst in a hydrogen atmosphere. Examples of the catalyst include palladium compounds (e.g., palladium carbon, palladium hydroxide carbon, palladium oxide and the like), nickel compounds (e.g., Raney nickel catalyst and the like), platinum compounds (e.g., platinum oxide, platinum carbon and the like), rhodium compounds (e.g., rhodium carbon and the like) and the like. Particularly, a palladium compound or a nickel compound is preferable. The amount thereof to be used is about 0.001 to about 1 molar equivalent, preferably about 0.01 to about 0.5 molar equivalent, per 1 mol of imine or iminium ion.

The catalytic hydrogenation reaction is generally performed in a solvent inert to the reaction. Examples of the solvent include alcohols (e.g., methanol, ethanol, propanol, butanol and the like), hydrocarbons (e.g., benzene, toluene, xylene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide and the like), carboxylic acids (e.g., acetic acid and the like), water and a mixture thereof.

The hydrogen pressure at which the reaction is performed is generally, about 1 to about 50 atm, preferably about 1 to about 10 atm. The reaction temperature is generally about 0° C. to about 150° C., preferably about 20° C. to about 100° C., and the reaction time is generally about 5 min to about 72 hr, preferably about 0.5 hr to about 40 hr.

The following reduction reaction can also be performed without isolating an intermediate imine or iminium ion. In this case, the pH of the reaction mixture is preferably from about 4 to about 5.

The TBDMS group can be removed according to the method described in step 1.
(Step 5)

In this step, a compound represented by the formula (XIV) or a salt thereof (hereinafter to be referred to as compound (XIV)) is converted to compound (XVI) by an amination reaction with amine compound (XX), and then removing the TBDMS group.

Compound (XIV) is commercially available, or can be produced by a known method. The amount of the amine compound (XX) to be used is about 1 to about 10 molar equivalents, preferably about 1 to about 2 molar equivalents, per 1 mol of compound (XIV).

The amination reaction can be performed by a method known per se, for example, by reacting a compound represented by the formula (XIVa):

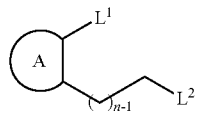

(XIVa)

wherein $L^2$ is a leaving group, and other symbols are as defined above, or a salt thereof (hereinafter to be referred to as reactive derivative (XIVa)), which is a reactive derivative of compound (XIV), with amine compound (XX).

As the leaving group for $L^2$, those similar to the above-mentioned leaving group $L^1$ can be mentioned. Particularly, chlorine atom, bromine atom and iodine atom are preferable.

Compound (XIV) can be converted to reactive derivative (XIVa) by a method similar to the method described in the aforementioned "method using a reactive derivative".

This reaction can be generally performed by reacting reactive derivative (XIVa) with amine compound (XX) in a solvent in the presence of a base.

Examples of the solvent include alcohols (e.g., methanol, ethanol, propanol and the like), ethers (e.g., dimethoxyethane, dioxane, tetrahydrofuran and the like), ketones (e.g., acetone, 2-butanone and the like), nitriles (e.g., acetonitrile and the like), amides (e.g., N,N-dimethylformamide), sulfoxides (e.g., dimethyl sulfoxide and the like), water and a mixture thereof.

Examples of the base include organic base (e.g., trimethylamine, triethylamine, N-methylmorpholine, pyridine, picoline, N,N-dimethylaniline and the like), inorganic base (e.g., potassium carbonate, sodium carbonate, potassium hydroxide, sodium hydroxide and the like) and the like. The amount of the base to be used is, for example, about 1 to about 100 molar equivalents, preferably about 1 to about 10 molar equivalents, per 1 mol of amine compound (XX).

The amount of reactive derivative (XIVa) to be used is, for example, about 1 to about 5 molar equivalents, preferably about 1 to about 3 molar equivalents, per 1 mol of amine compound (XX).

Where necessary, the reaction can also be promoted by adding an additive. Examples of the additive include iodide salt (e.g., sodium iodide, potassium iodide and the like) and the like, and the amount thereof to be used is about 0.1 to about 10 molar equivalents, preferably about 0.1 to about 5 molar equivalents, per 1 mol of amine compound (XX).

The reaction temperature is generally about −10° C. to about 200° C., preferably about 0° C. to about 100° C., and the reaction time is generally about 0.5 hr to about 48 hr, preferably about 0.5 hr to about 16 hr.

The TBDMS group can be removed according to the method described in step 1.
(Step 6)

In this step, a compound represented by the formula (XV) or a salt thereof (hereinafter to be referred to as compound (XV)) is converted to compound (XVI) by a reductive alkylation reaction with a compound represented by the formula (XXI):

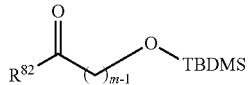

(XXI)

wherein $R^{82}$ is a hydrogen atom, and other symbols are as defined above, or a salt thereof (hereinafter to be referred to as carbonyl compound (XXI)), and then removing the TBDMS group.

Compound (XV) and carbonyl compound (XXI) are commercially available, or can be produced by a known method. The amount of carbonyl compound (XXI) to be used is generally about 1 to about 10 molar equivalents, preferably about 1 to about 2 molar equivalents, per 1 mol of compound (XV).

The reductive alkylation reaction can be performed by a method known per se, for example, by reacting compound (XV) with carbonyl compound (XXI), and reducing the resulting imine or iminium ion.

The conversion of compound (XV) to imine or iminium ion and the reduction reaction can be performed in the same manner as in the method described in step 4, and the following reduction reaction can also be performed without isolating an intermediate imine or iminium ion.

The TBDMS group can be removed according to the method described in step 1.

(Step 7)

In this step, compound (XVI) is converted to compound (Ia) by an intramolecular ring closure reaction, which can be performed in the same manner as in the method described in step 2.

(Step 8)

In this step, compound (XV) and a compound represented by the formula (XXII):

(XXII)

wherein each symbol is as defined above, or a salt thereof (hereinafter to be referred to as compound (XXII)) are subjected to a dehydrative condensation, and then the TBDMS group is removed to give a compound represented by the formula (XVII) or a salt thereof (hereinafter to be referred to as compound (XVII)).

Compound (XV) and compound (XXII) are commercially available, or can be produced by a known method. The amount of compound (XXII) to be used is about 1 to about 10 molar equivalents, preferably about 1 to about 2 molar equivalents, per 1 mol of compound (XV).

The dehydrative condensation can be performed in the same manner as in the method described in step 1.

The TBDMS group can be removed in the same manner as in the method described in step 1.

(Step 9)

In this step, compound (XVII) is converted to a compound represented by the formula (XVIII) or a salt thereof (hereinafter to be referred to as compound (XVIII)) by an intramolecular ring closure response in the same manner as in the method described in step 2.

(Step 10)

In this step, compound (XI) is converted to compound (XVI) by a reduction reaction, which can be performed in the same manner as in the method described in step 3.

(Step 11)

In this step, compound (XVII) is converted to compound (XVI) by a reduction reaction, which can be performed in the same manner as in the method described in step 3.

(Step 12)

In this step, compound (XVIII) is converted to compound (Ia) by a reduction reaction, which can be performed in the same manner as in the method described in step 3.

(Step 13)

In this step, compound (Ia) is converted to a compound represented by the formula (Ib) or a salt thereof (hereinafter to be referred to as compound (Ib)) by removing a benzyl group.

The benzyl group can be removed by a method known per se or the method described in Wiley-InterScience, 1999 "Protective Groups in Organic Synthesis, 3rd Ed." (by Theodora W. Greene, Peter G. M. Wuts) and the like, or a method analogous thereto. For example, a method including a catalytic hydrogenation reaction or a treatment with acid halide and the like can be used.

The catalytic hydrogenation reaction can be performed in a hydrogen atmosphere in the presence of a catalyst. Examples of the catalyst include palladium compounds (e.g., palladium carbon, palladium hydroxide carbon, palladium oxide and the like), nickel compounds (e.g., Raney nickel catalyst and the like), platinum compounds (e.g., platinum oxide, platinum carbon and the like), rhodium compounds (e.g., rhodium carbon and the like) and the like. The amount thereof to be used is about 0.001 to about 1 molar equivalent, preferably about 0.01 to about 0.5 molar equivalent, per 1 mol of compound (Ia).

The catalytic hydrogenation reaction is generally performed in a solvent inert to the reaction. Examples of the solvent include alcohols (e.g., methanol, ethanol, propanol, butanol and the like), hydrocarbons (e.g., benzene, toluene, xylene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide and the like), carboxylic acids (e.g., acetic acid and the like), water and a mixture thereof.

The hydrogen pressure at which the reaction is performed is generally about 1 to about 50 atm, preferably about 1 to about 10 atm. The reaction temperature is generally about 0° C. to about 150° C., preferably about 20° C. to about 100° C., and the reaction time is generally about 5 min to about 72 hr, preferably about 0.5 hr to about 40 hr.

For the treatment with acid halide, for example, 1-chloroethyl chloroformate, 2,2,2-trichloro-1,1-dimethylethyl chloroformate, β-trimethylsilylethyl chloroformate and the like are used. Particularly, a method using 1-chloroethyl chloroformate is preferable. The amount of 1-chloroethyl chloroformate to be used is about 1 to about 10 molar equivalents, preferably about 1 to about 2 molar equivalents, per 1 mol of compound (Ia). The reaction can be generally performed in a solvent inert to the reaction. Examples of the solvent include hydrocarbons (e.g., benzene, toluene, xylene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide and the like), nitriles (e.g., acetonitrile and the like) and a mixture thereof. The reaction temperature is generally about −80° C. to about 150° C., preferably about 0° C. to about 100° C., and the reaction time is generally about 5 min to about 72 hr, preferably about 0.5 hr to about 20 hr.

When 1-chloroethyl chloroformate is used, compound (Ia) is reacted with 1-chloroethyl chloroformate, and treated with alcohols (e.g., methanol, ethanol and the like), aqueous solution (e.g., aqueous sodium hydroxide solution and the like) or water to give compound (Ib). The reaction temperature is generally about 0° C. to about 150° C., preferably about 5° C. to about 100° C., and the reaction time is generally about 5 min to about 24 hr, preferably about 0.5 hr to about 5 hr.

(Step 14)

In this step, compound (Ib) is converted to a compound represented by the formula (Ic) or a salt thereof (hereinafter to be referred to as compound (Ic)) by an alkylation reaction or a reductive alkylation reaction.

The alkylation reaction can be performed by a method known per se, for example, by reacting compound (Ib) with a compound represented by the formula (XXIII):

$R^{81}$—OH (XXIII)

wherein $R^{81}$ is as defined above, or a salt thereof (hereinafter to be referred to as compound (XXIII)) or a reactive derivative thereof, which is an alkylating agent, to produce compound (Ic).

Examples of the reactive derivative of compound (XXIII) include a compound represented by the formula (XXIIIa):

$R^{81}$-$L^3$ (XXIIIa)

wherein $L^3$ is a leaving group, and $R^{81}$ is as defined above, or a salt thereof (hereinafter to be referred to as reactive derivative (XXIIIa)).

As the leaving group for $L^3$, a group similar to the above-mentioned leaving group $L^1$ is used.

The reaction using the above-mentioned reactive derivative as an alkylating agent can be generally performed by reacting compound (Ib) with a reactive derivative in a solvent in the presence of a base. Examples of the solvent include alcohols (e.g., methanol, ethanol, propanol and the like), ethers (e.g., dimethoxyethane, dioxane, tetrahydrofuran and the like), ketones (e.g., acetone, 2-butanone and the like), nitriles (e.g., acetonitrile and the like), amides (e.g., N,N-dimethylformamide and the like), sulfoxides (e.g., dimethyl sulfoxide and the like), water and a mixture thereof. Examples of the base include organic base (e.g., trimethylamine, triethylamine, N-methylmorpholine, pyridine, picoline, N,N-dimethylaniline and the like), inorganic base (e.g., potassium carbonate, sodium carbonate, potassium hydroxide, sodium hydroxide and the like) and the like. The amount of the base to be used is, for example, about 1 to about 100 molar equivalents, preferably about 1 to about 10 molar equivalents, per 1 mol of compound (Ib).

Examples of the reactive derivative include halides (e.g., chloride, bromide, iodide and the like), sulfuric acid esters, sulfonic acid esters (e.g., methanesulfonate, p-toluenesulfonate, benzenesulfonate and the like) and the like. Particularly, halides are preferably used. The amount of the reactive derivative to be used is, for example, about 1 to about 5 molar equivalents, preferably about 1 to about 3 molar equivalents, per 1 mol of compound (Ib).

Where necessary, the reaction can also be promoted by adding an additive. Examples of the additive include iodide salt (e.g., sodium iodide, potassium iodide and the like) and the like, and the amount thereof to be used is about 0.1 to about 10 molar equivalents, preferably about 0.1 to about 5 molar equivalents, per 1 mol of compound (Ib).

The reaction temperature is generally about −10° C. to about 200° C., preferably about 0° C. to about 110° C., and the reaction time is generally about 0.5 hr to about 48 hr, preferably about 0.5 hr to about 16 hr.

The reductive alkylation reaction can be performed by a method known per se, for example, by reacting compound (Ib) with a compound represented by the formula (XXIV):

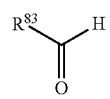

(XXIV)

wherein $R^{83}$ is a hydrogen atom, a $C_{1-5}$ alkyl group optionally having substituent(s), a phenyl group optionally having substituent(s) or a $C_{7-11}$ aralkyl group optionally having substituent(s), or a salt thereof (hereinafter to be referred to as carbonyl compound (XXIV)) and subjecting the resulting imine or iminium ion to a reduction reaction.

The formation reaction of imine or iminium ion and a reduction reaction thereof can be performed according to the method described in step 4.

In this step, the following reduction reaction may be performed without isolating an intermediate imine or iminium ion to directly obtain compound (Ic) from compound (Ib). In this case, the pH of the reaction mixture is preferably about 4 to about 5.

When leaving group $L^4$ is present at the ring A moiety of compound (Ia), Ar can be introduced by the following Method B.

[Method B]

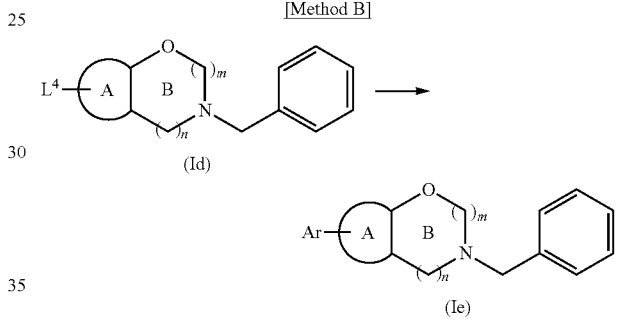

wherein $L^4$ is a leaving group, Ar is an aryl group optionally having substituent(s) or a heterocyclic group optionally having substituent(s), and other symbols are as defined above.

As the leaving group for $L^4$, a group similar to the leaving group for the aforementioned $L^1$ can be mentioned. Particularly, a halogen atom (e.g., fluorine atom, chlorine atom, bromine atom, iodine atom and the like), a substituted sulfinyl group (e.g., methylsulfinyl and the like), a substituted sulfonyloxy group (e.g., trifluoromethanesulfonyloxy and the like) and the like are preferable.

Examples of the aryl group optionally having substituent(s) for Ar include those similar to the aforementioned "aryl group optionally having substituent(s)".

Examples of the heterocyclic group optionally having substituent(s) for Ar include those similar to the aforementioned "heterocyclic group optionally having substituent(s)".

Compound (Ie) can be produced, for example, by subjecting a compound represented by the formula (Id):

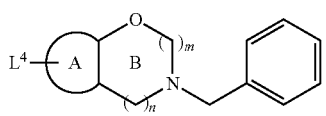

(Id)

wherein each symbol is as defined above, or a salt thereof (hereinafter to be referred to as compound (Id)) to a coupling reaction with a compound represented by the formula (XXV):

ArB(OH)$_2$ (XXV)

wherein Ar is as defined above, or a salt thereof.

This reaction can be performed according to a method known per se [e.g., Chemical Reviews, 1995, vol. 95, page 2457 and the like], for example, in the presence of a transition metal catalyst and a base, in a solvent that does not adversely influence the reaction.

Examples of the transition metal catalyst to be used include palladium catalyst (e.g., palladium(II) acetate, tris(dibenzylideneacetone)dipalladium(0), palladium(II) chloride, tetrakis(triphenylphosphine)palladium(0) and the like), nickel catalyst (e.g., nickel chloride and the like) and the like and, where necessary, a ligand (e.g., triphenylphosphine, tri-tert-butylphosphine and the like) may be added, or metal oxide (e.g., copper oxide, silver oxide and the like) and the like may be used as a cocatalyst. While the amount of the catalyst to be used varies depending on the kind of the catalyst, it is generally about 0.0001 to about 1 molar equivalent, preferably about 0.01 to about 0.5 molar equivalent, per 1 mol of compound (Id), the amount of the ligand to be used is generally about 0.0001 to about 4 molar equivalents, preferably about 0.01 to about 2 molar equivalents, per 1 mol of compound (Id), and the amount of the cocatalyst to be used is about 0.0001 to about 4 molar equivalents, preferably about 0.01 to about 2 molar equivalents, per 1 mol of compound (Id).

Examples of the base to be used include organic amines (e.g., trimethylamine, triethylamine, diisopropylamine, N-methylmorpholine, 1,8-diazabicyclo[5.4.0]undec-7-ene, pyridine, N,N-dimethylaniline and the like), alkali metal salt (e.g., sodium hydrogen carbonate, potassium hydrogen carbonate, sodium carbonate, potassium carbonate, cesium carbonate, sodium phosphate, potassium phosphate, sodium hydroxide, potassium hydroxide and the like), metal hydride (potassium hydride, sodium hydride and the like), alkali metal alkoxide (sodium methoxide, sodium ethoxide, sodium tert-butoxide, potassium tert-butoxide and the like), alkali disilazide (e.g., lithium disilazide, sodium disilazide, potassium disilazide and the like) and the like. Particularly, alkali metal salts such as potassium carbonate, cesium carbonate, sodium phosphate, potassium phosphate and the like; alkali metal alkoxides such as sodium tert-butoxide, potassium tert-butoxide and the like; organic amines such as triethylamine, diisopropylamine and the like; and the like are preferable. The amount of the base to be used is about 0.1 to about 10 molar equivalents, preferably about 1 to about 5 molar equivalents, per 1 mol of compound (Id).

The solvent to be used may be any as long as it does not adversely influence the reaction and, for example, hydrocarbons (e.g., benzene, toluene, xylene and the like), halogenated hydrocarbons (e.g., chloroform, 1,2-dichloroethane and the like), nitriles (e.g., acetonitrile and the like), ethers (e.g., dimethoxyethane, tetrahydrofuran and the like), alcohols (e.g., methanol, ethanol and the like), aprotic polar solvents (e.g., N,N-dimethylformamide, dimethyl sulfoxide, hexamethylphosphoramide and the like), water or a mixture thereof are used. The reaction temperature is generally about −10° C. to about 200° C., preferably about 0° C. to about 150° C., and the reaction time is generally about 0.5 to about 48 hr, preferably about 0.5 to about 16 hr.

Compound (Ie) obtained in this step can be led to compound (Ib) or compound (Ic) by the methods described in step 13 and step 14.

When leaving group $L^4$ is present at the ring A moiety of compound (Ia), $R^{85}$ can be introduced by the following Method C.

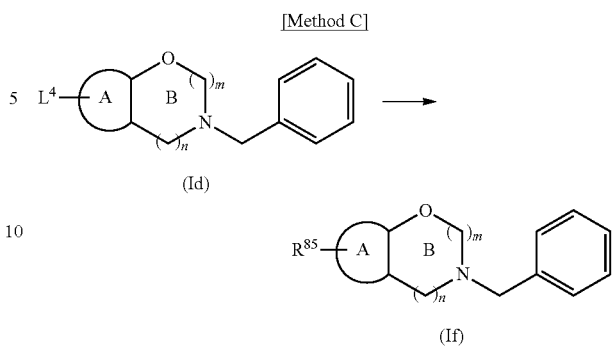

wherein $R^{85}$ is an amino group optionally having substituent(s), and other symbols are as defined above.

Examples of the amino group optionally having substituent(s) for $R^{85}$ include those similar to the aforementioned "amino group optionally having substituent(s)".

This step can be performed according to a method known per se [e.g., J. Am. Soc. Chem. 2003, vol. 125, page 6653 or J. Org. Chem. 2000, vol. 65, page 1174 and the like], for example, in the presence of a transition metal catalyst and a base in a solvent that does not adversely influence the reaction.

Examples of the transition metal catalyst to be used include palladium catalyst (e.g., palladium(II) acetate, tris(dibenzylideneacetone)dipalladium(0), palladium(II) chloride, tetrakis(triphenylphosphine)palladium(0) and the like), nickel catalyst (e.g., nickel chloride and the like) and the like and, where necessary, a ligand (e.g., 2-dicyclohexylphosphino-2', 4',6'-triisopropyl-1,1'-biphenyl, triphenylphosphine, tri-tert-butylphosphine and the like) may be added. While the amount of the catalyst to be used varies depending on the kind of the catalyst, it is generally about 0.0001 to about 1 molar equivalent, preferably about 0.01 to about 0.5 molar equivalent, per 1 mol of compound (Id), and the amount of the ligand to be used is generally about 0.0001 to about 4 molar equivalents, preferably about 0.01 to about 0.2 molar equivalent, per 1 mol of compound (Id).

Examples of the base to be used include organic amines (e.g., trimethylamine, triethylamine, diisopropylamine, N-methylmorpholine, 1,8-diazabicyclo[5.4.0]undec-7-ene, pyridine, N,N-dimethylaniline and the like), alkali metal salt (e.g., sodium hydrogen carbonate, potassium hydrogen carbonate, sodium carbonate, potassium carbonate, cesium carbonate, sodium phosphate, potassium phosphate, sodium hydroxide, potassium hydroxide and the like), metal hydride (potassium hydride, sodium hydride and the like), alkali metal alkoxide (sodium methoxide, sodium ethoxide, sodium tert-butoxide, potassium tert-butoxide and the like), alkali disilazide (e.g., lithium disilazide, sodium disilazide, potassium disilazide and the like) and the like. Particularly, alkali metal salts such as potassium carbonate, cesium carbonate, sodium phosphate, potassium phosphate and the like; alkali metal alkoxide such as sodium tert-butoxide, potassium tert-butoxide and the like; organic amines such as triethylamine, diisopropylamine and the like; and the like are preferable. The amount of the base to be used is about 0.1 to about 10 molar equivalents, preferably about 1 to about 5 molar equivalents, per 1 mol of compound (Id).

The solvent to be used may be any as long as it does not adversely influence the reaction and, for example, hydrocarbons (e.g., benzene, toluene, xylene and the like), halogenated hydrocarbons (e.g., chloroform, 1,2-dichloroethane and the like), nitriles (e.g., acetonitrile and the like), ethers (e.g., dimethoxyethane, tetrahydrofuran and the like), aprotic polar solvents (e.g., N,N-dimethylformamide, dimethyl sulfoxide, hexamethylphosphoramide and the like) or a mixture thereof are used. The reaction temperature is generally about −10° C. to about 200° C., preferably about 0° C. to about 150° C., and the reaction time is generally about 0.5 to about 48 hr, preferably about 0.5 to about 16 hr.

Compound (If) obtained in this step can be led to compound (Ib) or compound (Ic) by the methods described in step 13 and step 14.

When a reactive amino group is present at the ring A moiety of compound (Ia), $R^{86}$ can be introduced by the following Method D.

[Method D]

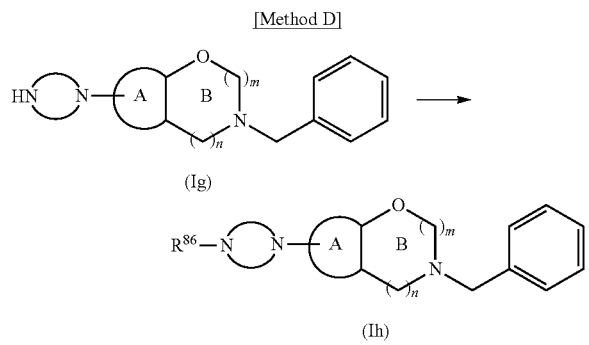

wherein $R^{86}$ is an alkyl group optionally having substituent(s), an alkyl-carbonyl group optionally having substituent(s) or an alkyl-sulfonyl group optionally having substituent(s), the ring represented by the formula:

is, for example, a group represented by the formula:

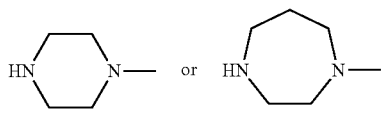

optionally having substituent(s), and other symbols are as defined above.

In this step, a compound represented by the formula (Ig) or a salt thereof (hereinafter to be referred to as compound (Ig)) is converted to a compound represented by the formula (Ih) or a salt thereof (hereinafter to be referred to as compound (Ih)) by reacting the compound with a compound represented by the formula:

$R^{86}$—OH                                           (XXVI)

wherein each symbol is as defined above, or a salt thereof (hereinafter to be referred to as compound (XXVI)) or a reactive derivative thereof, which is an alkylating agent, acylating agent or sulfonylating agent.

Examples of the alkyl group optionally having substituent(s) for $R^{86}$ include those similar to the aforementioned "alkyl group optionally having substituent(s)".

Examples of the reactive derivative of compound (XXVI) include a compound represented by the formula:

$R^{86}$-$L^5$                                           (XXVIa)

wherein $L^5$ is a leaving group, and $R^{86}$ is as defined above, or a salt thereof (hereinafter to be referred to as reactive derivative (XXVIa)).

Examples of the leaving group for $L^5$ include those similar to the aforementioned leaving group $L^1$.

The reaction using the above-mentioned reactive derivative as an alkylating agent can be generally performed by reacting compound (Ih) with a reactive derivative (XXVIa) in a solvent in the presence of a base. Examples of the solvent include alcohols (e.g., methanol, ethanol, propanol and the like), ethers (e.g., dimethoxyethane, dioxane, tetrahydrofuran and the like), ketones (e.g., acetone, 2-butanone and the like), nitriles (e.g., acetonitrile and the like), amides (e.g., N,N-dimethylformamide and the like), sulfoxides (e.g., dimethyl sulfoxide and the like), water and a mixture thereof. Examples of the base include organic base (e.g., trimethylamine, triethylamine, N-methylmorpholine, pyridine, picoline, N,N-dimethylaniline and the like), inorganic base (e.g., potassium carbonate, sodium carbonate, potassium hydroxide, sodium hydroxide and the like). The amount of the base to be used is, for example, about 1 to about 100 molar equivalents, preferably about 1 to about 10 molar equivalents, per 1 mol of compound (Ig).

Examples of the reactive derivative (XXVIa) include halides (e.g., chloride, bromide, iodide and the like), sulfuric acid esters, sulfonic acid esters (e.g., methanesulfonate, p-toluenesulfonate, benzenesulfonate and the like) and the like, and halide is particularly preferable. The amount of the reactive derivative (XXVIa) to be used is, for example, about 1 to about 5 molar equivalents, preferably about 1 to about 3 molar equivalents, per 1 mol of compound (Ig).

Where necessary, the reaction can also be promoted by adding an additive. Examples of the additive include iodide salt (e.g., sodium iodide, potassium iodide and the like) and the like, and the amount thereof to be used is about 0.1 to about 10 molar equivalents, preferably about 0.1 to about 5 molar equivalents, per 1 mol of compound (Ig).

The reaction temperature is generally about −10° C. to about 200° C., preferably about 0° C. to about 110° C., and the reaction time is generally about 0.5 hr to about 48 hr, preferably about 0.5 hr to about 16 hr.

The reaction using reactive derivative (XXVIa) as an acylating agent or sulfonylating agent varies depending on the kind of reactive derivative (XXVIa) or compound (Ig), but generally performed in a solvent, and an appropriate base may be added to promote the reaction. Examples of the solvent include hydrocarbons (e.g., benzene, toluene and the like), ethers (e.g., diethyl ether, dioxane, tetrahydrofuran and the like), esters (e.g., ethyl acetate and the like), halogenated hydrocarbons (e.g., chloroform, dichloromethane and the like), esters (e.g., ethyl acetate and the like), amides (e.g., N,N-dimethylformamide and the like), aromatic amines (e.g., pyridine and the like), water and a mixture thereof. Examples of the base include alkali metal hydroxide (e.g., sodium hydroxide, potassium hydroxide and the like), hydrogen carbonate (e.g., sodium hydrogen carbonate, potassium hydrogen carbonate and the like), carbonate (e.g., sodium carbonate, potassium carbonate and the like), acetate (e.g., sodium acetate and the like), tertiary amines (e.g., trimethylamine, triethylamine, N-methylmorpholine and the like), aromatic amines (e.g., pyridine, picoline, N,N-dimethylaniline and the like) and the like. The amount of the base to be used is, for example, about 1 to about 100 molar equivalents, preferably about 1 to about 10 molar equivalents, per 1 mol of compound (Ig).

Examples of the acylating agent include carboxylic acid, sulfonic acid, phosphoric acid, carbonic acid or a reactive derivative thereof (e.g., acid halide, acid anhydride, mixed acid anhydride, active ester and the like), isocyanic acid ester, isothiocyanic acid ester and the like.

The amount of the acylating agent or sulfonylating agent to be used is generally about 1 to about 10 molar equivalents, preferably about 1 to about 3 molar equivalents, per 1 mol of compound (Ig). The reaction temperature is generally about −10° C. to about 150° C., preferably about 0° C. to about 100° C., and the reaction time is generally about 15 min to about 24 hr, preferably about 30 min to about 16 hr.

Compound (Ih) obtained in this step can be led to compound (Ib) or compound (Ic) by the methods described in step 13 and step 14.

When compound (I) is obtained as a free compound by the above-mentioned method, for example, a salt with inorganic acid (e.g., hydrochloric acid, sulfuric acid, hydrobromic acid and the like), organic acid (e.g., methanesulfonic acid, benzenesulfonic acid, toluenesulfonic acid, oxalic acid, fumaric acid, maleic acid, tartaric acid and the like), inorganic base (e.g., alkali metal such as sodium, potassium and the like, alkaline earth metal such as calcium, magnesium and the like, aluminum, ammonium or the like) or organic base (e.g., trimethylamine, triethylamine, pyridine, picoline, ethanolamine, diethanolamine, triethanolamine, dicyclohexylamine, N,N'-dibenzylethylenediamine or the like) and the like can be formed according to a conventional method and, when compound (I) is obtained as a salt, it can also be converted to a free compound or other salt according to a conventional method.

When a starting material compound can form a salt in each of the aforementioned reactions, the compound can be used as a salt. Examples of the salt include those exemplified as the salt of compound (I).

When leaving group $L^4$ is present at the ring A moiety of compound (Ia), $R^{87}$ can be introduced by the following Method E.

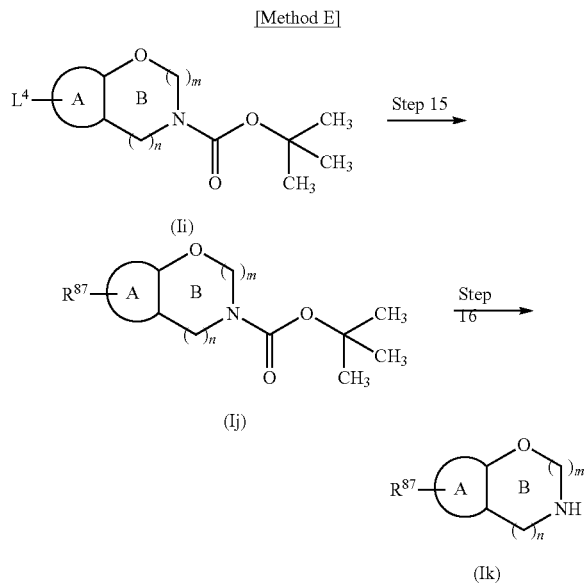

wherein $R^{87}$ is an alkyl group optionally having substituent(s), and other symbols are as defined above.

Examples of the alkyl group optionally having substituent(s) for $R^{87}$ include those similar to the aforementioned "alkyl group optionally having substituent(s)".

(Step 15)

In this step, a compound represented by the formula (Ij) or a salt thereof (hereinafter to be referred to as compound (Ij)) is produced by subjecting a compound represented by the formula (Ii) or a salt thereof (hereinafter to be referred to as compound (Ii)) and an organic metal compound ($R^{87}$MgX, $R^{87}_3$ZnMgX, $R^{87}$MnX, $R^{87}_2$Mn, $R^{87}_3$MnMgX and the like wherein $R^{87}$ is as defined above, X is a halogen atom), or a salt thereof to, for example, a coupling reaction in the presence of a transition metal catalyst in a solvent that does not adversely influence the reaction.

Examples of the organic metal compound to be used include Grignard reagent, organic zinc reagent, organic manganese reagent and the like. Examples of the transition metal catalyst to be used include iron catalyst (e.g., iron(II) chloride, iron(III) chloride, iron(II) acetylacetonate, iron(III) acetylacetonate and the like), nickel catalyst (e.g., dichloro[1,2-bis(diphenylphosphino)ethane]nickel(II) and the like) and the like and, where necessary, a ligand (e.g., triphenylphosphine, tri-tert-butylphosphine and the like) may be added or metal oxide (e.g., copper oxide, silver oxide and the like) and the like may be used as a cocatalyst. While the amount of the catalyst to be used varies depending on the kind of the catalyst, it is generally about 0.0001 to about 1 molar equivalent, preferably about 0.01 to about 0.5 molar equivalent, per 1 mol of compound (Ii), the amount of the ligand to be used is generally about 0.0001 to about 4 molar equivalents, preferably about 0.01 to about 2 molar equivalents, per 1 mol of compound (Ii), and the amount of the cocatalyst to be used is about 0.0001 to about 4 molar equivalents, preferably about 0.01 to about 2 molar equivalents, per 1 mol of compound (Ii).

The solvent to be used may be any as long as it does not adversely influence the reaction and, for example, hydrocarbons (e.g., benzene, toluene, xylene and the like), halogenated hydrocarbons (e.g., chloroform, 1,2-dichloroethane and the like), nitriles (e.g., acetonitrile and the like), ethers (e.g., dimethoxyethane, tetrahydrofuran and the like), aprotic polar solvents (e.g., N,N-dimethylformamide, dimethyl sulfoxide, hexamethylphosphoramide and the like) or a mixture thereof is used. The reaction temperature is generally about −10° C. to about 200° C., preferably about 0° C. to about 150° C., and the reaction time is generally about 0.5 to about 48 hr, preferably about 0.5 to about 16 hr.

Thus-obtained compound (Ij) can be isolated and purified by a known separation and purification means, for example, concentration, concentration under reduced pressure, solvent extraction, crystallization, recrystallization, phase transfer, chromatography and the like.

(Step 16)

In this step, a compound represented by the formula (Ik) or a salt thereof (hereinafter to be referred to as compound (Ik)) is produced by removing a tert-butoxycarbonyl group of compound (Ij). This reaction can be performed by a method known per se and generally performed by reaction with an acid in a solvent that does not adversely influence the reaction.

Examples of the acid include hydrochloric acid, hydrobromic acid, sulfuric acid, trifluoroacetic acid, trifluoromethanesulfonic acid, hydrogen chloride and the like. The amount of the acid to be used is preferably about 1 mol to about 100 mol, per 1 mol of compound (Ij).

Examples of the solvent that does not adversely influence the reaction include alcohols (e.g., methanol etc.), ethers (e.g., tetrahydrofuran etc.), halogenated hydrocarbons (e.g., chloroform etc.), aromatic hydrocarbons (e.g., toluene etc.), amides (e.g., N,N-dimethylformamide etc.), sulfoxides (e.g., dimethyl sulfoxide etc.), esters (e.g., ethyl acetate etc.) and the like. These solvents may be used in a mixture of two or more kinds at an appropriate ratio. The amount of the solvent to be used is generally 1-fold volume to 100-fold volume, relative to compound (Ij).

The reaction temperature is, generally about −50° C. to about 250° C., preferably about 0° C. to about 120° C. The reaction time is generally about 0.5 hr to about 24 hr.

Thus-obtained compound (Ik) can be isolated and purified by a known separation and purification means, for example, concentration, concentration under reduced pressure, solvent extraction, crystallization, recrystallization, phase transfer, chromatography and the like.

Compound (Ik) obtained in this step can be led to compound (Ic) by the method described in step 14.

Compound (I) produced by such method, can be isolated and purified by a typical separation means such as recrystallization, distillation, chromatography, etc.

When compound (I) contains an optical isomer, a stereoisomer, a regioisomer or a rotamer, these are also encompassed in compound (I), and can be obtained as a single product according to synthesis and separation methods known per se (e.g., concentration, solvent extraction, column chromatography, recrystallization, etc.). For example, when compound (I) has an optical isomer, an optical isomer resolved from this compound is also encompassed in compound (I).

The optical isomer can be produced by a method known per se. To be specific, an optically active synthetic intermediate is used, or the final racemate product is subjected to optical resolution according to a conventional method to give an optical isomer.

The method of optical resolution may be a method known per se, such as a fractional recrystallization method, a chiral column method, a diastereomer method, etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.) is formed, which is separated by a fractional recrystallization method, and if desired, a free optical isomer is obtained by a neutralization step.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, isopropanol, acetonitrile, trifluoroacetic acid, diethylamine, etc.) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method, etc.) and the like, and is subjected to a chemical treatment such as hydrolysis and the like to separate an optically active reagent moiety, whereby an optical isomer is obtained. For example, when compound (I) contains hydroxy, or primary or secondary amino in a molecule, the compound and an optically active organic acid (e.g., MTPA [α-methoxy-α-(trifluoromethyl)phenylacetic acid], (−)-menthoxyacetic acid, etc.) and the like are subjected to condensation reaction to give diastereomers in the ester form or in the amide form, respectively. When compound (I) has a carboxylic acid group, this compound and an optically active amine or alcohol reagent are subjected to condensation reaction to give diastereomers in the amide form or in the ester form, respectively. The separated diastereomer is converted to an optical isomer of the original compound by acid hydrolysis or base hydrolysis.

The compound (I) may be a crystal.

The crystal of the compound (I) can be produced by crystallization of compound (I) according to crystallization methods known per se.

Examples of the crystallization method include a method of crystallization from a solution, a method of crystallization from vapor, a method of crystallization from the melts and the like.

The "crystallization from a solution" is typically a method of shifting a non-saturated state to supersaturated state by varying factors involved in solubility of compounds (solvent composition, pH, temperature, ionic strength, redox state, etc.) or the amount of solvent. To be specific, for example, a concentration method, a slow cooling method, a reaction method (a diffusion method, an electrolysis method), a hydrothermal growth method, a flux method and the like can be mentioned. Examples of the solvent to be used include aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, diisopropyl ether, tetrahydrofuran, dioxane, etc.), nitriles (e.g., acetonitrile, etc.), ketones (e.g., acetone, etc.), sulfoxides (e.g., dimethyl sulfoxide, etc.), acid amides (e.g., N,N-dimethylformamide, etc.), esters (e.g., ethyl acetate, etc.), alcohols (e.g., methanol, ethanol, isopropyl alcohol, etc.), water and the like. These solvents are used alone or in a combination of two or more at a suitable ratio (e.g., 1:1 to 1:100 (a volume ratio)). Where necessary, a seed crystal can be used.

The "crystallization from vapor" is, for example, a vaporization method (a sealed tube method, a gas stream method), a gas phase reaction method, a chemical transportation method and the like.

The "crystallization from the melts" is, for example, a normal freezing method (a Czockralski method, a temperature gradient method and a Bridgman method, etc.), a zone melting method (a zone leveling method and a floating zone method, etc.), a special growth method (a VLS method and a liquid phase epitaxy method, etc.) and the like.

Preferable examples of the crystallization method include a method of dissolving compound (I) in a suitable solvent (e.g., alcohols such as methanol, ethanol, etc., and the like) at a temperature of 20 to 120° C., and cooling the resulting solution to a temperature not higher than the temperature of dissolution (e.g., 0 to 50° C., preferably 0 to 20° C.) and the like.

The thus obtained crystals of the present invention can be isolated, for example, by filtration and the like.

As an analysis method of the obtained crystal is generally a method of crystal analysis by powder X-ray diffraction. As a method of determining crystal orientation, a mechanical method or an optical method and the like can also be used.

The crystal of compound (I) obtained by the above-mentioned production method (hereinafter to be abbreviated as "the crystal of the present invention") has high purity, high quality, and low hygroscopicity, is not denatured even after a long-term preservation under general conditions, and is extremely superior in the stability. In addition, it is also superior in the biological properties (e.g., pharmacokinetics (absorption, distribution, metabolism, excretion), efficacy expression etc.) and is extremely useful as a pharmaceutical agent.

In the present specification, the specific rotation ($[\alpha]_D$) means, for example, a specific rotation measured using a polarimeter (JASCO, P-1030 polarimeter (No. AP-2)) and the like.

In the present specification, the melting point means a melting point measured using, for example, a micro melting point apparatus (YANACO, MP-500D), a DSC (differential scanning calorimetry) apparatus (SEIKO, EXSTAR6000) and the like.

A prodrug of the compound (I) means a compound which is converted to the compound (I) with a reaction due to an enzyme, an gastric acid, etc. under the physiological condition in the living body, that is, a compound which is converted to the compound (I) with oxidation, reduction, hydrolysis, etc. according to an enzyme; a compound which is converted to the compound (I) by hydrolysis etc. due to gastric acid, etc. A prodrug for compound (I) may be a compound obtained by subjecting an amino group in compound (I) to an acylation, alkylation or phosphorylation [e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.]; a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation, dimethylaminomethylcarbonylation, etc.); a compound obtained by subjecting a carboxy group in compound (I) to an esterification or amidation [e.g., a compound obtained by subjecting a carboxy group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.] and the like. Any of these compounds can be produced from compound (I) by a method known per se.

A prodrug for compound (I) may also be one which is converted into compound (I) under a physiological condition, such as those described in IYAKUHIN no KAIHATSU (Development of Pharmaceuticals), Vol. 7, Design of Molecules, p. 163-198, Published by HIROKAWA SHOTEN (1990).

Compound (I) of the present invention or a salt thereof or a prodrug thereof (hereinafter to be abbreviated as compound (I)) has a superior serotonin 5-$HT_{2C}$ receptor activating action.

In addition, compound (I) of the present invention has low toxicity and is safe.

Accordingly, compound (I) of the present invention having a superior serotonin 5-$HT_{2C}$ receptor activation action is useful as a prophylaxis or therapeutic drug for all serotonin 5-$HT_{2C}$ associated diseases in mammals (e.g., mouse, rat, hamster, rabbit, cat, dog, bovine, sheep, monkey, human and the like), for example, (1) lower urinary tract symptoms [for example, overactive bladder, stress urinary incontinence, mixed urinary incontinence, lower urinary tract symptoms associated with benign prostatic hyperplasia, pelvic visceral pain, lower urinary tract symptoms associated with chronic prostatitis, lower urinary tract symptoms associated with interstitial cystitis, abnormal urination such as post-micturition dribble and the like]

(2) metabolic diseases [for example, diabetes (insulin dependent diabetes, diabetic complications, diabetic retinopathy, diabetic microangiopathy, diabetic neuropathy etc.), impaired glucose tolerance, obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity], benign prostatic hyperplasia, sexual dysfunction and the like]

(3) central nervous system diseases [for example, neurodegenerative diseases (e.g., Alzheimer's disease, Down's disease, Parkinson's disease, Creutzfeldt-Jakob disease, amyotrophic lateral sclerosis (ALS), Huntington chorea, diabetic neuropathy, multiple sclerosis etc.), mental diseases (e.g., schizophrenia, depression, mania, anxiety neurosis, obsessive-compulsive neurosis, panic disorder, epilepsy, alcohol dependence, drug dependence, anxiety, anxious mental state, emotional abnormality, cyclothymia, nervous erethism, autism, faint, addiction, low sex drive etc.), disorders such as central nervous system and peripheral nerve disorders (e.g., head trauma, spinal trauma, brain edema, disorders of sensory function, abnormality of sensory function, disorders of autonomic nervous function, abnormality of autonomic nervous function, whiplash injury etc.), memory disorders (e.g., senile dementia, amnesia, cerebrovascular dementia etc.), cerebrovascular disorder (e.g., cerebral hemorrhage, cerebral infarction and the like and sequelae or complication thereof, asymptomatic cerebrovascular accident, transient cerebral ischemic attack, hypertensive encephalopathia, blood-brain barrier disorder, etc.), recurrence and sequelae of cerebrovascular disorders (e.g., neural symptoms, mental symptoms, subjective symptoms, disorders of daily living activities etc.), central nervous system hypofunction after brain blood vessel occlusion, disorder or abnormality of autoregulation ability of brain circulation or renal circulation etc.], sleep disorder (4) genital insufficiency diseases [for example, male erectile dysfunction, dysspermia, female genital insufficiency etc.]

(5) digestive organ diseases [for example, an irritable bowel syndrome, inflammatory bowel disease, ulcerative colitis, Crohn's disease, diseases caused by a spiral urease-positive gram-negative bacterium (e.g., *Helicobacter pylori*, etc.) (e.g., gastritis, gastric ulcer, etc.), gastric cancer, postgastrostomy disorder, indigestion, esophageal ulcer, pancreatitis, polyp of the colon, cholelithiasis, hemorrhoids, peptic ulcer, situational ileitis, gluttony, constipation, diarrhea, borborygmus, etc.]

(6) inflammatory or allergic diseases [for example, allergic rhinitis, conjunctivitis, gastrointestinal allergy, pollinosis, anaphylaxis, dermatitis, herpes, psoriasis, bronchitis, expectoration, retinopathy, postoperative and posttraumatic inflammation, regression of puffiness, pharyngitis, cystitis, meningitidis, inflammatory ophthalmic diseases, etc.]

(7) osteoarthropathy diseases [for example, rheumatoid arthritis (chronic rheumatoid arthritis), arthritis deformans, rheumatoid myelitis, osteoporosis, abnormal growth of cells, bone fracture, bone refracture, osteomalacia, osteopenia, Paget's disease of bone, rigid myelitis, articular tissue destruction by gonarthrosis deformans and similar diseases thereto, etc.]

(8) respiratory diseases [for example, cold syndrome, pneumonia, asthma, pulmonary hypertension, pulmonary thrombi/pulmonary obliteration, pulmonary sarcoidosis, pulmonary tuberculosis, interstitial pneumonia, silicosis, adult respiratory distress syndrome, chronic obstructive pulmonary disease, cough, etc.]

(9) infectious diseases [HIV infectious diseases, virus infectious diseases due to cytomegalo virus, influenza virus, herpes virus and the like, rickettsia infectious diseases, bacterial infectious diseases, sexually-transmitted diseases, carinii pneumonia, *Helicobacter pylori* infectious disease, systemic fungal infectious diseases, tuberculosis, invasive staphylococcal infectious diseases, acute viral encephalitis, acute bacterial meningitidis, AIDS encephalitis, septicemia, sepsis, sepsis gravis, septic shock, endotoxin shock, toxic shock syndromes, etc.]

(10) cancers [for example, primary, metastatic or recurrent breast cancer, prostatic cancer, pancreatic cancer, gastric cancer, lung cancer, colorectal cancer (colon cancer, rectal cancer, anal cancer), esophagus cancer, duodenal cancer, head and neck cancer (tongue cancer, pharynx cancer, larynx cancer), brain tumor, neurinoma, non-small cell lung cancer, small cell lung cancer, hepatic cancer, renal cancer, colic cancer, uterine cancer (cancer of the uterine body, uterine cervical cancer), ovarian cancer, bladder cancer, skin cancer, hemangioma, malignant lymphoma, malignant melanoma, thyroid cancer, bone tumor, hemangioma, angiofibroma, retinosarcoma, penis cancer, pediatric solid cancer, Kaposi's sarcoma, Kaposi's sarcoma caused by AIDS, tumor of the maxillary sinus, fibrous histiocytoma, smooth muscle sarcoma, rhabdomyosarcoma, liposarcoma, fibroid tumors of the uterus, osteoblastoma, osteosarcoma, chondrosarcoma, carcinomatous mesothelial tumor, tumors such as leukemia, Hodgkin's disease, etc.]

(11) circulatory diseases [for example, acute coronary artery syndromes (e.g., acute cardiac infarction, unstable angina, etc.), peripheral arterial occlusion, Raynaud's disease, Buerger's disease, restenosis after coronary-artery intervention (percutaneous transluminal coronary angioplasty (PTCA), directional coronary atherectomy (DCA), stenting, etc.), restenosis after coronary-artery bypass operation, restenosis after intervention (angioplasty, atherectomy, stenting, etc.) or bypass operation in other peripheral artery, ischemic cardiac diseases (e.g., cardiac infarction, angina, etc.), myocarditis, intermittent claudication, lacunar infarction, arteriosclerosis (e.g., atherosclerosis, etc.), cardiac failure (acute cardiac failure, chronic cardiac failure including congestive cardiac failure), arrhythmia, progress of atherosclerotic plaque, thrombosis, hypertension, hypertensive tinnitus, hypotension, etc.]

(12) pains [e.g., headache, migraine, neuralgia, pelvic visceral pain (including cystalgia), etc.]

(13) autoimmune diseases [for example, collagen disease, systemic lupus erythematosus, scleroderma, polyarteritis, myasthenia gravis, multiple sclerosis, Sjogren's syndrome, Behcet's disease, etc.]

(14) hepatic diseases [e.g., hepatitis (including chronic hepatitis), cirrhosis, interstitial hepatic diseases, etc.]

(15) pancreatic diseases [e.g., pancreatitis (including chronic pancreatitis), etc.]

(16) renal diseases [e.g., nephritis, glomerulonephritis, glomerulosclerosis, renal failure, thrombotic microangiopathy, dialysis complications, organ disorders including nephropathia by radiation, diabetic nephropathy, etc.]

(17) endocrine diseases [e.g., Addison's disease, Cushing's syndrome, melanocytoma, primary aldosteronism, etc.]

(18) other diseases (a) transplant rejection [e.g., posttransplantational rejection, posttransplantational polycythemia, hypertension, organ disorder and/or vascular hypertrophy, graft-versus-host disease, etc.]

(b) abnormality in characteristic of blood and/or blood components [e.g., enhancement in platelet aggregation, abnormality of erythrocyte deformability, enhancement in leukocyte adhesiveness, increase in blood viscosity, polycythemia, vascular peliosis, autoimmune hemolytic anemia, disseminated intravascular coagulation syndrome (DIC), multiple myelopathy, etc.]

(c) gynecologic diseases [e.g., climacteric disorder, gestational toxicosis, endometriosis, hysteromyoma, ovarian disease, mammary disease, premenstrual syndrome, pelvic organ prolapse, rectal prolapse, etc.]

(d) dermatic diseases [e.g., keloid, angioma, psoriasis, pruritus, etc.]

(e) ophthalmic diseases [e.g., glaucoma, ocular hypertension disease, etc.]

(f) otolaryngological diseases [e.g., Menuel syndrome, tinnitus, gustation disorder, dizziness, disequilibrium, dysphagia, etc.]

(g) diseases due to environmental and/or occupational factors (e.g., radiation disorder, disorders by ultraviolet ray/infrared ray/laser ray, altitude sickness, etc.)

(h) ataxia, stiffness, tremor, motion impairment, akinesia (i) chronic fatigue syndrome (j) sudden infant death syndrome (k) hiccup (l) diseases causing palpitation, vertigo, heartburn and the like.

In these diseases, the compound of the present invention is particularly useful as a serotonin 5-HT$_{2C}$ receptor activator, as an ameliorator for lower urinary tract symptoms such as overactive bladder and/or stress urinary incontinence, and as a prophylactic or therapeutic drug for these lower urinary tract symptoms.

Serotonin 5-HT$_{2C}$ receptor activators, including the compound of the present invention, can also be used for the prevention or treatment of diseases resulting from the weakening of the pelvic floor muscles as a cause thereof, such as pelvic organ prolapses (for example, prolapse of the anterior wall of the vagina, prolapse of the vaginal apex, prolapse of the posterior wall of the vagina, prolapse of the uterus and the like), rectal prolapse and post-micturition dribble.

Pelvic organ prolapse and rectal prolapse are diseases characterized by the protrusion of a pelvic organ (uterus and the like) or the rectum beyond the vaginal orifice or the rectal orifice due to a lack of the contractile force of the pelvic floor muscles.

As a serotonin 5-HT$_{2C}$ receptor activator other than the compound of the present invention, for example, one having an inhibitory activity as evidenced by 50% inhibitory concentration (IC$_{50}$) of not more than about 1000 nM, preferably not more than about 100 nM, by a binding assay is more preferable. Specifically, as the serotonin 5-HT$_{2C}$ receptor agonist, compounds described in EP0572863, EP0863136, EP1213017, U.S. Pat. No. 3,253,989, U.S. Pat. No. 3,676,558, U.S. Pat. No. 3,652,588, U.S. Pat. No. 4,082,844, U.S. Pat. No. 4,971,969, U.S. Pat. No. 5,494,928, U.S. Pat. No. 5,646,173, U.S. Pat. No. 6,310,208, WO97/42183, WO98/30546, WO98/30548, WO98/33504, WO99/02159, WO99/43647 (U.S. Pat. No. 6,281,243), WO00/12475 (U.S. Pat. No. 6,380,238), WO00/12502 (U.S.

Pat. No. 6,365,598), WO00/12510 (U.S. Pat. No. 6,433,175), WO00/12475, WO00/12481 (U.S. Pat. No. 6,552,062), WO00/12482, WO00/12502, WO00/16761, WO00/17170, WO00/28993, WO00/35922 (U.S. Pat. No. 6,372,745), WO00/44737, WO00/44753, WO00/64899, WO00/77001, WO00/77002, WO00/77010, WO00/76984 (U.S. Pat. No. 6,465,467), WO01/09111, WO01/09122, WO01/09123 (U.S. Pat. No. 6,638,936), WO01/09126, WO01/12602, WO01/12603 (U.S. Pat. No. 6,706,750), WO01/40183, WO01/66548 (U.S. Pat. No. 6,583,134), WO01/70207, WO01/70223, WO01/72752 (U.S. Pat. No. 6,734,301), WO01/83487, WO02/04456, WO02/04457, WO02/08178, WO02/10169, WO02/24700, WO02/24701, WO02/36596, WO02/40456, WO02/40457, WO02/42304, WO02/44152 (U.S. Pat. No. 6,479,534), WO02/48124, WO02/51844 (U.S. Pat. No. 6,610,685), WO02/59124, WO02/59127, WO02/59129, WO02/72584, WO02/74746, WO02/83863, WO02/98350, WO02/98400, WO02/98860, WO03/00663, WO03/00666, WO03/04501, WO03/06466, WO03/11281, WO03/14118, WO03/14125, WO03/24976, WO03/28733, WO03/33497, WO03/57161, WO03/57213, WO03/57673, WO03/57674, WO03/62205, WO03/64423, WO03/86306, WO03/87086, WO03/89409, WO03/91250, WO03/91251, WO03/91257, WO03/97636, WO04/00829, WO04/00830 (U.S. Pat. No. 6,667,303), WO04/56324, WO04/78718, WO04/81010, WO04/087156, WO04/87662, WO04/87692, WO04/89897, WO04/096196, WO04/96201, WO04/112769, US2004/192754, WO05/00849, WO05/03096, EP1500391, WO05/16902, WO05/19180, US2005/080074, WO05/40146, WO05/41856, WO05/42490, WO05/42491, WO05/44812, WO05/082859, WO05/000309, WO05/019179, WO05/121113, WO05/049623, WO05/105082, WO05/109987, WO05/121113, WO05/113535, US2006/003990, US2006/014777, US2006/014778, WO06/000902, WO06/028961, WO06/020817, WO06/020049, WO06/019940, WO06/004931, US2006/025601, WO06/044762, WO06/047032, WO06/050007, WO06/052887, WO06/077025, WO06/065600, WO06/103511, WO06/116165, WO06/047228, WO06/117304, US2006/241172, US2006/241176, WO06/116136, WO06/116148, WO06/116151, WO06/116171, WO06/116170, WO06/116218, WO06/116169, WO06/077025, US2007/032481, WO07/025,144, WO07/028,082, WO07/028,132, WO07/028,131, WO07/028,083, WO07/030,150, US2007/0049613 and the like are used. Among these, particularly, (1) WAY-161503

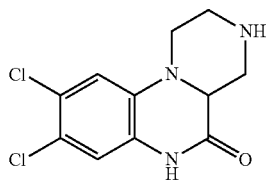 [SMILES: O=C1Nc2cc(Cl)c(Cl)cc2N2CCNCC12]

(2) m-CPP

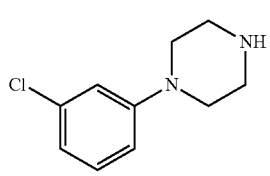 [SMILES: Clc1cccc(N2CCNCC2)c1]

(3) PNU-22394A

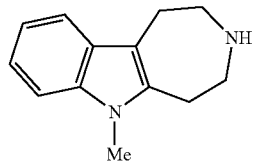 [SMILES: Cn1c2c(c3ccccc31)CCNCC2]

(4) Ro60-0175

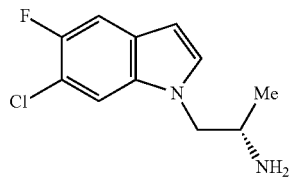 [SMILES: C[C@H](N)Cn1ccc2cc(F)c(Cl)cc21]

(5) ORG-12962

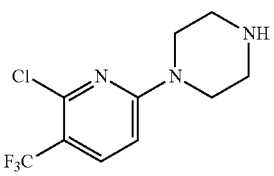

(6) Nordexfenfluramine

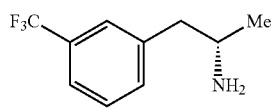

(7) MK-212

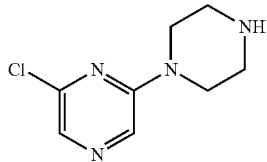 [SMILES: Clc1cncc(N2CCNCC2)n1]

(8) Oxaflozane

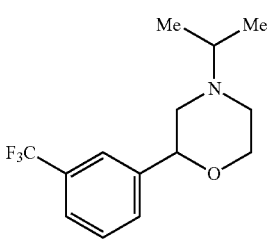 [SMILES: CC(C)N1CCOC(c2cccc(C(F)(F)F)c2)C1]

(9) a compound represented by the following structural formula described in WO00/12510 (U.S. Pat. No. 6,433,175)

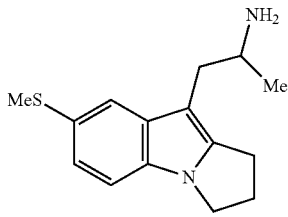 [SMILES: CSc1ccc2c(c1)c(CC(C)N)c1n2CCC1]

(10) a compound represented by the following structural formula described in WO02/51844 (U.S. Pat. No. 6,610,685)

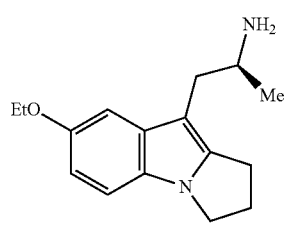 [SMILES: CCOc1ccc2c(c1)c(C[C@H](C)N)c1n2CCC1]

(11) a compound represented by the following structural formula described in WO01/66548 (U.S. Pat. No. 6,583,134)

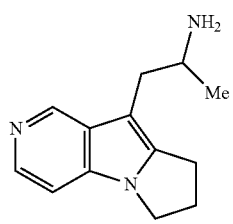 [SMILES: CC(N)Cc1c2n(c3ccncc13)CCC2]

(12) a compound represented by the following structural formula described in WO00/12482

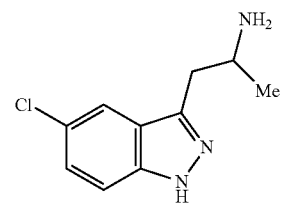 [SMILES: CC(N)Cc1n[nH]c2ccc(Cl)cc12]

(13) a compound represented by the following structural formula described in WO03/24976

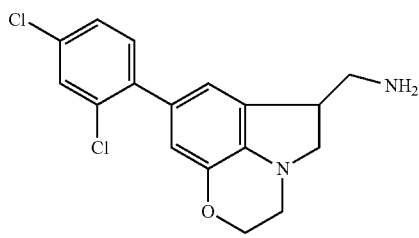 [SMILES: NCC1CN2CCOc3cc(-c4ccc(Cl)cc4Cl)cc1c32]

(14) ALX-2218

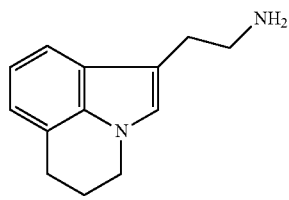 [SMILES: NCCc1cn2c3c(cccc13)CCC2]

(15) ALX-2226

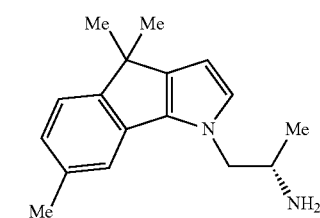 [SMILES: Cc1ccc2c(c1)-c1c(ccn1C[C@H](C)N)C2(C)C]

(16) Ro60-0332

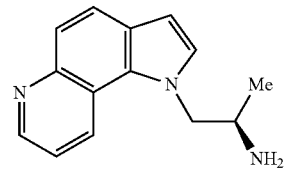 [SMILES: C[C@@H](N)Cn1ccc2ccc3ncccc3c21]

(17) VER-2692

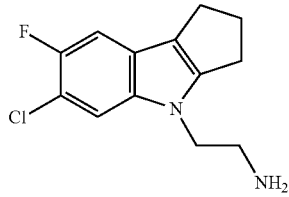 [SMILES: NCCn1c2c(c3cc(F)c(Cl)cc31)CCC2]

(18) VER-6925

(19) VER-7397

(20) VER-7499

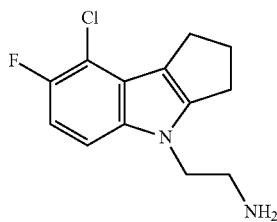 [SMILES: NCCn1c2c(c3c(Cl)c(F)ccc31)CCC2]

(21) VER-7443

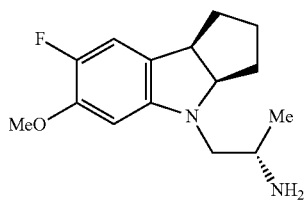 [SMILES: COc1cc2c(cc1F)[C@H]1CCC[C@H]1N2C[C@H](C)N]

(22) VER-3993

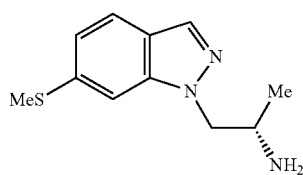 [SMILES: CSc1ccc2cnn(C[C@H](C)N)c2c1]

(23) YM-348

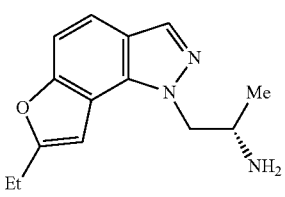 [SMILES: CCc1cc2c(ccc3cnn(C[C@H](C)N)c32)o1]

(24) a compound represented by the following structural formula described in WO03/57213

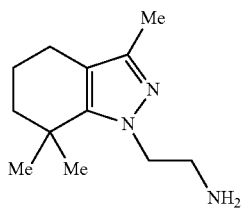

(25) a compound represented by the following structural formula described in WO03/57674

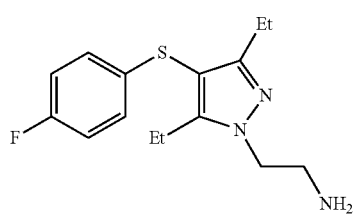 [SMILES: CCc1nn(CCN)c(CC)c1Sc1ccc(F)cc1]

(26) a compound represented by the following structural formula described in WO02/98860

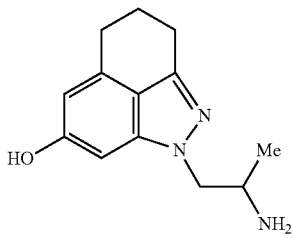 [SMILES: CC(N)Cn1nc2c3c(cc(O)cc31)CCC2]

(27) VER-5593

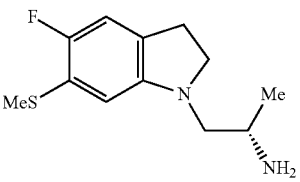 [SMILES: CSc1cc2c(cc1F)CCN2C[C@H](C)N]

(28) VER-5384

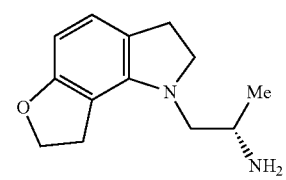 [SMILES: C[C@H](N)CN1CCc2ccc3c(c21)CCO3]

(29) VER-3323

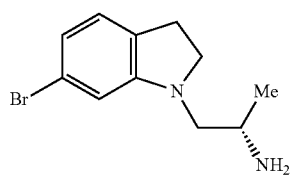 [SMILES: C[C@H](N)CN1CCc2ccc(Br)cc21]

(30) a compound represented by the following structural formula described in WO02/44152 (U.S. Pat. No. 6,479,534)

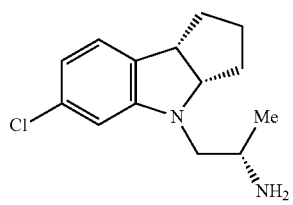 [SMILES: C[C@H](N)CN1c2cc(Cl)ccc2[C@@H]2CCC[C@@H]21]

(31) a compound represented by the following structural formula described in WO00/44737

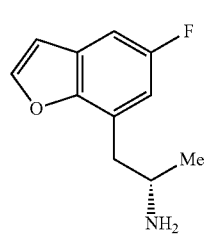 [SMILES: C[C@H](N)Cc1cc(F)cc2ccoc12]

(32) APD-356

(33) AR-10A

(34) a compound represented by the following structural formula described in WO02/40456

(35) BVT-933

(36) a compound represented by the following structural formula described in WO02/08178

(37) PNU-243922

(38) a compound represented by the following structural formula described in WO03/00666

(39) a compound represented by the following structural formula described in WO01/09123 (U.S. Pat. No. 6,638,936)

(40) a compound represented by the following structural formula described in WO01/09122

(41) a compound represented by the following structural formula described in WO01/09126

(42) Org-37684

(43) Org-36262 (Ro60-0527)

(44) a compound represented by the following structural formula described in EP0572863

(45) Ro60-0017 (Org-35013)
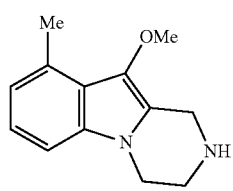 [SMILES: COc1c2n(c3cccc(C)c13)CCNC2]
(46) VER-3881
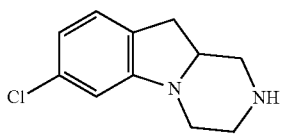 [SMILES: Clc1ccc2c(c1)N1CCNCC1C2]
(47) a compound represented by the following structural formula described in WO02/72584
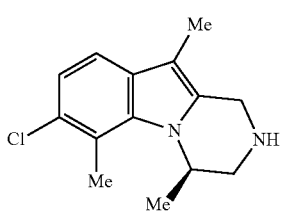 [SMILES: Cc1c2n(c3c(C)c(Cl)ccc13)[C@H](C)CNC2]
(48) Ro0721256
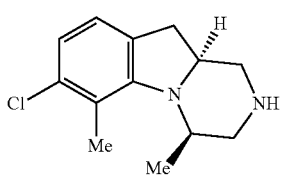 [SMILES: Cc1c(Cl)ccc2c1N1[C@H](CNC[C@H]1C)C2]
(49) PNU-181731A
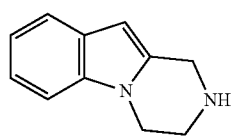 [SMILES: c1ccc2c(c1)cc1n2CCNC1]
(50) a compound represented by the following structural formula described in WO02/59127
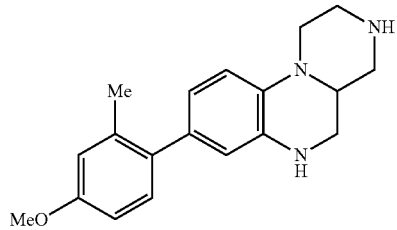 [SMILES: COc1ccc(-c2ccc3c(c2)NCC2CNCCN32)c(C)c1]
(51) a compound represented by the following structural formula described in WO03/14118
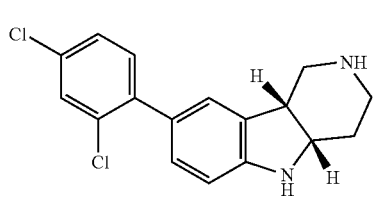 [SMILES: Clc1ccc(-c2ccc3c(c2)[C@@H]2CNCC[C@@H]2N3)c(Cl)c1]
(52) a compound represented by the following structural formula described in WO03/33497
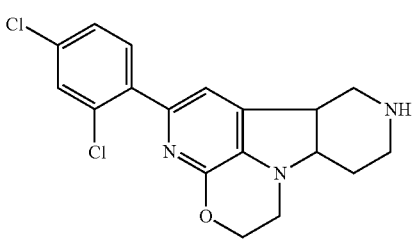 [SMILES: Clc1ccc(-c2cc3c4c(n2)OCCN4C2CCNCC32)c(Cl)c1]
(53) IL-639
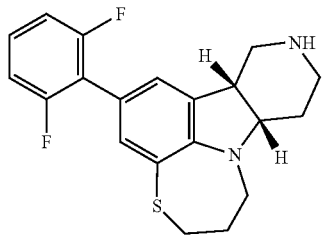 [SMILES: Fc1cccc(F)c1-c1cc2c3c(c1)[C@@H]1CNCC[C@@H]1N3CCCS2]
(54) IK-264
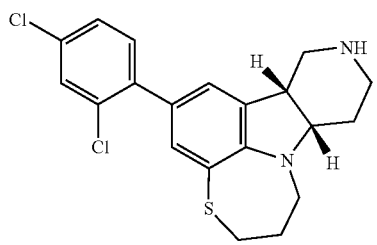 [SMILES: Clc1ccc(-c2cc3c4c(c2)[C@@H]2CNCC[C@@H]2N4CCCS3)c(Cl)c1]
(55) VR-1065
(56) Ro60-0759
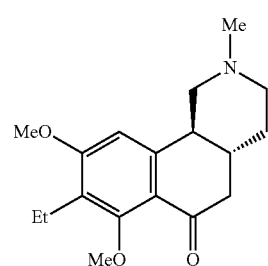 [SMILES: CCc1c(OC)cc2c(c1OC)C(=O)C[C@H]1CCN(C)C[C@H]21]

(57) Ro60-0869

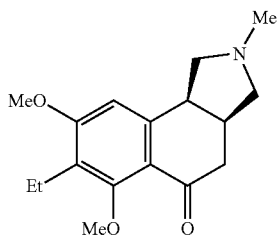 [SMILES: CCc1c(OC)cc2c(c1OC)C(=O)C[C@@H]1CN(C)C[C@H]21]

(58) a compound represented by the following structural formula described in WO00/64899

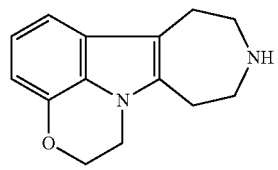 [SMILES: c1cc2c3c(c1)c1c(n3CCO2)CCNCC1]

(59) PNU-57378E

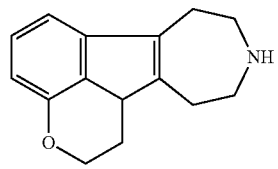

(60) a compound represented by the following structural formula described in WO03/06466

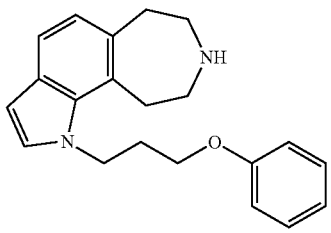 [SMILES: c1ccc(OCCCn2ccc3ccc4c(c32)CCNCC4)cc1]

(61) a compound represented by the following structural formula described in WO02/74746

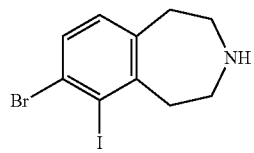

(62) a compound represented by the following structural formula described in WO02/42304

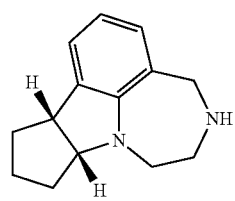 [SMILES: c1cc2c3c(c1)[C@H]1CCC[C@H]1N3CCNC2]

(63) WAY-470

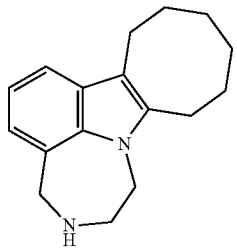 [SMILES: c1cc2c3c(c1)c1c(n3CCNC2)CCCCCC1]

(64) WAY-629

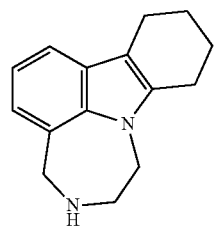 [SMILES: c1cc2c3c(c1)c1c(n3CCNC2)CCCC1]

(65) a compound represented by the following structural formula described in WO97/42183

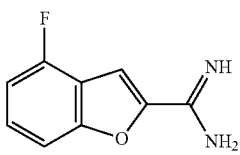 [SMILES: N=C(N)c1cc2c(F)cccc2o1]

(66) a compound represented by the following structural formula described in WO02/48124

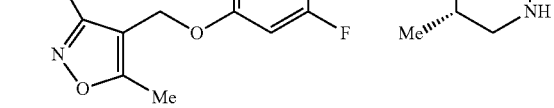

(67) WAY-162545

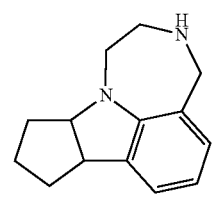 [SMILES: c1cc2c3c(c1)C1CCCC1N3CCNC2]

(68) WAY-163909

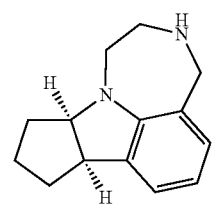 [SMILES: c1cc2c3c(c1)[C@H]1CCC[C@H]1N3CCNC2]

(69) IX-065

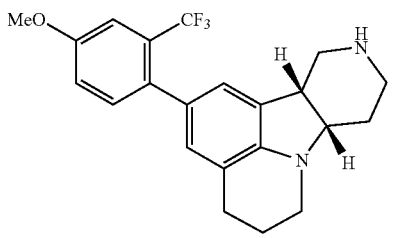 [SMILES: COc1ccc(-c2cc3c4c(c2)[C@@H]2CNCC[C@@H]2N4CCC3)c(C(F)(F)F)c1]

(70) A-37215

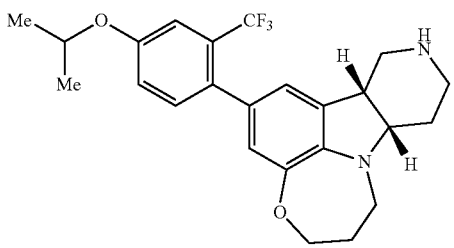 [SMILES: CC(C)Oc1ccc(-c2cc3c4c(c2)[C@@H]2CNCC[C@@H]2N4CCCO3)c(C(F)(F)F)c1]

(71) a compound represented by the following structural formula described in WO05/42491

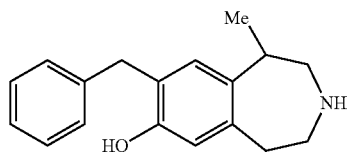 [SMILES: CC1CNCCc2cc(O)c(Cc3ccccc3)cc21]

(72) a compound represented by the following structural formula described in WO05/16902

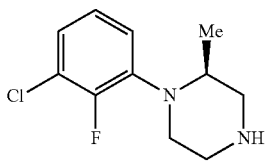 [SMILES: C[C@H]1CNCCN1c1cccc(Cl)c1F]

(73) a compound represented by the following structural formula described in WO04/99150

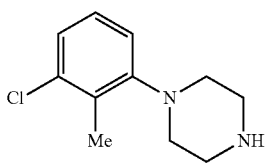 [SMILES: Cc1c(Cl)cccc1N1CCNCC1]

(74) PAL-287
(75) SCA-136

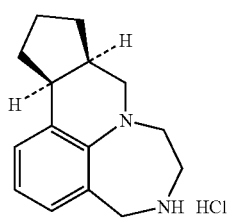

and the like are preferably used.

Preparations comprising compound (I) of the present invention may be in any solid forms of powders, granules, tablets, capsules, etc., and in any liquid forms of syrups, emulsions, injections, etc.

The preparations of the present invention for prophylaxis or treatment can be produced by any conventional methods, for example, blending, kneading, granulation, tableting, coating, sterilization, emulsification, etc., in accordance with the forms of the preparations to be produced. For the production of such pharmaceutical preparations, for example, each of the items in General Rules for Preparations in the Japanese Pharmacopoeia, can be made reference to. In addition, the preparations of the present invention may be formulated into a sustained release preparation containing active ingredients and biodegradable polymer compounds. The sustained release preparation can be produced according to the method described in JP-A-9-263545.

In the preparations of the present invention, the content of the compound (I) varies depending on the forms of the preparations, but is generally in the order of 0.01 to 100% by weight, preferably 0.1 to 50% by weight, more preferably 0.5 to 20% by weight, relative to the total weight of each preparation.

When the compound (I) of the present invention is used in the above-mentioned pharmaceutical products, it may be used alone, or in admixture with a suitable, pharmacologically acceptable carrier, for example, excipients (e.g., starch, lactose, sucrose, calcium carbonate, calcium phosphate, etc.), binders (e.g., starch, arabic gum, carboxymethyl cellulose, hydroxypropyl cellulose, crystalline cellulose, alginic acid, gelatin, polyvinylpyrrolidone, etc.), lubricants (e.g., stearic acid, magnesium stearate, calcium stearate, talc, etc.), disintegrants (e.g., calcium carboxymethylcellulose, talc, etc.), diluents (e.g., water for injection, physiological saline, etc.) and if desired, with the additives (e.g., a stabilizer, a preservative, a colorant, a fragrance, a dissolution aid, an emulsifier, a buffer, an isotonic agent, etc.) and the like, by ordinary methods. It can be formulated into the solid preparations such as powders, fine granules, granules, tablets, capsules, etc., or into the liquid preparations such as injections, etc., and can be administered orally or parenterally. When compound (I) is formed as a preparation for topical administration and administered, it can also be directly administered to the affected part of an articular disease. In this case, an injection is preferable. It can also be administered as a parenteral agent for topical administration (e.g., intramuscular injection, subcutaneous injection, organ injection, injection to the vicinity of a joint and the like, solid preparation such as implant, granule, powder and the like, liquid such as suspension and the like, ointment etc.) and the like.

For formulation into an injection, for example, compound (I) is formulated into an aqueous suspension with a dispersing agent (e.g., surfactant such as Tween 80, HCO-60 and the like, polysaccharides such as carboxymethylcellulose, sodium alginate, hyaluronic acid and the like, polysorbate etc.), preservative (e.g., methylparaben, propylparaben etc.), isotonic agent (e.g., sodium chloride, mannitol, sorbitol, glucose etc.), buffer (e.g., calcium carbonate etc.), pH adjuster (e.g., sodium phosphate, potassium phosphate etc.) and the like to give a preparation for practical injection. In addition, an oily suspension can be obtained by dispersing compound (I) together with vegetable oil such as sesame oil, corn oil and the like or a mixture thereof with a phospholipid such as lecithin and the like, or medium-chain triglyceride (e.g., miglyol 812 etc.) to give an injection to be actually used.

An agent for the prophylaxis or treatment of the present invention can be used along with other pharmaceutical agent.

As the drug that can be mixed with or concomitantly used with the substance of the present invention (hereinafter to be abbreviated as concomitant drug), for example, the following drugs can be used.

(1) Other Drugs for Treating Stress Urinary Incontinence

Adrenaline α1 receptor agonists (e.g., ephedrine hydrochloride, midodrine hydrochloride), adrenaline β2 receptor agonists (e.g., Clenbuterol), noradrenaline uptake inhibitory substances, noradrenaline and serotonin uptake inhibitory substances (e.g., duloxetine), tricyclic antidepressants (e.g., imipramine hydrochloride), anticholinergic agents or smooth muscle stimulants (e.g., oxybutynin hydrochloride, propiverine hydrochloride, celimeverine hydrochloride), female hormone drugs (e.g., conjugated estrogen (premarin), estriol) and the like.

(2) Agent for Treating Diabetes

Insulin preparations [e.g., animal insulin preparations extracted from the bovine or swine pancreas; human insulin preparations synthesized by a genetic engineering technique using *Escherichia coli* or a yeast; insulin zinc; protamine zinc insulin; a fragment or a derivative of insulin (e.g., INS-1, etc.)], insulin sensitizers (e.g., pioglitazone hydrochloride, troglitazone, rosiglitazone or its maleate, JTT-501, MCC-555, YM-440, KRP-297, FK-614, CS-011, etc.), α-glucosidase inhibitors (e.g., voglibose, acarbose, miglitol, emiglitate, etc.), biguanides (e.g., phenformin, metformin, buformin, etc.), sulfonylureas (e.g., tolbutamide, glibenclamide, gliclazide, chlorpropamide, tolazamide, acetohexamide, glyclopyramide, glimepiride, etc.) and other insulin secretagogues (e.g., repaglinide, senaglinide, mitiglinide or its calcium salt hydrate, GLP-1, nateglinide, etc.), dipeptidylpeptidase IV inhibitors (e.g., vildagliptin, sitagliptin, saxagliptin, alogliptin, NVP-DPP-728, PT-100, P32/98, etc.), β3 agonists (e.g., CL-316243, SR-58611-A, UL-TG-307, AJ-9677, AZ40140, etc.), amylin agonists (e.g., pramlintide, etc.), phosphotyrosine phosphatase inhibitors (e.g., vanadic acid, etc.), gluconeogenesis inhibitors (e.g., glycogen phosphorylase inhibitors, glucose-6-phosphatase inhibitors, glucagon antagonists, etc.), SGLT (sodium-glucose cotransporter) inhibitors (e.g., T-1095, etc.) and the like.

(3) Agent for Treating Diabetic Complications

Aldose reductase inhibitors (e.g., tolrestat, epalrestat, zenarestat, zopolrestat, fidarestat (SNK-860), minalrestat (ARI-509), CT-112, etc.), neurotrophic factors (e.g., NGF, NT-3, etc.), AGE inhibitors (e.g., ALT-945, pimagedine, pyratoxathine, N-phenacylthiazolium bromide (ALT-766), EXO-226, etc.), active oxygen scavengers (e.g., thioctic acid, etc.), cerebral vasodilators (e.g., tiapride, etc.) and the like.

(4) Antihyperlipidemic Agent

Statin compounds inhibiting cholesterol synthesis (e.g., pravastatin, simvastatin, lovastatin, atorvastatin, fluvastatin, cerivastatin or their salt (e.g., sodium salt, etc.), etc.), squalene synthase inhibitors or fibrate compounds having triglyceride lowering action (e.g., bezafibrate, clofibrate, simfibrate, clinofibrate, etc.) and the like.

(5) Hypotensive Agent

Angiotensin converting enzyme inhibitors (e.g., captopril, enalapril, delapril, etc.), angiotensin II antagonists (e.g., losartan, candesartan cilexetil, etc.), calcium antagonists (e.g., manidipine, nifedipine, amlodipine, efonidipine, nicardipine, etc.), clonidine, and the like.

(6) Antiobesity Agent

Antiobesity drugs acting on the central nervous system (e.g. dexfenfluramine, fenfluramine, phentermine, sibutramine, anfepramone, dexamphetamine, mazindol, phenylpropanolamine, clobenzorex, etc.), pancreatic lipase inhibitors (e.g. orlistat, etc.), β3 agonists (e.g. CL-316243, SR-58611- A, UL-TG-307, AJ-9677, AZ40140, etc.), anorectic peptides (e.g. leptin, CNTF (Ciliary Neurotrophic Factor), etc.), cholecystokinin agonists (e.g. lintitript, FPL-15849, etc.).

(7) Diuretic Agent

Xanthine derivatives (e.g., theobromine sodium salicylate, theobromine calcium salicylate, etc.), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide, etc.), antialdosterone preparations (e.g., spironolactone, triamterene, etc.), carbonic anhydrase inhibitors (e.g., acetazolamide, etc.), chlorobenzenesulfonamide preparations (e.g., chlorthalidone, mefruside, indapamide, etc.), azosemide, isosorbide, ethacrynic acid, piretanide, bumetanide, furosemide, etc.

(8) Chemotherapeutic Agent

Alkylating agents (e.g., cyclophosphamide, ifosamide, etc.), metabolic antagonists (e.g., methotrexate, 5-fluorouracil, etc.), antitumor antibiotics (e.g., mitomycin, adriamycin, etc.), plant-derived antitumor agents (e.g., vincristine, vindesine, taxol, etc.), cisplatin, carboplatin, etoposide, etc. Among these, 5-fluorouracil derivatives such as Furtulon and Neo-Furtulon are preferred.

(9) Immunotherapeutic Agent

Microorganism- or bacterium-derived components (e.g., muramyl dipeptide derivatives, Picibanil, etc.), immunopotentiator polysaccharides (e.g., lentinan, schizophyllan, krestin, etc.), genetically engineered cytokines (e.g., interferons, interleukins (IL), etc.), colony stimulating factors (e.g., granulocyte colony stimulating factor, erythropoietin, etc.) and the like. Among these, IL-1, IL-2, IL-12, etc. are preferred.

(10) Therapeutic Agent Recognized to Ameliorate Cachexia in Animal Models or Clinical Practice Progesterone derivatives (e.g., megestrol acetate) [Journal of Clinical Oncology, vol. 12, pp. 213-225, 1994], metoclopramide pharmaceuticals, tetrahydrocannabinol pharmaceuticals (the above references are applied to both), fat metabolism ameliorating agents (e.g., eicosapentaenoic acid) [British Journal of Cancer, vol. 68, pp. 314-318, 1993], growth hormones, IGF-1, and antibodies to the cachexia-inducing factors such as TNF-", LIF, IL-6 and oncostatin M.

(11) Antiinflammatory Agent

Steroids (e.g., dexamethasone, etc.), sodium hyaluronate, cyclooxygenase inhibitors (e.g., indomethacin, ketoprofen, loxoprofen, meloxicam, ampiroxicam, celecoxib, rofecoxib, etc.) and the like.

(12) Miscellaneous

Glycosylation inhibitors (e.g., ALT-711, etc.), nerve regeneration promoting drugs (e.g., Y-128, VX853, prosaptide, etc.), drugs acting on the central nervous system (e.g., antidepressants such as desipramine, amitriptyline, imipramine, fluoxetine, paroxetine, doxepin, etc.), anticonvulsants (e.g., lamotrigine, carbamazepine), antiarrhythmic drugs (e.g., mexiletine), acetylcholine receptor ligands (e.g., ABT-594), endothelin receptor antagonists (e.g., ABT-627), monoamine uptake inhibitors (e.g., tramadol), indoleamine uptake inhibitors (e.g., fluoxetine, paroxetine), narcotic analgesics (e.g., morphine), GABA receptor agonists (e.g., gabapentin), GABA uptake inhibitors (e.g., tiagabine), $\alpha_2$ receptor agonists (e.g., clonidine), local analgesics (e.g., capsaicin), protein kinase C inhibitors (e.g., LY-333531), antianxiety drugs (e.g., benzodiazepines), phosphodiesterase inhibitors (e.g., sildenafil), dopamine receptor agonists (e.g., apomorphine), dopamine receptor antagonists (e.g., haloperidol), serotonin receptor agonists (e.g., tandospirone citrate, sumatryptan), serotonin receptor antagonists (e.g., cyproheptadine hydrochloride, ondansetron), serotonin uptake inhibitors (e.g., fluvoxamine maleate, fluoxetine, paroxetine), hypnotics (e.g., triazolam, zolpidem), anticholinergic agents, $\alpha_1$ receptor blocking agents (e.g., tamsulosin, silodosin, naftopidil), muscle relaxants (e.g., baclofen), potassium channel openers (e.g., nicorandil), calcium channel blocking agents (e.g., nifedipine), agents for preventing and/or treating Alzheimer's disease (e.g., donepezil, rivastigmine, galanthamine), agents for treating Parkinson's disease (e.g., L-dopa), agents for preventing and/or treating multiple sclerosis (e.g., interferon β-1a), histamine $H_1$ receptor inhibitors (e.g., promethazine hydrochloride), proton pump inhibitors (e.g., lansoprazole, omeprazole), antithrombotic agents (e.g., aspirin, cilostazol), NK-2 receptor antagonists, agents of treating HIV infection (saquinavir, zidovudine, lamivudine, nevirapine), agents of treating chronic obstructive pulmonary diseases (salmeterol, thiotropium bromide, cilomilast), etc.

Anticholinergic agents include, for example, atropine, scopolamine, homatropine, tropicamide, cyclopentolate, butylscopolamine bromide, propantheline bromide, methylbenactyzium bromide, mepenzolate bromide, flavoxate, pirenzepine, ipratropium bromide, trihexyphenidyl, oxybutynin, propiverine, darifenacin, tolterodine, temiverine, trospium chloride or a salt thereof (e.g., atropine sulfate, scopolamine hydrogen bromide, homatropine hydrogen bromide, cyclopentolate hydrochloride, flavoxate hydrochloride, pirenzepine hydrochloride, trihexyphenidyl hydrochloride, oxybutynin hydrochloride, tolterodine tartrate, etc.), preferably, oxybutynin, propiverine, darifenacin, tolterodine, temiverine, trospium chloride or a salt thereof (e.g., oxybutynin hydrochloride, tolterodine tartrate, etc.). In addition, acetylcholinesterase inhibitors (e.g., distigmine, etc.) and the like can be used.

NK-2 receptor antagonists include, for example, a piperidine derivative such as GR159897, GR149861, SR48968 (saredutant), SR144190, YM35375, YM38336, ZD7944, L-743986, MDL105212A, ZD6021, MDL105172A, SCH205528, SCH62373, R-113281, etc., a perhydroisoindole derivative such as RPR-106145, etc., a quinoline derivative such as SB-414240, etc., a pyrrolopyrimidine derivative such as ZM-253270, etc., a pseudopeptide derivative such as MEN11420 (nepadutant), SCH217048, L-659877, PD-147714 (CAM-2291), MEN10376, S16474, etc., and others such as GR100679, DNK333, GR94800, UK-224671, MEN10376, MEN10627, or a salt thereof, and the like.

In combination of the compound of the present invention and the concomitant drug, the administration time of the compound (I) and the concomitant drug is not restricted, and the compound (I) or a pharmaceutical composition thereof and the concomitant drug or a pharmaceutical composition thereof can be administered to the administration subject simultaneously, or may be administered at different times. The dosage of the concomitant drug may be determined according to the administration amount clinically used, and can be appropriately selected depending on the administration subject, administration route, disease, combination and the like.

The concomitant administration mode is not particularly restricted, and it is sufficient that the compound (I) and the concomitant drug are combined in administration. Examples of such administration mode include the following methods: (1) The compound (I) or a pharmaceutical composition thereof and the concomitant drug are simultaneously produced to give a single preparation which is administered. (2) The compound (I) or a pharmaceutical composition thereof and the concomitant drug or a pharmaceutical composition thereof are separately produced to give two kinds of preparations which are administered simultaneously by the same administration route. (3) The compound (I) or a pharmaceutical composition thereof and the concomitant drug or a pharmaceutical composition thereof are separately produced to give two kinds of preparations which are administered by the same administration route only at the different times. (4) The compound (I) or a pharmaceutical composition thereof and the concomitant drug or a pharmaceutical composition thereof are separately produced to give two kinds of preparations which are administered simultaneously by different administration routes. (5) The compound (I) or a pharmaceutical composition thereof and the concomitant drug or a pharmaceutical composition thereof are separately produced to give two kinds of preparations which are administered by different administration routes at different times (for example, the compound (I) or a pharmaceutical composition thereof; the concomitant drug or a pharmaceutical composition thereof are administered in this order, or in the reverse order).

The mixing ratio of compound (I) and a concomitant drug in the combination drug of the present invention can be appropriately determined according to the subject of administration, administration route, disease and the like.

For example, while the content of compound (I) in the combination drug of the present invention varies depending on the form of the preparation, it is generally about 0.01 to about 100 wt %, preferably about 0.1 to about 50 wt %, more preferably about 0.5 to about 20 wt %, relative to the whole preparation.

While the content of the concomitant drug in the combination drug of the present invention varies depending on the form of the preparation, it is generally about 0.01 to about 100 wt %, preferably about 0.1 to about 50 wt %, more preferably about 0.5 to about 20 wt %, relative to the whole preparation.

While the content of the additive such as a carrier and the like in the combination drug of the present invention varies depending on the form of the preparation, it is generally about 1 to about 99.99 wt %, preferably about 10 to about 90 wt %, relative to the whole preparation.

Similar contents can be employed when compound (I) and the concomitant drug are independently formulated.

While the dose varies depending on the kind of compound (I) or a pharmaceutically acceptable a salt thereof, administration route, symptom, age of patients and the like, for example, for oral administration to an adult patient with stress urinary incontinence and/or obesity, it is about 0.005-50 mg, preferably about 0.05-10 mg, more preferably about 0.2-4 mg/kg body weight/day as compound (I), which can be administered in 1 to about 3 portions.

When the pharmaceutical composition of the present invention is a sustained-release preparation, the dose varies depending on the kind and content of compound (I), dosage form, period of sustained drug release, subject animal of administration (e.g., mammals such as human, rat, mouse, cat, dog, rabbit, bovine, swine and the like) and administration object. For parenteral administration, for example, about 0.1-about 100 mg of compound (I) only needs to be released in one week from the administered preparation.

The dose of the concomitant drug may be set within the range such that it causes no problems of side effects. The daily dose as the concomitant drug varies depending on severity of symptoms, age, sex, weight and sensitivity of the subject to be administered, time and interval of administration, property, formulation and kinds of pharmaceutical preparation, kinds of active ingredients, etc., and is not particularly limited. In the case of oral administration, a daily dosage in terms of drugs is usually in the order of about 0.001 to 2000 mg, preferably about 0.01 to 500 mg, and more preferably about 0.1 to 100 mg, per 1 kg body weight of mammals, which may be administered once a day or in two to four divided portions a day.

In administering the combination drug of the present invention, it may be administered at the same time or, the concomitant drug may be administered before administering the compound (I), and vice versa. In case of staggered administration, the time interval varies depending on the active ingredients to be administered, a formulation and an administration route. For example, if the concomitant drug is administered first, the compound (I) may be administered 1 minute to 3 days, preferably 10 minutes to 1 day, more preferably 15 minutes to 1 hour after administering the concomitant drug. If the compound (I) is administered first, the concomitant drug may be administered 1 minute to 1 day, preferably 10 minutes to 6 hours, more preferably 15 minutes to 1 hour after administering the compound (I).

The pharmaceutical composition of the present invention shows low toxicity and can be used safely. Particularly, since the Example compounds shown below are superior in the absorption by oral administration, they can be advantageously used for oral preparations.

Described below are a screening method for a prophylactic or therapeutic agent for pelvic organ prolapse, rectal prolapse or post-micturition dribble, and a screening method for a substance that increases the contractile force of the pelvic floor muscles.

The screening methods of the present invention can be performed by administering a test substance to a test animal and without administration thereof, and examining the influence of the test substance on the contractile responses of the pelvic floor muscles in the animal (e.g., non-human mammal) in terms of reflex closure responses in the urethra or urethral resistance (leak point pressure) upon a rise in intravesical pressure. The animals used in the screening methods of the present invention have the hypogastric nerve and the pudendal nerve cut bilaterally. Muscular tissues that influence urethral closure pressure include the internal urethral sphincter, which is a smooth muscle, the external urethral sphincter and the pelvic floor muscles, which are striated muscles, and the like; the pelvic floor muscles include the iliococcygeus muscle and the pubococcygeus muscle. The internal urethral sphincter is under the control of the hypogastric nerve, the external urethral sphincter is under the control of the pudendal nerve, and the iliococcygeus muscle and the pubococcygeus muscle are under the control of the nerves that lead to the iliococcygeus muscle and the pubococcygeus muscle (no unified names across species available). When a water reservoir connected to the urinary bladder is raised to a given height, a reflex urethral contractile response is observed in the middle urethra (see "American Journal of Physiology Renal Physiology", 2004, vol. 287, p. F434-441); by increasing the intravesical pressure in an animal having the hypogastric nerve and the pudendal nerve cut bilaterally, and monitoring the resulting urethral contractile responses or leak point pressure, urethral closure responses or urethral resistance, which are attributed mainly to the pelvic floor muscles (the iliococcygeus muscle and the pubococcygeus muscle), can be measured, and the contractile responses of the pelvic floor muscles can be evaluated.

A specific method of measuring "the reflex contractile responses of the pelvic floor muscles upon a rise in intravesical pressure" is described in detail in an Example below. "Leak point pressure upon a rise in intravesical pressure" refers to an intravesical pressure upon occurrence of urine leakage without contraction of the detrusor, showing the maximum urethral resistance against rises in intravesical pressure.

Applying "the reflex contractile responses of the pelvic floor muscles upon a rise in intravesical pressure", the reflex contractile responses of the pelvic floor muscles can be evaluated also by measuring reflex closure responses in the rectum or the vagina.

As the gender of the "animal" to be used in the present invention, female is preferable, and the species is a non-human animal such as monkey, dog, cat, rabbit, guinea pig, hamster, rat, mouse, Mongolian gerbil and the like can be mentioned, and rat (Wistar, SD and the like) is most preferable.

While the age in weeks, body weight, delivery or non-delivery and the like of the "animal" to be used in the present invention are not particularly limited as long as they are applicable to the objective screening, these conditions may be appropriately changed. As the "animal" to be used in the present invention, normal animals (animals free of pathosis and the like) may be used. In addition, those having partially sectioned or injured nerve involved in the contraction of the pelvic floor muscles or having decreased weight of the pelvic floor muscles can also be used. To decrease the reflex contractile force of the pelvic floor muscles, a part of the nerve involved in the reflex contraction of the pelvic floor muscles (e.g., pelvic nerve, nerve to iliococcygeous muscle/pubococcygeous muscle and the like) is physically, chemically or biologically sectioned or injured, the animal is made to deliver, the ovary is removed, vagina is mechanically expanded, diabetes is induced, a drug is administered, or these may be combined.

As the drug, for example, α-bungarotoxin, d-tubocurarine, pancuronium, decamethonium, suxamethonium and the like, which are neuromuscular junction blockers, are used.

These model animals can be produced according to a known method, for example, the method described in Urology, 1998, vol. 52, p. 143-151, Journal of Urology, 2001, vol. 166, p. 311-317.

As the test substance, a known or novel synthetic compound, a physiological active substance derived from a naturally occurring substance, peptide, protein and the like and, for example, tissue extract, cell culture supernatant and the like of warm-blooded mammals (e.g., mouse, rat, swine, bovine, sheep, monkey, human and the like) are used.

Using this screening method, a substance that increases the contractile force of the pelvic floor muscles can be screened for using, as an index, the fact that the reflex closure response or the leak point pressure increases when a test substance is administered than without administration.

For example, by performing the present screening method using rats, a test substance can be evaluated to have an improving effect on pelvic organ prolapse, rectal prolapse or post-micturition dribble when the contractile response of the pelvic floor muscles increased by not less than about 10%, preferably not less than about 20%, more preferably not less than about 50%, with administration of the test substance as compared to the absence of administration of the test substance.

The screening method of the present invention measures the contractile response of the pelvic floor muscles during an abrupt increase in abdominal pressure in an animal, and is useful for and efficiently applicable to the screening for a substance usable for the prophylaxis or treatment of pelvic organ prolapse, rectal prolapse or post-micturition dribble.

For example, in the screening method of the present invention, about 0.0001-about 1000 mg/kg (preferably about 0.001-about 100 mg/kg) of a test substance is administered to a non-human mammal, and the treatment effect of the test substance is examined with the contractile response of the pelvic floor muscles as an index, whereby a drug for the prophylaxis or treatment of pelvic organ prolapse, rectal prolapse or post-micturition dribble can be evaluated. Here, the concept of the treatment of pelvic organ prolapse, rectal prolapse or post-micturition dribble includes improvement, suppression of progression and prophylaxis of aggravation of pelvic organ prolapse, rectal prolapse or post-micturition dribble. In the evaluation method of the present invention, a test substance is administered to an animal before or after the treatment for decreasing the reflex contractile force of pelvic floor muscles (or leak point pressure), or during the measurement of contractile force (or leak point pressure) and the like. A drug can be evaluated for the purpose of preventing or treating pelvic organ prolapse, rectal prolapse or post-micturition dribble according to each administration period.

While the animals to be used in the present invention may be a normal animal (animal free of pathosis), for example, an animal (e.g., overweight rat (Wistar Fatty rat) and the like) showing the pathosis of urinary incontinence, overactive bladder, benign prostatic hyperplasia, detrusor underactivity, diabetes, diabetes neuropathy, hypertension, obesity, hyperlipidemia, arteriosclerosis, gastric ulcer, asthma, chronic obstructive respiratory disease, uterus cancer, cerebrovascular disorder, brain damage, spinal cord injury and the like may be used for the measurement of the aforementioned reflex contraction of the pelvic floor muscles. When animals showing such pathosis are subjected to the aforementioned measurement of the contractile force of the pelvic floor muscles (or leak point pressure), a new model animal of pelvic organ prolapse, rectal prolapse or post-micturition dribble can be searched for, and the measurement can be effectively applied to the screening for a pharmaceutical substance for the prophylaxis or treatment of the complications. For example, the measurement is applicable to the screening for a pharmaceutical substance effective only for the aforementioned pathosis (e.g., digestive disease such as gastric ulcer etc., and the like) and free of an influence on the pelvic organ prolapse, rectal prolapse and post-micturition dribble, and also applicable to the screening for the purpose of removing a test substance inducing pelvic organ prolapse, rectal prolapse or post-micturition dribble from a pharmaceutical substance to be selected.

Furthermore, the screening method of the present invention can be effectively applied to the screening for a pharmaceutical substance for the prophylaxis or treatment of pelvic organ prolapse, rectal prolapse or post-micturition dribble by applying a test substance and testing increasing effect on the contractile force of pelvic floor muscles (or leak point pressure), as well as effectively applied to the screening for the purpose of applying a test substance and selecting a test substance showing an improving effect on pelvic organ prolapse, rectal prolapse or post-micturition dribble, as a pharmaceutical substance for the prophylaxis or treatment of pelvic organ prolapse, rectal prolapse or post-micturition dribble or the complications of pelvic organ prolapse, rectal prolapse or post-micturition dribble with a certain kind of disease; and the like. The substance obtained by the screening method of the present invention can be formed as a preparation in the same manner as in the aforementioned substance of the present invention and can be used as an agent for the prophylaxis or treatment of pelvic organ prolapse, rectal prolapse or post-micturition dribble.

EXAMPLES

The present invention is further described in detail in with reference to Reference Examples, Examples, Formulation Examples and Experimental Examples which are not intended to restrict the invention and may be modified without departing from the scope of the invention.

Elution in the column chromatography in the following Reference Examples and Examples was conducted under observation by TLC (thin layer chromatography), unless otherwise specifically indicated. In the TLC observation, 60F254, TLC plates, produced by Merck & Co., Inc. was used, and the solvent employed as an elution solvent in the column chromatography was used as an eluent. For the detection, a UV detector was used. As silica gel for the column chromatography, Silica Gel 60 (70 to 230 mesh) produced by Merck & Co., Inc. was used. The room temperature referred herein means temperature generally from about 10° C. to 30° C. For drying extract, sodium sulfate or magnesium sulfate was used.

The abbreviations in Examples and Reference Examples mean the following.
LC: liquid chromatography
MS: mass spectrometry spectrum
ESI: electrospray method
M: molecular ion peak
NMR: nuclear magnetic resonance spectrum
Hz: hertz
J: coupling constant
m: multiplet
q: quartet
t: triplet
d: doublet
dd: double doublet
ddd: double double doublet
s: singlet
br: broad
dt: double triplet
brs: broad singlet
Ac: acetyl group
$^t$Bu: tert-butyl group
Boc: tert-butyloxycarbonyl group
Et: ethyl group
Ph: phenyl group
N: normal concentration
DMF: N,N-dimethylformamide
THF: tetrahydrofuran
MeOH: methanol
EtOH: ethanol
DMSO: dimethyl sulfoxide
DME: dimethoxyethane
IPE: diisopropyl ether
TFA: trifluoroacetic acid
HOBt.H$_2$O: 1-hydroxybenzotriazole monohydrate
WSC.HCl: 1-ethyl-3-(3-dimethylaminopropyl)carbodiimide hydrochloride
5-HT: serotonin (or 5-hydroxytryptamine)
LC-MS in Examples and Reference Examples was measured under the following conditions.
Analysis by LC-MS
Measurement device: Waters LC-MS system
HPLC: Agilent HP1100
MS: Micromass ZMD
HPLC Conditions
Column: CAPCELL PAK C18UG120, S-3 μm, 1.5×35 mm (Shiseido)
Solvent: Solution A; water containing 0.05% trifluoroacetic acid, Solution B; acetonitrile containing 0.05% trifluoroacetic acid
Gradient cycle: 0.00 min (Solution A/Solution B=90/10), 2.00 min (Solution A/Solution B=5/95), 2.75 min (Solution A/Solution B=5/95), 2.76 min (Solution A/Solution B=90/10), 3.60 min (Solution A/Solution B=90/10)

Injection volume: 2 μL, flow rate: 0.5 mL/min, detection method: UV 220 nm

MS Conditions

Ionization method: ESI

Purification by preparative HPLC in Examples and Reference Examples was carried out under the following conditions.

Instrument: Gilson high-throughput purification system
Column: CombiPrep ODS-AS-5 μm, 50×20 mm (YMC)
Solvent: Solution A; water containing 0.1% trifluoroacetic acid, Solution B; acetonitrile containing 0.1% trifluoroacetic acid
Gradient cycle: 0.00 min (Solution A/Solution B=95/5), 1.00 min (Solution A/Solution B=95/5), 5.20 min (Solution A/Solution B=5/95), 6.40 min (Solution A/Solution B=5/95), 6.50 min (Solution A/Solution B=95/5), 6.60 min (Solution A/Solution B=95/5)
Flow rate: 25 mL/min, detection method: UV 220 nm Purification by high-resolution preparative HPLC in the following Examples was carried out under the following conditions.

Instrument: Gilson high-throughput purification system
Column: Combiprep Hydrosphere C18, 50×20 mm (YMC)
Solvent: Solution A; water containing 0.1% trifluoroacetic acid, Solution B; acetonitrile containing 0.1% trifluoroacetic acid
Gradient cycle: 0.00 min (Solution A/Solution B=98/2), 1.00 min (Solution A/Solution B=98/2), 5.20 min (Solution A/Solution B=60/40), 5.40 min (Solution A/Solution B=5/95), 6.40 min (Solution A/Solution B=5/95), 6.50 min (Solution A/Solution B=98/2), 6.60 min (Solution A/Solution B=98/2)
Flow rate: 20 mL/min, detection method: UV 220 nm Example 1

4-benzyl-2,3,4,5-tetrahydropyrido[3,2-f][1,4]oxazepine (Step 1)

To a solution of 2-chloronicotinic acid (7.88 g), N-benzyl-2-{[tert-butyl(dimethyl)silyl]oxy}ethanamine (13.3 g) synthesized by known method (e.g., the method described in WO99/31085) and HOBt.H₂O (11.5 g) in DMF (50 mL) was added WSC.HCl (14.4 g), and the mixture was stirred at room temperature for 14 hr. The reaction mixture was poured into water, and the mixture was extracted with ethyl acetate. The organic layer was washed with saturated aqueous sodium hydrogen carbonate solution and brine, and concentrated. The residue was purified by silica gel column chromatography (solvent gradient; 10→33% ethyl acetate/hexane) to give N-benzyl-N-(2-{[tert-butyl(dimethyl)silyl]oxy}ethyl)-2-chloronicotinamide (11.8 g, 58%) as a colorless oil.

¹H-NMR (CDCl₃): δ 0.00-0.10 (6H, m), 0.85-0.93 (9H, m), 3.00-4.70 & 5.32-5.37 (6H, m), 7.08-7.74 (7H, m), 8.38-8.44 (1H, m)

(Step 2)

To a solution of the compound (11.8 g) obtained in step 1 in THF (30 mL) was added 1M BH₃.THF complex/THF solution (134 mL) at 0° C., and the mixture was stirred at 90° C. for 1 hr. After the reaction mixture was cooled to 10° C., MeOH (20 mL) was added, and the mixture was concentrated under reduced pressure. The residue was suspended in 6N hydrochloric acid (43 mL), and the mixture was stirred at 90° C. for 2 hr. The reaction mixture was cooled to 10° C., and made basic with aqueous sodium hydroxide solution, and the resultant product was extracted with ethyl acetate. The organic layer was washed with saturated aqueous ammonium chloride solution and brine, and concentrated. The residue was purified by silica gel column chromatography (solvent gradient; 10→33% ethyl acetate/hexane) to give 2-{benzyl[(2-chloropyridin-3-yl)methyl]amino}ethanol (6.92 g, 86%) as a colorless oil.

¹H-NMR (CDCl₃): δ 2.71 (2H, t), 3.56-3.76 (7H, m), 7.21-7.35 (6H, m), 7.83 (1H, dd, J=7.5, 1.8 Hz), 8.29 (1H, dd, J=4.8, 1.8 Hz)

(Step 3)

Under a nitrogen atmosphere, to a suspension of sodium hydride (60% in oil, 1.99 g) in THF (30 ml) was added a solution of the compound (6.90 g) obtained in step 2 in THF (20 mL) at 0° C., and the mixture was stirred at 90° C. for 1 hr. The reaction mixture was cooled to 10° C., and poured into water, and the mixture was extracted with ethyl acetate. The organic layer was washed with saturated aqueous ammonium chloride solution and brine, and concentrated. The residue was purified by silica gel column chromatography (solvent gradient; 10→66% ethyl acetate/hexane) to give the title compound (4.51 g, 75%) as a pale-yellow oil.

¹H-NMR (CDCl₃): δ 3.08-3.12 (2H, m), 3.67 (2H, s), 3.74 (2H, s), 4.20-4.25 (2H, m), 6.98 (1H, dd, J=7.5, 5.1 Hz), 7.25-7.40 (6H, m), 8.17 (1H, dd, J=5.1, 2.1 Hz)

MS (ESI+): 241 (M+H)

Example 2

4-benzyl-8-methyl-2,3,4,5-tetrahydropyrido[3,2-f][1,4]oxazepine

The title compound was obtained in the same manner as in Example 1 and using 2-chloro-6-methylnicotinic acid.

¹H-NMR (CDCl₃): δ 2.47 (3H, s), 3.08-3.11 (2H, m), 3.66 (2H, s), 3.71 (2H, s), 4.19-4.22 (2H, m), 6.83 (1H, d, J=7.5 Hz), 7.25-7.38 (6H, m)

MS (ESI+): 255 (M+H)

Example 3

4-benzyl-8-chloro-2,3,4,5-tetrahydropyrido[3,2-f][1,4]oxazepine

The title compound was obtained in the same manner as in Example 1 and using 2,6-dichloronicotinic acid.

¹H-NMR (CDCl₃): δ 3.08-3.12 (2H, m), 3.67 (2H, s), 3.72 (2H, s), 4.21-4.25 (2H, m), 7.01 (1H, d, J=7.8 Hz), 7.25-7.35 (6H, m)

MS (ESI+): 275 (M+H)

Example 4

4-benzyl-8-chloro-7-fluoro-2,3,4,5-tetrahydropyrido[3,2-f][1,4]oxazepine

The title compound was obtained in the same manner as in Example 1 and using 2,6-dichloro-5-fluoronicotinic acid.

¹H-NMR (CDCl₃): δ 3.10-3.13 (2H, m), 3.67 (2H, s), 3.70 (2H, s), 4.18-4.22 (2H, m), 7.18 (1H, d, J=7.5 Hz), 7.25-7.40 (5H, m)

MS (ESI+): 293 (M+H)

Example 5

4-benzyl-8-chloro-3-methyl-2,3,4,5-tetrahydropyrido[3,2-f][1,4]oxazepine

The title compound was obtained in the same manner as in Example 1 and using 2,6-dichloronicotinic acid and N-benzyl-1-{[tert-butyl(dimethyl)silyl]oxy}propan-2-amine.

$^1$H-NMR (CDCl$_3$): δ 1.24 (3H, d, J=6.7 Hz), 3.25-3.40 (1H, m), 3.61 (1H, d, J=15.8 Hz), 3.68 (2H, d like), 4.10 (1H, d, J=15.8 Hz), 4.09-4.20 (1H, m), 4.29 (1H, dd, J=12.8, 3.0 Hz), 6.97 (1H, d, J=7.6 Hz), 7.20-7.40 (6H, m)
MS (ESI+): 289 (M+H)

Example 6

4-benzyl-8-chloro-2-methyl-2,3,4,5-tetrahydropyrido[3,2-f][1,4]oxazepine

The title compound was obtained in the same manner as in Example 1 and using 2,6-dichloronicotinic acid and N-benzyl-2-{[tert-butyl(dimethyl)silyl]oxy}propan-1-amine.

$^1$H-NMR (CDCl$_3$): δ 1.39 (3H, d, J=6.4 Hz), 2.91-3.04 (2H, m), 3.66 (2H, s), 3.67 (1H, d, J=14.0 Hz), 3.76 (1H, d, J=14.3 Hz), 4.25-4.40 (1H, m), 7.00 (1H, d, J=7.6 Hz), 7.25-7.36 (6H, m)
MS (ESI+): 289 (M+H)

Example 7

4-benzyl-2,3,4,5-tetrahydropyrido[4,3-f][1,4]oxazepine

The title compound was obtained in the same manner as in Example 1 and using 3-fluoroisonicotinic acid.

$^1$H-NMR (CDCl$_3$): δ 3.11-3.14 (2H, m), 3.66 (2H, s), 3.79 (2H, s), 4.10-4.14 (2H, m), 6.93 (1H, d, J=4.5 Hz), 7.25-7.37 (5H, m), 8.23 (1H, d, J=4.5 Hz), 8.35 (1H, s)
MS (ESI+): 241 (M+H)

Example 8

4-benzyl-9-chloro-2,3,4,5-tetrahydropyrido[4,3-f][1,4]oxazepine (Step 1)
To a solution of 3-fluoroisonicotinic acid (10.0 g) and DMF (0.155 mL) in toluene (50 mL) was added thionyl chloride (20.5 ml), and the mixture was stirred at 110° C. for 2 hr. The reaction mixture was concentrated under reduced pressure, and THF (20 mL) was added to the residue. After the THF solution was cooled to −78° C., a solution of N-benzyl-2-{[tert-butyl(dimethyl)silyl]oxy}ethanamine (20.7 g) and Et$_3$N (11.0 mL) in THF (50 mL) was added, and the mixture was stirred at room temperature for 30 min. The reaction mixture was poured into water, and the mixture was extracted with ethyl acetate. The organic layer was washed with brine, and concentrated. The residue was purified by silica gel column chromatography (solvent gradient; 10→20% ethyl acetate/hexane) to give N-benzyl-N-(2-{[tert-butyl(dimethyl)silyl]oxy}ethyl)-3-fluoroisonicotinamide (27.2 g, 99%) as a pale-yellow oil.

$^1$H-NMR (CDCl$_3$): δ 0.00-0.10 (6H, m), 0.85-0.93 (9H, m), 2.74 & 3.23 & 3.56-3.91 & 4.56 & 4.88 (6H, m), 7.08-7.40 (6H, m), 8.42-8.54 (2H, m)

(Step 2)
To a solution of the compound (26.2 g) obtained in step 1 in THF (135 mL) was added 70% m-chloroperbenzoic acid (m-CPBA) (16.2 g) at 0° C., and the mixture was stirred at room temperature for 4 hr. m-CPBA (16.2 g) was further added, and the mixture was stirred at room temperature for 4 hr. The reaction mixture was poured into aqueous sodium thiosulfate solution, and the mixture was extracted three times with ethyl acetate. The organic layer was washed with brine, and concentrated. The residue was purified by silica gel column chromatography (solvent gradient; 10→80% ethyl acetate/hexane) to give N-benzyl-N-(2-{[tert-butyl(dimethyl)silyl]oxy}ethyl)-3-fluoroisonicotinamide 1-oxide (19.0 g, 70%) as a pale-yellow oil.

$^1$H-NMR (CDCl$_3$): δ −0.01-0.09 (6H, m), 0.85-0.93 (9H, m), 3.21-3.31 & 3.56-3.68 & 3.86-3.94 (4H, m), 4.56-4.90 (2H, m), 7.07-7.60 (6H, m), 7.94-8.20 (2H, m)

(Step 3)
To a solution of the compound (1.20 g) obtained in step 2 in MeOH (5 mL) was added 6N hydrochloric acid (5 mL), and the mixture was stirred at 60° C. for 30 min. The reaction mixture was concentrated under reduced pressure, and the residue was dissolved in a mixture of ethyl acetate and THF. The solution was neutralized with aqueous sodium hydroxide solution, and the resultant product was extracted three times with a mixture of ethyl acetate and THF, and concentrated. The residue was purified by silica gel column chromatography (solvent gradient; 66% ethyl acetate/hexane→5% ammonia/ethyl acetate) to give N-benzyl-3-fluoro-N-(2-hydroxyethyl)isonicotinamide 1-oxide (0.63 g, 73%) as a white powder.

$^1$H-NMR (CDCl$_3$): δ 2.09 & 2.49 (1H, brs), 3.25-3.40 (1H, m), 3.60-3.75 (2H, m), 3.80-3.90 (1H, m), 4.50-4.83 (2H, m), 7.11-7.15 (1H, m), 7.25-7.48 (5H, m), 8.00-8.10 (1H, m), 8.12-8.15 (1H, m)

(Step 4)
To a solution of the compound (0.60 g) obtained in step 3 in THF (15 mL) was added sodium hydride (60% in oil, 0.34 g), and the mixture was stirred at 80° C. for 4 hr. The reaction mixture was poured into water, and the resultant product was extracted three times with ethyl acetate. The organic layer was washed with brine, and concentrated. The residue was purified by silica gel column chromatography (solvent gradient; 80% ethyl acetate/hexane→5% ammonia/ethyl acetate) to give 4-benzyl-3,4-dihydropyrido[4,3-f][1,4]oxazepin-5(2H)-one 8-oxide (0.27 g, 48%) as a white powder.

$^1$H-NMR (CDCl$_3$): δ 3.58-3.61 (2H, m), 4.28-4.31 (2H, m), 4.81 (2H, s), 7.30-7.42 (5H, m), 7.90-8.00 (3H, m)

(Step 5)
A solution of the compound (0.23 g) obtained in step 4 in phosphorus oxychloride (1.0 mL) was stirred at 80° C. for 30 min. The reaction mixture was poured into water, and the resultant product was extracted twice with ethyl acetate. The organic layer was washed with saturated aqueous sodium hydrogen carbonate solution and brine, and concentrated. The residue was purified by silica gel column chromatography (solvent gradient; 5→20% ethyl acetate/hexane) to give 4-benzyl-9-chloro-3,4-dihydropyrido[4,3-f][1,4]oxazepin-5(2H)-one (0.23 g, 94%) as a colorless oil.

$^1$H-NMR (CDCl$_3$): δ 3.51 (2H, t, J=4.9 Hz), 4.31 (2H, t, J=4.9 Hz), 4.83 (2H, s), 7.32-7.42 (5H, m), 7.71 (1H, d, J=4.8 Hz), 8.20 (1H, d, J=4.8 Hz)

(Step 6)
To a solution of the compound (2.40 g) obtained in step 5 in THF (30 mL) was added 1M BH$_3$.THF complex/THF solution (41.5 mL) was added at 0° C., and the mixture was stirred at 90° C. for 1 hr. After the reaction mixture was cooled to 10°

C., MeOH (10 mL) was added, and the mixture was concentrated under reduced pressure. The residue was suspended in MeOH (15 mL) and 6N hydrochloric acid (15 mL), and the mixture was stirred at 80° C. for 1 hr. The reaction mixture was cooled to 10° C., and made basic with aqueous sodium hydroxide solution, and the resultant product was extracted with ethyl acetate. The organic layer was washed with brine, and concentrated. The residue was purified by silica gel column chromatography (solvent; 5% ethyl acetate/hexane) to give the title compound (1.80 g, 79%) as a colorless oil.

$^1$H-NMR (CDCl$_3$): δ 3.14-3.18 (2H, m), 3.66 (2H, s), 3.81 (2H, s), 4.17-4.20 (2H, m), 6.87 (1H, d, J=4.8 Hz), 7.25-7.38 (5H, m), 8.01 (1H, d, J=4.8 Hz)

MS (ESI+): 275 (M+H)

Example 9

4-benzyl-3,4,5,6-tetrahydro-2H-pyrido[3,2-g][1,4]oxazocine (Step 1)

To a suspension of lithium aluminum hydride (8.60 g) in THF (200 mL) was added a solution of 2-chloronicotinic acid (22.4 g) in THF (30 mL) at 0° C., and the mixture was stirred at 50° C. for 1 hr. After the reaction mixture was cooled to 0° C., 1N aqueous sodium hydroxide solution (9 mL) was added. The precipitate was filtered off, and the filtrate was concentrated. The residue was purified by silica gel column chromatography (solvent gradient; 10→25% ethyl acetate/hexane) to give (2-chloropyridin-3-yl)methanol (14.0 g, 68%) as a colorless oil.

$^1$H-NMR (CDCl$_3$): δ 2.42-2.75 (1H, m), 4.80 (2H, d, J=4.8 Hz), 7.29 (1H, dd, J=7.8, 4.8 Hz), 7.88-7.93 (1H, m), 8.29-8.32 (1H, m)

(Step 2)

To a solution of the compound (18.5 g) obtained in step 1 in a mixture of chloroform (95 mL) and DMF (0.63 mL) was added thionyl chloride (14.0 mL) at 0° C., and the mixture was stirred at room temperature for 4 hr. The reaction mixture was concentrated under reduced pressure, and the residue was poured into a mixture of water and ethyl acetate. The solution was neutralized with sodium hydrogen carbonate, and the resultant product was extracted with ethyl acetate. The organic layer was washed with brine, and concentrated to give 2-chloro-3-(chloromethyl)pyridine (20.5 g, 89%) as a white powder.

$^1$H-NMR (CDCl$_3$): δ 4.74 (2H, s), 7.53 (1H, dd, J=7.6, 5.0 Hz), 8.11 (1H, dd, J=7.6, 1.8 Hz), 8.51 (1H, dd, J=5.0, 1.8 Hz)

(Step 3)

To a solution of the compound (20.5 g) obtained in step 2 in DMSO (100 mL) was added sodium cyanide (12.4 g), and the mixture was stirred at 50° C. for 4 hr. The reaction mixture was concentrated under reduced pressure, and the residue was poured into a mixture of water and ethyl acetate. The organic layer was washed with brine, and concentrated. The residue was purified by silica gel column chromatography (solvent gradient; 10→25% ethyl acetate/hexane) to give (2-chloropyridin-3-yl)acetonitrile (11.7 g, 61%) as a white powder.

$^1$H-NMR (CDCl$_3$): δ 3.87 (2H, s), 7.34 (1H, dd, J=7.6, 4.8 Hz), 7.88-7.93 (1H, ddd like), 8.41 (1H, dd, J=4.8, 1.8 Hz)

(Step 4)

To a solution of the compound (11.7 g) obtained in step 3 in water (66 mL) was added concentrated sulfuric acid (55.6 mL) at 0° C., and the mixture was stirred at 90° C. for 4 hr. The reaction mixture was poured into ice-cold water, and the precipitate was filtered off. The filtrate was extracted three times with ethyl acetate. The organic layer was washed with brine, and concentrated to give (2-chloropyridin-3-yl)acetic acid (10.5 g, 80%) as a white powder.

$^1$H-NMR (CDCl$_3$+DMSO-d$_6$): δ 3.75 (2H, s), 7.25 (1H, dd, J=7.4, 4.8 Hz), 7.69 (1H, dd, J=7.4, 1.8 Hz), 8.31 (1H, dd, J=4.8, 1.8 Hz)

(Step 5)

To a solution of the compound (3.40 g) obtained in step 4, N-benzylethanolamine (4.53 g) and HOBt.H$_2$O (4.60 g) in DMF (50 mL) was added WSC.HCl (5.80 g), and the mixture was stirred at room temperature for 4 days. The reaction mixture was poured into water, and the mixture was extracted with ethyl acetate. The organic layer was washed with saturated aqueous sodium hydrogen carbonate solution and brine, and concentrated. The residue was purified by silica gel column chromatography (solvent gradient; 80% ethyl acetate/hexane→2% methanol/ethyl acetate) to give N-benzyl-2-(2-chloropyridin-3-yl)-N-(2-hydroxyethyl)acetamide (6.20 g, 100%) as a pale-yellow oil.

$^1$H-NMR (CDCl$_3$): δ 3.49-3.98 (6H, m), 4.69-4.71 (2H, m), 7.20-7.46 (6H, m), 7.63-7.69 (1H, m), 8.30 (1H, dd, J=4.8, 1.8 Hz)

(Step 6)

To a solution of the compound (2.00 g) obtained in step 5 in THF (30 mL) was added 1M BH$_3$.THF complex/THF solution (32.0 mL) at 0° C., and the mixture was stirred at 90° C. for 1 hr. After the reaction mixture was cooled to 10° C., MeOH (10 mL) was added, and the mixture was concentrated under reduced pressure. The residue was suspended in 6N hydrochloric acid (32 mL), and the mixture was stirred at 100° C. for 2 hr. The reaction mixture was cooled to 10° C., and made basic with aqueous sodium hydroxide solution, and the resultant product was extracted with ethyl acetate. The organic layer was washed with brine, and concentrated. The residue was purified by silica gel column chromatography (solvent gradient; 33→50% ethyl acetate/hexane) to give 2-(benzyl(2-(2-chloropyridin-3-yl)ethyl)amino)ethanol (0.88 g, 46%) as a colorless oil.

$^1$H-NMR (CDCl$_3$): δ 2.40-2.60 (1H, br), 2.74-2.84 (4H, m), 2.85-2.95 (2H, m), 3.59 (2H, t, J=5.3 Hz), 3.71 (2H, s), 7.15 (1H, dd, J=7.5, 4.5 Hz), 7.20-7.35 (5H, m), 7.46 (1H, dd, J=7.5, 2.1 Hz), 8.25 (1H, dd, J=4.5, 1.8 Hz)

(Step 7)

Under a nitrogen atmosphere, to a suspension of sodium hydride (60% in oil, 0.24 g) in THF (5 mL) was added a solution of the compound (0.88 g) obtained in step 6 in THF (10 mL) at 0° C., and the mixture was stirred at 80° C. for 6 hr. The reaction mixture was cooled to 10° C., and poured into water. The resultant product was extracted with ethyl acetate. The organic layer was washed with saturated aqueous ammonium chloride solution and brine, and concentrated. The residue was purified by silica gel column chromatography (solvent gradient; 20→33% ethyl acetate/hexane) to give the title compound (0.59 g, 77%) as a colorless oil.

$^1$H-NMR (CDCl$_3$): δ 2.77-2.87 (6H, m), 3.73 (2H, s), 4.15-4.18 (2H, dt like), 7.00-7.08 (3H, m), 7.16-7.25 (3H, m), 7.43 (1H, dd, J=7.5, 2.1 Hz), 8.23 (1H, dd, J=4.8, 1.8 Hz)

MS (ESI+): 255 (M+H)

Example 10

4-benzyl-9-methyl-3,4,5,6-tetrahydro-2H-pyrido[3,2-g][1,4]oxazocine monohydrochloride The title compound was obtained by reaction in the same manner as in Example 9 and using 2-chloro-6-methylnicotinic acid, and treating the obtained product with 1 equivalent of 4N hydrogen chloride/ethyl acetate.

MS (ESI+): 269 (M−HCl+H)

Example 11 tert-butyl 4-(4-benzyl-2,3,4,5-tetrahydropyrido[3,2-f][1,4]oxazepin-8-yl)piperazine-1-carboxylate (Method 1)

A solution of the compound (0.275 g) obtained in Example 3, N-Boc-piperazine (0.205 g), 2-dicyclohexylphosphino-2',4',6'-triisopropyl-1,1'-biphenyl (XPhos) (0.048 g) and $^t$BuONa (0.134 g) in toluene (5 mL) was degassed with argon gas, tris(dibenzylideneacetone)dipalladium(0) (Pd$_2$(dba)$_3$) (0.046 g) was added, and the mixture was stirred at 50° C. for 3 hr under an argon atmosphere. The reaction mixture was poured into water, and the resultant product was extracted with ethyl acetate. The organic layer was washed with saturated aqueous ammonium chloride solution and brine, and concentrated. The residue was purified by silica gel column chromatography (solvent gradient; 10→33% ethyl acetate/hexane) to give the title compound (0.270 g, 64%) as a white powder.

(Method 2)

A solution of the compound (1.30 g) obtained in Example 3, N-Boc-piperazine (0.97 g), XPhos (0.113 g) and $^t$BuONa (0.637 g) in toluene (25 mL) was degassed with argon gas, palladium acetate (Pd(OAc)$_2$) (0.053 g) was added and the mixture was stirred at 50° C. for 6 hr under argon atmosphere. The reaction mixture was poured into water, and the resultant product was extracted with ethyl acetate. The organic layer was washed with saturated aqueous ammonium chloride solution and brine, and concentrated. The residue was purified by silica gel column chromatography (solvent gradient; 10→33% ethyl acetate/hexane) to give the title compound (0.795 g, 40%) as a white powder.

$^1$H-NMR (CDCl$_3$): δ 1.48 (9H, s), 3.04-3.07 (2H, m), 3.47-3.56 (8H, m), 3.64 (2H, s), 3.66 (2H, s), 4.18-4.22 (2H, m), 6.28 (1H, d, J=8.4 Hz), 7.20 (1H, d, J=8.4 Hz), 7.24-7.35 (5H, m)

MS (ESI+): 425 (M+H)

Example 12 tert-butyl 4-(4-benzyl-7-fluoro-2,3,4,5-tetrahydropyrido[3,2-f][1,4]oxazepin-8-yl)piperazine-1-carboxylate The title compound was obtained in the same manner as in Example 11, method 2, and using the compound obtained in Example 4.

$^1$H-NMR (CDCl$_3$): δ 1.48 (9H, s), 3.04-3.08 (2H, m), 3.40-3.50 (4H, m), 3.50-3.60 (4H, m), 3.61 (2H, s), 3.66 (2H, s), 4.15-4.20 (2H, m), 6.97 (1H, d, J=12.0 Hz), 7.25-7.38 (5H, m)

MS (ESI+): 443 (M+H)

Example 13

4-benzyl-8-piperazin-1-yl-2,3,4,5-tetrahydropyrido[3,2-f][1,4]oxazepine trihydrochloride To a solution of the compound (0.15 g) in MeOH (10 mL) was added 4N hydrogen chloride/ethyl acetate (0.35 mL), and the mixture was stirred at 50° C. for 2 hr. The reaction mixture was concentrated under reduced pressure, and the residue was triturated with ethyl acetate to give the title compound (0.15 g, 100%) as white amorphous.

$^1$H-NMR (DMSO-d$_6$): δ 3.10-3.20 (4H, m), 3.34-3.55 (2H, m), 3.70-3.80 (4H, m), 4.15-4.60 (6H, m), 6.67 (1H, d, J=8.1 Hz), 7.44-7.50 (3H, m), 7.53 (1H, d, J=8.1 Hz), 7.62-7.70 (2H, m), 9.46 (2H, brs), 11.62 (1H, brs)

MS (ESI+): 325 (M−3HCl+H)

Example 14 tert-butyl 4-(4-benzyl-2,3,4,5-tetrahydropyrido[3,2-f][1,4]oxazepin-8-yl)-1,4-diazepane-1-carboxylate The title compound was obtained in the same manner as in method 2 of Example 11 and Using the compound obtained in Example 3 and 1-Boc-homopiperazine.

$^1$H-NMR (CDCl$_3$): δ 1.40-1.44 (9H, m), 1.90-2.00 (2H, m), 3.02-3.05 (2H, m), 3.20-3.38 (2H, m), 3.50-3.70 (8H, m), 3.73-3.77 (2H, m), 4.17-4.20 (2H, m), 6.15 (1H, d, J=8.1 Hz), 7.14 (1H, d, J=8.1 Hz), 7.20-7.35 (5H, m)

MS (ESI+): 439 (M+H)

Example 15

4-benzyl-8-(1,4-diazepan-1-yl)-2,3,4,5-tetrahydropyrido[3,2-f][1,4]oxazepine trihydrochloride The title compound was obtained in the same manner as in Example 13 and using the compound obtained in Example 14.

$^1$H-NMR (DMSO-d$_6$): δ 2.00-2.20 (2H, m), 3.05-3.30 (4H, m), 3.30-3.55 (2H, m), 3.60-3.70 (2H, m), 3.85-4.00 (4H, m), 4.10-4.65 (6H, m), 6.50 (1H, d, J=8.4 Hz), 7.45-7.48 (4H, m), 7.60-7.80 (2H, m), 9.36 (3H, brs), 11.60 (2H, brs)

MS (ESI+): 339 (M−3HCl+H)

Example 16 tert-butyl 4-(4-benzyl-3-methyl-2,3,4,5-tetrahydropyrido[3,2-f][1,4]oxazepin-8-yl)piperazine-1-carboxylate The title compound was obtained in the same manner as in method 1 of Example 11 and using the compound obtained in Example 5.

$^1$H-NMR (CDCl$_3$): δ 1.22 (3H, d, J=6.4 Hz), 1.48 (9H, s), 3.20-3.30 (1H, m), 3.51 (9H, m), 3.69 (2H, s), 4.03 (1H, d, J=15.6 Hz), 4.12 (1H, dd, J=12.8, 7.3 Hz), 4.24 (1H, dd, J=12.8, 3.0 Hz), 6.26 (1H, d, J=8.1 Hz), 7.11 (1H, d, J=8.1 Hz), 7.24-7.35 (5H, m)

MS (ESI+): 439 (M+H)

Example 17

4-benzyl-3-methyl-8-piperazin-1-yl-2,3,4,5-tetrahydropyrido[3,2-f][1,4]oxazepine trihydrochloride The title compound was obtained in the same manner as in Example 13 and using the compound obtained in Example 16.

$^1$H-NMR (DMSO-d$_6$): δ 1.44 & 1.53 (total 3H, d, J=6.9 Hz), 3.13 (4H, brs), 3.75 (4H, brs), 4.10-4.40 (4H, m), 4.55 (1H, t like), 6.68 (1H, d, J=4.6 Hz), 7.46 (3H, brs), 7.54 (1H, d, J=8.3 Hz), 7.70 (2H, brs), 9.56 (3H, brs), 11.40 & 11.76 (total 3H, brs)

MS (ESI+): 339 (M−3HCl+H)

Example 18 tert-butyl 4-(4-benzyl-2-methyl-2,3,4,5-tetrahydropyrido[3,2-f][1,4]oxazepin-8-yl)piperazine-1-carboxylate The title compound was obtained in the same manner as in method 1 of Example 11 and using the compound obtained in Example 6.

¹H-NMR (CDCl₃): δ 1.35 (3H, d, J=6.4 Hz), 1.48 (9H, s), 2.85-3.00 (2H, m), 3.50 (8H, brs), 3.62 (2H, d, J=10.9 Hz), 3.66 (2H, d, J=4.5 Hz), 4.31 (1H, m), 6.27 (1H, d, J=7.9 Hz), 7.16 (1H, d, J=8.3 Hz), 7.25-7.35 (5H, m)
MS (ESI+): 439 (M+H)

Example 19

4-benzyl-2-methyl-8-piperazin-1-yl-2,3,4,5-tetrahydropyrido[3,2-f][1,4]oxazepine trihydrochloride The title compound was obtained in the same manner as in Example 13 and using the compound obtained in Example 18.
¹H-NMR (DMSO-d₆): δ 1.32 (3H, d, J=6.4 Hz), 3.14 (4H, brs), 3.20-3.50 (2H, m), 3.72 (4H, brs), 3.85-4.80 (7H, m), 6.66 (1H, d like), 7.45-7.50 (4H, m), 7.60-7.70 (2H, m), 9.32 (2H, brs)
MS (ESI+): 339 (M−3HCl+H)

Example 20

4-benzyl-2-methyl-8-morpholin-4-yl-2,3,4,5-tetrahydropyrido[3,2-f][1,4]oxazepine The title compound was obtained in the same manner as in method 1 of Example 11 and using the compound obtained in Example 6 and morpholine.
¹H-NMR (CDCl₃): δ 1.36 (3H, d, J=6.4 Hz), 2.92 (2H, ddd like), 3.47 (4H, m), 3.55-3.75 (4H, m), 3.80 (4H, t, J=4.9 Hz), 4.25-4.40 (1H, m), 6.26 (1H, d, J=8.3 Hz), 7.18 (1H, d, J=8.0 Hz), 7.25-7.40 (5H, m)
MS (ESI+): 340 (M+H)

Example 21

4-benzyl-2-methyl-8-piperidin-1-yl-2,3,4,5-tetrahydropyrido[3,2-f][1,4]oxazepine The title compound was obtained in the same manner as in method 1 of Example 11 and using the compound obtained in Example 6 and piperidine.
¹H-NMR (CDCl₃): δ 1.35 (3H, d, J=6.4 Hz), 1.57-1.65 (6H, m), 2.85-2.95 (2H, m), 3.64 (4H, brs), 3.60-3.75 (4H, m), 4.25-4.35 (1H, m), 6.27 (1H, d, J=8.3 Hz), 7.12 (1H, d, J=8.3 Hz), 7.25-7.40 (5H, m)
MS (ESI+): 338 (M+H)

Example 22 tert-butyl 4-(3-methyl-2,3,4,5-tetrahydropyrido[3,2-f][1,4]oxazepin-8-yl)piperazine-1-carboxylate To a solution of the compound (0.23 g) obtained in Example 16 in MeOH (5 mL) was added 10% palladium hydroxide (0.023 g), and the mixture was stirred at room temperature for 20 hr under a hydrogen atmosphere (1 atm). The catalyst was filtered off, and the filtrate was concentrated under reduced pressure to give the title compound (0.17 g, 92%) as a white powder.
¹H-NMR (CDCl₃): δ 1.12 (3H, d, J=6.6 Hz), 1.48 (9H, s), 1.64 (1H, brs), 3.25-3.35 (1H, m), 3.49 (8H, brs like), 3.67 (1H, dd, J=12.3, 8.0 Hz), 3.85 (2H, dt like), 4.36 (1H, dd like), 6.28 (1H, d, J=8.1 Hz), 7.29 (1H, d, J=8.1 Hz)
MS (ESI+): 349 (M+H)

Example 23 tert-butyl 4-(3,4-dimethyl-2,3,4,5-tetrahydropyrido[3,2-f][1,4]oxazepin-8-yl)piperazine-1-carboxylate To a solution of the compound (0.30 g) obtained in Example 22 and paraformaldehyde (0.052 g) in a mixture of acetic acid (0.20 mL) and CH₂Cl₂ (4 mL) was added NaBH(OAc)₃ (0.274 g), and the mixture was stirred at room temperature for 25 hr. Paraformaldehyde (0.052 g) and NaBH(OAc)₃ (0.274 g) were further added, and the mixture was stirred at room temperature for 3 days. The reaction mixture was poured into water, and the resultant product was extracted with CH₂Cl₂. The organic layer was washed with water and brine, and concentrated. The residue was purified by silica gel column chromatography (solvent gradient; 30→60% ethyl acetate/hexane) to give the title compound (0.122 g, 39%) as a colorless oil.
¹H-NMR (CDCl₂): δ 1.17 (3H, d, J=6.8 Hz), 1.48 (9H, s), 2.34 (3H, s), 3.04 (1H, m), 3.49 (8H, brs like), 3.71 (1H, d, J=15.0 Hz), 3.88 (1H, d, J=15.0 Hz), 3.96 (1H, dd, J=12.9, 7.0 Hz), 4.20 (1H, dd, J=12.9, 2.2 Hz), 6.29 (1H, d, J=8.1 Hz), 7.30 (1H, d, J=8.6 Hz)
MS (ESI+): 363 (M+H)

Example 24

3,4-dimethyl-8-piperazin-1-yl-2,3,4,5-tetrahydropyrido[3,2-f][1,4]oxazepine trihydrochloride The compound (0.086 g) obtained in Example 23 in 4N hydrogen chloride/ethyl acetate (3.0 mL) was stirred at room temperature for 2 hr. The precipitate was collected by filtration, and recrystallized from MeOH-ethyl acetate to give the title compound (0.063 g, 71%) as a white powder.
¹H-NMR (DMSO-d₆): δ 1.25 & 1.47 (total 3H, d×2, J=6.8 & 6.4 Hz), 2.78 (1H, brs like), 3.15 (4H, brs like), 3.73 (1H, brs like), 3.90-4.20 (2H, m), 4.24 & 4.18 (total 3H, s×2), 4.44 (2H, t like), 6.68 & 6.72 (total 1H, d×2, J=8.3 & 8.5 Hz), 7.66 & 7.72 (total 1H, d×2, J=8.3 & 8.3 Hz), 9.38 (2H, brs), 11.08 & 11.69 (total 1H, brs×2)
MS (ESI+): 263 (M−3HCl+H)

Example 25 tert-butyl 4-(4-benzyl-2,3,4,5-tetrahydropyrido[4,3-f][1,4]oxazepin-9-yl)piperazine-1-carboxylate The title compound was obtained in the same manner as in Example 11, method 2, and using the compound obtained in Example 8.
¹H-NMR (CDCl₃): δ 1.48 (9H, s), 3.09-3.12 (2H, m), 3.37-3.43 (4H, m), 3.53-3.60 (4H, m), 3.65 (2H, s), 3.74 (2H, s), 4.05-4.09 (2H, m), 6.51 (1H, d, J=4.8 Hz), 7.25-7.38 (5H, m), 7.87 (1H, d, J=4.8 Hz)
MS (ESI+): 425 (M+H)

Example 26

4-benzyl-9-piperazin-1-yl-2,3,4,5-tetrahydropyrido[4,3-f][1,4]oxazepine monohydrochloride A solution of the compound (0.450 g) obtained in Example 25 in a mixture of 4N hydrogen chloride/ethyl acetate (5 mL) and MeOH (5 mL) was stirred at room temperature for 14 hr.

The reaction mixture was concentrated under reduced pressure, water and ethyl acetate were added to the residue, and the mixture was made basic with aqueous sodium hydroxide solution. The organic layer was washed with brine, and concentrated. The residue was purified by silica gel column chromatography (solvent gradient; 50% ethyl acetate/hexane→1% ammonia/ethyl acetate) to give 4-benzyl-9-piperazin-1-yl-2,3,4,5-tetrahydropyrido[4,3-f][1,4]oxazepine (0.21 g, 61%) as a colorless oil.

$^1$H-NMR (CDCl$_3$): δ 3.01-3.60 (4H, m), 3.09-3.12 (2H, m), 3.39-3.43 (4H, m), 3.65 (2H, s), 3.74 (2H, s), 4.05-4.09 (2H, m), 6.50 (1H, d, J=4.8 Hz), 7.25-7.40 (5H, m), 7.88 (1H, d, J=4.8 Hz)

The obtained oil (0.21 g) was treated with 1 equivalent of 4N hydrogen chloride/ethyl acetate to give the title compound (0.125 g) as a white powder.

MS (ESI+): 325 (M−HCl+H)

Example 27

2,3,4,5-tetrahydropyrido[3,2-f][1,4]oxazepine dihydrochloride (Step 1)

To a solution of the compound (4.36 g) obtained in Example 1 in 1,2-dichloroethane (30 mL) was added 1-chloroethyl chloroformate (2.4 mL) at room temperature, and the mixture was stirred at 100° C. for 2 hr. The reaction mixture was concentrated under reduced pressure, the obtained residue was dissolved in MeOH (30 mL), and the mixture was stirred at 80° C. for 1 hr. The reaction mixture was concentrated under reduced pressure, and the obtained residue was dissolved in acetonitrile (20 mL). Et$_3$N (0.64 and Boc$_2$O (1.0 g) were added, and the mixture was stirred at room temperature for 14 hr. The reaction mixture was poured into water, and the resultant product was extracted with ethyl acetate. The organic layer was washed with saturated aqueous ammonium chloride solution and brine and dried, and the solvent was evaporated under reduced pressure. The obtained residue was purified by silica gel column chromatography (solvent gradient; 20→66% ethyl acetate/hexane) to give tert-butyl 2,3-dihydropyrido[3,2-f][1,4]oxazepine-4(5H)-carboxylate (2.4 g, 54%) as a white powder.

$^1$H-NMR (CDCl$_3$): δ 1.42 (9H, s), 3.84 (2H, t, J=4.5 Hz), 4.21 (2H, t, J=4.5 Hz), 4.38-4.52 (2H, m), 7.00-7.04 (1H, m), 7.53-7.70 (1H, m), 8.14-8.24 (1H, br)

(Step 2)

The title compound was obtained in the same manner as in Example 13 and using the compound obtained in step 1.

$^1$H-NMR (DMSO-d$_6$): δ 3.44-3.54 (2H, m), 4.30-4.42 (4H, m), 7.23 (1H, dd, J=6.9, 4.5 Hz), 7.96 (1H, dd, J=6.9, 1.5 Hz), 8.24 (1H, dd, J=4.5, 1.5 Hz), 9.97 (3H, brs)

MS (ESI+): 151 (M−2HCl+H)

Example 28

8-methyl-2,3,4,5-tetrahydropyrido[3,2-f][1,4]oxazepine dihydrochloride

The title compound was obtained in the same manner as in Example 27 and using the compound obtained in Example 2.

$^1$H-NMR (DMSO-d$_6$): δ 2.41 (3H, s), 3.48 (2H, brs), 4.26-4.40 (4H, m), 6.60-7.30 (1H, br), 7.11 (1H, d, J=7.5 Hz), 7.86 (1H, d, J=7.5 Hz), 9.92 (2H, brs)

MS (ESI+): 165 (M−2HCl+H)

Example 29

8-chloro-2,3,4,5-tetrahydropyrido[3,2-f][1,4]oxazepine monohydrochloride (Step 1)

tert-Butyl 8-chloro-2,3-dihydropyrido[3,2-f][1,4]oxazepine-4(5H)-carboxylate was obtained as a white powder in the same manner as in Example 27, step 1, and using the compound obtained in Example 3.

$^1$H-NMR (CDCl$_3$): δ 1.42 (9H, s), 3.84 (2H, t like, J=4.5 Hz), 4.22 (2H, t like, J=4.5 Hz), 4.35-4.50 (2H, m), 7.05 (1H, d like, J=7.2 Hz), 7.45-7.64 (1H, m)

(Step 2)

The title compound was obtained in the same manner as in Example 13 and using the compound obtained in step 1.

$^1$H-NMR (DMSO-d$_6$): δ 3.49-3.52 (2H, m), 4.36 (2H, s), 4.39-4.43 (2H, m), 7.35 (1H, d, J=7.8 Hz), 7.97 (1H, d, J=7.8 Hz), 9.80 (2H, brs)

MS (ESI+): 185 (M−HCl+H)

Example 30 tert-butyl 4-(2,3,4,5-tetrahydropyrido[3,2-f][1,4]oxazepin-8-yl)piperazine-1-carboxylate The title compound was obtained in the same manner as in Example 22 and using the compound obtained in Example 11.

$^1$H-NMR (CDCl$_3$): δ 1.47 (9H, s), 3.22 (2H, t, J=4.5 Hz), 3.49 (8H, s like), 3.83 (2H, s), 4.18 (2H, t, J=4.5 Hz), 6.28 (1H, d, J=8.1 Hz), 7.31 (1H, d, J=8.1 Hz)

MS (ESI+): 335 (M+H)

Example 31

8-piperazin-1-yl-2,3,4,5-tetrahydropyrido[3,2-f][1,4]oxazepine trihydrochloride

The title compound was obtained in the same manner as in Example 13 and using the compound obtained in Example 30.

$^1$H-NMR (DMSO-d$_6$): δ 3.11 (4H, brs), 3.40-3.50 (2H, m), 3.70-3.80 (4H, m), 4.17 (2H, brs), 4.28 (2H, brs), 6.66 (1H, d, J=8.4 Hz), 7.69 (1H, d, J=8.4 Hz), 9.40-9.85 (4H, m)

MS (ESI+): 235 (M−3HCl+H)

Example 32 benzyl 4-(2,3,4,5-tetrahydropyrido[3,2-f][1,4]oxazepin-8-yl)piperazine-1-carboxylate dihydrochloride (Step 1)

tert-Butyl 8-{4-[(benzyloxy)carbonyl]piperazin-1-yl}-2,3-dihydropyrido[3,2-f][1,4]oxazepine-4(5H)-carboxylate was obtained in the same manner as in Example 11, method 2, and using the compound obtained in Example 29, step 1 and benzyl 1-piperazinecarboxylate.

$^1$H-NMR (CDCl$_3$): δ 1.42 (9H, s), 3.48-3.65 (8H, m), 3.78 (2H, t, J=4.5 Hz), 4.15-4.44 (4H, m), 5.16 (2H, s), 6.29 (1H, d, J=7.8 Hz), 7.28-7.40 (6H, m)

(Step 2)

The title compound was obtained in the same manner as in Example 26 and using the compound obtained in step 1.

$^1$H-NMR (DMSO-d$_6$): δ 3.35-3.58 (6H, m), 4.15 (2H, brs), 4.25 (2H, brs), 4.90-5.20 (4H, br), 5.11 (2H, s), 6.58 (1H, d, J=8.4 Hz), 7.30-7.45 (5H, m), 7.63 (1H, d, J=8.4 Hz), 9.62 (2H, brs)

MS (ESI+): 369 (M−2HCl+H)

Example 33 methyl 4-(2,3,4,5-tetrahydropyrido[3,2-f][1,4]ox-azepin-8-yl)piperazine-1-carboxylate (Step 1)

To a solution of the compound (1.11 g) obtained in Example 32, step 1 in EtOH (30 mL) was added 10% palladium hydroxide (0.20 g), and the mixture was stirred at room temperature for 14 hr under a hydrogen atmosphere (1 atm). The catalyst was filtered off, and the filtrate was concentrated under reduced pressure to give tert-butyl 8-piperazin-1-yl-2,3-dihydropyrido[3,2-f][1,4]oxazepine-4(5H)-carboxylate (0.45 g, 57%) as a white powder.

$^1$H-NMR (CDCl$_3$): δ 1.42 (9H, s), 2.98 (4H, t, J=5.0 Hz). 3.50 (4H, t, J=5.0 Hz), 3.79 (2H, t, J=4.5 Hz), 4.15-4.42 (4H, m), 6.30 (1H, d, J=8.4 Hz), 7.30-7.45 (1H, m)

(Step 2)

To a solution of the compound (0.26 g) obtained in step 1 and Et$_3$N (0.21 mL) in THF (10 mL) was added methyl chloroformate (0.12 mL) at 0° C., and the mixture was stirred at 0° C. for 1 hr. The reaction mixture was poured into water, and the resultant product was extracted with ethyl acetate. The organic layer was washed with saturated aqueous ammonium chloride solution and brine and dried, and the solvent was evaporated under reduced pressure. The obtained residue was purified by silica gel column chromatography (solvent gradient; 10→50% ethyl acetate/hexane) to give tert-butyl 8-[4-(methoxycarbonyl)piperazin-1-yl]-2,3-dihydropyrido[3,2-f][1,4]oxazepine-4(5H)-carboxylate (0.21 g, 69%) as a colorless oil.

$^1$H-NMR(CDCl$_3$): δ 1.42 (9H, s), 3.48-3.60 (8H, m), 3.73 (3H, s), 3.77-3.81 (2H, m), 4.15-4.42 (4H, m), 6.30 (1H, d, J=8.0 Hz), 7.30-7.50 (1H, m)

(Step 3)

A solution of the compound (0.21 g) obtained in step 2 in a mixture of 4N hydrogen chloride/ethyl acetate (5 mL) and ethyl acetate (5 mL) was stirred at room temperature for 3 hr. The reaction mixture was concentrated under reduced pressure, water and ethyl acetate were added to the residue, and the mixture was made basic with aqueous sodium hydroxide solution. The organic layer was washed with brine, and concentrated to give the title compound (0.13 g, 83%) as a white powder.

$^1$H-NMR (CDCl$_3$): δ 3.20-3.23 (2H, m), 3.47-3.60 (8H, m), 3.73 (3H, s), 3.83 (2H, s), 4.16-4.20 (2H, m), 6.29 (1H, d, J=8.4 Hz), 7.31 (1H, d, J=8.4 Hz)

MS (ESI+): 293 (M+H)

Example 34 isopropyl 4-(2,3,4,5-tetrahydropyrido[3,2-f][1,4]oxazepin-8-yl)piperazine-1-carboxylate The title compound was obtained in the same manner as in Example 33, steps 2 and 3, and using the compound obtained in Example 33, step 1 and isopropyl chloroformate.

$^1$H-NMR (CDCl$_3$): δ 1.27 (6H, d, J=6.3 Hz), 1.42 (9H, s), 3.45-3.60 (8H, m), 3.77-3.81 (2H, m), 4.15-4.45 (4H, m), 4.95 (1H, septet, J=6.3 Hz), 6.30 (1H, d, J=8.1 Hz), 7.30-7.50 (1H, m)

MS (ESI+): 321 (M+H)

Example 35

8-(4-acetylpiperazin-1-yl)-2,3,4,5-tetrahydropyrido[3,2-f][1,4]oxazepine

The title compound was obtained in the same manner as in Example 33, steps 2 and 3, and using the compound obtained in Example 33, step 1 and acetyl chloride.

$^1$H-NMR (CDCl$_3$): δ 2.14 (3H, s), 3.20-3.24 (2H, m), 3.43-3.50 (2H, m), 3.52-3.64 (4H, m), 3.70-3.75 (2H, m), 3.84 (2H, s), 4.17-4.20 (2H, m), 6.29 (1H, d, J=8.1 Hz), 7.33 (1H, J=8.1 Hz)

MS (ESI+): 277 (M+H)

Example 36

8-(4-isobutyrylpiperazin-1-yl)-2,3,4,5-tetrahydropyrido[3,2-f][1,4]oxazepine The title compound was obtained in the same manner as in Example 33, steps 2 and 3, and using the compound obtained in Example 33, step 1 and isobutyryl chloride.

$^1$H-NMR (CDCl$_3$): δ 1.15 (6H, d, J=6.6 Hz), 2.83 (1H, septet, J=6.6 Hz), 3.20-3.23 (2H, m), 3.40-3.50 (2H, m), 3.60 (4H, s like), 3.68-3.80 (2H, m), 3.84 (2H, s), 4.16-4.20 (2H, m), 6.30 (1H, d, J=8.4 Hz), 7.33 (1H, d, J=8.4 Hz)

MS (ESI+): 305 (M+H)

Example 37

8-[4-(3,3-dimethylbutanoyl)piperazin-1-yl]-2,3,4,5-tetrahydropyrido[3,2-f][1,4]oxazepine The title compound was obtained in the same manner as in Example 33, steps 2 and 3, and using the compound obtained in Example 33, step 1 and tert-butylacetyl chloride.

$^1$H-NMR (CDCl$_3$): δ 1.07 (9H, s), 2.30 (2H, s), 3.20-3.23 (2H, m), 3.43-3.47 (2H, m), 3.54-3.64 (4H, m), 3.72-3.76 (2H, m), 3.84 (2H, s), 4.16-4.20 (2H, m), 6.29 (1H, d, J=8.1 Hz), 7.32 (1H, d, J=8.1 Hz)

MS (ESI+): 333 (M+H)

Example 38

N-isopropyl-4-(2,3,4,5-tetrahydropyrido[3,2-f][1,4]oxazepin-8-yl)piperazine-1-carboxamide The title compound was obtained in the same manner as in Example 33, steps 2 and 3, and using the compound obtained in Example 33, step 1 and isopropyl isocyanate.

$^1$H-NMR (CDCl$_3$): δ 1.17 (6H, d, J=6.6 Hz), 3.20-3.23 (2H, m), 3.44-3.50 (4H, m), 3.52-3.58 (4H, m), 3.83 (2H, s), 4.00 (1H, septet, J=6.6 Hz), 4.16-4.28 (3H, m), 6.27 (1H, d, J=8.1 Hz), 7.31 (1H, d, J=8.1 Hz)

MS (ESI+): 320 (M+H)

Example 39

8-(4-isopropylsulfonylpiperazin-1-yl)-2,3,4,5-tetrahydropyrido[3,2-f][1,4]oxazepine The title compound was obtained in the same manner as in Example 33, steps 2 and 3, and using the compound obtained in Example 33, step 1 and isopropylsulfonyl chloride.

$^1$H-NMR (CDCl$_3$): δ 1.36 (6H, d, J=6.9 Hz), 3.16-3.26 (3H, m), 3.42-3.45 (4H, m), 3.56-3.60 (4H, m), 3.84 (2H, s), 4.16-4.20 (2H, m), 6.29 (1H, d, J=7.8 Hz), 7.33 (1H, d, J=7.8 Hz)

MS (ESI+): 341 (M+H)

Example 40

8-piperidin-1-yl-2,3,4,5-tetrahydropyrido[3,2-f][1,4]oxazepine (Step 1)
tert-Butyl 8-piperidin-1-yl-2,3-dihydropyrido[3,2-f][1,4]oxazepine-4(5H)-carboxylate was obtained in the same manner as in Example 11, method 2, and using the compound obtained in Example 29, step 1 and piperidine.
$^1$H-NMR (CDCl$_3$): δ 1.42 (9H, s), 1.62 (6H, brs), 3.48 (4H, brs), 3.76-3.79 (2H, m), 4.12-4.40 (4H, m), 6.30 (1H, d, J=8.4 Hz), 7.25-7.40 (1H, m)
(Step 2)
The title compound was obtained in the same manner as in Example 33, step 3, and using the compound obtained in step 1.
$^1$H-NMR (CDCl$_3$): δ 1.62 (6H, s like), 3.18-3.22 (2H, m), 3.44-4.54 (4H, brs), 3.81 (2H, s), 4.15-4.19 (2H, m), 6.28 (1H, d, J=8.1 Hz), 7.26 (1H, d, J=8.1 Hz)
MS (ESI+): 234 (M+H)

Example 41

8-morpholin-4-yl-2,3,4,5-tetrahydropyrido[3,2-f][1,4]oxazepine

The title compound was obtained in the same manner as in Example 40 and using the compound obtained in Example 29, step 1 and morpholine.
$^1$H-NMR (CDCl$_3$): δ 3.20-3.23 (2H, m), 3.44-3.48 (4H, m), 3.77-3.81 (4H, m), 3.84 (2H, s), 4.16-4.20 (2H, m), 6.28 (1H, d, J=8.1 Hz), 7.32 (1H, d, J=8.1 Hz)
MS (ESI+): 236 (M+H)

Example 42 tert-butyl 4-(2,3,4,5-tetrahydropyrido[3,2-f][1,4]oxazepin-8-yl)-1,4-diazepane-1-carboxylate The title compound was obtained in the same manner as in Example 11, method 2 and Example 22, and using the compound obtained in Example 3 and 1-Boc-homopiperazine.
$^1$H-NMR (CDCl$_3$): δ 1.40-1.44 (9H, m), 1.90-2.00 (2H, m), 3.18-3.38 (4H, m), 3.50-3.68 (4H, m), 3.74 (2H, t, J=4.5 Hz), 3.81 (2H, s), 4.17 (2H, t, J=4.5 Hz), 6.15 (1H, d, J=8.4 Hz), 7.25 (1H, d, J=8.4 Hz)
MS (ESI+): 349 (M+H)

Example 43

8-pyrrolidin-1-yl-2,3,4,5-tetrahydropyrido[3,2-f][1,4]oxazepine bis(trifluoroacetate)

To a solution of the compound obtained in Example 29, step 1 in toluene (0.20 mol/L, 500 μL) were added a solution of pyrrolidine in toluene (0.22 mol/L, 500 μL), XPhos (14.4 mg), Pd(OAc)$_2$ (2.4 mg) and $^t$BuONa (13.5 mg) at room temperature, and the reaction container was degassed with argon gas. The reaction container was irradiated in a microwave reaction apparatus at 80° C. for 6 min. Water (2 mL) was added to the reaction mixture, and the mixture was extracted with ethyl acetate (3 mL). Ethyl acetate was evaporated under reduced pressure, and the residue was dissolved in DMSO (1 mL) and purified by preparative HPLC. TFA (1.5 mL) was added to the obtained residue, and the mixture was stirred at room temperature for 14 hr. TFA was evaporated under reduced pressure, and the residue was dissolved in water (1 mL) and purified by high-resolution preparative HPLC to give the title compound (2.5 mg).
MS (ESI+): 220 (M−2TFA+H)

The compounds described in the following Examples 44-75 were synthesized using the compound obtained in Example 29, step 1 and the corresponding amine derivatives, and reacting and treating in the same manner as in Example 43.

Example 44

N,N-diethyl-2,3,4,5-tetrahydropyrido[3,2-f][1,4]oxazepin-8-amine bis(trifluoroacetate)

MS (ESI+): 222 (M−2TFA+H)

Example 45

N-(2-methoxyethyl)-N-methyl-2,3,4,5-tetrahydropyrido[3,2-f][1,4]oxazepin-8-amine bis(trifluoroacetate)

MS (ESI+): 238 (M−2TFA+H)

Example 46

8-azepan-1-yl-2,3,4,5-tetrahydropyrido[3,2-f][1,4]oxazepine bis(trifluoroacetate)

MS (ESI+): 248 (M−2TFA+H)

Example 47

N-cyclohexyl-N-methyl-2,3,4,5-tetrahydropyrido[3,2-f][1,4]oxazepin-8-amine bis(trifluoroacetate)

MS (ESI+): 262 (M−2TFA+H)

Example 48

N-benzyl-N-methyl-2,3,4,5-tetrahydropyrido[3,2-f][1,4]oxazepin-8-amine bis(trifluoroacetate)

MS (ESI+): 270 (M−2TFA+H)

Example 49

8-(2-methylpiperidin-1-yl)-2,3,4,5-tetrahydropyrido[3,2-f][1,4]oxazepine bis(trifluoroacetate)

MS (ESI+): 248 (M−2TFA+H)

Example 50

8-(3,5-dimethylpiperidin-1-yl)-2,3,4,5-tetrahydropyrido[3,2-f][1,4]oxazepine bis(trifluoroacetate)

MS (ESI+): 262 (M−2TFA+H)

Example 51

8-[(2R,6S)-2,6-dimethylmorpholin-4-yl]-2,3,4,5-tetrahydropyrido[3,2-f][1,4]oxazepine bis(trifluoroacetate)

MS (ESI+): 264 (M−2TFA+H)

Example 52

8-[(2R)-2-(methoxymethyl)pyrrolidin-1-yl]-2,3,4,5-tetrahydropyrido[3,2-f][1,4]oxazepine bis(trifluoroacetate)

MS (ESI+): 264 (M−2TFA+H)

Example 53

8-(4-methylpiperazin-1-yl)-2,3,4,5-tetrahydropyrido[3,2-f][1,4]oxazepine tris(trifluoroacetate)

MS (ESI+): 249 (M−3TFA+H)

Example 54

8-[4-(pyrrolidin-1-yl)piperidin-1-yl]-2,3,4,5-tetrahydropyrido[3,2-f][1,4]oxazepine tris(trifluoroacetate)

MS (ESI+): 303 (M−3TFA+H)

Example 55

8-[4-(pyrimidin-2-yl)piperazin-1-yl]-2,3,4,5-tetrahydropyrido[3,2-f][1,4]oxazepine bis(trifluoroacetate)

MS (ESI+): 313 (M−2TFA+H)

Example 56

N-(1-benzylpyrrolidin-3-yl)-N-methyl-2,3,4,5-tetrahydropyrido[3,2-f][1,4]oxazepin-8-amine tris(trifluoroacetate)

MS (ESI+): 339 (M−3TFA+H)

Example 57

8-(3,4-dihydroquinolin-1(2H)-yl)-2,3,4,5-tetrahydropyrido[3,2-f][1,4]oxazepine bis(trifluoroacetate)

MS (ESI+): 282 (M−2TFA+H)

Example 58

8-[4-(2-phenylethyl)piperazin-1-yl]-2,3,4,5-tetrahydropyrido[3,2-f][1,4]oxazepine tris(trifluoroacetate)

MS (ESI+): 339 (M−3TFA+H)

Example 59

8-(4-phenoxypiperidin-1-yl)-2,3,4,5-tetrahydropyrido[3,2-f][1,4]oxazepine bis(trifluoroacetate)

MS (ESI+): 326 (M−2TFA+H)

Example 60

8-[4-(2-thienylcarbonyl)piperazin-1-yl]-2,3,4,5-tetrahydropyrido[3,2-f][1,4]oxazepine bis(trifluoroacetate)

MS (ESI+): 345 (M−2TFA+H)

Example 61

8-(5,5-dimethyl-1,3,4,5-tetrahydro-2H-2-benzoazepin-2-yl)-2,3,4,5-tetrahydropyrido[3,2-f][1,4]oxazepine bis(trifluoroacetate)

MS (ESI+): 324 (M−2TFA+H)

Example 62

8-(3-phenylpyrrolidin-1-yl)-2,3,4,5-tetrahydropyrido[3,2-f][1,4]oxazepine bis(trifluoroacetate)

MS (ESI+): 296 (M−2TFA+H)

Example 63

N-methyl-N-(3-phenylpropyl)-2,3,4,5-tetrahydropyrido[3,2-f][1,4]oxazepin-8-amine bis(trifluoroacetate)

MS (ESI+): 298 (M−2TFA+H)

Example 64

8-{4-[2-(phenylsulfonyl)ethyl]piperazin-1-yl}-2,3,4,5-tetrahydropyrido[3,2-f][1,4]oxazepine tris(trifluoroacetate)

MS (ESI+): 403 (M−3TFA+H)

Example 65

8-[4-(1H-imidazo[4,5-c]pyridin-1-ylmethyl)piperidin-1-yl]-2,3,4,5-tetrahydropyrido[3,2-f][1,4]oxazepine tris(trifluoroacetate)

MS (ESI+): 365 (M−3TFA+H)

Example 66

8-[4-(2-morpholin-4-ylethyl)piperazin-1-yl]-2,3,4,5-tetrahydropyrido[3,2-f][1,4]oxazepine tetrakis(trifluoroacetate)

MS (ESI+): 348 (M−4TFA+H)

Example 67

8-[4-(4-phenylbutyl)piperazin-1-yl]-2,3,4,5-tetrahydropyrido[3,2-f][1,4]oxazepine tris(trifluoroacetate)

MS (ESI+): 367 (M−3TFA+H)

Example 68

8-[4-(2-pyridin-2-ylethyl)piperazin-1-yl]-2,3,4,5-tetrahydropyrido[3,2-f][1,4]oxazepine tetrakis(trifluoroacetate)

MS (ESI+): 340 (M−4TFA+H)

Example 69

1'-(2,3,4,5-tetrahydropyrido[3,2-f][1,4]oxazepin-8-yl)-2,3-dihydrospiro[indene-1,4'-piperidine]bis(trifluoroacetate)

MS (ESI+): 336 (M−2TFA+H)

Example 70

8-(4-tert-butylpiperidin-1-yl)-2,3,4,5-tetrahydropyrido[3,2-f][1,4]oxazepine bis(trifluoroacetate)

MS (ESI+): 290 (M−2TFA+H)

Example 71

8-(2-phenylmorpholin-4-yl)-2,3,4,5-tetrahydropyrido[3,2-f][1,4]oxazepine bis(trifluoroacetate)

MS (ESI+): 312 (M−2TFA+H)

Example 72

8-[2-(4-methoxyphenyl)morpholin-4-yl]-2,3,4,5-tetrahydropyrido[3,2-f][1,4]oxazepine bis(trifluoroacetate)

MS (ESI+): 342 (M−2TFA+H)

Example 73

8-[2-(2-chlorophenyl)morpholin-4-yl]-2,3,4,5-tetrahydropyrido[3,2-f][1,4]oxazepine bis(trifluoroacetate)

MS (ESI+): 346 (M−2TFA+H)

Example 74

N-(3,3-diphenylbutyl)-N-methyl-2,3,4,5-tetrahydropyrido[3,2-f][1,4]oxazepin-8-amine bis(trifluoroacetate)

MS (ESI+): 388 (M−2TFA+H)

Example 75

8-(octahydroquinolin-1(2H)-yl)-2,3,4,5-tetrahydropyrido[3,2-f][1,4]oxazepine bis(trifluoroacetate)

MS (ESI+): 288 (M−2TFA+H)

Example 76

8-phenyl-2,3,4,5-tetrahydropyrido[3,2-f][1,4]oxazepine (Step 1)

A solution of the compound (0.285 g) obtained in Example 29, step 1, phenylboronic acid (0.183 g) and potassium carbonate (0.138 g) in: a mixture of toluene (10 mL) and water (0.5 mL) was degassed with argon gas, tetrakis(triphenylphosphine)palladium(0) (Pd(PPh$_3$)$_4$) (0.116 g) was added, and the mixture was stirred under argon atmosphere at 90° C. for 14 hr. The reaction mixture was poured into water, and the resultant product was extracted with ethyl acetate. The organic layer was washed with saturated aqueous ammonium chloride solution and brine, and concentrated. The residue was purified by silica gel column chromatography (solvent gradient; 10→33% ethyl acetate/hexane) to give tert-butyl 8-phenyl-2,3-dihydropyrido[3,2-f][1,4]oxazepine-4(5H)-carboxylate (0.040 g, 12%) as a white powder.

$^1$H-NMR (CDCl$_3$): δ 1.43 (9H, s), 3.85-3.88 (2H, m), 4.26-4.29 (2H, m), 4.42-4.58 (2H, m), 7.38-7.75 (5H, m), 7.98 (2H, d, J=7.2 Hz)

(Step 2)

The title compound was obtained in the same manner as in Example 33, step 3, and using the compound obtained in step 1.

$^1$H-NMR (CDCl$_3$): δ 3.27-3.31 (2H, m), 3.99 (2H, s), 4.23-4.28 (2H, m), 7.36-7.50 (4H, m), 7.57 (1H, d, J=7.5 Hz), 7.97-8.02 (2H, m)

MS (ESI+): 227 (M+H)

Example 77

8-(4-methoxyphenyl)-2,3,4,5-tetrahydropyrido[3,2-f][1,4]oxazepine

The title compound was obtained in the same manner as in Example 76 and using the compound obtained in Example 29, step 1 and 4-methoxyphenylboronic acid.

$^1$H-NMR (CDCl$_3$): δ 3.26-3.30 (2H, m), 3.85 (3H, s), 3.97 (2H, s), 4.23-4.26 (2H, m), 6.96 (2H, d, J=8.7 Hz), 7.36 (1H, d, J=7.5 Hz), 7.52 (1H, d, J=7.5 Hz), 7.94 (2H, d, J=8.7 Hz)

MS (ESI+): 257 (M+H)

Example 78

8-(4-methylphenyl)-2,3,4,5-tetrahydropyrido[3,2-f][1,4]oxazepine

The title compound was obtained in the same manner as in Example 76 and using the compound obtained in Example 29, step 1 and 4-methylphenylboronic acid.

$^1$H-NMR (CDCl$_3$): δ 2.39 (3H, s), 3.26-3.30 (2H, m), 3.97 (2H, s), 4.23-4.26 (2H, m), 7.25 (2H, d, J=8.4 Hz), 7.40 (1H, d, J=7.5 Hz), 7.54 (1H, d, J=7.5 Hz), 7.89 (2H, d, J=8.4 Hz)

MS (ESI+): 241 (M+H)

Example 79

8-(4-chlorophenyl)-2,3,4,5-tetrahydropyrido[3,2-f][1,4]oxazepine

The title compound was obtained in the same manner as in Example 76 and using the compound obtained in Example 29, step 1 and 4-chlorophenylboronic acid.

$^1$H-NMR (CDCl$_3$): δ 3.27-3.31 (2H, m), 3.99 (2H, s), 4.24-4.27 (2H, m), 7.38-7.44 (3H, m), 7.57 (1H, d, J=7.8 Hz), 7.93 (2H, d, J=9.0 Hz)

MS (ESI+): 261 (M+H)

Example 80

4-(2,3,4,5-tetrahydropyrido[3,2-f][1,4]oxazepin-8-yl)benzonitrile

The title compound was obtained in the same manner as in Example 76 and using the compound obtained in Example 29, step 1 and 4-cyanophenylboronic acid.

¹H-NMR (CDCl₃): δ 3.29-3.32 (2H, m), 4.01 (2H, s), 4.25-4.29 (2H, m), 7.47 (1H, d, J=7.5 Hz), 7.62 (1H, d, J=7.5 Hz), 7.73 (2H, d, J=8.7 Hz), 8.10 (2H, d, J=8.7 Hz)
MS (ESI+): 252 (M+H)

Example 81

8-(4-fluorophenyl)-2,3,4,5-tetrahydropyrido[3,2-f][1,4]oxazepine bis(trifluoroacetate)

To a solution of the compound obtained in Example 29, step 1 in DME (1.0 mol/L, 1.0 mL) were added 4-fluorophenylboronic acid (210 mg), Pd(PPh₃)₄ (12 mg) and 2.0 mol/L aqueous potassium carbonate solution (0.050 mL) at room temperature, and the reaction container was degassed with argon gas. The reaction container was irradiated in a microwave reaction apparatus at 150° C. for 6 min. Water (2 mL) was added to the reaction mixture, and the mixture was extracted with ethyl acetate (3 ml). Ethyl acetate was evaporated under reduced pressure, and the residue was dissolved in DMSO (1 mL) and purified by preparative HPLC. TFA (1.5 mL) was added to the obtained residue, and the mixture was stirred at room temperature for 14 hr. TFA was evaporated under reduced pressure, and the residue was dissolved in water (1 mL) and purified by high-resolution preparative HPLC to give the title compound (8.4 mg).
MS (ESI+): 245 (M−2TFA+H)

The compounds described in the following Examples 82-120 were synthesized using the compound obtained in Example 29, step 1 and the corresponding phenylboronic acid derivatives, and reacting and treating in the same manner as in Example 81.

Example 82

8-(3-chlorophenyl)-2,3,4,5-tetrahydropyrido[3,2-f][1,4]oxazepine bis(trifluoroacetate)

MS (ESI+): 261 (M−2TFA+H)

Example 83

8-(2-chlorophenyl)-2,3,4,5-tetrahydropyrido[3,2-f][1,4]oxazepine bis(trifluoroacetate)

MS (ESI+): 261 (M−2TFA+H)

Example 84

8-(3-chloro-4-fluorophenyl)-2,3,4,5-tetrahydropyrido[3,2-f][1,4]oxazepine bis(trifluoroacetate)

MS (ESI+): 279 (M−2TFA+H)

Example 85

8-(3,5-dichlorophenyl)-2,3,4,5-tetrahydropyrido[3,2-f][1,4]oxazepine bis(trifluoroacetate)

MS (ESI+): 296 (M−2TFA+H)

Example 86

8-(2,6-dichlorophenyl)-2,3,4,5-tetrahydropyrido[3,2-f][1,4]oxazepine bis(trifluoroacetate)

MS (ESI+): 296 (M−2TFA+H)

Example 87

8-(2,4-dichlorophenyl)-2,3,4,5-tetrahydropyrido[3,2-f][1,4]oxazepine bis(trifluoroacetate)

MS (ESI+): 296 (M−2TFA+H)

Example 88

8-(4-chloro-2-methylphenyl)-2,3,4,5-tetrahydropyrido[3,2-f][1,4]oxazepine bis(trifluoroacetate)

MS (ESI+): 275 (M−2TFA+H)

Example 89

8-(3-chloro-2-methylphenyl)-2,3,4,5-tetrahydropyrido[3,2-f][1,4]oxazepine bis(trifluoroacetate)

MS (ESI+): 275 (M−2TFA+H)

Example 90

8-(3,5-dimethylphenyl)-2,3,4,5-tetrahydropyrido[3,2-f][1,4]oxazepine bis(trifluoroacetate)

MS (ESI+): 255 (M−2TFA+H)

Example 91

8-(2,4-dimethylphenyl)-2,3,4,5-tetrahydropyrido[3,2-f][1,4]oxazepine bis(trifluoroacetate)

MS (ESI+): 255 (M−2TFA+H)

Example 92

8-(4-methoxy-2-methylphenyl)-2,3,4,5-tetrahydropyrido[3,2-f][1,4]oxazepine bis(trifluoroacetate)

MS (ESI+): 271 (M−2TFA+H)

Example 93

8-(3-methoxyphenyl)-2,3,4,5-tetrahydropyrido[3,2-f][1,4]oxazepine bis(trifluoroacetate)

MS (ESI+): 257 (M−2TFA+H)

Example 94

8-(2-ethoxyphenyl)-2,3,4,5-tetrahydropyrido[3,2-f][1,4]oxazepine bis(trifluoroacetate)

MS (ESI+): 271 (M−2TFA+H)

Example 95

8-(1,3-benzodioxol-5-yl)-2,3,4,5-tetrahydropyrido[3,2-f][1,4]oxazepine bis(trifluoroacetate)

MS (ESI+): 271 (M−2TFA+H)

Example 96

8-[4-(methylthio)phenyl]-2,3,4,5-tetrahydropyrido[3,2-f][1,4]oxazepine bis(trifluoroacetate)

MS (ESI+): 273 (M−2TFA+H)

Example 97

3-(2,3,4,5-tetrahydropyrido[3,2-f][1,4]oxazepin-8-yl)aniline tris(trifluoroacetate)

MS (ESI+): 242 (M−3TFA+H)

Example 98

1-[3-(2,3,4,5-tetrahydropyrido[3,2-f][1,4]oxazepin-8-yl)phenyl]ethanone bis(trifluoroacetate)

MS (ESI+): 269 (M−2TFA+H)

Example 99

4-(2,3,4,5-tetrahydropyrido[3,2-f][1,4]oxazepin-8-yl)benzamide bis(trifluoroacetate)

MS (ESI+): 270 (M−2TFA+H)

Example 100

N,N-dimethyl-4-(2,3,4,5-tetrahydropyrido[3,2-f][1,4]oxazepin-8-yl)aniline tris(trifluoroacetate)

MS (ESI+): 270 (M−3TFA+H)

Example 101

N-[3-(2,3,4,5-tetrahydropyrido[3,2-f][1,4]oxazepin-8-yl)phenyl]acetamide bis(trifluoroacetate)

MS (ESI+): 284 (M−2TFA+H)

Example 102 methyl 4-(2,3,4,5-tetrahydropyrido[3,2-f][1,4]oxazepin-8-yl)benzoate bis(trifluoroacetate)

MS (ESI+): 285 (M−2TFA+H)

Example 103

8-[3-(trifluoromethyl)phenyl]-2,3,4,5-tetrahydropyrido[3,2-f][1,4]oxazepine bis(trifluoroacetate)

MS (ESI+): 295 (M−2TFA+H)

Example 104

8-[4-(trifluoromethoxy)phenyl]-2,3,4,5-tetrahydropyrido[3,2-f][1,4]oxazepine bis(trifluoroacetate)

MS (ESI+): 311 (M−2TFA+H)

Example 105

8-[2-(trifluoromethyl)phenyl]-2,3,4,5-tetrahydropyrido[3,2-f][1,4]oxazepine bis(trifluoroacetate)

MS (ESI+): 295 (M−2TFA+H)

Example 106

8-dibenzo[b,d]furan-4-yl-2,3,4,5-tetrahydropyrido[3,2-f][1,4]oxazepine bis(trifluoroacetate)

MS (ESI+): 317 (M−2TFA+H)

Example 107

8-[3-(benzyloxy)phenyl]-2,3,4,5-tetrahydropyrido[3,2-f][1,4]oxazepine bis(trifluoroacetate)

MS (ESI+): 333 (M−2TFA+H)

Example 108

8-biphenyl-3-yl-2,3,4,5-tetrahydropyrido[3,2-f][1,4]oxazepine bis(trifluoroacetate)

MS (ESI+): 303 (M−2TFA+H)

Example 109

8-(1-benzothien-2-yl)-2,3,4,5-tetrahydropyrido[3,2-f][1,4]oxazepine bis(trifluoroacetate)

MS (ESI+): 283 (M−2TFA+H)

Example 110

8-(1-naphthyl)-2,3,4,5-tetrahydropyrido[3,2-f][1,4]oxazepine bis(trifluoroacetate)

MS (ESI+): 277 (M−2TFA+H)

Example 111

8-(2-naphthyl)-2,3,4,5-tetrahydropyrido[3,2-f][1,4]oxazepine bis(trifluoroacetate)

MS (ESI+): 277 (M−2TFA+H)

Example 112

8-(3-furyl)-2,3,4,5-tetrahydropyrido[3,2-f][1,4]oxazepine bis(trifluoroacetate)

MS (ESI+): 217 (M−2TFA+H)

Example 113

3-(2,3,4,5-tetrahydropyrido[3,2-f][1,4]oxazepin-8-yl)phenol bis(trifluoroacetate)

MS (ESI+): 243 (M−2TFA+H)

Example 114

5-(2,3,4,5-tetrahydropyrido[3,2-f][1,4]oxazepin-8-yl)thiophene-2-carbonitrile bis(trifluoroacetate)

MS (ESI+): 258 (M−2TFA+H)

Example 115

8-pyridin-3-yl-2,3,4,5-tetrahydropyrido[3,2-f][1,4]oxazepine tris(trifluoroacetate)

MS (ESI+): 228 (M−3TFA+H)

Example 116

8-pyridin-4-yl-2,3,4,5-tetrahydropyrido[3,2-f][1,4]oxazepine tris(trifluoroacetate)

MS (ESI+): 228 (M−3TFA+H)

Example 117

8-(1-methyl-1H-pyrazol-4-yl)-2,3,4,5-tetrahydropyrido[3,2-f][1,4]oxazepine tris(trifluoroacetate)

MS (ESI+): 231 (M−3TFA+H)

Example 118

8-(3-bromo-2-fluorophenyl)-2,3,4,5-tetrahydropyrido[3,2-f][1,4]oxazepine bis(trifluoroacetate)

MS (ESI+): 324, 326 (M−2TFA+H)

Example 119

8-[6-(morpholin-4-yl)pyridin-3-yl]-2,3,4,5-tetrahydropyrido[3,2-f][1,4]oxazepine tris(trifluoroacetate)

MS (ESI+): 313 (M−3TFA+H)

Example 120 tetrahydropyrido[3,2-f][1,4]oxazepine tris(trifluoroacetate)

MS (ESI+): 297 (M−3TFA+H)

Example 121

8-chloro-7-fluoro-2,3,4,5-tetrahydropyrido[3,2-f][1,4]oxazepine (Step 1)
tert-Butyl 8-chloro-7-fluoro-2,3-dihydropyrido[3,2-f][1,4]oxazepine-4(5H)-carboxylate was obtained in the same manner as in Example 27, step 1 and using the compound obtained in Example 4.

$^1$H-NMR (CDCl$_3$): δ 1.43 (9H, s), 3.82-3.86 (2H, m), 4.15-4.19 (2H, m), 4.36-4.48 (2H, m), 7.30-7.50 (1H, m)
(Step 2)
The title compound was obtained in the same manner as in Example 33, step 3, and using the compound obtained in step 1.

$^1$H-NMR (CDCl$_3$): δ 3.24-3.28 (2H, m), 3.91 (2H, s), 4.15-4.18 (2H, m), 7.32 (1H, d, J=7.5 Hz)
MS (ESI+): 203 (M+H)

Example 122 tert-butyl 4-(7-fluoro-2,3,4,5-tetrahydropyrido[3,2-f][1,4]oxazepin-8-yl)piperazine-1-carboxylate The title compound was obtained in the same manner as in Example 11, method 2 and Example 22, and using the compound obtained in Example 4.

$^1$H-NMR (CDCl$_3$): δ 1.47 (9H, s), 3.24-3.28 (2H, m), 3.40-3.46 (4H, m), 3.50-3.54 (4H, m), 3.86 (2H, s), 4.15-4.18 (2H, m), 7.20 (1H, d, J=11.7 Hz)
MS (ESI+): 353 (M+H)

Example 123

8-chloro-3-methyl-2,3,4,5-tetrahydropyrido[3,2-f][1,4]oxazepine monohydrochloride To a solution of the compound (0.20 g) obtained in Example 5 in 1,2-dichloroethane (3 mL) was added 1-chloroethyl chloroformate (0.082 mL) at, room temperature, and the mixture was stirred at 90° C. for 2 hr. The reaction mixture was concentrated under reduced pressure, the obtained residue was dissolved in MeOH (3 mL), and the mixture was stirred at 80° C. for 1 hr. The reaction mixture was concentrated under reduced pressure, and the obtained residue was dissolved in ethyl acetate and water, and made basic with aqueous sodium hydroxide solution. The resultant product was extracted with ethyl acetate, and concentrated. The residue was purified by basic silica gel column chromatography (solvent gradient; 40→60% ethyl acetate/hexane) to give a colorless oil. To the obtained oil was added 1 equivalent of 4N hydrogen chloride/ethyl acetate solution to give the title compound (0.066 g, 59%) as a white powder.

$^1$H-NMR (DMSO-d$_6$): δ 1.30 (3H, d, J=6.8 Hz), 3.79 (1H, t like), 4.40 (1H, dd, J=13.4, 8.0 Hz), 4.27 (1H, d, J=15.1 Hz), 4.43 (1H, d, J=15.1 Hz), 4.49 (1H, dd, J=13.4, 2.6 Hz), 7.36 (1H, J=7.7 Hz), 8.00 (1H, d, J=7.9 Hz), 9.83 (1H, brs)
MS (ESI+): 199 (M−HCl+H)

Example 124

3-methyl-8-piperazin-1-yl-2,3,4,5-tetrahydropyrido[3,2-f][1,4]oxazepine dihydrochloride The title compound was obtained in the same manner as in Example 24 and using the compound obtained in Example 22.

$^1$H-NMR (DMSO-d$_6$): δ 1.28 (3H, d, J=6.6 Hz), 3.10-3.20 (4H, m), 3.65-3.75 (5H, m), 3.86 (1H, d, J=8.4 Hz), 4.08 (1H, dd like), 4.21 (1H, dd like), 4.36 (1H, dd, J=13.4, 2.2 Hz), 6.69 (1H, d, J=8.5 Hz), 7.72 (1H, d, J=8.3 Hz), 9.10-9.40 (3H, m), 9.95 (1H, brs)
MS (ESI+): 249 (M−2HCl+H)

Example 125

8-chloro-2-methyl-2,3,4,5-tetrahydropyrido[3,2-f][1,4]oxazepine monohydrochloride The title compound was obtained in the same manner as in Example 123 and using the compound obtained in Example 6.

$^1$H-NMR (DMSO-d$_6$): δ 1.39 (3H, d, J=6.4 Hz), 3.32 (1H, t like), 3.40-3.60 (1H, m), 4.22 (1H, d, J=14.9 Hz), 4.50 (1H, d, J=14.7 Hz), 4.50-4.60 (1H, m), 7.35 (1H, d, J=7.7 Hz), 7.95 (1H, d, J=7.7 Hz), 9.80 (2H, brs)
MS (ESI+): 199 (M−HCl+H)

Example 126 tert-butyl 4-(2-methyl-2,3,4,5-tetrahydropyrido[3,2-f][1,4]oxazepin-8-yl)piperazine-1-carboxylate The title compound was obtained in the same manner as in Example 22 and using the compound obtained in Example 18.
$^1$H-NMR (CDCl$_3$): δ 1.37 (3H, d, J=6.4 Hz), 1.48 (9H, s), 2.96 (1H, dd, J=14.1, 9.3 Hz), 3.17 (1H, d, J=14.1 Hz), 3.49 (8H, brs), 3.82 (2H, dd like), 4.05-4.25 (1H, m), 6.27 (1H, d, J=7.9 Hz), 7.27 (1H, d, J=8.3 Hz)
MS (ESI+): 349 (M+H)

Example 127

2-methyl-8-piperazin-1-yl-2,3,4,5-tetrahydropyrido[3,2-f][1,4]oxazepine trihydrochloride The title compound was obtained in the same manner as in Example 24 and using the compound obtained in Example 126.
$^1$H-NMR (DMSO-d$_6$): δ 1.36 (3H, d, J=6.4 Hz), 3.10 (4H, brs), 3.15-3.25 (1H, m), 3.40-3.50 (1H, m), 3.71 (4H, brs), 4.03 (1H, dd, J=14.1, 7.2 Hz), 4.25-4.40 (2H, m), 6.66 (1H, d, J=8.3 Hz), 7.66 (1H, d, J=8.4 Hz), 9.39 (1H, brs), 9.56 (1H, brs), 9.81 (1H, brs)
MS (ESI+): 249 (M−3HCl+H)

Example 128

2-methyl-8-morpholin-4-yl-2,3,4,5-tetrahydropyrido[3,2-f][1,4]oxazepine

The title compound was obtained in the same manner as in Example 22 and using the compound obtained in Example 20.
$^1$H-NMR (CDCl$_3$): δ 1.38 (3H, d, J=8.4 Hz), 1.66 (1H, brs), 2.97 (1H, dd, J=14.1, 9.4 Hz), 3.18 (1H, dd, J=14.1, 1.8 Hz), 3.40-3.50 (4H, m), 3.75-3.85 (6H, m), 4.10-4.20 (1H, m), 6.26 (1H, d, J=8.1 Hz), 7.28 (1H, d, J=8.1 Hz)
MS (ESI+): 250 (M+H)

Example 129

2-methyl-8-piperidin-1-yl-2,3,4,5-tetrahydropyrido[3,2-f][1,4]oxazepine

The title compound was obtained in the same manner as in Example 22 and using the compound obtained in Example 21.
$^1$H-NMR (CDCl$_3$): δ 1.37 (3H, d, J=6.4 Hz), 1.61 (6H, s like), 1.76 (1H, brs), 2.95 (1H, dd, J=14.1, 9.4 Hz), 3.16 (1H, d, J=14.1 Hz), 3.47 (4H, brs), 3.80 (2H, dd, J=22.4, 15.2 Hz), 4.10-4.20 (1H, m), 6.26 (1H, d, J=8.3 Hz), 7.22 (1H, d, J=8.3 Hz)
MS (ESI+): 248 (M+H)

Example 130

(+)-(R)-2-methyl-8-morpholin-4-yl-2,3,4,5-tetrahydropyrido[3,2-f][1,4]oxazepine

The compound (1.30 g) obtained in Example 128 was optically resolved by chiral HPLC. The fraction with a short retention time was concentrated under reduced pressure to give the title compound (0.44 g) as a white powder.
Chiral HPLC Conditions
Column: CHIRALPAK AD 50 mmID×500 mL
Solvent: hexane/ethanol/diethylamine=85/15/0.1
Flow rate: 85 mL/min
Temperature: 35° C.
Detection method: UV 254 nm
$[α]_D^{25}$+77.2 (c 1.0, MeOH)
MS (ESI+): 250 (M+H)

Example 131

(−)-(S)-2-methyl-8-morpholin-4-yl-2,3,4,5-tetrahydropyrido[3,2-f][1,4]oxazepine

The compound (1.30 g) obtained in Example 128 was optically resolved by chiral HPLC. The fraction with a long retention time was concentrated under reduced pressure to give the title compound (0.51 g) as a white powder.
Chiral HPLC Conditions
Same as in Example 130
$[α]_D^{25}$−78.6 (c 1.0, MeOH)
MS (ESI+): 250 (M+H)

Example 132

2,3,4,5-tetrahydropyrido[4,3-f][1,4]oxazepine

The title compound was obtained in the same manner as in Example 22 and using the compound obtained in Example 7.
$^1$H-NMR (CDCl$_3$): δ 3.24-3.27 (2H, m), 3.97 (2H, s), 4.06-4.10 (2H, m), 7.05 (1H, dd, J=4.5, 0.6 Hz), 8.23 (1H, d, J=4.5 Hz), 8.36 (1H, s)
MS (ESI+): 151 (M+H)

Example 133 tert-butyl 4-(2,3,4,5-tetrahydropyrido[4,3-f][1,4]oxazepin-9-yl)piperazine-1-carboxylate The title compound was obtained in the same manner as in Example 11, method 2 and Example 22, and using the compound obtained in Example 8.
$^1$H-NMR (CDCl$_3$): δ 1.48 (9H, s), 3.32-3.26 (2H, m), 3.34-3.42 (4H, m), 3.52-3.60 (4H, m), 3.90 (2H, s), 4.02-4.06 (2H, m), 6.64 (1H, d, J=4.8 Hz), 7.87 (1H, d, J=4.8 Hz)
MS (ESI+): 335 (M+H)

Example 134

9-chloro-2,3,4,5-tetrahydropyrido[4,3-f][1,4]oxazepine

To a solution of the compound (0.30 g) obtained in Example 8 in acetonitrile (10 mL) was added 1-chloroethyl chloroformate (0.13 mL) at room temperature, and the mixture was stirred at 90° C. for 2 hr. The reaction mixture was concentrated under reduced pressure, and then the obtained residue was dissolved in MeOH (10 mL), and the mixture was stirred at 80° C. for 1 hr. The reaction mixture was concentrated under reduced pressure, and the obtained residue was dissolved in ethyl acetate and water, and made basic with aqueous sodium hydroxide solution. The resultant product was extracted with ethyl acetate, and concentrated. The residue was purified by silica gel column chromatography (solvent gradient; 50% ethyl acetate/hexane→0.1% aqueous ammonia/ethyl acetate) to give the title compound (0.085 g, 42%) as a white powder.
$^1$H-NMR (CDCl$_3$): δ 3.29 (2H, t, J=4.4 Hz), 3.98 (2H, s), 4.15 (2H, t, J=4.4 Hz), 7.01 (1H, d, J=4.8 Hz), 8.01 (1H, d, J=4.8 Hz)
MS (ESI+): 185 (M+H)

Example 135

9-morpholin-4-yl-2,3,4,5-tetrahydropyrido[4,3-f][1,4]oxazepine monohydrochloride The title compound was obtained by reaction and purification in the same manner as in Example 11, method 2 and Example 22 and using the compound obtained in Example 8 and morpholine, and treating the obtained product with 1 equivalent of 4N hydrogen chloride/ethyl acetate.
MS (ESI+): 236 (M−HCl+H)

Example 136

9-piperidin-1-yl-2,3,4,5-tetrahydropyrido[4,3-f][1,4]oxazepine monohydrochloride The title compound was obtained by reaction and purification in the same manner as in Example 11, method 2 and Example 22 and using the compound obtained in Example 8 and piperidine, and treating the obtained product with 1 equivalent of 4N hydrogen chloride/ethyl acetate.
MS (ESI+): 234 (M−HCl+H)

Example 137

3,4,5,6-tetrahydro-2H-pyrido[3,2-g][1,4]oxazocine monohydrochloride

The title compound was obtained in the same manner as in Example 27 and using the compound obtained in Example 9.
$^1$H-NMR (DMSO-$d_6$): δ 2.97-3.10 (4H, m), 3.14-3.30 (2H, m), 4.20-4.60 (2H, m), 7.23-7.30 (1H, m), 7.79-7.83 (1H, m), 8.26-8.30 (1H, m), 9.56 (2H, brs)
MS (ESI+): 165 (M−HCl+H)

Example 138

9-methyl-3,4,5,6-tetrahydro-2H-pyrido[3,2-g][1,4]oxazocine monohydrochloride

The title compound was obtained in the same manner as in Example 27 and using the compound obtained in Example 10.
$^1$H-NMR (DMSO-$d_6$): δ 2.43 (3H, s), 2.94-3.10 (4H, m), 3.14-3.24 (2H, m), 4.36 (2H, t, J=5.3 Hz), 7.15 (1H, d, J=7.5 Hz), 7.71 (1H, d, J=7.5 Hz), 9.56 (2H, brs)
MS (ESI+): 179 (M−HCl+H)

The compounds described in Examples 1-138 are as follows (Tables 1-14).

TABLE 1

| Example No. | Structural formula | Salt | MS (ESI) |
|---|---|---|---|
| 1 | | | 241 |
| 2 | | | 255 |
| 3 | | | 275 |
| 4 | | | 293 |
| 5 | | | 289 |
| 6 | | | 289 |
| 7 | | | 241 |
| 8 | | | 275 |
| 9 | | | 255 |
| 10 | | HCl | 269 |

TABLE 2

| Example No. | Structural formula | Salt | MS (ESI) |
|---|---|---|---|
| 11 | | | 425 |
| 12 | | | 443 |
| 13 | | 3HCl | 325 |
| 14 | | | 439 |
| 15 | | 3HCl | 339 |
| 16 | | | 439 |

TABLE 2-continued

| Example No. | Structural formula | Salt | MS (ESI) |
|---|---|---|---|
| 17 | (piperazine)-pyrido-oxazepine-CH₃-N-benzyl | 3HCl | 339 |
| 18 | Boc-piperazine-pyrido-oxazepine-CH₃-N-benzyl | | 439 |
| 19 | (piperazine)-pyrido-oxazepine-CH₃-N-benzyl | 3HCl | 339 |
| 20 | morpholine-pyrido-oxazepine-CH₃-N-benzyl | | 340 |

TABLE 3

| Example No. | Structural formula | Salt | MS (ESI) |
|---|---|---|---|
| 21 | piperidine-pyrido-oxazepine-CH₃-N-benzyl | | 338 |
| 22 | Boc-piperazine-pyrido-oxazepine-CH₃-NH | | 349 |
| 23 | Boc-piperazine-pyrido-oxazepine-CH₃-N-CH₃ | | 363 |
| 24 | piperazine-pyrido-oxazepine-CH₃-N-CH₃ | 3HCl | 263 |

TABLE 3-continued

| Example No. | Structural formula | Salt | MS (ESI) |
|---|---|---|---|
| 25 | | | 425 |
| 26 | | HCl | 325 |
| 27 | | 2HCl | 151 |
| 28 | | 2HCl | 165 |
| 29 | | HCl | 185 |
| 30 | | | 335 |

TABLE 4

| Example No. | Structural formula | Salt | MS (ESI) |
|---|---|---|---|
| 31 | | 3HCl | 235 |

TABLE 4-continued

| Example No. | Structural formula | Salt | MS (ESI) |
|---|---|---|---|
| 32 | | 2HCl | 369 |
| 33 | | | 293 |
| 34 | | | 321 |
| 35 | | | 277 |
| 36 | | | 305 |
| 37 | | | 333 |
| 38 | | | 320 |
| 39 | | | 341 |

TABLE 4-continued

| Example No. | Structural formula | Salt | MS (ESI) |
|---|---|---|---|
| 40 | ![structure] | | 234 |

TABLE 5

| Example No. | Structural formula | Salt | MS (ESI) |
|---|---|---|---|
| 41 | ![structure] | | 236 |
| 42 | ![structure] | | 349 |
| 43 | ![structure] | 2CF3COOH | 220 |
| 44 | ![structure] | 2CF3COOH | 222 |
| 45 | ![structure] | 2CF3COOH | 238 |
| 46 | ![structure] | 2CF3COOH | 248 |
| 47 | ![structure] | 2CF3COOH | 262 |

TABLE 5-continued

| Example No. | Structural formula | Salt | MS (ESI) |
|---|---|---|---|
| 48 | | 2CF3COOH | 270 |
| 49 | | 2CF3COOH | 248 |
| 50 | | 2CF3COOH | 262 |

TABLE 6

| Example No. | Structural formula | Salt | MS (ESI) |
|---|---|---|---|
| 51 | | 2CF3COOH | 264 |
| 52 | | 2CF3COOH | 264 |
| 53 | | 3CF3COOH | 249 |
| 54 | | 3CF3COOH | 303 |

TABLE 6-continued

| Example No. | Structural formula | Salt | MS (ESI) |
|---|---|---|---|
| 55 | | 2CF3COOH | 313 |
| 56 | | 3CF3COOH | 339 |
| 57 | | 2CF3COOH | 282 |
| 58 | | 3CF3COOH | 339 |
| 59 | | 2CF3COOH | 326 |
| 60 | | 2CF3COOH | 345 |

TABLE 7
| Example No. | Structural formula | Salt | MS (ESI) |
|---|---|---|---|
| 61 | 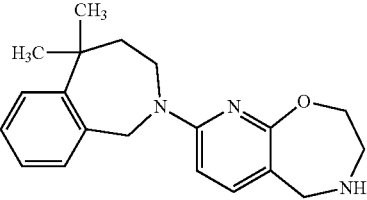 [SMILES: CC1(C)CCN(c2ccc3c(n2)OCCNC3)Cc2ccccc21] | 2CF3COOH | 324 |
| 62 | 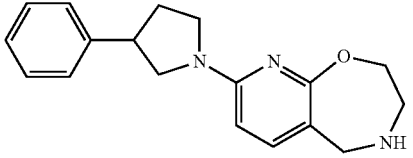 [SMILES: c1ccc(C2CCN(c3ccc4c(n3)OCCNC4)C2)cc1] | 2CF3COOH | 296 |
| 63 | 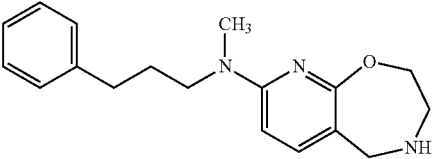 [SMILES: CN(CCCc1ccccc1)c1ccc2c(n1)OCCNC2] | 2CF3COOH | 298 |
| 64 | 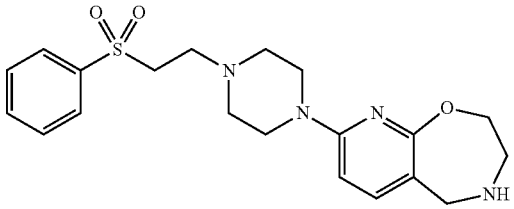 [SMILES: O=S(=O)(CCN1CCN(c2ccc3c(n2)OCCNC3)CC1)c1ccccc1] | 3CF3COOH | 403 |
| 65 | 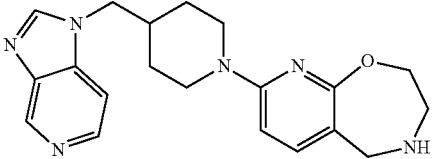 [SMILES: c1cc2c(cn1)ncn2CC1CCN(c2ccc3c(n2)OCCNC3)CC1] | 3CF3COOH | 365 |
| 66 | 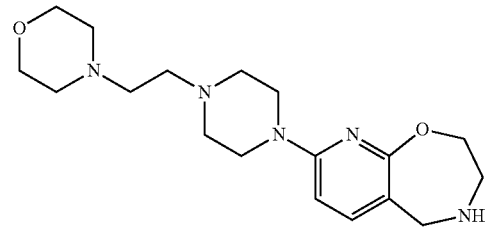 [SMILES: c1cc2c(nc1N1CCN(CCN3CCOCC3)CC1)OCCNC2] | 4CF3COOH | 348 |
| 67 | 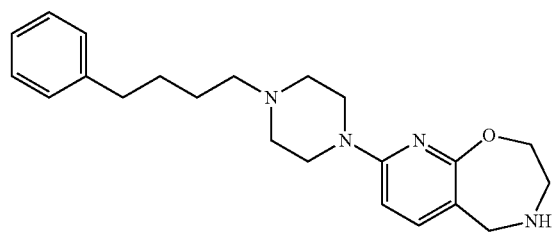 [SMILES: c1ccc(CCCCN2CCN(c3ccc4c(n3)OCCNC4)CC2)cc1] | 3CF3COOH | 367 |

TABLE 7-continued
| Example No. | Structural formula | Salt | MS (ESI) |
|---|---|---|---|
| 68 | 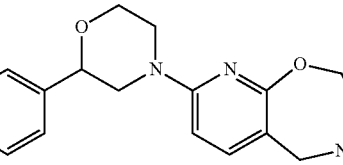 | 4CF3COOH | 340 |
| 69 | 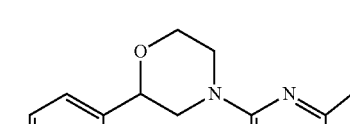 | 2CF3COOH | 336 |
| 70 | 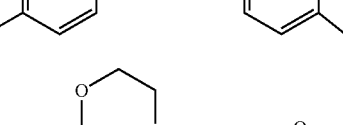 | 2CF3COOH | 290 |
TABLE 8
| Example No. | Structural formula | Salt | MS (ESI) |
|---|---|---|---|
| 71 | 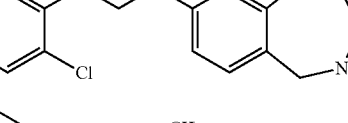 | 2CF3COOH | 312 |
| 72 | | 2CF3COOH | 342 |
| 73 | | 2CF3COOH | 346 |
| 74 | | 2CF3COOH | 388 |

TABLE 8-continued

| Example No. | Structural formula | Salt | MS (ESI) |
|---|---|---|---|
| 75 | | 2CF3COOH | 288 |
| 76 | | | 227 |
| 77 | | | 257 |
| 78 | | | 241 |
| 79 | | | 261 |
| 80 | | | 252 |

TABLE 9

| Example No. | Structural formula | Salt | MS (ESI) |
|---|---|---|---|
| 81 | | 2CF3COOH | 245 |
| 82 | | 2CF3COOH | 261 |

TABLE 9-continued

| Example No. | Structural formula | Salt | MS (ESI) |
|---|---|---|---|
| 83 | 2-chlorophenyl pyrido-oxazepine | 2CF3COOH | 261 |
| 84 | 3-chloro-4-fluorophenyl pyrido-oxazepine | 2CF3COOH | 279 |
| 85 | 3,5-dichlorophenyl pyrido-oxazepine | 2CF3COOH | 296 |
| 86 | 2,6-dichlorophenyl pyrido-oxazepine | 2CF3COOH | 296 |
| 87 | 2,4-dichlorophenyl pyrido-oxazepine | 2CF3COOH | 296 |
| 88 | 4-chloro-2-methylphenyl pyrido-oxazepine | 2CF3COOH | 275 |
| 89 | 3-chloro-2-methylphenyl pyrido-oxazepine | 2CF3COOH | 275 |
| 90 | 3,5-dimethylphenyl pyrido-oxazepine | 2CF3COOH | 255 |

TABLE 10

| Example No. | Structural formula | Salt | MS (ESI) |
|---|---|---|---|
| 91 | 2,4-dimethylphenyl pyrido-oxazepine | 2CF3COOH | 255 |
| 92 | 4-methoxy-2-methylphenyl pyrido-oxazepine | 2CF3COOH | 271 |
| 93 | 3-methoxyphenyl pyrido-oxazepine | 2CF3COOH | 257 |

TABLE 10-continued

| Example No. | Structural formula | Salt | MS (ESI) |
| --- | --- | --- | --- |
| 94 | | 2CF3COOH | 271 |
| 95 | | 2CF3COOH | 271 |
| 96 | | 2CF3COOH | 273 |
| 97 | | 2CF3COOH | 242 |
| 98 | | 2CF3COOH | 269 |
| 99 | | 2CF3COOH | 270 |
| 100 | | 2CF3COOH | 270 |

TABLE 11

| Example No. | Structural formula | Salt | MS (ESI) |
|---|---|---|---|
| 101 | | 2CF3COOH | 284 |
| 102 | | 2CF3COOH | 285 |
| 103 | | 2CF3COOH | 295 |
| 104 | | 2CF3COOH | 311 |
| 105 | | 2CF3COOH | 295 |
| 106 | | 2CF3COOH | 317 |
| 107 | | 2CF3COOH | 333 |
| 108 | | 2CF3COOH | 303 |

TABLE 11-continued

| Example No. | Structural formula | Salt | MS (ESI) |
|---|---|---|---|
| 109 | | 2CF3COOH | 283 |
| 110 | | 2CF3COOH | 277 |

TABLE 12

| Example No. | Structural formula | Salt | MS (ESI) |
|---|---|---|---|
| 111 | | 2CF3COOH | 277 |
| 112 | | 2CF3COOH | 217 |
| 113 | | 2CF3COOH | 243 |
| 114 | | 2CF3COOH | 258 |
| 115 | | 3CF3COOH | 228 |
| 116 | | 3CF3COOH | 228 |

TABLE 12-continued

| Example No. | Structural formula | Salt | MS (ESI) |
|---|---|---|---|
| 117 | (1-methylpyrazol-4-yl)-pyrido-oxazepine | 3CF3COOH | 231 |
| 118 | (3-bromo-2-fluorophenyl)-pyrido-oxazepine | 2CF3COOH | 324, 326 |
| 119 | (6-morpholinopyridin-3-yl)-pyrido-oxazepine | 3CF3COOH | 313 |
| 120 | (6-pyrrolidin-1-yl-pyridin-3-yl)-pyrido-oxazepine | 3CF3COOH | 297 |

TABLE 13

| Example No. | Structural formula | Salt | MS(ESI) |
|---|---|---|---|
| 121 | 7-chloro-8-fluoro-pyrido-oxazepine | | 203 |
| 122 | tert-butyl 4-(3-fluoro-pyrido-oxazepin-7-yl)piperazine-1-carboxylate | | 353 |
| 123 | 7-chloro-4-methyl-pyrido-oxazepine | HCl | 199 |

TABLE 13-continued

| Example No. | Structural formula | Salt | MS(ESI) |
|---|---|---|---|
| 124 | | 2HCl | 249 |
| 125 | | HCl | 199 |
| 126 | | | 349 |
| 127 | | 3HCl | 249 |
| 128 | | | 250 |
| 129 | | | 248 |
| 130 | (+)- | | 250 |

TABLE 14

| Example No. | Structural formula | Salt | MS(ESI) |
|---|---|---|---|
| 131 | (-)- | | 250 |
| 132 | | | 151 |

TABLE 14-continued

| Example No. | Structural formula | Salt | MS(ESI) |
|---|---|---|---|
| 133 | [structure: tert-butyl piperazine carboxylate linked to pyrido-oxazepine] | | 335 |
| 134 | [structure: Cl-substituted pyrido-oxazepine] | | 185 |
| 135 | [structure: morpholine linked to pyrido-oxazepine] | HCl | 236 |
| 136 | [structure: piperidine linked to pyrido-oxazepine] | HCl | 234 |
| 137 | [structure: pyrido-oxazocine] | HCl | 165 |
| 138 | [structure: methyl-substituted pyrido-oxazocine] | HCl | 179 |

Example 139

2,3,4,5-tetrahydropyrido[3,2-f][1,4]oxazepin-8-amine dihydrochloride (Step 1)

A solution of the compound (0.300 g) obtained in Example 29, step 1, lithium amide (0.242 g), (R)-1-[(S)-2-(dicyclohexylphosphino)ferrocenyl]ethyldi-tert-butylphosphine (SL-J009-1) (0.018 g) and $^t$BuONa (0.203 g) in DME (20 mL) was degassed with argon gas, Pd(OAc)$_2$ (0.007 g) was added, and the mixture was refluxed for 1.5 hr under an argon atmosphere. The reaction mixture was poured into water, and the resultant product was extracted with ethyl acetate. The organic layer was washed with water and brine and dried, and the solvent was evaporated under reduced pressure. The residue was purified by silica gel column chromatography (solvent gradient; 20→40% ethyl acetate/hexane) to give 2,3,4,5-tetrahydropyrido[3,2-f][1,4]oxazepin-8-amine (0.120 g, 43%) as a yellow oil.

$^1$H-NMR (CDCl$_3$): δ 1.42 (9H, s), 3.79 (2H, t like), 4.16 (2H, brs like), 4.29-4.40 (4H, m), 6.19 (1H, d, J=7.9 Hz), 7.27-7.40 (1H, m)

(Step 2)

The title compound was obtained in the same manner as in Example 24 and using the compound obtained in step 1.

$^1$H-NMR (CD$_3$OD): δ 3.75 (2H, t like), 4.42 (2H, s), 4.72 (2H, t like), 4.87 (5H, s), 6.69 (1H, d, J=9.0 Hz), 7.88 (1H, d, J=9.1 Hz)

MS (ESI+): 166 (M−2HCl+H)

Example 140

8-(3-methylpiperidin-1-yl)-2,3,4,5-tetrahydropyrido[3,2-f][1,4]oxazepine (Step 1)

A mixture of the compound (0.30 g) obtained in Example 29, step 1 and 3-methylpiperidine (1.2 mL) was stirred at 100° C. for 20 hr. The reaction mixture was poured into water, and the resultant product was extracted with ethyl acetate. The organic layer was washed with brine and dried, and the solvent was evaporated under reduced pressure. The residue was recrystallized from ethyl acetate-hexane to give tert-butyl 8-(3-methylpiperidin-1-yl)-2,3-dihydropyrido[3,2-f][1,4]oxazepine-4(5H)-carboxylate (0.22 g, 61%) as a white powder.

$^1$H-NMR (CDCl$_3$): δ 0.93 (3H, d, J=6.6 Hz), 1.12 (1H, dt like), 1.42 (9H, s), 1.50-1.80 (4H, m), 2.42 (1H, t like), 2.73 (1H, dt like), 3.78 (2H, t like), 4.10-4.45 (6H, m), 6.30 (1H, d, J=8.3 Hz), 7.26-7.40 (1H, m)

(Step 2)

A mixture of the compound (0.15 g) obtained in step 1 and 4N hydrogen chloride/ethyl acetate (2 mL) was stirred at room temperature for 3 hr. The precipitate was collected by filtration, and the aqueous layer was made basic with ethyl acetate and aqueous sodium hydroxide solution. The organic layer was washed with brine and dried, and the solvent was evaporated under reduced pressure. The residue was recrystallized from pentane to give the title compound (0.07 g, 67%) as a white powder.

$^1$H-NMR (CDCl$_3$): δ 0.93 (3H, d, J=6.6 Hz), 1.02-1.16 (1H, m), 1.48-1.85 (5H, m), 2.41 (1H, dd, J=10.8, 12.8 Hz), 2.73 (1H, dt, J=2.5, 12.8 Hz), 3.20 (2H, dd like), 3.80 (2H, s), 4.10-4.20 (4H, m), 6.28 (1H, d, J=8.1 Hz), 7.25 (1H, d, J=8.3 Hz)

MS (ESI+): 248 (M+H)

Example 141

8-(4-methylpiperidin-1-yl)-2,3,4,5-tetrahydropyrido[3,2-f][1,4]oxazepine

The title compound was obtained in the same manner as in Example 140 and using the compound obtained in Example 29, step 1, and 4-methylpiperidine.

$^1$H-NMR (CDCl$_3$): δ 0.95 (3H, d, J=6.5 Hz), 1.13-1.27 (2H, m), 1.50-1.75 (4H, m), 2.77 (2H, dt, J=2.6, 12.6 Hz), 3.20 (2H, dd like), 3.81 (2H, s), 4.15-4.25 (4H, m), 6.29 (1H, d, J=8.3 Hz), 7.24 (1H, d like)

MS (ESI+): 248 (M+H)

Example 142

8-(4-methoxypiperidin-1-yl)-2,3,4,5-tetrahydropyrido[3,2-f][1,4]oxazepine monohydrochloride The title compound was obtained in the same manner as in Example 140, step 1 and Example 24, and using the compound obtained in Example 29, step 1 and 4-methoxypiperidine.
$^1$H-NMR (DMSO-$d_6$): δ 1.25-1.45 (2H, m), 1.80-1.90 (2H, m), 3.15 (2H, t like), 3.26 (3H, s), 3.35-3.45 (5H, m), 3.84-3.95 (2H, m), 4.22-4.25 (2H, m), 6.59 (1H, d, J=8.3 Hz), 7.58 (1H, d, J=8.3 Hz), 9.42 (2H, brs)
MS (ESI+): 264 (M−HCl+H)

Example 143

(S)-(+)-8-(2-methylpiperidin-1-yl)-2,3,4,5-tetrahydropyrido[3,2-f][1,4]oxazepine monohydrochloride (Step 1)
A solution of the compound (0.300 g) obtained in Example 29, step 1, 2-methylpiperidine (185.7 μL), XPhos (0.030 g) and $^t$BuONa (0.152 g) in toluene (10 mL) was degassed with argon gas, Pd$_2$(dba)$_3$ (0.019 g) was added, and the mixture was stirred at 100° C. for 1.5 hr under an argon atmosphere. The reaction mixture was poured into water, and the resultant product was extracted with ethyl acetate. The organic layer was washed with water and brine and dried, and the solvent was evaporated under reduced pressure. The residue was purified by silica gel column chromatography (solvent gradient; 20→40% ethyl acetate/hexane) and recrystallized from pentane to give tert-butyl 8-(2-methylpiperidin-1-yl)-2,3-dihydropyrido[3,2-f][1,4]oxazepine-4(5H)-carboxylate (0.106 g, 29%) as a white powder.
$^1$H-NMR (CDCl$_3$): δ 1.12 (3H, d, J=6.8 Hz), 1.42 (9H, s), 1.40-1.80 (6H, m), 2.88 (1H, dt, J=2.7, 12.9 Hz), 3.75-3.85 (2H, m), 4.05-4.38 (5H, m), 4.58 (1H, brs like), 6.26 (1H, d, J=8.3 Hz), 7.60 (1H, d like)

(Step 2)
A mixture of the compound (0.09 g) obtained in step 1 and 4N hydrogen chloride/ethyl acetate (3 mL) was stirred at room temperature for 3 hr. An aqueous sodium hydroxide solution was added until the aqueous layer became alkaline. The organic layer was washed with brine and dried, and the solvent was evaporated under reduced pressure. The residue was purified by basic silica gel column chromatography (solvent gradient; 10→40% ethyl acetate/hexane) to give 8-(2-methylpiperidin-1-yl)-2,3,4,5-tetrahydropyrido[3,2-f][1,4]oxazepine (0.034 g, 52%) as a pale-yellow powder.
$^1$H-NMR (CDCl$_3$): δ 1.11 (3H, d, J=6.8 Hz), 1.20-1.90 (7H, m), 2.88 (1H, dt, J=2.8, 12.8 Hz), 3.19 (2H, t, J=4.4 Hz), 3.80 (2H, s), 4.03-4.50 (3H, m), 4.58 (1H, t like), 6.24 (1H, d, J=8.3 Hz), 7.25 (1H, d, J=8.3 Hz)

(Step 3)
The compound (0.077 g) obtained by repeating step 1 and step 2 was optically resolved by chiral HPLC. A fraction having a short retention time was concentrated under reduced pressure to give (S)-(+)-8-(2-methylpiperidin-1-yl)-2,3,4,5-tetrahydropyrido[3,2-f][1,4]oxazepine (0.033 g) as a white powder.
Chiral HPLC Conditions
 Column: CHIRALCEL OJ 50 mmID×500 mL
 Solvent: hexane/isopropyl alcohol/diethylamine=85/15/0.1
 Flow rate: 60 mL/min
 Temperature: 30° C.
 Detection method: UV 260 nm
MS (ESI+): 248 (M+H)

(Step 4)
To a solution of the compound (0.033 g) obtained in step 3 in diethyl ether (2 mL) was added 4N hydrogen chloride/ethyl acetate. The precipitate was collected by filtration to give the title compound (0.040 g, quant.) as a white powder.
$^1$H-NMR (DMSO-$d_6$): δ 1.06 (3H, d, J=6.6 Hz), 1.38 & 1.50-1.75 (total 6H, m), 2.84 (1H, t like), 3.40 (2H, t like), 4.00-4.10 (1H, m), 4.13 (2H, brs like), 4.25 (2H, brs like), 4.52 (1H, brs like), 6.53 (1H, brs like), 7.56 (1H, d like), 9.56 (2H, brs)
$[α]_D^{25}$+67.3 (c 1.0, MeOH)
MS (ESI+): 248 (M−HCl+H)

Example 144

(R)-(−)-8-(2-methylpiperidin-1-yl)-2,3,4,5-tetrahydropyrido[3,2-f][1,4]oxazepine monohydrochloride (Step 1)
The compound (0.077 g) obtained by repeating Example 143, step 1 and step 2 was optically resolved by chiral HPLC. A fraction having a long retention time was concentrated under reduced pressure to give (R)-(−)-8-(2-methylpiperidin-1-yl)-2,3,4,5-tetrahydropyrido[3,2-f][1,4]oxazepine (0.033 g) as a white powder.
Chiral HPLC Conditions
 Same as Example 143, step 3
MS (ESI+): 248 (M+H)

(Step 2)
The title compound was obtained in the same manner as in Example 143, step 4 and using the compound obtained in step 1.
$[α]_D^{25}$−67.4 (c 1.0, MeOH)
MS (ESI+): 248 (M−HCl+H)

Example 145

8-(2-ethylpiperidin-1-yl)-2,3,4,5-tetrahydropyrido[3,2-f][1,4]oxazepine dihydrobromide (Step 1)
tert-Butyl 8-(2-ethylpiperidin-1-yl)-2,3-dihydropyrido[3,2-f][1,4]oxazepine-4(5H)-carboxylate was obtained as a yellow oil in the same manner as in Example 143, step 1, and using the compound obtained in Example 29, step 1 and 2-ethylpiperidine.
$^1$H-NMR (CDCl$_3$): δ 0.86 (3H, t, J=7.5 Hz), 1.42 (9H, s), 1.49-1.75 (8H, m), 2.88 (1H, dt like), 3.77 (2H, t like), 4.11-4.37 (6H, m), 6.23 (1H, d, J=8.2 Hz), 7.25-7.36 (1H, m)

(Step 2)
A mixture of the compound (0.10 g) obtained in step 1 and 4N hydrogen chloride/ethyl acetate (3 mL) was stirred at room temperature for 3 hr. The precipitate was collected by filtration, and the aqueous layer was made basic with ethyl acetate and aqueous sodium hydroxide solution. The organic layer was washed with brine and dried, and the solvent was evaporated under reduced pressure. Ethyl acetate was added to the residue, and hydrobromic acid-ethanol solution was added. The precipitate was collected by filtration and recrystallized from methanol-ethyl acetate to give the title compound (0.054 g, 45%) as a white powder.
$^1$H-NMR (CD$_3$OD): δ 0.86 (3H, brs like), 1.38 & 1.50-2.00 (8H, m), 3.30 (1H, br), 3.69 (2H, brs like), 3.94 (1H, brs like), 4.21 (1H, brs like), 4.39 (2H, s), 4.58 (2H, br), 4.86 (3H, s), 6.99 (1H, d, J=7.5 Hz), 7.85 (1H, d like)
MS (ESI+): 262 (M−2HBr+H)

Example 146

8-(3,3-dimethylpiperidin-1-yl)-2,3,4,5-tetrahydropyrido[3,2-f][1,4]oxazepine dihydrochloride (Step 1)

tert-Butyl 8-(3,3-dimethylpiperidin-1-yl)-2,3-dihydropyrido[3,2-f][1,4]oxazepine-4(5H)-carboxylate was obtained as a white powder in the same manner as in Example 143, step 1, and using the compound obtained in Example 29, step 1 and 3,3-dimethylpiperidine.

$^1$H-NMR (CDCl$_3$): δ 0.94 (6H, s), 1.42 (9H, s), 1.38-1.70 (4H, m), 3.18 (2H, s), 3.47 (2H, t like), 3.77 (2H, t like), 4.20-4.40 (4H, m), 6.38 (1H, d, J=8.4 Hz), 7.26-7.40 (1H, m)

(Step 2)

A mixture of the compound (0.15 g) obtained in step 1 and 4N hydrogen chloride/ethyl acetate (3 mL) was stirred at room temperature for 3 hr. The precipitate was collected by filtration, and the aqueous layer was made basic with ethyl acetate and aqueous sodium hydroxide solution. The organic layer was washed with brine and dried, and the solvent was evaporated under reduced pressure. Ethyl acetate was added to the residue, and 4N hydrogen chloride/ethyl acetate was added. The precipitate was collected by filtration and recrystallized from methanol-ethyl acetate to give the title compound (0.10 g, 76%) as a white powder.

$^1$H-NMR (CD$_3$OD): δ 0.97 (6H, s), 1.52 (2H, t like), 1.65-1.80 (2H, m), 3.39 (2H, s), 3.61 (2H, t, J=5.6 Hz), 3.67 (2H, t like), 4.33 (2H, s), 4.55 (2H, brs like), 4.86 (3H, s), 6.86 (1H, d, J=8.9 Hz), 7.75 (1H, d, J=9.1 Hz)

MS (ESI+): 262 (M−2HCl+H)

Example 147

8-morpholin-4-yl-2,3,4,5-tetrahydropyrido[3,2-f][1,4]oxazepine monohydrochloride To a solution of the compound (1.0 g) obtained in Example 41 in ethyl acetate solution was added 4N hydrogen chloride/ethyl acetate (1.28 mL, 1.2 equivalent). The solvent was evaporated under reduced pressure. The residue was recrystallized from methanol-ethanol-IPE to give the title compound (0.99 g, 86%) as a pale-yellow powder.

$^1$H-NMR (CD$_3$OD): δ 3.49 (4H, t like), 3.56-3.59 (2H, m), 3.73-3.77 (4H, m), 4.25 (2H, s), 4.30-4.33 (2H, m), 4.83 (2H, s), 6.57 (1H, d, J=8.3 Hz), 7.60 (1H, d, J=8.3 Hz)

MS (ESI+): 236 (M−HCl+H)

Example 148

8-morpholin-4-yl-2,3,4,5-tetrahydropyrido[3,2-f][1,4]oxazepine monohydrobromide The title compound was obtained in the same manner as in Example 147 and using the compound obtained in Example 41 and hydrobromic acid-ethanol solution.

$^1$H-NMR (CD$_3$OD): δ 3.49 (4H, t like), 3.58 (2H, t like), 3.75 (4H, t like), 4.25 (2H, s), 4.29-4.35 (2H, m), 4.83 (2H, s), 6.57 (1H, d, J=8.3 Hz), 7.60 (1H, d, J=8.7 Hz)

MS (ESI+): 236 (M−HBr+H)

Example 149

7-fluoro-8-morpholin-4-yl-2,3,4,5-tetrahydropyrido[3,2-f][1,4]oxazepine monohydrochloride (Step 1)

tert-Butyl 8-morpholin-4-yl-2,3-dihydropyrido[3,2-f][1,4]oxazepine-4(5H)-carboxylate was obtained as a white powder in the same manner as in Example 140, step 1, and using the compound obtained in Example 29, step 1 and morpholine.

$^1$H-NMR (DMSO-d$_6$): δ 1.33 (9H, brs), 3.35 (4H, t like), 3.60-3.70 (6H, m), 4.10-4.20 (2H, m), 4.30-4.34 (2H, m), 6.45-6.50 (1H, m), 7.42 (1H, d, J=8.3 Hz)

(Step 2)

To a solution of the compound (0.100 g) obtained in step 1 in 1,2-dichloroethane (3 mL) was added 1-fluoropyridine triflate (0.08 g), and the mixture was stirred at room temperature for 18 hr. Ethyl acetate was added to the reaction mixture. The organic layer was washed with brine and dried, and the solvent was evaporated under reduced pressure. The residue was purified by silica gel column chromatography (solvent gradient; 0→40% ethyl acetate/hexane) to give tert-butyl 7-fluoro-8-morpholin-4-yl-2,3-dihydropyrido[3,2-f][1,4]oxazepine-4(5H)-carboxylate (0.34 g, quant.) as a colorless oil.

$^1$H-NMR (CDCl$_3$): δ 1.43 (9H, s), 3.47 (4H, br), 3.80 (6H, t like), 4.15 (2H, brs like), 4.28-4.36 (2H, m), 7.10-7.27 (1H, m)

(Step 3)

The title compound was obtained in the same manner as in Example 146, step 2, using the compound obtained in step 2 and recrystallized from ethanol-diethyl ether.

$^1$H-NMR (CD$_3$OD): δ 3.51 (4H, t like), 3.56-3.60 (2H, m), 3.76 (4H, t like), 4.25 (2H, s), 4.27-4.30 (2H, m), 4.83 (2H, s), 7.48 (1H, d, J=12.5 Hz)

MS (ESI+): 254 (M−HCl+H)

Example 150

7-chloro-8-morpholin-4-yl-2,3,4,5-tetrahydropyrido[3,2-f][1,4]oxazepine monohydrobromide (Step 1)

To a solution of the compound (0.300 g) obtained in Example 149, step 1 in dichloromethane (3 mL) was added N-chlorosuccinimide (0.143 g), and the mixture was stirred at room temperature for 18 hr. Ethyl acetate was added to the reaction mixture. The organic layer was washed with brine and dried, and the solvent was evaporated under reduced pressure. The residue was purified by silica gel column chromatography (solvent gradient; 10→40% ethyl acetate/hexane) to give tert-butyl 7-chloro-8-morpholin-4-yl-2,3-dihydropyrido[3,2-f][1,4]oxazepine-4(5H)-carboxylate (0.34 g, quant.) as a colorless oil.

$^1$H-NMR (CDCl$_3$): δ 1.43 (9H, s), 3.35 (4H, brs like), 3.79-3.85 (6H, m), 4.17-4.50 (4H, m), 7.42-7.53 (1H, m)

(Step 2)

To a solution of the compound (0.10 g) obtained in step 1 in ethanol (1 mL) was added hydrobromic acid-ethanol solution (1 mL), and the mixture was stirred at room temperature for 4 hr. The solvent was evaporated under reduced pressure, and the aqueous layer was made basic with ethyl acetate and aqueous sodium hydroxide solution. The organic layer was washed with brine and dried, and the solvent was evaporated under reduced pressure. Ethyl acetate was added to the residue, and hydrobromic acid-ethanol solution was added. The precipitate was collected by filtration to give the title compound (0.03 g, 25%) as a white powder.

$^1$H-NMR (CD$_3$OD): δ 3.38 (4H, t like), 3.60-3.63 (2H, m), 3.80 (4H, t like), 4.31 (2H, s), 4.34-4.39 (2H, m), 4.85 (2H, s), 7.79 (1H, s)

MS (ESI+): 270 (M−HBr+H)

Example 151

7-bromo-8-morpholin-4-yl-2,3,4,5-tetrahydropyrido[3,2-f][1,4]oxazepine monohydrochloride The title compound was obtained in the same manner as in Example 150, step 1 and Example 146, step 2, using the compound obtained in Example 149, step 1 and N-bromosuccinimide, and recrystallized from ethanol-diethyl ether.
$^1$H-NMR (CD$_3$OD): δ 3.35 (4H, t like), 3.62 (2H, t like), 3.80 (4H, t like), 4.32 (2H, s), 4.35-4.38 (2H, m), 4.83 (2H, s), 7.97 (1H, s)
MS (ESI+): 314 (M−HCl+H)

Example 152

8-thiomorpholin-4-yl-2,3,4,5-tetrahydropyrido[3,2-f][1,4]oxazepine dihydrochloride (Step 1)
tert-Butyl 8-thiomorpholin-4-yl-2,3-dihydropyrido[3,2-f][1,4]oxazepine-4(5H)-carboxylate was obtained as a white powder in the same manner as in Example 143, step 1, and using the compound obtained in Example 29, step 1 and thiomorpholine.
$^1$H-NMR (CDCl$_3$): δ 1.43 (9H, s), 2.66 (4H, t like), 3.79 (2H, dd like), 3.91 (4H, dd like), 4.20-4.40 (4H, m), 6.27 (1H, d, J=7.9 Hz), 7.26-7.50 (1H, m)
(Step 2)
The title compound was obtained in the same manner as in Example 146, step 2, and using the compound obtained in step 1.
$^1$H-NMR (CD$_3$OD): δ 2.76 (4H, dd like), 3.71 (2H, m), 4.00 (4H, dd like), 4.38 (2H, s), 4.61 (2H, m), 4.90 (3H, s), 6.90 (1H, d, J=9.0 Hz), 7.86 (1H, d, J=9.0 Hz)
MS (ESI+): 252 (M−2HCl+H)

Example 153

8-(1-oxidothiomorpholin-4-yl)-2,3,4,5-tetrahydropyrido[3,2-f][1,4]oxazepine dihydrobromide (Step 1)
To a solution of the compound (0.33 g) obtained in Example 152, step 1 in dichloromethane (10 mL) was added m-chloroperbenzoic acid (0.24 g), and the mixture was stirred at room temperature for 18 hr under a nitrogen atmosphere. Ethyl acetate and water were added to the reaction mixture. The organic layer was washed with brine and dried, and the solvent was evaporated under reduced pressure. The residue was washed with ethyl acetate and methanol to give tert-butyl 8-(1-oxidothiomorpholin-4-yl)-2,3-dihydropyrido[3,2-f][1,4]oxazepine-4(5H)-carboxylate as a white powder.
$^1$H-NMR (CDCl$_3$): δ 1.43 (9H, s), 2.79 (4H, br), 3.80 (2H, t like), 4.00-4.25 (6H, m), 4.25-4.50 (2H, m), 6.39 (1H, d, J=8.0 Hz), 7.35-7.50 (1H, m)
(Step 2)
A mixture of the compound (0.12 g) obtained in step 1 and 4N hydrogen chloride/ethyl acetate (3 mL) was stirred at room temperature for 3 hr. The precipitate was collected by filtration, and the aqueous layer was made basic with ethyl acetate and aqueous sodium hydroxide solution. The organic layer was washed with brine and dried, and the solvent was evaporated under reduced pressure. Ethyl acetate was added to the residue, and hydrobromic acid-ethanol solution was added. The precipitate was collected by filtration and recrystallized from methanol-ethyl acetate to give the title compound (0.04 g, 29%) as a white powder.
$^1$H-NMR (CD$_3$OD): δ 2.61 (4H, t like), 3.56 (2H, t like), 3.94 (4H, m), 4.24-4.33 (4H, m), 4.83 (3H, s), 6.57 (1H, d, J=8.7 Hz), 7.57 (1H, d, J=8.3 Hz)
MS (ESI+): 267 (M−2HBr)

Example 154

8-(1,1-dioxidothiomorpholin-4-yl)-2,3,4,5-tetrahydropyrido[3,2-f][1,4]oxazepine dihydrochloride The title compound was obtained in the same manner as in Example 143, step 1 and Example 146, step 2, and using the compound obtained in Example 29, step 1 and 1,1-dioxidothiomorpholine.
$^1$H-NMR (DMSO-d$_6$): δ 3.09 (4H, br), 3.39-3.57 (2H, m), 3.57 (1H, s like), 4.00 (4H, br), 4.18 (2H, brs like), 4.28 (2H, t like), 6.78 (1H, d, J=8.3 Hz), 7.69 (1H, d, J=8.3 Hz), 9.46 (2H, brs)
MS (ESI+): 284 (M−2HCl+H)

Example 155

8-(2,5-dimethylpyrrolidin-1-yl)-2,3,4,5-tetrahydropyrido[3,2-f][1,4]oxazepine (Step 1)
A solution of the compound (0.300 g) obtained in Example 29, step 1, 2,5-dimethylpyrrolidine (258.0 μL) and $^t$BuONa (0.152 g) in DME (2 mL) was degassed with argon gas, 1,3-bis-(2,4,6-trimethylphenyl)imidazol-2-ylidene-(allyl)-palladium(2)-chloride (0.051 g) was added, and the mixture was refluxed under argon atmosphere for 2 hr. The reaction mixture was poured into water, and the resultant product was extracted with ethyl acetate. The organic layer was washed with water and brine and dried, and the solvent was evaporated under reduced pressure. The residue was purified by silica gel column chromatography (solvent gradient; 0→35% ethyl acetate/hexane) and basic silica gel column chromatography (solvent gradient; 0→35% ethyl acetate/hexane) to give tert-butyl 8-(2,5-dimethylpyrrolidin-1-yl)-2,3-dihydropyrido[3,2-f][1,4]oxazepine-4(5H)-carboxylate (0.314 g, 86%) as a colorless oil.
$^1$H-NMR (CDCl$_3$): δ 1.29 (6H, d, J=6.4 Hz), 1.43 (9H, s), 1.60-1.75 (2H, m), 1.95-2.10 (2H, m), 3.77 (2H, t like), 4.09 (2H, brs like), 4.19-4.40 (4H, m), 6.06 (1H, d, J=8.3 Hz), 7.20-7.40 (1H, m)
(Step 2)
The title compound was obtained in the same manner as in Example 143, step 2, and using the compound obtained in step 1.
$^1$H-NMR (CDCl$_3$): δ 1.29 (6H, d, J=6.2 Hz), 1.65-1.80 (3H, m), 1.95-2.10 (2H, m), 3.20 (2H, t like), 3.81 (2H, s), 4.04 (2H, q like), 4.17 (2H, dd like), 6.05 (1H, d, J=8.3 Hz), 7.22 (1H, d, J=8.1 Hz)
MS (ESI+): 248 (M+H)

Example 156

8-(2,5-dimethylpyrrolidin-1-yl)-2,3,4,5-tetrahydropyrido[3,2-f][1,4]oxazepine monohydrobromide The title compound was obtained in the same manner as in Example 153, step 2, and using the compound obtained in Example 155, step 1.

¹H-NMR (DMSO-d₆): δ 1.22 (6H, d, J=6.2 Hz), 1.60-1.75 (2H, m), 1.95-2.10 (2H, m), 3.46 (2H, t like), 3.90-4.00 (2H, m), 4.15 (2H, s), 4.22 (2H, t like), 6.23 (1H, d, J=8.3 Hz), 7.52 (1H, d, J=8.3 Hz), 8.93 (2H, brs)
MS (ESI+): 248 (M−HBr+H)

Example 157

8-(2-methylpyrrolidin-1-yl)-2,3,4,5-tetrahydropyrido[3,2-f][1,4]oxazepine

The title compound was obtained in the same manner as in Example 143, steps 1 to 3, and using the compound obtained in Example 29, step 1 and 2-methylpyrrolidine.
Chiral HPLC Conditions
Same as Example 143, step 3, short retention time
MS (ESI+): 234 (M+H)

Example 158

8-(2-methylpyrrolidin-1-yl)-2,3,4,5-tetrahydropyrido[3,2-f][1,4]oxazepine

The title compound was obtained in the same manner as in Example 143, steps 1 to 3, and using the compound obtained in Example 29, step 1 and 2-methylpyrrolidine.
Chiral HPLC Conditions
Same as Example 143, step 3, long retention time
MS (ESI+): 234 (M+H)

Example 159

8-(1,4-oxazepan-4-yl)-2,3,4,5-tetrahydropyrido[3,2-f][1,4]oxazepine monohydrochloride The title compound was obtained in the same manner as in Example 143, step 1 and Example 146, step 2, and using the compound obtained in Example 29, step 1 and homomorpholine monohydrochloride.
¹H-NMR (DMSO-d₆): δ 1.75-1.90 (2H, m), 3.45 (2H, br), 3.57 (2H, t, J=5.5 Hz), 3.64-3.70 (6H, m), 4.10-4.18 (2H, m), 4.21-4.25 (2H, m), 6.45 (1H, d, J=8.3 Hz), 7.56 (1H, d, J=8.5 Hz), 9.07 (2H, brs)
MS (ESI+): 250 (M−HCl+H)

Example 160

N-isopropyl-2,3,4,5-tetrahydropyrido[3,2-f][1,4]oxazepin-8-amine dihydrobromide (Step 1)
A solution of the compound (0.300 g) obtained in Example 29, step 1, isopropylamine (0.136 mL), SL-J009-1 (0.006 g) and ᵗBuONa (0.152 g) in DME (2 mL) was degassed with argon gas, Pd(OAc)₂ (0.002 g) was added, and the mixture was refluxed under argon atmosphere for 1.5 hr. The reaction mixture was poured into water, and the resultant product was extracted with ethyl acetate. The organic layer was washed with water and brine and dried, and the solvent was evaporated under reduced pressure. The residue was purified by silica gel column chromatography (solvent gradient; 20→40% ethyl acetate/hexane) to give tert-butyl 8-isopropylamino-2,3-dihydropyrido[3,2-f][1,4]oxazepine-4(5H)-carboxylate (0.202 g, 63%) as a white powder.
¹H-NMR (CDCl₃): δ 1.20 (6H, d, J=6.4 Hz), 1.42 (9H, s), 3.57 (2H, dd like), 3.75-3.89 (1H, m), 4.13 (2H, brs like), 4.27-4.40 (3H, m), 6.04 (1H, d, J=7.9 Hz), 7.25-7.40 (1H, m)

(Step 2)
The title compound was obtained in the same manner as in Example 145, step 2, and using the compound obtained in step 1.
¹H-NMR (CD₃OD): δ 1.30 (6H, d, J=6.4 Hz), 3.75 (2H, t like), 3.91-4.04 (1H, m), 4.40 (2H, s), 4.69 (2H, brs like), 4.86 (4H, s), 6.68 (1H, d, J=9.1 Hz), 7.81 (1H, d, J=9.0 Hz)
MS (ESI+): 208 (M−2HBr+H)

Example 161

7-chloro-N-isopropyl-2,3,4,5-tetrahydropyrido[3,2-f][1,4]oxazepin-8-amine dihydrochloride The title compound was obtained in the same manner as in Example 150, step 1 and Example 146, step 2, and using the compound obtained in Example 160, step 1 and N-chlorosuccinimide.
¹H-NMR (CD₃OD): δ 1.23 (6H, d, J=6.4 Hz), 3.59 (2H, t like), 4.16-4.29 (1H, m), 4.21 (2H, s), 4.33 (2H, t like), 4.85 (4H, s), 7.59 (1H, s)
MS (ESI+): 242 (M−2HCl+H)

Example 162

(2S)—N-isopropyl-2-methyl-2,3,4,5-tetrahydropyrido[3,2-f][1,4]oxazepin-8-amine 0.5 succinate (Step 1)
To a solution of (S)-1-aminopropan-2-ol (5.0 g) and imidazole (5.0 g) in dichloromethane (200 mL) was added tert-butyldimethylchlorosilane (10.0 g), and the mixture was stirred at room temperature for 1 hr. The precipitate was filtered off, and the solvent was evaporated under reduced pressure. Benzaldehyde (6.8 mL) and toluene (200 mL) were added to the residue, and the mixture was refluxed for 4 hr while evaporating water by a Dean-Stark apparatus. The solvent was evaporated under reduced pressure, and methanol (200 mL) was added. Sodium tetrahydroborate (2.0 g) was added, and the mixture was stirred at room temperature for 13 hr. Water was added, and the solvent was evaporated under reduced pressure. Ethyl acetate was added. The organic layer was washed with water and brine and dried, and the solvent was evaporated under reduced pressure. The residue was purified by basic silica gel column chromatography (solvent gradient; 0→10% ethyl acetate/hexane) to give (2S)—N-benzyl-2-{[tert-butyl(dimethyl)silyl]oxy}propan-1-amine (12.9 g, 69%) as a colorless oil.
¹H-NMR (CDCl₃): δ 0.07 (6H, s), 0.88 (9H, s), 1.14 (3H, d, J=6.0 Hz), 1.60 (1H, brs), 2.58 (2H, d like), 3.80 (2H, d like), 3.94-4.05 (1H, m), 7.20-7.32 (5H, m)
(Step 2)
To 2-chloronicotinic acid (6.87 g) and DMF/toluene (2 mL/170 mL) was added dropwise oxalyl chloride (3.07 mL), and the mixture was stirred at room temperature for 1 hr. The reaction mixture was concentrated under reduced pressure, and triethylamine (12.49 mL) and THF (170 mL) were added. The compound (10.0 g) obtained in step 1 was added to the mixture at 0° C., and the mixture was stirred at room temperature for 2 hr. The reaction mixture was washed with 1N hydrochloric acid and brine and dried, and the solvent was evaporated under reduced pressure. The residue was purified by silica gel column chromatography (solvent gradient; 5→35% ethyl acetate/hexane) to give (2S)—N-benzyl-N-(2-{[tert-butyl(dimethyl)silyl]oxy}propyl)-2,6-dichloronicotinamide (14.99 g, 92%) as a pale-yellow oil.

¹H-NMR (CDCl₃): δ 0.10 (6H, s), 0.91 (9H, s), 0.80-0.97 (3H, m), 2.75-3.25 & 3.50-5.00 & 5.25-5.60 (total 5H, m), 7.04-7.80 (7H, m)
(Step 3)
tert-Butyl (2S)-8-chloro-2-methyl-2,3-dihydropyrido[3,2-f][1,4]oxazepine-4(5H)-carboxylate was obtained in the same manner as in Example 1, steps 2 and 3 and Example 27, step 1, and using the compound obtained in step 2.
¹H-NMR (CDCl₃): δ 1.41 (9H, s), 1.39-1.44 (3H, m), 3.25-3.40 & 3.45-3.60 (total 1H, m), 3.80-3.95 & 4.00-4.10 (total 1H, m), 4.22 (2H, t like), 4.50-4.65 (1H, m), 7.06 (1H, d, J=7.9 Hz), 7.45-7.61 (1H, m)
(Step 4)
tert-Butyl (2S)-8-(isopropylamino)-2-methyl-2,3-dihydropyrido[3,2-f][1,4]oxazepine-4(5H)-carboxylate was obtained in the same manner as in Example 160, step 1, and using the compound obtained in step 3 and isopropylamine.
¹H-NMR (CDCl₃): δ 1.20 (6H, d, J=6.4 Hz), 1.38 (3H, d, J=6.0 Hz), 1.42 (9H, s), 3.20-3.30 & 3.35-3.50 & 3.65-3.85 & 3.98-4.25 & 4.30-4.50 (total 7H, m), 6.04 (1H, d, J=8.1 Hz), 7.25-7.40 (1H, m)
(Step 5)
A mixture of the compound (0.10 g) obtained in step 4 and 4N hydrogen chloride/ethyl acetate (3 mL) was stirred at room temperature for 3 hr. The precipitate was collected by filtration, and the aqueous layer was made basic with ethyl acetate and aqueous sodium hydroxide solution. The organic layer was washed with brine and dried, and the solvent was evaporated under reduced pressure. Ethyl acetate was added to the residue, and 0.5M succinic acid-methanol solution was added. The precipitate was collected by filtration and recrystallized from methanol-ethyl acetate to give the title compound (0.07 g, 78%) as a white powder.
¹H-NMR (DMSO-d₆): δ 1.08 (3H, d, J=6.8 Hz), 1.10 (3H, d, J=6.8 Hz), 1.23 (3H, d, J=6.4 Hz), 2.33 (2H, s), 2.80 (1H, dd, J=9.4, 14.0 Hz), 3.12 (1H, d like), 3.50 (2H, br), 3.63 (1H, d, J=14.6 Hz), 3.76 (1H, d, J=14.6 Hz), 3.80-3.90 (1H, m), 3.93-4.05 (1H, m), 6.07 (1H, d, J=8.1 Hz), 6.23 (1H, d, J=8.1 Hz), 7.22 (1H, d, J=8.1 Hz)
MS (ESI+): 222 (M−0.5C₄H₆O₄+H)

Example 163

(2R)—N-isopropyl-2-methyl-2,3,4,5-tetrahydropyrido[3,2-f][1,4]oxazepin-8-amine 0.5 succinate The title compound was obtained in the same manner as in Example 162 and using (R)-1-aminopropan-2-ol.
¹H-NMR (DMSO-d₆): δ 1.08 (3H, d, J=7.0 Hz), 1.10 (3H, d, J=7.0 Hz), 1.23 (3H, d, J=6.4 Hz), 2.33 (2H, s), 2.81 (1H, dd, J=9.4, 14.0 Hz), 3.12 (1H, d like), 3.50 (2H, br), 3.63 (1H, d, J=14.7 Hz), 3.77 (1H, d, J=14.5 Hz), 3.84 (1H, q like), 3.98 (1H, dt like), 6.07 (1H, d, J=8.1 Hz), 6.23 (1H, d, J=7.9 Hz), 7.22 (1H, d, J=8.1 Hz)
MS (ESI+): 222 (M−0.5C₄H₆O₄+H)

Example 164

N-ethyl-N-isopropyl-2,3,4,5-tetrahydropyrido[3,2-f][1,4]oxazepin-8-amine monohydrochloride The title compound was obtained in the same manner as in Example 143, step 1 and Example 146, step 2, and using the compound obtained in Example 29, step 1 and N-ethylisopropylamine.
¹H-NMR (DMSO-d₆): δ 1.09 (3H, d, J=6.9 Hz), 1.12 (6H, d, J=6.8 Hz), 3.28-3.45 (4H, m), 4.13 (2H, brs like), 4.23 (2H, t like), 4.60-4.70 (1H, m), 6.34 (1H, d, J=8.5 Hz), 7.53 (1H, d, J=8.5 Hz), 9.29 (2H, brs)
MS (ESI+): 236 (M−HCl+H)

Example 165

N-ethyl-N-isopropyl-2,3,4,5-tetrahydropyrido[3,2-f][1,4]oxazepin-8-amine monohydrobromide The title compound was obtained in the same manner as in Example 143, step 1 and Example 145, step 2, and using the compound obtained in Example 29, step 1 and N-ethylisopropylamine.
¹H-NMR (CD₃OD): δ 1.13-1.20 (9H, m), 3.38 (2H, q, J=7.0 Hz), 3.52 (2H, dd like), 4.19 (2H, s), 4.25-4.30 (2H, m), 4.69-4.80 (1H, m), 4.85 (2H, s), 6.37 (1H, d, J=8.7 Hz), 7.49 (1H, d, J=8.5 Hz)
MS (ESI+): 236 (M−HBr+H)

Example 166

N-ethyl-N-propyl-2,3,4,5-tetrahydropyrido[3,2-f][1,4]oxazepin-8-amine monohydrochloride The title compound was obtained in the same manner as in Example 143, step 1 and Example 146, step 2, and using the compound obtained in Example 29, step 1 and N-ethylpropylamine.
¹H-NMR (DMSO-d₆): δ 0.86 (3H, t, J=7.2 Hz), 1.06 (3H, t, J=7.0 Hz), 1.53 (2H, q like), 3.33 (2H, t, J=7.6 Hz), 3.39 (2H, brs like), 3.44 (2H, q, J=6.8 Hz), 4.10 (2H, brs like), 4.24 (2H, brs like), 6.34 (1H, d, J=8.3 Hz), 7.53 (1H, d, J=8.3 Hz), 9.61 (2H, brs)
MS (ESI+): 236 (M−HCl+H)

Example 167

N-benzyl-N-isopropyl-2,3,4,5-tetrahydropyrido[3,2-f][1,4]oxazepin-8-amine

The title compound was obtained in the same manner as in Example 143, step 1 and Example 140, step 2, and using the compound obtained in Example 29, step 1 and N-benzylisopropylamine.
¹H-NMR (CDCl₃): δ 1.17 (6H, d, J=6.8 Hz), 2.05 (1H, s), 3.47 (2H, dd like), 4.05 (2H, s), 4.34-4.40 (2H, m), 4.49 (2H, s), 5.05-5.20 (1H, m), 5.98 (1H, d, J=8.3 Hz), 7.19-7.31 (6H, m)
MS (ESI+): 298 (M+H)

Example 168

N-(sec-butyl)-2,3,4,5-tetrahydropyrido[3,2-f][1,4]oxazepin-8-amine dihydrobromide (Step 1)
The title compound was obtained in the same manner as in Example 160, step 1 and Example 145, step 2, and using the compound obtained in Example 29, step 1 and sec-butylamine.
¹H-NMR (CD₃OD): δ 0.96 (3H, t, J=7.1 Hz), 1.23 (3H, d, J=6.4 Hz), 1.50-1.70 (2H, m), 3.62-3.70 (2H, m), 3.71-3.82 (1H, m), 4.33 (2H, s), 4.56 (2H, s like), 4.83 (4H, s), 6.58 (1H, d, J=8.7 Hz), 7.69 (1H, d, J=9.1 Hz)
MS (ESI+): 222 (M−2HBr+H)

Example 169

N-[(1R)-1-methylpropyl]-2,3,4,5-tetrahydropyrido[3,2-f][1,4]oxazepin-8-amine dihydrobromide The title compound was obtained in the same manner as in Example 160, step 1 and Example 145, step 2, and using the compound obtained in Example 29, step 1 and (R)-2-aminobutane.

$^1$H-NMR (CD$_3$OD): δ 0.98 (3H, t, J=7.4 Hz), 1.25 (3H, d, J=6.4 Hz), 1.50-1.75 (2H, m), 3.73 (2H, t like), 3.75-3.82 (1H, m), 4.38 (2H, s), 4.60-4.70 (2H, m), 4.83 (4H, s like), 6.68 (1H, d, J=9.0 Hz), 7.79 (1H, d, J=9.1 Hz)

MS (ESI+): 222 (M−2HBr+H)

Example 170

N-[(1S)-1-methylpropyl]-2,3,4,5-tetrahydropyrido[3,2-f][1,4]oxazepin-8-amine dihydrobromide The title compound was obtained in the same manner as in Example 160, step 1 and Example 145, step 2, and using the compound obtained in Example 29, step 1 and (S)-2-aminobutane.

$^1$H-NMR (CD$_3$OD): δ 0.96 (3H, t, J=7.6 Hz), 1.22 (3H, d, J=6.4 Hz), 1.55-1.75 (2H, m), 3.68 (2H, br), 3.75-3.85 (1H, m), 4.33 (2H, s), 4.56 (2H, br), 4.83 (4H, s like), 6.58 (1H, d, J=8.7 Hz), 7.69 (1H, d, J=9.4 Hz)

MS (ESI+): 222 (M−2HBr+H)

Example 171

N-(sec-butyl)-N-methyl-2,3,4,5-tetrahydropyrido[3,2-f][1,4]oxazepin-8-amine monohydrobromide tert-Butyl 8-(sec-butylamino)-2,3-dihydropyrido[3,2-f][1,4]oxazepine-4(5H)-carboxylate was obtained in the same manner as in Example 160, step 1, and using the compound obtained in Example 29, step 1 and sec-butylamine.

$^1$H-NMR (CDCl$_3$): δ 0.94 (3H, t, J=7.5 Hz), 1.17 (3H, d, J=6.4 Hz), 1.43 (9H, s), 1.45-1.60 (2H, m), 3.55-3.69 (1H, br), 3.78 (2H, t like), 4.13 (2H, br), 4.27-4.35 (3H, br), 6.04 (1H, d, J=8.1 Hz), 7.25-7.37 (1H, m)

(Step 2)

To a solution of the compound (0.68 g) obtained in step 1 in THF (6 mL) was added sodium hydride (0.13 g), and the mixture was stirred at room temperature for 15 min. Then, methyl iodide (397 μL) was added, and the mixture was stirred at room temperature for 4 days. Ethyl acetate and water were poured into the reaction mixture. The organic layer was washed with water and brine and dried, and the solvent was evaporated under reduced pressure. The residue was purified by silica gel column chromatography (solvent gradient; 0→40% ethyl acetate/hexane) to give tert-butyl 8-[sec-butyl(methyl)amino]-2,3-dihydropyrido[3,2-f][1,4]oxazepine-4(5H)-carboxylate (0.21 g, 29%) as a yellow oil.

$^1$H-NMR (CDCl$_3$): δ 0.83 (3H, t, J=7.4 Hz), 1.10 (3H, d, J=6.4 Hz), 1.43 (9H, s), 1.45-1.60 (2H, m), 2.77 (3H, s), 3.77 (2H, t like), 4.20 (2H, br), 4.29-4.38 (2H, br), 4.57 (1H, br), 6.16 (1H, d, J=7.9 Hz), 7.26-7.40 (1H, m)

(Step 3)

The title compound was obtained in the same manner as in Example 145, step 2, and using the compound obtained in step 2.

$^1$H-NMR (CD$_3$OD): δ 0.81 (3H, t, J=7.6 Hz), 1.13 (3H, d, J=6.4 Hz), 1.50-1.70 (2H, m), 2.81 (3H, s), 3.50-3.70 (2H, m), 4.21 (2H, s), 4.2-4.35 (2H, m), 4.50-4.65 (1H, m), 4.83 (2H, s like), 6.41 (1H, d, J=8.3 Hz), 7.52 (1H, d, J=8.3 Hz)

MS (ESI+): 236 (M−HBr+H)

Example 172

N-(sec-butyl)-N-methyl-2,3,4,5-tetrahydropyrido[3,2-f][1,4]oxazepin-8-amine monohydrochloride To the compound (0.010 g) obtained in Example 171 were added ethyl acetate and aqueous sodium hydroxide solution to make the aqueous layer basic. The organic layer was washed with brine and dried, and the solvent was evaporated under reduced pressure. Diethyl ether was added to the residue, and 4N hydrogen chloride/ethyl acetate (1.2 equivalent) was added. The precipitate was collected by filtration and recrystallized from ethanol-IPE to give the title compound (0.006 g, 69%) as a white powder.

$^1$H-NMR (CD$_3$OD): δ 0.81 (3H, t, J=7.4 Hz), 1.13 (3H, d, J=6.8 Hz), 1.50-1.60 (2H, m), 2.80 (3H, s), 3.55 (2H, br), 4.19-4.23 (2H, m), 4.26-4.32 (2H, m), 4.52-4.62 (1H, m), 4.86 (2H, s), 6.41 (1H, d, J=8.3 Hz), 7.51 (1H, d, J=8.4 Hz)

MS (ESI+): 236 (M−HCl+H)

Example 173

N-(sec-butyl)-N-methyl-2,3,4,5-tetrahydropyrido[3,2-f][1,4]oxazepin-8-amine dihydrochloride The title compound was obtained in the same manner as in Example 146, step 2, and using the compound obtained in Example 171, step 2.

$^1$H-NMR (CD$_3$OD): δ 0.90 (3H, brs like), 1.15 (3H, d, J=6.1 Hz), 1.69 (2H, brs like), 3.02 (3H, s), 3.73 (2H, brs like), 3.87-3.98 (1H, m), 4.39 (2H, brs like), 4.64 (2H, brs like), 4.92 (3H, s), 6.89 (1H, brs like), 7.84 (1H, brs like)

MS (ESI+): 236 (M−2HCl+H)

Example 174

N-(cyclopropylmethyl)-2,3,4,5-tetrahydropyrido[3,2-f][1,4]oxazepin-8-amine

The title compound was obtained in the same manner as in Example 160, step 1 and Example 143, step 2, and using the compound obtained in Example 29, step 1 and cyclopropylmethylamine.

$^1$H-NMR (CDCl$_3$): δ 0.23 (2H, q like), 0.53 (2H, q like), 1.00-1.10 (1H, m), 1.65 (1H, s), 3.08 (2H, t like), 3.21 (2H, t like), 3.81 (2H, s), 4.15 (2H, dd like), 4.55 (1H, brs), 6.05 (1H, d, J=8.1 Hz), 7.25 (1H, d, J=8.1 Hz)

MS (ESI+): 220 (M+H)

Example 175

N-(cyclopropylmethyl)-N-methyl-2,3,4,5-tetrahydropyrido[3,2-f][1,4]oxazepin-8-amine dihydrobromide The title compound was obtained in the same manner as in Example 171 and using the compound obtained in Example 29, step 1 and cyclopropylmethylamine.

$^1$H-NMR (CD$_3$OD): δ 0.30 (2H, q like), 0.52 (2H, q like), 1.00-1.11 (1H, m), 3.12 (3H, s), 3.45 (2H, d, J=6.6 Hz), 3.62 (2H, t like), 4.27 (2H, s), 4.35-4.41 (2H, m), 4.85 (3H, s), 6.55 (1H, d, J=8.4 Hz), 7.62 (1H, d, J=8.7 Hz)

MS (ESI+): 234 (M−2HBr+H)

Example 176

N-(cyclopropylmethyl)-N-propyl-2,3,4,5-tetrahydropyrido[3,2-f][1,4]oxazepin-8-amine The title compound was obtained in the same manner as in Example 143, step 1 and Example 143, step 2, and using the compound obtained in Example 29, step 1 and N-(cyclopropylmethyl)propylamine.
$^1$H-NMR (CDCl$_3$): δ 0.24 (2H, q like), 0.49 (2H, q like), 0.91 (3H, t, J=7.4 Hz), 0.95-1.15 (1H, m), 1.25 (1H, br), 1.50-1.70 (2H, m), 3.20 (2H, t like), 3.36-3.44 (4H, m), 3.81 (2H, s), 4.17 (2H, t like), 6.15 (1H, d, J=8.2 Hz), 7.22 (1H, d, J=8.3 Hz)
MS (ESI+): 262 (M+H)

Example 177

N-isopropyl-N-methyl-2,3,4,5-tetrahydropyrido[3,2-f][1,4]oxazepin-8-amine

The title compound was obtained in the same manner as in Example 155, step 1 and Example 143, step 2, and using the compound obtained in Example 29, step 1 and N-isopropylmethylamine.
$^1$H-NMR (CDCl$_3$): δ 1.14 (6H, d, J=6.6 Hz), 1.82 (1H, brs), 2.80 (3H, s), 3.20 (2H, brs like), 3.81 (2H, s like), 4.18 (2H, t like), 4.60-4.95 (1H, m), 6.14 (1H, d, J=8.1 Hz), 7.25 (1H, d, J=8.3 Hz)
MS (ESI+): 222 (M+H)

Example 178

N-isopropyl-N-methyl-2,3,4,5-tetrahydropyrido[3,2-f][1,4]oxazepin-8-amine monohydrobromide The title compound was obtained in the same manner as in Example 160, step 1, Example 171, step 2 and Example 145, step 2, and using the compound obtained in Example 29, step 1 and isopropylamine.
$^1$H-NMR (DMSO-d$_6$): δ 1.09 (6H, d, J=6.8 Hz), 2.76 (3H, s), 3.40-3.50 (2H, m), 4.15 (2H, s), 4.20-4.25 (2H, m), 4.65-4.80 (1H, m), 6.37 (1H, d, J=8.5 Hz), 7.55 (1H, d, J=8.3 Hz), 8.94 (2H, brs)
MS (ESI+): 222 (M−HBr+H)

Example 179

7-chloro-N-isopropyl-N-methyl-2,3,4,5-tetrahydropyrido[3,2-f][1,4]oxazepin-8-amine monohydrochloride (Step 1)
tert-Butyl 8-[isopropyl(methyl)amino]-2,3-dihydropyrido[3,2-f][1,4]oxazepine-4(5H)-carboxylate was obtained in the same manner as in Example 171, step 2, and using the compound obtained in Example 160, step 1.
$^1$H-NMR (CDCl$_3$): δ 1.17 (6H, d, J=6.8 Hz), 1.43 (9H, s), 2.79 (3H, s), 3.78 (2H, t like), 4.15-4.40 (5H, m), 7.36-7.46 (1H, m)
(Step 2)
The title compound was obtained in the same manner as in Example 161 and using the compound obtained in step 1.
$^1$H-NMR (CDCl$_3$): δ 1.21 (6H, d, J=6.8 Hz), 2.86 (3H, s), 3.61 (2H, t like), 4.29 (2H, s), 4.29-4.40 (3H, m), 4.85 (2H, s), 7.75 (1H, s like)
MS (ESI+): 256 (M−HCl+H)

Example 180

7-bromo-N-isopropyl-N-methyl-2,3,4,5-tetrahydropyrido[3,2-f][1,4]oxazepin-8-amine monohydrochloride The title compound was obtained in the same manner as in Example 179 and using the compound obtained in Example 160, step 1.
$^1$H-NMR (CDCl$_3$): δ 1.20 (6H, d, J=6.6 Hz), 2.82 (3H, s), 3.61 (2H, s like), 4.28 (2H, s), 4.28-4.50 (3H, m), 4.85 (2H, s), 7.90 (1H, s like)
MS (ESI+): 300 (M−HCl+H)

Example 181

(2S)—N-isopropyl-N,2-dimethyl-2,3,4,5-tetrahydropyrido[3,2-f][1,4]oxazepin-8-amine monosuccinate (Step 1)
To a solution of the compound (0.39 g) obtained in Example 162, step 4 and acetic acid (105 μL) in dichloromethane (5 mL) were added paraformaldehyde (0.11 g) and sodium triacetoxyborohydride (0.39 g), and the mixture was stirred at room temperature. The reaction was monitored by thin layer chromatography and paraformaldehyde, acetic acid and sodium triacetoxyborohydride were added until the starting materials were consumed. The solvent was evaporated under reduced pressure, and ethyl acetate was added. The organic layer was washed with water and brine and dried, and the solvent was evaporated under reduced pressure. The residue was purified by silica gel column chromatography (solvent gradient; 0→40% ethyl acetate/hexane) to give tert-butyl (2S)-8-[isopropyl(methyl)amino]-2-methyl-2,3-dihydropyrido[3,2-f][1,4]oxazepine-4(5H)-carboxylate (0.36 g, 86%) as a colorless oil.
$^1$H-NMR (CDCl$_3$): δ 1.13 (6H, t like), 1.37 (3H, d like), 1.42 (9H, s), 2.80 (3H, s), 3.25-3.40 & 3.45-3.60 (total 1H, m), 3.70-3.80 & 3.90-4.00 (total 1H, m), 4.09-4.42 (3H, m), 4.75-4.90 (1H, m), 6.15 (1H, d, J=8.3 Hz), 7.21-7.37 (1H, m)
(Step 2)
The title compound was obtained in the same manner as in Example 162, step 5, and using the compound obtained in step 1.
$^1$H-NMR (DMSO-d$_6$): δ 1.05 (3H, d, J=6.7 Hz), 1.09 (3H, d, J=6.7 Hz), 1.26 (3H, d, J=6.4 Hz), 2.35 (4H, s), 2.72 (3H, s), 2.87 (1H, dd like), 3.16 (1H, dd like), 3.69 (1H, d, J=14.6 Hz), 3.87 (1H, d, J=14.6 Hz), 4.06 (1H, t like), 4.65-4.80 (1H, m), 6.24 (1H, d, J=8.3 Hz), 7.36 (1H, d, J=8.1 Hz), 10.00 (br, 3H)
MS (ESI+): 236 (M−C$_4$H$_6$O$_4$+H)

Example 182

(2R)—N-isopropyl-N,2-dimethyl-2,3,4,5-tetrahydropyrido[3,2-f][1,4]oxazepin-8-amine 0.5 succinate The title compound was obtained in the same manner as in Example 162, steps 1 to 4 and Example 181, and using (R)-1-aminopropan-2-ol.
$^1$H-NMR (DMSO-d$_6$): δ 1.05 (3H, d, J=6.8 Hz), 1.09 (3H, d, J=6.8 Hz), 1.24 (3H, d, J=6.4 Hz), 2.34 (2H, s), 2.72 (3H, s), 2.81 (1H, dd like), 3.12 (1H, dd like), 3.61 (1H, d, J=14.4

Hz), 3.80 (1H, d, J=14.4 Hz), 3.95-4.10 (1H, m), 4.65-4.80 (1H, m), 6.22 (1H, d, J=8.3 Hz), 7.33 (1H, d, J=8.3 Hz), 8.50 (br, 2H)
MS (ESI+): 236 (M−0.5C$_4$H$_6$O$_4$+H)

Example 183

N-(tert-butyl)-2,3,4,5-tetrahydropyrido[3,2-f][1,4]oxazepin-8-amine dihydrobromide The title compound was obtained in the same manner as in Example 160, step 1 and Example 153, step 2, and using the compound obtained in Example 29, step 1 and tert-butylamine.
$^1$H-NMR (CD$_3$OD): δ 1.47 (9H, s), 3.70-3.78 (2H, m), 4.45 (2H, s), 4.65 (2H, brs like), 4.86 (4H, s), 6.95 (1H, brs like), 7.92 (1H, brs like)
MS (ESI+): 222 (M−2HBr+H)

Example 184

N-isobutyl-2,3,4,5-tetrahydropyrido[3,2-f][1,4]oxazepin-8-amine monohydrobromide The title compound was obtained in the same manner as in Example 160, step 1 and Example 153, step 2, and using the compound obtained in Example 29, step 1 and isobutylamine.
$^1$H-NMR (CD$_3$OD): δ 0.98 (6H, d, J=6.8 Hz), 1.80-1.95 (1H, m), 3.13 (2H, d, J=6.8 Hz), 3.60-3.70 (2H, m), 4.29 (2H, s), 4.47 (2H, m), 4.85 (3H, s), 6.50 (1H, d, J=8.7 Hz), 7.61 (1H, d, J=8.6 Hz)
MS (ESI+): 222 (M−HBr+H)

Example 185

N-isobutyl-N-methyl-2,3,4,5-tetrahydropyrido[3,2-f][1,4]oxazepin-8-amine dihydrobromide The title compound was obtained in the same manner as in Example 160, step 1, Example 181, step 1 and Example 145, step 2, and using the compound obtained in Example 29, step 1 and isobutylamine.
$^1$H-NMR (CD$_3$OD): δ 0.90 (6H, d, J=6.4 Hz), 1.95-2.10 (1H, m), 3.05 (3H, s), 3.25-3.40 (2H, m), 3.57 (2H, t like), 4.23 (2H, s), 4.33 (2H, t like), 4.83 (3H, s), 6.42 (1H, d, J=8.3 Hz), 7.53 (1H, d, J=8.3 Hz)
MS (ESI+): 236 (M−2HBr+H)

Example 186

N-ethyl-N-methyl-2,3,4,5-tetrahydropyrido[3,2-f][1,4]oxazepin-8-amine dihydrobromide The title compound was obtained in the same manner as in Example 143, step 1 and Example 145, step 2, and using the compound obtained in Example 29, step 1 and ethylmethylamine.
$^1$H-NMR (CD$_3$OD): δ 1.25 (3H, t, J=7.2 Hz), 3.30 (3H, s), 3.67 (2H, q), 3.74 (2H, t like), 4.41 (2H, s), 4.67 (2H, t like), 4.84 (3H, s), 6.85 (1H, d, J=9.1 Hz), 7.87 (1H, d, J=9.1 Hz)
MS (ESI+): 208 (M−2HBr+H)

Example 187

N,N-dimethyl-2,3,4,5-tetrahydropyrido[3,2-f][1,4]oxazepin-8-amine dihydrobromide The title compound was obtained in the same manner as in Example 143, step 1 and Example 153, step 2, and using the compound obtained in Example 29, step 1 and 2.0M dimethylamine-tetrahydrofuran solution.
$^1$H-NMR (CD$_3$OD): δ 3.12 (6H, s), 3.66 (2H, t like), 4.28 (2H, s), 4.42 (2H, t like), 4.85 (3H, s), 6.55 (1H, d, J=9.0 Hz), 7.64 (1H, d, J=8.4 Hz)
MS (ESI+): 194 (M−2HBr+H)

Example 188

N-methyl-N-(tetrahydro-2H-pyran-4-yl)-2,3,4,5-tetrahydropyrido[3,2-f][1,4]oxazepin-8-amine dihydrochloride The title compound was obtained in the same manner as in Example 143, step 1 and Example 146, step 2, and using the compound obtained in Example 29, step 1 and N-methyltetrahydro-2H-pyran-4-yl-amine.
$^1$H-NMR (CD$_3$OD): δ 1.73 (2H, d like), 1.90-2.10 (2H, m), 3.11 (3H, s), 3.58 (2H, t like), 3.75 (2H, dd like), 4.04 (2H, dd, J=4.5, 11.5 Hz), 4.25-4.40 (1H, m), 4.43 (2H, s), 4.65-4.75 (2H, m), 4.91 (3H, s), 7.06 (1H, d, J=9.4 Hz), 7.94 (1H, d, J=9.2 Hz)
MS (ESI+): 264 (M−2HCl+H)

Example 189

N-cyclopropyl-2,3,4,5-tetrahydropyrido[3,2-f][1,4]oxazepin-8-amine dihydrobromide The title compound was obtained in the same manner as in Example 160, step 1 and Example 145, step 2, and using the compound obtained in Example 29, step 1 and cyclopropylamine.
$^1$H-NMR (CD$_3$OD): δ 0.45-0.51 (2H, m), 0.75-0.81 (2H, m), 2.45-2.55 (1H, m), 3.56 (2H, dd like), 4.23 (2H, s), 4.30 (2H, dd like), 4.85 (4H, s), 6.52 (1H, d, J=8.3 Hz), 7.55 (1H, d, J=8.3 Hz)
MS (ESI+): 206 (M−2HBr+H)

Example 190

N-cyclopropyl-N-methyl-2,3,4,5-tetrahydropyrido[3,2-f][1,4]oxazepin-8-amine dihydrobromide The title compound was obtained in the same manner as in Example 160, step 1, Example 171, step 2 and Example 145, step 2, and using the compound obtained in Example 29, step 1 and cyclopropylamine.
$^1$H-NMR (CD$_3$OD): δ 0.6-0.75 (2H, m), 0.90-1.00 (2H, m), 2.50-2.70 (1H, m), 3.11 (3H, s), 3.50-3.70 (2H, m), 4.28 (2H, s), 4.30-4.45 (2H, m), 4.85 (3H, s), 6.86 (1H, br), 7.62 (1H, br)
MS (ESI+): 220 (M−2HBr+H)

Example 191

N-cyclobutyl-2,3,4,5-tetrahydropyrido[3,2-f][1,4]oxazepin-8-amine dihydrobromide The title compound was obtained in the same manner as in Example 160, step 1 and Example 153, step 2, and using the compound obtained in Example 29, step 1 and cyclobutylamine.
$^1$H-NMR (CD$_3$OD): δ 1.70-1.83 (2H, m), 1.85-2.00 (2H, m), 2.30-2.45 (2H, m), 3.58 (2H, brs like), 4.21 (2H, s), 4.30 (2H, brs like), 4.86 (4H, s), 4.89 (1H, m), 6.25 (1H, d like), 7.45 (1H, d like)
MS (ESI+): 220 (M−2HBr+H)

Example 192

N-cyclobutyl-N-methyl-2,3,4,5-tetrahydropyrido[3,2-f][1,4]oxazepin-8-amine dihydrobromide The title compound was obtained in the same manner as in Example 160, step 1, Example 171, step 2 and Example 145, step 2, and using the compound obtained in Example 29, step 1 and cyclobutylamine.

$^1$H-NMR (CD$_3$OD): δ 1.65-1.79 (2H, m), 2.21 (4H, q like), 2.99 (3H, s), 3.57 (2H, br), 4.21 (2H, s), 4.26-4.34 (2H, m), 4.65-4.80 (1H, m), 4.85 (3H, s), 6.40 (1H, d, J=8.3 Hz), 7.52 (1H, d, J=8.5 Hz)

MS (ESI+): 234 (M−2HBr+H)

Example 193

N-cyclopentyl-2,3,4,5-tetrahydropyrido[3,2-f][1,4]oxazepin-8-amine dihydrobromide The title compound was obtained in the same manner as in Example 160, step 1 and Example 153, step 2, and using the compound obtained in Example 29, step 1 and cyclopentylamine.

$^1$H-NMR (CD$_3$OD): δ 1.50-1.85 (6H, m), 2.07 (2H, brs like), 3.72 (2H, brs like), 4.04-4.15 (1H, m), 4.37 (2H, brs like), 4.86 (4H, s), 4.55-4.72 (2H, m), 6.65 (1H, br), 7.75 (1H, br)

MS (ESI+): 234 (M−2HBr+H)

Example 194

N-cyclopentyl-N-methyl-2,3,4,5-tetrahydropyrido[3,2-f][1,4]oxazepin-8-amine dihydrobromide The title compound was obtained in the same manner as in Example 160, step 1, Example 171, step 2 and Example 145, step 2, and using the compound obtained in Example 29, step 1 and cyclopentylamine.

$^1$H-NMR (CD$_3$OD): δ 1.50-1.95 (8H, m), 2.94 (3H, s), 3.55-3.65 (2H, m), 4.29 (2H, s), 4.37-4.46 (2H, m), 4.74 (1H, brs like), 4.85 (3H, s), 6.63 (1H, d, J=8.7 Hz), 7.65 (1H, d, J=8.7 Hz)

MS (ESI+): 248 (M−2HBr+H)

Example 195

N-(tert-butyl)-4-(2,3,4,5-tetrahydropyrido[3,2-f][1,4]oxazepin-8-yl)piperazine-1-carboxamide dihydrochloride (Step 1)

To a solution of the compound (0.10 g) obtained in Example 33, step 1 in THF (3 mL)/diethyl ether (3 mL) was added tert-butyl isocyanate (41 μL), and the mixture was stirred at room temperature for 16 hr. The solvent was evaporated under reduced pressure, and the obtained solid was washed with diethyl ether/hexane to give tert-butyl 8-{4-[(tert-butylamino)carbonyl]piperazin-1-yl}-2,3-dihydropyrido[3,2-f][1,4]oxazepine-4(5H)-carboxylate (0.11 g, 85%) as a white powder.

$^1$H-NMR (CDCl$_3$): δ 1.36 (9H, s), 1.42 (9H, s), 3.40-3.48 (4H, m), 3.50-3.60 (4H, m), 3.79 (2H, dd like), 4.21-4.40 (5H, m), 6.29 (1H, d, J=8.1 Hz), 7.26-7.50 (1H, m)

(Step 2)

The title compound was obtained in the same manner as in Example 146, step 2, and using the compound obtained in step 1.

$^1$H-NMR (DMSO-d$_6$): δ 1.26 (9H, s), 3.30-3.37 (4H, m), 3.44 (6H, brs like), 4.16 (2H, brs), 4.25 (2H, brs), 4.56 (1H, brs), 5.87 (1H, brs), 6.60 (1H, d, J=8.3 Hz), 7.62 (1H, d, J=8.5 Hz), 9.37 (2H, brs)

MS (ESI+): 334 (M−2HCl+H)

Example 196

8-[4-(3-phenylpropyl)piperazin-1-yl]-2,3,4,5-tetrahydropyrido[3,2-f][1,4]oxazepine dihydrochloride (Step 1)

To the compound (0.10 g) obtained in Example 33, step 1 and 3-phenylpropanal (118 μL) was added titanium tetraisopropoxide (664 μL), and the mixture was stirred at room temperature for 18 hr under a nitrogen atmosphere. A solution of poly(methylhydrosilane) (106 μL) in THF (5 mL) was added, and the mixture was stirred at room temperature for 3 hr. A 3N aqueous sodium hydroxide solution was added to the reaction mixture, and the mixture was extracted with ethyl acetate. The organic layer was washed with brine and dried, and the solvent was evaporated under reduced pressure. The residue was purified by basic silica gel column chromatography (solvent gradient; 10→40% ethyl acetate/hexane) to give tert-butyl 8-[4-(3-phenylpropyl)piperazin-1-yl]-2,3-dihydropyrido[3,2-f][1,4]oxazepine-4(5H)-carboxylate (0.02 g, 4%) as a yellow oil.

$^1$H-NMR (CDCl$_3$): δ 1.42 (9H, s), 1.80-1.91 (2H, m), 2.40 (2H, dd like), 2.51 (4H, t like), 2.65 (2H, t, J=7.6 Hz), 3.51 (4H, t like), 3.78 (2H, t like), 4.20-4.40 (4H, m), 6.30 (1H, d, J=8.3 Hz), 7.15-7.20 (3H, m), 7.25-7.30 (3H, m)

(Step 2)

The title compound was obtained in the same manner as in Example 146, step 2, and using the compound obtained in step 1.

$^1$H-NMR (DMSO-d$_6$): δ 1.99-2.15 (2H, m), 2.65 (2H, t, J=7.7 Hz), 3.01 (2H, q like), 3.08-3.13 (2H, m), 3.33 (2H, t like), 3.43 (2H, brs like), 3.55 (2H, d like), 4.00-4.40 (6H, m), 6.69 (1H, d, J=8.3 Hz), 7.19-7.34 (5H, m), 7.70 (1H, d, J=8.3 Hz), 9.66 (2H, brs), 11.28 (1H, brs)

Example 197

8-(4-benzylpiperazin-1-yl)-2,3,4,5-tetrahydropyrido[3,2-f][1,4]oxazepine (Step 1)

To a mixture of the compound (0.28 g) obtained in Example 33, step 1, potassium carbonate (0.23 g) and DMF (5 mL) was added benzyl bromide (109 μL), and the mixture was stirred at room temperature for 18 hr. Ethyl acetate and water were added to the reaction mixture. The organic layer was washed with water and brine and dried, and the solvent was evaporated under reduced pressure. The residue was purified by silica gel column chromatography (solvent gradient; 0→30% ethyl acetate/hexane) to give tert-butyl 8-(4-benzylpiperazin-1-yl)-2,3-dihydropyrido[3,2-f][1,4]oxazepine-4(5H)-carboxylate (0.24 g, 68%) as a white powder.

$^1$H-NMR (CDCl$_3$): δ 1.42 (9H, s), 2.53 (4H, t like), 3.51 (4H, t like), 3.54 (2H, s), 3.78 (2H, dd like), 4.20-4.39 (4H, m), 6.28 (1H, d, J=8.3 Hz), 7.25-7.40 (6H, m)

(Step 2)

The title compound was obtained in the same manner as in Example 143, step 2, and using the compound obtained in step 1.

¹H-NMR (CDCl₃): δ 1.59 (1H, brs), 2.53 (4H, t, J=5.1 Hz), 3.21 (2H, t like), 3.51 (4H, t, J=5.1 Hz), 3.54 (2H, s), 3.82 (2H, s), 4.17 (2H, dd like), 6.27 (1H, d, J=8.3 Hz), 7.26-7.34 (6H, m)

MS (ESI+): 325 (M+H)

Example 198 ethyl 2-[4-(2,3,4,5-tetrahydropyrido[3,2-f][1,4]oxazepin-8-yl)piperazin-1-yl]propanoate 1.4 hydrobromide The title compound was obtained in the same manner as in Example 143, step 1 and Example 145, step 2, and using the compound obtained in Example 29, step 1 and ethyl 2-piperazin-1-ylpropanoate.

¹H-NMR (CD₃OD): δ 1.19 (3H, t, J=7.2 Hz), 1.45 (3H, br), 2.99 (4H, brs like), 3.59 (2H, t like), 3.70 (4H, brs like), 4.27 (2H, s), 4.20-4.34 (5H, m), 4.82 (2.4H, s), 6.63 (1H, d, J=8.4 Hz), 7.63 (1H, d, J=8.4 Hz)

MS (ESI+): 335 (M−1.4HBr+H)

Example 199

8-[4-(benzyloxy)phenyl]-2,3,4,5-tetrahydropyrido[3,2-f][1,4]oxazepine dihydrochloride (Step 1)

A solution of the compound (0.500 g) obtained in Example 29, step 1,4-benzyloxyphenylboronic acid (0.600 g) and potassium carbonate (0.243 g) in DME (10 mL) and water (1 mL) was degassed with argon gas, tetrakis(triphenylphosphine)palladium(0) (Pd(PPh₃)₄) (0.203 g) was added, and the reaction container was irradiated in a microwave reaction apparatus at 150° C. for 10 min. The reaction mixture was poured into water, and the resultant product was extracted with ethyl acetate. The organic layer was washed with brine, dried over magnesium sulfate, and concentrated. The obtained solid was recrystallized from a mixed solution of ethyl acetate and hexane to give tert-butyl 8-[(benzyloxy)phenyl]-2,3-dihydropyrido[3,2-f][1,4]oxazepine-4(5H)-carboxylate (0.483 g, 64%) as a white powder.

¹H-NMR (CDCl₃): δ 1.32 (9H, brs), 3.74 (2H, brs), 4.24 (2H, brs), 4.47 (2H, brs), 5.17 (2H, s), 7.09 (2H, d, J=8.7 Hz), 7.31-7.52 (5H, m), 7.58 (1H, m), 7.71 (1H, m), 7.97 (2H, d, J=8.7 Hz)

MS (ESI+): 433 (M+H)

(Step 2)

The title compound was obtained in the same manner as in Example 33, step 3, and using the compound obtained in step 1.

¹H-NMR (DMSO-d₆): δ 3.52 (2H, brs), 4.30-4.43 (4H, m), 5.18 (2H, s), 7.12 (2H, d, J=8.9 Hz), 7.30-7.50 (5H, m), 7.73 (1H, d, J=7.9 Hz), 7.94 (1H, d, J=7.9 Hz), 8.02 (2H, d, J=8.9 Hz), 9.63 (2H, brs)

MS (ESI+): 333 (M−2HCl+H)

Example 200

8-(1H-pyrazol-4-yl)-2,3,4,5-tetrahydropyrido[3,2-f][1,4]oxazepine trihydrochloride The title compound was obtained in the same manner as in Example 199 and using the compound obtained in Example 29, step 1 and 4-(4,4,5,5-tetramethyl-1,3,2-dioxaborolan-2-yl)-1H-pyrazole.

¹H-NMR (DMSO-d₆): δ 3.50 (2H, brs), 4.32-4.36 (4H, m), 7.51 (1H, d, J=7.7 Hz), 7.87 (1H, d, J=7.7 Hz), 8.18 (2H, s), 9.64 (2H, brs)

MS (ESI+): 217 (M−3HCl+H)

Example 201

8-(3,5-dimethylisoxazol-4-yl)-2,3,4,5-tetrahydropyrido[3,2-f][1,4]oxazepine dihydrochloride The title compound was obtained in the same manner as in Example 199 and using the compound obtained in Example 29, step 1 and 3,5-dimethylisoxazole-4-boronic acid.

¹H-NMR (DMSO-d₆): δ 2.37 (3H, s), 2.57 (3H, s), 3.50-3.60 (2H, m) 4.35-4.45 (4H, m), 7.38 (1H, d, J=8.0 Hz), 8.00 (1H, d, J=8.0 Hz), 9.70 (2H, brs)

MS (ESI+): 246 (M−2HCl+H)

Example 202

8-(1H-indol-5-yl)-2,3,4,5-tetrahydropyrido[3,2-f][1,4]oxazepine trihydrochloride The title compound was obtained in the same manner as in Example 199 and using the compound obtained in Example 29, step 1 and indole-5-boronic acid.

¹H-NMR (DMSO-d₆): δ 3.53 (2H, brs), 4.31-4.43 (4H, m), 6.53 (1H, brs), 7.40 (1H, t, J=2.7 Hz), 7.46 (1H, d, J=8.5 Hz), 7.77 (1H, d, J=8.0 Hz), 7.84 (1H, dd, J=8.5, 1.7 Hz), 7.92 (1H, d, J=8.0 Hz), 8.28-8.31 (1H, m), 9.54 (2H, brs), 11.26 (1H, brs)

MS (ESI+): 266 (M−3HCl+H)

Example 203

8-(1H-indol-6-yl)-2,3,4,5-tetrahydropyrido[3,2-f][1,4]oxazepine trihydrochloride The title compound was obtained in the same manner as in Example 199 and using the compound obtained in Example 29, step 1 and indole-6-boronic acid;

¹H-NMR (DMSO-d₆): δ 3.53 (2H, brs), 4.32-4.44 (4H, m), 6.47 (1H, brs), 7.46 (1H, t, J=2.8 Hz), 7.61 (1H, d, J=8.3 Hz), 7.69-7.75 (1H, m), 7.78 (1H, d, J=7.6 Hz), 7.94 (1H, d, J=7.6 Hz), 8.15 (1H, s), 9.64 (2H, brs), 11.31 (1H, brs)

MS (ESI+): 266 (M−3HCl+H)

Example 204

8-(2,3-dihydro-1-benzofuran-5-yl)-2,3,4,5-tetrahydropyrido[3,2-f][1,4]oxazepine dihydrochloride The title compound was obtained in the same manner as in Example 199 and using the compound obtained in Example 29, step 1 and 2,3-dihydro-1-benzofuran-5-ylboronic acid.

¹H-NMR (DMSO-d₆): δ 3.24 (2H, t, J=8.7 Hz), 3.49-3.57 (2H, m), 4.33-4.41 (4H, m), 4.60 (2H, t, J=8.7 Hz), 6.85 (1H, d, J=8.3 Hz), 7.69 (1H, d, J=7.6 Hz), 7.84 (1H, dd, J=8.3, 1.9 Hz), 7.91 (1H, d, J=7.6 Hz), 7.96 (1H, d, J=1.9 Hz), 9.54 (2H, brs)

MS (ESI+): 269 (M−2HCl+H)

Example 205

8-isopropyl-2,3,4,5-tetrahydropyrido[3,2-f][1,4]oxazepine dihydrochloride (Step 1)

To a solution of the compound (0.500 g) obtained in Example 29, step 1 and iron(III) acetylacetonate (0.0620 g) in a mixture of THF (10 mL) and 1-methylpyrrolidinone (1 mL) was added 1M isopropylmagnesium chloride ether solution (8.78 mL), and the mixture was stirred at room temperature for 2 hr. The reaction mixture was poured into 1N hydrochloric acid, and the resultant product was extracted with ethyl acetate. The organic layer was washed with brine, dried over magnesium sulfate, and concentrated. The obtained residue was purified by silica gel column chromatography (solvent gradient; 5→100% ethyl acetate/hexane) to give tert-butyl 8-isopropyl-2,3-dihydropyrido[3,2-f][1,4]oxazepine-4(5H)-carboxylate (0.136 g, 27%) as an oil.

$^1$H-NMR (CDCl$_3$): δ 1.27 (6H, d, J=7.0 Hz), 1.42 (9H, s), 2.93-3.02 (1H, m), 3.82-3.84 (2H, m), 4.22 (2H, brs), 4.35-4.50 (2H, m), 6.88 (1H, d, J=7.5 Hz), 7.40-7.60 (1H, m)

MS (ESI+): 293 (M+H)

(Step 2)

The title compound was obtained in the same manner as in Example 33, step 3, and using the compound obtained in step 1.

$^1$H-NMR (DMSO-d$_6$): δ 1.19 (6H, d, J=6.8 Hz), 2.86-3.03 (1H, m), 3.44-3.53 (2H, m), 4.27-4.35 (4H, m), 7.10 (1H, d, J=7.5 Hz), 7.81 (1H, d, J=7.5 Hz), 9.56 (2H, brs)

MS (ESI+): 193 (M−2HCl+H)

Example 206

8-ethyl-2,3,4,5-tetrahydropyrido[3,2-f][1,4]oxazepine dihydrochloride

The title compound was obtained in the same manner as in Example 205 and using the compound obtained in Example 29, step 1 and 3-Methylmagnesium bromide ether solution.

$^1$H-NMR (DMSO-d$_6$): δ 1.18 (3H, t, J=7.6 Hz), 2.67 (2H, q, J=7.6 Hz), 3.48 (2H, brs), 4.25-4.35 (4H, m), 7.09 (1H, d, J=7.5 Hz), 7.82 (1H, d, J=7.5 Hz), 9.71 (2H, brs)

MS (ESI+): 179 (M−2HCl+H)

Example 207

8-sec-butyl-2,3,4,5-tetrahydropyrido[3,2-f][1,4]oxazepine dihydrochloride

The title compound was obtained in the same manner as in Example 205 and using the compound obtained in Example 29, step 1 and 1M sec-butylmagnesium bromide THF solution.

$^1$H-NMR (DMSO-d$_6$): δ 0.76 (3H, t, J=7.4 Hz), 1.16 (3H, d, J=6.8 Hz), 1.43-1.73 (2H, m), 2.62-2.77 (1H, m), 3.41-3.54 (2H, m), 4.24-4.38 (4H, m), 7.06 (1H, d, J=7.5 Hz), 7.82 (1H, d, J=7.5 Hz), 9.66 (2H, brs)

MS (ESI+): 207 (M−2HCl+H)

Example 208

8-(1-methylbutyl)-2,3,4,5-tetrahydropyrido[3,2-f][1,4]oxazepine dihydrochloride (Step 1)

To a mixture of 2-bromopentane (5.00 g), magnesium turnings (4.02 g) and THF (20 mL) was added iodine (1 piece), and the mixture was heated under reflux for 10 min. A solution of 2-bromopentane (20.0 g) in THF (80 mL) was added dropwise to the reaction mixture. The mixture was further heated under reflux for 16 hr and cooled to room temperature.

(Step 2)

To a solution of the compound (0.500 g) obtained in Example 29, step 1 and iron(III) acetylacetonate (0.0620 g) in a mixture of THF (10 mL) and 1-methylpyrrolidinone (1 mL) was added the solution (8.78 mL) obtained in step 1, and the mixture was stirred at room temperature for 2 hr. The reaction mixture was poured into 1N hydrochloric acid, and the resultant product was extracted with ethyl acetate. The organic layer was washed with brine, dried over magnesium sulfate, and concentrated. The obtained residue was purified by silica gel column chromatography (solvent gradient; 5→100% ethyl acetate/hexane) to give tert-butyl 8-(1-methylbutyl)-2,3-dihydropyrido[3,2-f][1,4]oxazepine-4(5H)-carboxylate (0.172 g, 30%) as an oil.

$^1$H-NMR (CDCl$_3$): δ 0.86 (3H, t, J=7.4 Hz), 1.09-1.34 (1H, m), 1.24 (3H, d, J=7.0 Hz), 1.42 (9H, s), 1.46-1.80 (3H, m), 2.72-2.88 (1H, m), 3.80-3.86 (2H, m), 4.19-4.25 (2H, m), 4.35-4.51 (2H, m), 6.84 (1H, d, J=7.5 Hz), 7.40-7.58 (1H, m)

MS (ESI+): 321 (M+H)

(Step 3)

The title compound was obtained in the same manner as in Example 33, step 3, and using the compound obtained in step 2.

$^1$H-NMR (DMSO-d$_6$): δ 0.83 (3H, t, J=7.3 Hz), 1.01-1.24 (2H, m), 1.16 (3H, d, J=6.9 Hz), 1.39-1.53 (1H, m), 1.54-1.68 (1H, m), 2.72-2.86 (1H, m), 3.47 (2H, brs), 4.28-4.34 (4H, m), 7.07 (1H, d, J=7.6 Hz), 7.82 (1H, d, J=7.6 Hz), 9.74 (2H, brs)

MS (ESI+): 221 (M−2HCl+H)

Example 209

8-(1-ethylpropyl)-2,3,4,5-tetrahydropyrido[3,2-f][1,4]oxazepine dihydrochloride

The title compound was obtained in the same manner as in Example 208 and using the compound obtained in Example 29, step 1 and 3-bromopentane.

$^1$H-NMR (DMSO-d$_6$): δ 0.70 (6H, t, J=7.4 Hz), 1.54-1.65 (4H, m), 2.42-2.50 (1H, m), 3.47 (2H, brs), 4.30-4.35 (4H, m), 7.03 (1H, d, J=7.6 Hz), 7.81 (1H, d, J=7.6 Hz), 9.61 (2H, brs)

MS (ESI+): 221 (M−2HCl+H)

Example 210

8-cyclopropyl-2,3,4,5-tetrahydropyrido[3,2-f][1,4]oxazepine dihydrochloride

The title compound was obtained in the same manner as in Example 205 and using the compound obtained in Example 29, step 1 and 0.5M cyclopropylmagnesium bromide ether solution.

$^1$H-NMR (DMSO-d$_6$): δ 0.80-0.89 (2H, m), 0.90-0.98 (2H, m), 2.01-2.10 (1H, m), 3.45 (2H, brs), 4.25-4.30 (4H, m), 7.11 (1H, d, J=7.6 Hz), 7.74 (1H, d, J=7.6 Hz), 9.70 (2H, brs)

MS (ESI+): 191 (M−2HCl+H)

Example 211

8-cyclobutyl-2,3,4,5-tetrahydropyrido[3,2-f][1,4]oxazepine dihydrochloride

The title compound was obtained in the same manner as in Example 208 and using the compound obtained in Example 29, step 1 and chlorocyclobutane.

$^1$H-NMR (DMSO-d$_6$): δ 1.74-1.89 (1H, m), 1.88-2.07 (1H, m), 2.11-2.29 (4H, m), 3.43-3.53 (2H, m), 3.53-3.65 (1H, m), 4.25-4.38 (4H, m), 7.06 (1H, d, J=7.6 Hz), 7.81 (1H, d, J=7.6 Hz), 9.69 (2H, brs)

MS (ESI+): 205 (M−2HCl+H)

Example 212

8-cyclopentyl-2,3,4,5-tetrahydropyrido[3,2-f][1,4]oxazepine dihydrochloride

The title compound was obtained in the same manner as in Example 205 and using the compound obtained in Example 29, step 1 and 1M cyclopentylmagnesium bromide THF solution.

$^1$H-NMR (DMSO-d$_6$): δ 1.60-1.80 (6H, m), 1.90-2.00 (2H, m), 3.03-3.15 (1H, m), 3.47 (2H, brs), 4.25-4.35 (4H, m), 7.10 (1H, d, J=7.5 Hz), 7.79 (1H, d, J=7.5 Hz), 9.64 (2H, brs)
MS (ESI+): 219 (M−2HCl+H)

Example 213

8-cyclopentyl-2,3,4,5-tetrahydropyrido[3,2-f][1,4]oxazepine

The compound obtained in Example 212 was dissolved in 8N aqueous sodium hydroxide solution, and the mixture was extracted with ethyl acetate. The organic layer was washed with brine, dried over magnesium sulfate, and concentrated. The obtained solid was recrystallized from a mixed solution of isopropyl ether and petroleum ether to give the title compound (0.209 g, 36%) as a pale-brown solid.

$^1$H-NMR (CDCl$_3$): δ 1.62-1.85 (6H, m), 1.96-2.10 (2H, m), 3.00-3.15 (1H, m), 3.23-3.26 (2H, m), 3.91 (2H, s), 4.18-4.21 (2H, m), 6.86 (1H, d, J=7.6 Hz), 7.39 (1H, d, J=7.6 Hz)
MS (ESI+): 219 (M+H)

Example 214

8-cyclohexyl-2,3,4,5-tetrahydropyrido[3,2-f][1,4]oxazepine dihydrochloride

The title compound was obtained in the same manner as in Example 205 and using the compound obtained in Example 29, step 1 and 1M cyclohexylmagnesium bromide THF solution.

$^1$H-NMR (DMSO-d$_6$): δ 1.15-1.50 (5H, m), 1.65-1.85 (5H, m), 2.55-2.65 (1H, m), 3.47 (2H, brs), 4.25-4.35 (4H, m), 7.07 (1H, d, J=7.6 Hz), 7.81 (1H, d, J=7.6 Hz), 9.64 (2H, br s)
MS (ESI+): 233 (M−2HCl+H)

Example 215

8-(tetrahydro-2H-pyran-4-yl)-2,3,4,5-tetrahydropyrido[3,2-f][1,4]oxazepine dihydrochloride The title compound was obtained in the same manner as in Example 208 and using the compound obtained in Example 29, step 1 and 4-chlorotetrahydropyran.

$^1$H-NMR (DMSO-d$_6$): δ 1.61-1.76 (4H, m), 2.80-2.95 (1H, m), 3.37-3.60 (4H, m), 3.90-3.97 (2H, m), 4.31 (4H, brs), 7.11 (1H, d, J=7.6 Hz), 7.83 (1H, d, J=7.6 Hz), 9.50-9.70 (2H, m)
MS (ESI+): 235 (M−2HCl+H)

Example 216

8-[(1E)-prop-1-en-1-yl]-2,3,4,5-tetrahydropyrido[3,2-f][1,4]oxazepine monohydrochloride The title compound was obtained in the same manner as in Example 199 and using the compound obtained in Example 29, step 1 and trans-propenylboronic acid.

$^1$H-NMR (DMSO-d$_6$): δ 1.88 (3H, dd, J=6.9, 1.6 Hz), 3.49 (2H, brs), 4.27-4.33 (4H, m), 6.43 (1H, dd, J=15.6, 1.6 Hz), 6.70-6.80 (1H, m), 7.16 (1H, d, J=7.6 Hz), 7.82 (1H, d, J=7.6 Hz), 9.50 (2H, brs)
MS (ESI+): 191 (M−HCl+H)

The compounds described in Examples 139-216 are as follows (Tables 15-22).

TABLE 15

| Example No. | Structural formula | Salt | MS (ESI) |
|---|---|---|---|
| 139 | H$_2$N-pyrido-oxazepine-NH | 2HCl | 166 |
| 140 | 3-methylpiperidinyl-pyrido-oxazepine-NH | | 248 |
| 141 | 4-methylpiperidinyl-pyrido-oxazepine-NH | | 248 |
| 142 | 4-methoxypiperidinyl-pyrido-oxazepine-NH | HCl | 264 |
| 143 | (+)-2-methylpiperidinyl-pyrido-oxazepine-NH | HCl | 248 |
| 144 | (−)-2-methylpiperidinyl-pyrido-oxazepine-NH | HCl | 248 |
| 145 | 2-ethylpiperidinyl-pyrido-oxazepine-NH | 2HBr | 262 |

TABLE 15-continued

| Example No. | Structural formula | Salt | MS (ESI) |
|---|---|---|---|
| 146 | | 2HCl | 262 |
| 147 | | HCl | 236 |
| 148 | | HBr | 236 |
| 149 | | HCl | 254 |
| 150 | | HBr | 270 |

TABLE 16

| Example No. | Structural formula | Salt | MS (ESI) |
|---|---|---|---|
| 151 | | HCl | 314 |
| 152 | | 2HCl | 252 |
| 153 | | 2HBr | 267 |

TABLE 16-continued

| Example No. | Structural formula | Salt | MS (ESI) |
|---|---|---|---|
| 154 | | 2HCl | 284 |
| 155 | | | 248 |
| 156 | | HBr | 248 |
| 157 | (short retention time) | | 234 |
| 158 | (long retention time) | | 234 |
| 159 | | HCl | 250 |
| 160 | | 2HBr | 208 |

TABLE 17

| Example No. | Structural formula | Salt | MS (ESI) |
|---|---|---|---|
| 161 | | 2HCl | 242 |

TABLE 17-continued

| Example No. | Structural formula | Salt | MS (ESI) |
|---|---|---|---|
| 162 | | 0.5 succinate | 222 |
| 163 | | 0.5 succinate | 222 |
| 164 | | HCl | 236 |
| 165 | | HBr | 236 |
| 166 | | HCl | 236 |
| 167 | | | 298 |
| 168 | | 2HBr | 222 |
| 169 | | 2HBr | 222 |

TABLE 17-continued

| Example No. | Structural formula | Salt | MS (ESI) |
|---|---|---|---|
| 170 | | 2HBr | 222 |

TABLE 18

| Example No. | Structural formula | Salt | MS (ESI) |
|---|---|---|---|
| 171 | | HBr | 236 |
| 172 | | HCl | 236 |
| 173 | | 2HCl | 236 |
| 174 | | | 220 |
| 175 | | 2HBr | 234 |
| 176 | | | 262 |
| 177 | | | 222 |

TABLE 18-continued

| Example No. | Structural formula | Salt | MS (ESI) |
|---|---|---|---|
| 178 | (H3C)(CH3)CH-N(CH3)-pyrido-oxazepine | HBr | 222 |
| 179 | (H3C)(CH3)CH-N(CH3)-pyrido-oxazepine, Cl substituent | HCl | 256 |
| 180 | (H3C)(CH3)CH-N(CH3)-pyrido-oxazepine, Br substituent | HCl | 300 |

TABLE 19

| Example No. | Structural formula | Salt | MS (ESI) |
|---|---|---|---|
| 181 | (H3C)(CH3)CH-N(CH3)-pyrido-oxazepine with CH3 | succinate | 236 |
| 182 | (H3C)(CH3)CH-N(CH3)-pyrido-oxazepine with CH3 | 0.5 succinate | 236 |
| 183 | (H3C)(CH3)(CH3)C-NH-pyrido-oxazepine | 2HBr | 222 |
| 184 | isobutyl-NH-pyrido-oxazepine | HBr | 222 |
| 185 | isobutyl-N(CH3)-pyrido-oxazepine | 2HBr | 236 |
| 186 | H3C-CH2-N(CH3)-pyrido-oxazepine | 2HBr | 208 |
| 187 | (H3C)(CH3)N-pyrido-oxazepine | 2HBr | 194 |
| 188 | tetrahydropyranyl-N(CH3)-pyrido-oxazepine | 2HCl | 264 |
| 189 | cyclopropyl-NH-pyrido-oxazepine | 2HBr | 206 |
| 190 | cyclopropyl-N(CH3)-pyrido-oxazepine | 2HBr | 220 |

TABLE 20

| Example No. | Structural formula | Salt | MS (ESI) |
|---|---|---|---|
| 191 | cyclobutyl-NH-pyrido-oxazepine | 2HBr | 220 |

TABLE 20-continued

| Example No. | Structural formula | Salt | MS (ESI) |
|---|---|---|---|
| 192 | | 2HBr | 234 |
| 193 | | 2HBr | 234 |
| 194 | | 2HBr | 248 |
| 195 | | 2HCl | 334 |
| 196 | | 2HCl | — |
| 197 | | | 325 |
| 198 | | 1.4HBr | 335 |
| 199 | | 2HCl | 333 |

TABLE 20-continued

| Example No. | Structural formula | Salt | MS (ESI) |
|---|---|---|---|
| 200 | | 3HCl | 217 |

TABLE 21

| Example No. | Structural formula | Salt | MS (ESI) |
|---|---|---|---|
| 201 | | 2HCl | 246 |
| 202 | | 3HCl | 266 |
| 203 | | 3HCl | 266 |
| 204 | | 2HCl | 269 |
| 205 | | 2HCl | 193 |
| 206 | | 2HCl | 179 |
| 207 | | 2HCl | 207 |

TABLE 21-continued

| Example No. | Structural formula | Salt | MS (ESI) |
|---|---|---|---|
| 208 | | 2HCl | 221 |
| 209 | | 2HCl | 221 |
| 210 | | 2HCl | 191 |

TABLE 22

| Example No. | Structural formula | Salt | MS (ESI) |
|---|---|---|---|
| 211 | | 2HCl | 205 |
| 212 | | 2HCl | 219 |
| 213 | | | 219 |

TABLE 22-continued

| Example No. | Structural formula | Salt | MS (ESI) |
|---|---|---|---|
| 214 | | 2HCl | 233 |
| 215 | | 2HCl | 235 |
| 216 | | HCl | 191 |

Formulation Example 1

| | |
|---|---|
| (1) Compound of Example 1 | 10 mg |
| (2) Lactose | 60 mg |
| (3) Cornstarch | 35 mg |
| (4) hydroxypropylmethylcellulose | 3 mg |
| (5) Magnesium stearate | 2 mg |

A mixture of 10 mg of the compound obtained in Example 1, 60 mg of lactose and 35 mg of corn starch is granulated using 0.03 mL of an aqueous solution of 10 wt % hydroxypropylmethylcellulose (3 mg as hydroxypropylmethylcellulose), and then dried at 40° C. and sieved. The obtained granules are mixed with 2 mg of magnesium stearate and compressed. The obtained uncoated tablets are sugar-coated with an aqueous suspension of sucrose, titanium dioxide, talc and gum arabic. The thus-coated tablets are glazed with beeswax to give finally-coated tablets.

Formulation Example 2

| | |
|---|---|
| (1) Compound of Example 1 | 10 mg |
| (2) Lactose | 70 mg |
| (3) Cornstarch | 50 mg |
| (4) Soluble starch | 7 mg |
| (5) Magnesium stearate | 3 mg |

The compound (10 mg) obtained in Example 1 and 3 mg of magnesium stearate are granulated with 0.07 mL of an aqueous solution of soluble starch (7 mg as soluble starch), dried, and mixed with 70 mg of lactose and 50 mg of corn starch. The mixture is compressed to give tablets.

Reference Formulation Example 1

| | |
|---|---|
| (1) Rofecoxib | 5.0 mg |
| (2) Sodium chloride | 20.0 mg |
| (3) Distilled water | amount to make total volume 2.0 mL |

Rofecoxib (5.0 mg) and 20.0 mg of Sodium chloride are dissolved in distilled water, and water is added to make the total volume 2.0 mL. The solution is filtered, and filled into 2 mL of ampoule under sterile condition. The ampoule is sterilized, and then sealed to give a solution for injection.

Reference Formulation Example 2

| | |
|---|---|
| (1) Rofecoxib | 50 mg |
| (2) Lactose | 34 mg |
| (3) Cornstarch | 10.6 mg |
| (4) Cornstarch (paste) | 5 mg |
| (5) Magnesium stearate | 0.4 mg |
| (6) Calcium carboxymethylcellulose | 20 mg |
| total | 120 mg |

The above-mentioned (1) to (6) are mixed according to a conventional method and the mixture is tableted by a tableting machine to give a tablet.

Formulation Example 3

The formulation prepared in Formulation Example 1 or 2, and the formulation prepared in Reference Formulation Example 1 or 2 are combined.

Experimental Example 1

The serotonin 5-HT$_{2C}$ receptor agonist activity of the Example compounds was evaluated based on the changes in the intracellular calcium concentration by the following method. After transcription, 5-HT$_{2C}$ undergoes RNA editing of the second intracellular loop, which results in the change of three amino acids and 14 receptor isoforms. 5-HT$_{2C}$ stably expressing CHO cell that expresses isoform type VSV stably was purchased from Euroscreen S.A., and cultured in a Ultra-CHO (BioWhittaker) medium containing 1% dialyzed bovine serum and 400 μg/mL G418. The cells were plated in a 384-well black clear bottom plate (PE Biosystems) at 5000 cells/well, cultured for 24 hr in a $CO_2$ incubator, and changes in the intracellular calcium concentration mediated by the 5-HT$_{2C}$ receptor were evaluated using Calcium Kit-Fluo 3 (Dojindo Laboratories). A calcium kit buffer containing 2.5 mM probenecid, 0.04% Pluronic F-127 and 2.5 μg Fluo-3 AM (calcium indicator fluorescent dye) was prepared and used as a Fluo-3 loading solution (contained in Dojindo Laboratories Calcium Kit). The loading solution was incubated at 37° C., the medium in the wells of the cell culture plate was removed, and the loading solution was added to each well by 40 μL. The cells were reacted at 37° C. for 1 hr to allow uptake of Fluo-3 AM into the cells and washed. The Example compound was diluted with a calcium kit buffer, and dispensed to each well of the 384-well plate (REMP) by 40 μL to give a Example compound plate. The cell culture plate and test compound plate were set on a Fluometric Imaging Plate Reader (FLIPR, Molecular Devices), and changes in the intracellular calcium concentration were measured. An increase in the fluorescence intensity of Fluo-3 matches with an increase in the intracellular calcium concentration mediated by a receptor. The changes in the intracellular fluorescence intensity were measured every second with a CCD camera of FLIPR and, after measurement for 5 seconds before addition of the compound, a diluted solution of the Example compound was added by 20 μL to each well of the cell culture plate using an automatic dispenser in FLIPR.

The agonist activity was evaluated based on the difference in the fluorescence level obtained by subtracting the fluorescence intensity before addition of the compound from the maximum fluorescence intensity after the addition thereof. The activity of the test compound is shown by the ratio relative to the maximum response by 5-HT (Table 23).

TABLE 23

| Example No. | ratio to maximum response by 5-HT (1 μM) |
|---|---|
| 30 | 99.4% |
| 40 | 80.8% |
| 41 | 83.0% |
| 43 | 97.0% |
| 44 | 95.1% |
| 46 | 100.2% |
| 49 | 89.5% |
| 58 | 87.1% |
| 67 | 123.5% |
| 79 | 91.1% |
| 81 | 92.1% |
| 96 | 90.3% |
| 102 | 91.3% |
| 104 | 94.6% |
| 112 | 93.0% |
| 122 | 109.7% |
| 126 | 108.9% |
| 128 | 106.6% |
| 129 | 111.4% |
| 130 | 105.4% |
| 131 | 94.2% |
| 147 | 93.9% |
| 148 | 93.5% |
| 155 | 85.4% |
| 156 | 93.4% |
| 171 | 99.6% |
| 172 | 95.3% |
| 173 | 95.1% |
| 177 | 91.5% |
| 178 | 94.6% |
| 205 | 93.5% |
| 210 | 107.7% |
| 211 | 98.0% |
| 212 | 91.9% |
| 213 | 96.6% |

From Table 23, it was found that the compound of the present invention has a superior serotonin 5-$HT_c$ receptor agonist activity.

Example 217

Experiment Method

Female SD rats (body weight 190-310 g) were anesthetized with urethane (Wako Pure Chemical Industries, Ltd.), and the spinal cord was transected at T8-9 level to eliminate the micturition reflex. During the operation, halothane (Takeda Pharmaceutical Company Limited) anesthesia was added when necessary. After abdominal section, bladder neck was ligated with a suture thread, and then the hypogastric nerve and pudendal nerve were bilaterally transected. In some animals, the nerves advancing toward the iliococcygeus muscle and pubococcygeus muscle were also bilaterally transected. A catheter (PE-90, Clay Adams) was placed in the bladder, and the other end of the bladder catheter was connected to a pressure transducer and a water reservoir (60 ml syringe) of saline via a three-way cock. A microchip transducer catheter (SPR-524, Millar Instruments Inc.) was inserted toward the bladder from the urethral opening, and adjusted using a scale on the catheter surface so that the transducer part is positioned in the urinary tract at 10.0-15.0 mm from the urethral opening.

The changes in the topical pressure within the urinary tract (hereinafter conveniently indicated as urethral internal pressure) as measured by the microchip transducer was transmitted to a computer via an amplifier (blood pressure amplification unit AP-641G; NIHON KOHDEN) and an analog-to-digital converter (MP-100; biopack; sampled at 500 Hz), and recorded on a hard disc. The intravesical pressure was rapidly increased to 50 $cmH_2O$ for 30 sec by setting the position of the water reservoir of saline at 50 cm higher, and changes in the urethral internal pressure were observed. The reaction of the urinary tract induced by an increased intravesical pressure was measured 3 times, and the average of the last 0.2 measures was taken as the value before drug administration. The evaluation item was reflex urethral closure response, and the recorded values were subjected to smoothing process at 500 points to calculate an average urethral internal pressure per 1 sec, after which the value immediately before increase of the intravesical pressure was subtracted from the maximum value on increase of the intravesical pressure and taken as the urethral closure response.

[Results]

Using rats in which the spinal cord was transected to eliminate the micturition reflex, and the hypogastric nerve and the pudendal nerve controlling the internal urethral sphincter, external urethral sphincter and coccygeus muscle were bilaterally transected, the intravesical pressure was rapidly increased from 0 $cmH_2O$ to 50 $cmH_2O$. As a result, a urethral internal pressure-increasing response (urethral closure response) was observed (FIG. 1). The mean±SEM of the urethral closure responses in 20 rats subjected to the experiment was 5.6±0.7 $cmH_2O$.

In rats in which the nerve advancing toward the iliococcygeus muscle and pubococcygeus muscle was bilaterally transected in addition to the hypogastric nerve and pudendal nerve, the mean±SEM of the urethral closure responses due to an increased intravesical pressure was 1.3±0.4 $cmH_2O$ (4 rats), which was significantly low ($P<0.05$, two-sided test, Student's t-test) as compared to the rats free of transection of the nerve advancing toward the iliococcygeus muscle and pubococcygeus muscle. The results reveal that the urethral closure response obtained by rapidly increasing the intravesical pressure from 0 $cmH_2O$ to 50 $cmH_2O$ in the rats with bilaterally transected hypogastric nerve and pudendal nerve is attributable to a contractile response mainly by the iliococcygeus muscle and pubococcygeus muscle.

Example 218

Experiment Method

Female SD rats (body weight 200-310 g) were anesthetized with urethane (Wako Pure Chemical Industries, Ltd.), and the spinal cord was transected at T8-9 level to eliminate the micturition reflex. During the operation, halothane (Takeda Pharmaceutical Company Limited) anesthesia was added when necessary. After abdominal section, bladder neck was ligated with a suture thread, and then the hypogastric nerve and pudendal nerve were bilaterally transected. A catheter (PE-90, Clay Adams) was placed in the bladder, and the other end of the bladder catheter was connected to a pressure transducer and a water reservoir (60 ml syringe) of saline via a three-way cock. A microchip transducer catheter (SPR-524, Millar Instruments Inc.) was inserted toward the bladder from the urethral opening, and adjusted using a scale on the catheter surface so that the transducer part is positioned in the urinary tract at 10.0-15.0 mm from the urethral opening.

The changes in the topical pressure within the urinary tract (hereinafter conveniently indicated as urethral internal pressure) as measured by the microchip transducer was transmitted to a computer via an amplifier (blood pressure amplification unit AP-641G; NIHON KOHDEN) and an analog-to-digital converter (MP-100; biopack; sampled at 500 Hz), and recorded on a hard disc. The intravesical pressure was rapidly increased to 50 cmH$_2$O for 30 sec by setting the position of the water reservoir of saline at 50 cm higher, and changes in the urethral internal pressure were observed. The reaction of the urinary tract induced by an increased intravesical pressure was measured 3 times, and the average of the last 2 measures was taken as the value before drug administration. The evaluation item was reflex urethral closure response, and the recorded values were subjected to smoothing process at 500 points to calculate an average urethral internal pressure per 1 sec, after which the value immediately before increase of the intravesical pressure was subtracted from the maximum value on increase of the intravesical pressure and taken as the urethral closure response. After measurement of the value before drug administration, WAY-163909, APD-356 or compound of Example 41, which are 5-HT$_{2C}$ receptor agonists, was intravenously administered, and the urethral closure response was evaluated again 10 min later. The drugs were all dissolved in N,N-dimethylformamide/polyethylene glycol 400 (1:1) and administered intravenously at a dose of 0.5 ml/kg.

[Results]

Using female spinal cord-transected rats in which the hypogastric nerve and pudendal nerve were bilaterally transected, the intravesical pressure was rapidly increased from 0 cmH$_2$O to 50 cmH$_2$O, and the action of various 5-HT$_{2C}$ receptor agonists (WAY-163909, APD-356 and compound of Example 41) on the urethral internal pressure-increasing response (urethral closure response) induced thereby was investigated. As a result, all of these three kinds of 5-HT$_{2C}$ receptor agonists different in the basic skeleton on the chemical structure enhanced the urethral closure response induced by the increased intravesical pressure (Table 24, FIG. 1). Particularly, WAY-163909 and compound of Example 41, which are selective 5-HT$_{2C}$ receptor agonists, enhanced the reflex urethral closure response. The results clarified that the urethral closure response by the iliococcygeus muscle and pubococcygeus muscle, which are pelvic floor muscles, is enhanced by stimulation of a 5-HT$_{2C}$ receptor.

TABLE 24

Action of 5-HT$_{2c}$ receptor agonist on urethral closure response (cmH$_2$O) induced by the increased intravesical pressure in female spinal cord-transected rats with bilaterally transected hypogastric nerve and pudendal nerve

|  | dose (mg/kg, i.v.) | urethral closure response (cmH$_2$O) | |
| --- | --- | --- | --- |
|  |  | before drug administration | after drug administration |
| solvent administration group | — | 7.9 ± 1.7 | 5.1 ± 2.2 |
| WAY-163909 | 3 | 4.4 ± 0.8 | 10.2 ± 1.6*** |
| APD-356 | 1 | 5.3 ± 1.7 | 8.6 ± 2.7* |
| Example 41 | 1 | 4.6 ± 0.8 | 7.5 ± 1.6* |

Data shows mean ± SEM of each group (n = 5).
*P < 0.05,
*** P < 0.001,
difference in urethral closure response between before and after drug administration was compared to that of solvent administration group (two-sided test, Dunnett test).

INDUSTRIAL APPLICABILITY

Since compound (I) of the present invention or a prodrug thereof has a superior serotonin 5-HT$_{2C}$ receptor activating action, it is useful as a safe prophylactic or therapeutic drug for all serotonin 5-HT$_{2C}$ associated diseases, for example, stress urinary incontinence and/or obesity and the like.

Since the screening method for a prophylactic or therapeutic drug for pelvic organ prolapse, rectal prolapse or post-micturition dribble of the present invention measures the contractile force of the pelvic floor muscles, it is superior as a practical in vivo evaluation system for the pathology, and can be usefully and efficiently applied to the screening for a substance that can be used for the prophylaxis or treatment of pelvic organ prolapse, rectal prolapse or post-micturition dribble. In addition, it is also useful as an evaluation system for determining that a substance used for the prophylaxis or treatment of other diseases does not induce pelvic organ prolapse, rectal prolapse and post-micturition dribble. Moreover, using the screening method of the present invention, various pathological physiological studies aiming at elucidation of the pathological mechanism of pelvic organ prolapse, rectal prolapse or post-micturition dribble, such as identification of a gene showing varying expressions depending on the pathology and pharmacokinetic elucidation, analysis of variation in protein expression, study of treatment effects of gene transfer for pelvic organ prolapse, rectal prolapse or post-micturition dribble and the like, can be efficiently performed with high precision.

This application is based on a patent application No. 2006-136236 filed in Japan, the contents of which are incorporated in full herein by this reference.

The invention claimed is:

1. A method of screening for a substance that increases a pelvic floor muscle contraction, consisting of:
    bilaterally transecting nerves selected from the group consisting of a hypogastric nerve and a pudendal nerve of an animal,
    then increasing an intravesical pressure in the animal, and
    then measuring changes in a urethral internal pressure using a microchip transducer catheter and a computer, and
    then calculating a urethral closure response from the changes in the urethral internal pressure in a urinary tract, rectum or vagina of the animal.

2. A method of screening for a substance that increases a pelvic floor muscle contraction, consisting essentially of:
    bilaterally transecting nerves selected from the group consisting of a hypogastric nerve and a pudendal nerve of an animal,
    then increasing an intravesical pressure in the animal, and
    then measuring a leak point pressure.

* * * * *

UNITED STATES PATENT AND TRADEMARK OFFICE
CERTIFICATE OF CORRECTION

Page 1 of 1

PATENT NO.         : 9,079,907 B2
APPLICATION NO.    : 13/410774
DATED              : July 14, 2015
INVENTOR(S)        : Kamo It is certified that error appears in the above-identified patent and that said Letters Patent is hereby corrected as shown below:

In the claims,

In column 176, line 41 (claim 1), "consisting of" should read

-- consisting essentially of --.

Signed and Sealed this
Fifth Day of January, 2016

Michelle K. Lee
*Director of the United States Patent and Trademark Office*